United States Patent
Yang et al.

(10) Patent No.: US 11,739,080 B2
(45) Date of Patent: Aug. 29, 2023

(54) MATRIX METALLOPROTEINASE (MMP) INHIBITORS AND METHODS OF USE THEREOF

(71) Applicant: Foresee Pharmaceuticals USA, Inc., Newark, DE (US)

(72) Inventors: Wenjin Yang, Newark, DE (US); Kai-Wei Chang, Newark, DE (US); Suying Liu, Newark, DE (US); Cheng-Han Tsai, Newark, DE (US)

(73) Assignee: Foresee Pharmaceuticals USA, Inc., Newark, DE (US)

( * ) Notice: Subject to any disclaimer, the term of this patent is extended or adjusted under 35 U.S.C. 154(b) by 0 days.

(21) Appl. No.: 17/055,459

(22) PCT Filed: May 14, 2019

(86) PCT No.: PCT/US2019/032127
§ 371 (c)(1),
(2) Date: Nov. 13, 2020

(87) PCT Pub. No.: WO2019/222154
PCT Pub. Date: Nov. 21, 2019

(65) Prior Publication Data
US 2021/0214340 A1    Jul. 15, 2021

Related U.S. Application Data

(60) Provisional application No. 62/671,753, filed on May 15, 2018.

(51) Int. Cl.
| | |
|---|---|
| C07D 407/14 | (2006.01) |
| C07D 407/04 | (2006.01) |
| C07D 233/74 | (2006.01) |
| C07D 401/04 | (2006.01) |
| C07D 401/14 | (2006.01) |
| C07D 403/04 | (2006.01) |
| C07D 405/04 | (2006.01) |
| C07D 409/04 | (2006.01) |
| C07D 409/14 | (2006.01) |
| C07D 413/04 | (2006.01) |
| C07D 413/14 | (2006.01) |

(52) U.S. Cl.
CPC ......... *C07D 407/14* (2013.01); *C07D 233/74* (2013.01); *C07D 401/04* (2013.01); *C07D 401/14* (2013.01); *C07D 403/04* (2013.01); *C07D 405/04* (2013.01); *C07D 407/04* (2013.01); *C07D 409/04* (2013.01); *C07D 409/14* (2013.01); *C07D 413/04* (2013.01); *C07D 413/14* (2013.01)

(58) Field of Classification Search
CPC .................................................... C07D 407/14
USPC .......................................................... 514/333
See application file for complete search history.

(56) References Cited

U.S. PATENT DOCUMENTS

| | | | |
|---|---|---|---|
| 6,352,976 | B1 | 3/2002 | Warshawsky |
| 7,179,831 | B2 * | 2/2007 | Yang ............... A61P 11/06 |
| | | | 548/317.1 |
| 2004/0067996 | A1 | 4/2004 | Sheppeck |
| 2004/0072871 | A1 | 4/2004 | Dublanchet |
| 2006/0041000 | A1 | 2/2006 | Yang |

FOREIGN PATENT DOCUMENTS

| | | |
|---|---|---|
| EP | 1288199 A1 | 3/2003 |
| EP | 1394159 A1 | 3/2004 |
| WO | 0040577 A1 | 7/2000 |
| WO | 02074752 A1 | 9/2002 |
| WO | 02096426 A1 | 12/2002 |
| WO | 2004020415 A1 | 3/2004 |
| WO | 2004108086 A2 | 12/2004 |

OTHER PUBLICATIONS

King, Med. Chem., Principle and Practice (1994), pp. 206-208.*
Morrison, K. "Physical Science Level 3" Pearson Education: Capetown, 2008, pp. 16-18, at p. 18.
Hautamaki, et al., "Requirement for macrophage elastase for cigarette smoke-induced emphysema in mice.", Science, vol. 277, 5334, pp. 2002-2004 (Sep. 1997).
Matute-Bello, et al. "Essential Role of MMP-12 in Fas-Induced Lung Fibrosis ", Am. Journal of Respir. Cell. Mol. Bio., vol. 37 (2); pp. 210-221, (Apr. 2007).
Madala, et al., "Matrix Metalloproteinases 12-Deficiency Augments Extracellular Matrix Degrading Metalloproteinase and Attenuates IL-13 Dependent Fibrosis", The Journal of Immunology, 184, pp. 3955-3963, (Feb. 2010).
Sand, et al., "MMP Mediated Degradation of Type IV Collagen Alpha 1 and Alpha 3 Chains Reflects Basement Membrane Remodeling in Experimental and Clinical Fibrosis—Validation of Two Novel Biomarker Assays", Plos One, 8:e84934, (2013), 12 pages.
Owen, et al., "The cell biology of leukocyte-mediated proteolysis.", J. Leukoc. Biology, vol. 65, pp. 137-150, (Feb. 1999).
Shapiro, et al., "Cloning and characterization of a unique elastolytic metalloproteinase produced by human alveolar macrophages.", J. Biol. Chem., vol. 268; 32, pp. 23824-9, (Nov. 1993).
Warner, et al., "Role of Metalloelastase in a Model of Allergic Lung Responses Induced by Cockroach Allergen", Am. J. Pathol., vol. 165; 6, pp. 1921-1930, (Dec. 2004).

(Continued)

*Primary Examiner* — Taofiq A Solola
(74) *Attorney, Agent, or Firm* — Ice Miller LLP

(57) ABSTRACT

Hydantoin based compounds useful as inhibitors of matrix metalloproteinases (MMPs), particularly macrophage elastase (MMP-12) are described. Also described are related compositions and methods of using the compounds to inhibit MMP-12 and treat diseases mediated by MMP-12, such as asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

13 Claims, 3 Drawing Sheets

(56) References Cited

OTHER PUBLICATIONS

Kaneko, et al., "Nephritis Anti-Glomerular Basement Membrane Factor for Glomerular Injury in Anti-Glomerular Basement Membrane Nephritis", The Journal of Immunology, 170:3377-3385, (2003).
Matsumoto, et al., "Expression and localization of matrix metalloproteinase-12 in the aorta of cholesterol-fed rabbits: relationship to lesion development.", vol. 153;1,pp. 109-119, (Jul. 1998).
Jormsjo, et al., "Allele-Specific Regulation of Matrix Metalloproteinase-12 Gene Activity Is Associated With Coronary Artery Luminal Dimensions in Diabetic Patients With Manifest Coronoary Artery Disease.", Circulation Research, 86:998-1003, (2000).
Pender, et al., "Role of macrophage metalloelastase in gut inflammation.", Ann. N.Y. Acad. Sci., vol. 1072:386-388, (Aug. 2006).
Makitalo, et al., "Matrix metalloproteinases in the restorative proctocolectomy pouch of pediatric ulcerative colitis", vol. 18, 30:4028-4036, (Aug. 2012).
International Search Report & Written Opinion issued in PCT/2019/032131 dated Jul. 5, 2019, 12 pages.
International Search Report & Written Opinion issued in PCT/US2019/032127 dated Jul. 19, 2019, 8 pages.

\* cited by examiner (I)

(II)

(I) Collagen I (II) Collagen IV (I) Collagen I (II) Collagen IV

MATRIX METALLOPROTEINASE (MMP) INHIBITORS AND METHODS OF USE THEREOF

CROSS REFERENCE TO RELATED APPLICATION

This application is entitled to priority under 35 U.S.C. § 119(e) to U.S. Provisional Patent Application No. 62/671,753, filed May 15, 2018, the disclosure of which is incorporated herein by reference.

BACKGROUND OF THE INVENTION

Matrix metalloproteinases (MMPs) are a superfamily of proteinase enzymes that are important for the degradation of most extracellular matrix proteins during organogenesis, growth, and normal tissue turnover. MMPs are also believed to be important in the uncontrolled breakdown of connective tissue, which relates to a few disease processes such as rheumatoid arthritis, osteoarthritis, gastric ulceration, asthma, emphysema, and tumor metastasis. Therefore, inhibition of one or more MMPs may be of benefit in these diseases.

Human macrophage elastase (MMP-12) is a particular MMP. MMP-12 exhibits all the characteristics of other MMPs, but is preferentially produced from macrophages infiltrating into tissues where injury or remodeling is occurring, and degrades extracellular matrix. For example, increased levels of MMP-12 have been observed during the onset of emphysema. Additionally, an MMP-12 knock-out mouse model showed no development of emphysema after being exposed for a lengthy period of time to cigarette smoke (Hautamkai et al. *Science*, 1997, 277: 2002-2004). These data suggest that MMP-12 plays a role in disease progression of emphysema. The involvement of MMP-12 in the development of chronic asthma has also been suggested based on studies in an MMP-12 deficient model of asthma (Warner et al. *Am J Pathol.* 2004; 165(6): 1921-1930). In the Fas-induced model of acute lung injury, MMP12-deficient mice are protected from developing pulmonary fibrosis (Matute-Bello et al., *Am J Respir Cell Mol Biol.* 2007; 37(2): 210-221). In a model of pulmonary and hepatic fibrosis induced by *Schistosoma mansoni* infection, MMP-12 has profibrotic activities in the lung and liver (Madala et al. *J Immunol* 2010; 184:3955-3963). MMP-12 may also contribute to Idiopathic pulmonary fibrosis (IPF) pathogenesis by cleaving extracellular matrix (ECM) proteins, as BALF levels of a type IV collagen fragment generated by MMP-12 are increased in patients with IPF (Sand et al. *PLoS One* 2013; 8:e84934), and human MMP-12 can cleave a number of human ECM proteins in vitro (Owen et al. *J Leukoc Biol* 1999; 65:137-150). Together, these results suggest that inhibitors of MMP-12 may be useful in the treatment of pulmonary diseases, such as chronic obstructive pulmonary disease (COPD), emphysema, asthma, acute lung injury, idiopathic pulmonary fibrosis (IPF), liver fibrosis and non-alcoholic steatohepatitis (NASH).

MMP-12 has been shown to be secreted from alveolar macrophages of smokers (Shapiro et al., *Journal of Biological Chemistry*, 1993, 268: 23824), in foam cells in atherosclerotic lesions (Matsumoto et al., *Am. J. Pathol.*, 1998, 153: 109), and in a nephritis rat model (Kaneko et al., *J. Immunol.*, 2003, 170:3377). MMP-12 also plays a role in coronary artery disease (Jormsjo et al., *Circulation Research*, 2000, 86: 998). MMP-12 was also shown to be upregulated in inflammatory bowel disease (IBD) patients as well as in a T-cell mediated model of colitis and contribute to epithelial degradation and MMP-12-/- mice were protected against TNBS induced colitis (Pender et al., *Ann N Y Acad Sci.* 2006, 1072:386-8.). Epithelial and stromal MMP-12 along with MMP-3 and -7 have been also upregulated in pouch mucosa of pediatric onset UC, suggesting that the expression of MMPs pediatric UC pouch in the long-term shares characteristics with IBD (Makitalo et al., *World J Gastroenterol.* 2012, 18(30):4028-36). Taken together, these observations suggest that MMP-12 could be a target for treatment of these diseases.

In view of the involvement of MMP-12 in a number of diseases, attempts have been made to prepare inhibitors of MMP-12. A number of MMP-12 inhibitors are known (see e.g., International Patent Application Publication WO 00/40577; European Patent Application Publication EP 1 288 199 A1; U.S. Pat. No. 6,352,976, and U.S. Patent Application Publication No. 2004/0072871; and European Patent Application Publication EP1394159).

A particular class of MMP inhibitors that have been described are the hydantoin derivatives. For example, International Patent Application Publication WO 02/096426 describes hydantoin derivatives of the general formula:

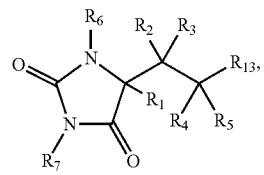

which are disclosed as being active as MMP inhibitors, particularly against tumor necrosis factor-alpha converting enzyme (TACE) and aggrecanase. A feature of the disclosed structures of these derivatives is a spiro-linkage between the hydantoin ring and its side chain. U.S. Patent Application Publication No. 2004/0067996 and International Patent Application Publication WO 2004/108086 describe similar hydantoin derivatives of the general formula:

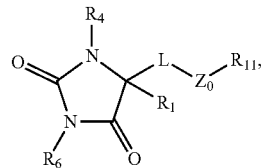

which are also described as MMP inhibitors, particularly for TACE and aggrecanase.

International Patent Application Publication WO 02/074752 describes the synthesis of MMP inhibitors and International Patent Application Publication WO 2004/020415 discloses MMP-12 inhibitors, which are hydantoin derivatives of the general formula:

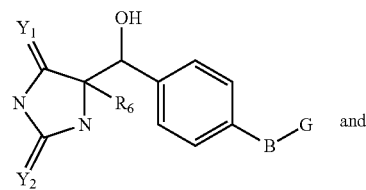

and

-continued $$\underset{Z_2}{\overset{Z_1}{\underset{HN}{\bigvee}}}\overset{R_2}{\underset{Y}{\bigvee}}\overset{R_3}{\underset{O}{\bigvee}}X_{L}G,$$

respectively. Some of the disclosed compounds showed MMP inhibitory activities, including MMP-12 inhibitory activity.

More recently, inhibitors of MMP-12 have been described in U.S. Pat. No. 7,179,831, which are hydantoin derivatives of the general formula:

[Structure of hydantoin derivative with furan and thioether-phenyl-O-CH₂-R]

Hydantoin derivatives are a useful class of MMP inhibitors. However, there is a need in the art to identify hydantoin derivatives having improved specificity, potency, and pharmacological properties.

BRIEF SUMMARY OF THE INVENTION

The application satisfies this need by providing hydantoin derivatives having high activity and specificity for MMPs, particularly macrophage elastase (MMP-12).

In a general aspect, the application relates to a compound of formula (I-b):

[Structure (I-b)]

or a tautomer, stereoisomer, pharmaceutically acceptable salt, or solvate thereof,
wherein:
ring B is an optionally substituted aryl or optionally substituted heteroaryl;
ring C is an optionally substituted aryl or optionally substituted heteroaryl;
ring D is an optionally substituted aryl or optionally substituted heteroaryl;
each of X, Y and Z is independently selected from the group consisting of $CH_2$, O, $NR_x$ and $S(O)_q$, wherein $R_x$ is hydrogen or alkyl;
$R_1$ is hydrogen or alkyl;
$R_4$ is hydrogen or alkyl;
$R_5$ is hydrogen; and
q is 0, 1, or 2,
provided that ring B is not furanyl.

In an embodiment, the application relates to a compound of formula (I):

[Structure (I)]

or a tautomer, stereoisomer, pharmaceutically acceptable salt, or solvate thereof,
wherein:
ring B is an optionally substituted aryl or optionally substituted heteroaryl;
ring C is aryl or heteroaryl;
ring D is aryl or heteroaryl;
each of X, Y and Z is independently selected from the group consisting of $CH_2$, O, $NR_x$ and $S(O)_q$, wherein $R_x$ is hydrogen or alkyl;
$R_1$ is hydrogen or alkyl;
each $R_2$ is independently selected from the group consisting of hydrogen, alkyl, halogen, hydroxyl, haloalkyl, alkoxy, alkylthio, amine, amide, alkylamine, aminoalkyl, cyano, hydroxyalkyl, —$(CH_2)_pC(O)OR_6$, and —$(CH_2)_pOC(O)R_6$;
each $R_3$ is independently selected from the group consisting of hydrogen, alkyl and halo;
$R_4$ is hydrogen or alkyl;
$R_5$ is hydrogen;
each $R_6$ is independently selected from the group consisting of hydrogen and alkyl, wherein the alkyl is unsubstituted or substituted with one or more groups independently selected from the group consisting of amine, hydroxyl, halogen, and alkoxy;
m is 1, 2, 3, or 4;
n is 1, 2, 3, 4, or 5;
p is 0, 1, 2, 3, 4, or 5; and
q is 0, 1, or 2,
provided that ring B is not furanyl.

In an embodiment, the application relates to a compound of formula (I), or a tautomer, stereoisomer, pharmaceutically acceptable salt, or solvate thereof, wherein ring C is phenyl.

In an embodiment, the application relates to a compound of formula (I), or a tautomer, stereoisomer, pharmaceutically acceptable salt, or solvate thereof, wherein ring D is pyridnyl or phenyl.

In an embodiment, the application relates to a compound of formula (I), or a tautomer, stereoisomer, pharmaceutically acceptable salt, or solvate thereof, wherein ring D is:

[Four ring D structures: methylphenyl, methylpyridyl, benzamide, hydroxymethylphenyl]

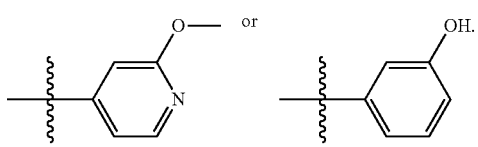

In an embodiment, the application relates to a compound of formula (I), or a tautomer, stereoisomer, pharmaceutically acceptable salt, or solvate thereof, wherein each of $R_1$, $R_4$ and $R_5$ is hydrogen.

In an embodiment, the application relates to a compound of formula (I), or a tautomer, stereoisomer, pharmaceutically acceptable salt, or solvate thereof, wherein X is S; Y is O; and Z is $CH_2$.

In an embodiment, the application relates to a compound of formula (I), or a tautomer, stereoisomer, pharmaceutically acceptable salt, or solvate thereof, wherein ring B is a five or six membered monocyclic heteroaryl having 1-2 heteroatoms independently selected from N, S, and O, wherein the five or six membered monocyclic heteroaryl is optionally substituted with —$CH_3$.

In an embodiment, the application relates to a compound of formula (I), or a tautomer, stereoisomer, pharmaceutically acceptable salt, or solvate thereof, wherein ring B is pyridinyl, thiophenyl, imidazolyl, pyrazolyl, or oxazolyl, wherein each of pyridinyl, thiophenyl, imidazolyl, pyrazolyl, and oxazolyl is optionally substituted with —$CH_3$.

In an embodiment, the application relates to a compound of formula (I), or a tautomer, stereoisomer, pharmaceutically acceptable salt, or solvate thereof, wherein ring B is pyridinyl.

In an embodiment, the application relates to a compound selected from the group consisting of a compound of formula (II-a), a compound of formula (II-b), a compound of formula (II-c), and a compound of formula (II-d):

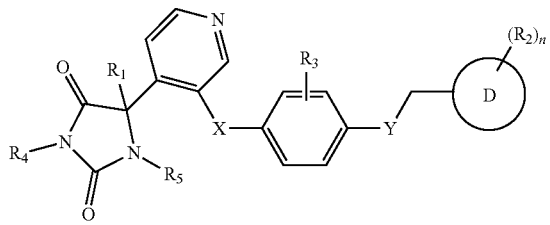

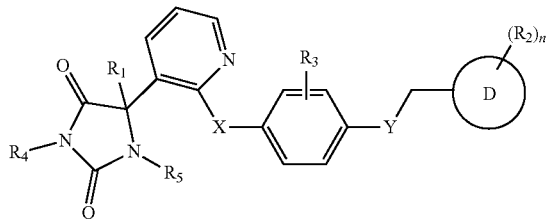

or a tautomer, stereoisomer, pharmaceutically acceptable salt, or solvate thereof,
wherein:
$R_1$ is hydrogen, —$CH_3$, or —$CH_2CH_3$;
$R_4$ is hydrogen or —$CH_3$;
$R_5$ is hydrogen or —$CH_3$;
$R_3$ is hydrogen, —F, —Cl, or $CH_3$;
X is S, SO, or $SO_2$;
Y is O, NH, $CH_2$, or $NHCH_3$;
ring D is pyridinyl or phenyl;
$R_2$ is —$CH_3$, —$CH_2OH$, —OH, $CH_2OC(O)CH(NH_2)CH(CH_3)_2$, —COOH, —$C(O)NH_2$, —$C(O)NHCH_3$, —$OCH_3$, —$OCH_2CH_3$, —$OCH(CH_3)_2$, or —$CH_2CH(CH_3)_2$; and
n is 0 or 1.

In an embodiment, the application relates to a compound of formula (I), or a tautomer, stereoisomer, pharmaceutically acceptable salt, or solvate thereof, wherein ring B is thiophenyl.

In an embodiment, the application relates to a compound of formula (IV):

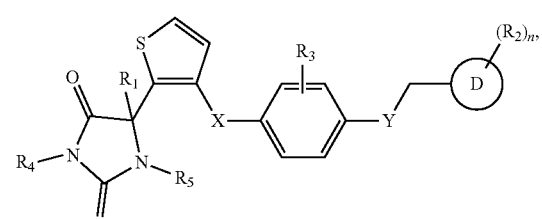

or a tautomer, stereoisomer, pharmaceutically acceptable salt, or solvate thereof,
wherein:
each of $R_1$, $R_4$ and $R_5$ is hydrogen;
X is S;
Y is O;
$R_3$ is hydrogen;
ring D is phenyl or pyridinyl;
$R_2$ is —$CH_3$, —$C(O)NH_2$, —$CH_2OH$, —$OCH_3$, or —OH; and
n is 0 or 1.

In an embodiment, the application relates to a compound selected from the group consisting of a compound of formula (Va), a compound of formula (Vb) and a compound of formula (VI):

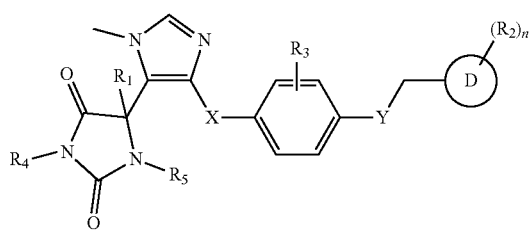
(Va)

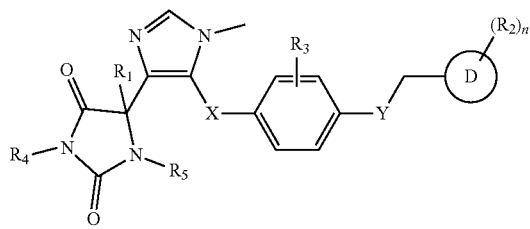
(Vb)

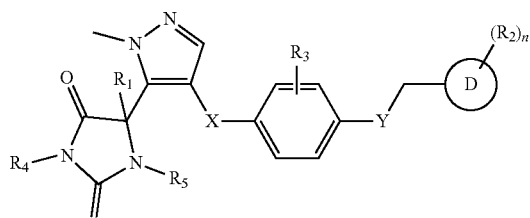
(VI)

or a tautomer, stereoisomer, pharmaceutically acceptable salt, or solvate thereof, wherein:

$R_1$ is hydrogen, —$CH_3$, or —$CH_2CH_3$;

$R_4$ is hydrogen or —$CH_3$;

$R_5$ is hydrogen or —$CH_3$;

$R_3$ is hydrogen, —F, —Cl, or $CH_3$;

X is S, SO, or $SO_2$;

Y is O, NH, $CH_2$, or $NHCH_3$;

ring D is pyridinyl or phenyl;

$R_2$ is —$CH_3$, —$CH_2OH$, —OH, $CH_2OC(O)CH(NH_2)CH(CH_3)_2$, —COOH, —C(O)$NH_2$, —C(O)$NHCH_3$, —$OCH_3$, —$OCH_2CH_3$, —$OCH(CH_3)_2$, or —$CH_2CH(CH_3)_2$; and n is 0 or 1.

In an embodiment, the application relates to a compound selected from the group consisting of a compound of formula (VII-a) and a compound of formula (VII-b):

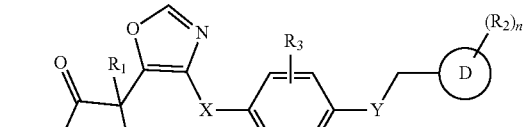
(VII-a)

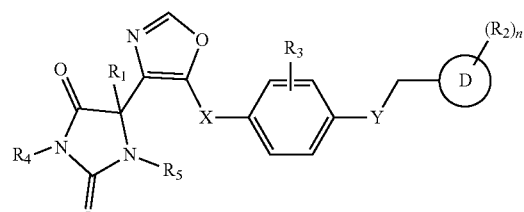
(VII-b)

or a tautomer, stereoisomer, pharmaceutically acceptable salt, or solvate thereof, wherein:

each of $R_1$, $R_3$, $R_4$, and $R_5$ is hydrogen;

X is S;

Y is O;

ring D is phenyl or pyridinyl;

$R_2$ is —$CH_3$, —C(O)$NH_2$, —$CH_2OH$, —$OCH_3$, or —OH; and n is 0 or 1.

In an embodiment, the application relates to a compound of formula (I-a):

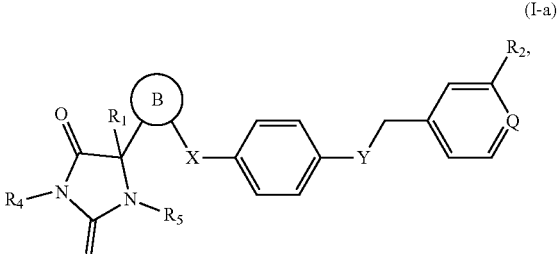
(I-a)

or a tautomer, stereoisomer, pharmaceutically acceptable salt, or solvate thereof, wherein:

ring B is pyridinyl;

Q is CH or N;

$R_1$ is hydrogen, —$CH_3$, or —$CH_2CH_3$;

$R_4$ is hydrogen or —$CH_3$;

$R_5$ is hydrogen or —$CH_3$;

$R_2$ is selected from the group consisting of —$CH_3$, —C(O)$NH_2$, —$CH_2OH$, —$OCH_3$, or —OH;

X is S; and

Y is O.

In an embodiment, the application relates to a compound selected from the group consisting of the compounds listed in Table 1, or a tautomer, stereoisomer, pharmaceutically acceptable salt, or solvate thereof.

In an embodiment, the application relates to a compound selected from the group consisting of the compounds listed in Table 1, or pharmaceutically acceptable salt thereof.

In another general aspect, the application relates to a pharmaceutical composition comprising a compound of the application as described herein, or a tautomer, stereoisomer, pharmaceutically acceptable salt, or solvate thereof, and at least one pharmaceutically acceptable carrier.

Other general aspects of the application relate to methods of inhibiting macrophage elastase (MMP-12) in a subject in need thereof, and methods of treating a disease mediated by macrophage elastase (MMP-12) in a subject in need thereof.

In an embodiment, the application relates to a method of inhibiting macrophage elastase (MMP-12) in a subject in need thereof, comprising administering to the subject a compound or pharmaceutical composition of the application.

In an embodiment, the application relates to a method of treating a disease mediated by macrophage elastase (MMP-12) in a subject in need thereof, comprising administering to the subject a compound or pharmaceutical composition of the application.

In some embodiments, the disease is selected from the group consisting of asthma, chronic obstructive pulmonary disease (COPD), emphysema, acute lung injury, and idiopathic pulmonary fibrosis (IPF), sarcoidosis, systemic sclerosis, liver fibrosis, nonalcoholic steatohepatitis (NASH), arthritis, cancer, heart disease, Inflammatory bowel disease (IBD), acute kidney injury (AKI), chronic kidney disease (CKD), Alport syndrome, and nephritis.

Also provided herein is a compound of the application or a tautomer, stereoisomer, pharmaceutically acceptable salt, or solvate thereof, or a composition of the application for use in a method of inhibiting macrophage elastase (MMP-12), or treating a disease mediated by macrophage elastase (MMP-12). In some embodiments, the disease is selected from the group consisting of asthma, chronic obstructive pulmonary disease (COPD), emphysema, acute lung injury, and idiopathic pulmonary fibrosis (IPF), sarcoidosis, systemic sclerosis, liver fibrosis, nonalcoholic steatohepatitis (NASH), arthritis, cancer, heart disease, Inflammatory bowel disease (IBD), acute kidney injury (AKI), chronic kidney disease (CKD), Alport syndrome, and nephritis.

Also provided herein is use of a compound of the application or a tautomer, stereoisomer, pharmaceutically acceptable salt, or solvate thereof, or a composition of the application in the manufacture of a medicament for inhibiting macrophage elastase (MMP-12) or treating a disease mediated by macrophage elastase (MMP-12). Preferably, the disease is selected from the group consisting of asthma, chronic obstructive pulmonary disease (COPD), emphysema, acute lung injury, and idiopathic pulmonary fibrosis (IPF), sarcoidosis, systemic sclerosis, liver fibrosis, nonalcoholic steatohepatitis (NASH), arthritis, cancer, heart disease, Inflammatory bowel disease (IBD), acute kidney injury (AKI), chronic kidney disease (CKD), Alport syndrome, and nephritis.

In yet another general aspect, the application relates to a method of preparing a pharmaceutical composition of the application, comprising combining a compound of the application, or a tautomer, stereoisomer, pharmaceutically acceptable salt, or solvate thereof, and at least one pharmaceutically acceptable carrier.

BRIEF DESCRIPTION OF THE FIGURES

The foregoing summary, as well as the following detailed description of the invention, will be better understood when read in conjunction with the appended FIGS. It should be understood that the invention is not limited to the precise embodiments shown in the drawings.

In the FIGS.:

FIG. 1A shows changes in serum BUN at 2 weeks as compared to pre-operation (pre-OP) for each of the experimental SD rat groups; FIG. 1B shows changes in serum creatine at 2 weeks as compared to pre-operation (pre-OP) for each of the experimental SD rat groups; FIG. 1C shows histology images of kidneys from H&E staining at ×200 magnification; panel A: right kidney as normal control, panel B: vehicle treated animals, panel C: PC-16 treated animals (2 mg/kg/day), panel D: PC-16 treated animals (6 mg/kg/day), panel E: PC-16 treated animals (20 mg/kg/day); FIG. 1D shows the renal tubular damage score (I) and the renal interstitial inflammatory score (II) for each of the experimental SD rat groups; T-test in (I): *$p<0.05$ vs. model, $$p<0.05$ vs. PC-16 (2 mg/kg/day), $$$p<0.01$ vs. PC-16 (6 mg/kg/day); T-test in (II): $p<0.05$ vs. model, *$p<0.001$ vs. model, FIG. 1E shows histology images in the kidneys from Masson Trichrome staining at a magnification of ×200; panels A-E correspond to panels A-E as described in FIG. 1C; FIG. 1F shows the interstitial fibrosis score for kidney interstitial fibrosis in the cortex; T-test: $p<0.01$ vs. model, *$p<0.001$ vs. model, $$p<0.05$ vs. PC-16 (2 mg/kg/day), $$$p<0.01$ vs. PC-16 (2 mg/kg/day); FIG. 1G shows collagen I deposition (I) and collagen IV deposition (II) in the cortex area of the left kidney by IHC staining at ×200 magnification; panels A-E correspond to panels A-E as described in FIG. 1C; FIG. 1H shows collagen I deposition positive staining (%) (I) and collagen IV deposition positive staining (%) (II) in the cortex area of the left kidney as determined from the IHC staining in FIG. 1G; One-way ANOVA: *$p<0.001$ vs. normal control; T-test: #$p<0.05$ vs. model.

DETAILED DESCRIPTION OF THE INVENTION

Figure 1A:
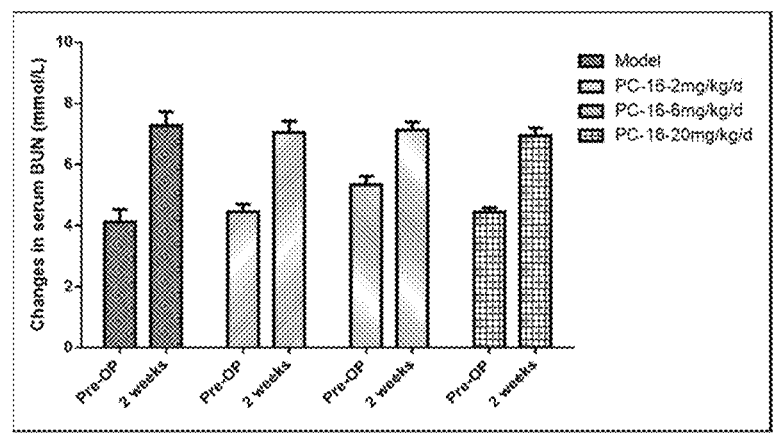
FIGS. 1A-1H depict the results of the efficacy study of MMP-12 inhibitors on SD rat kidney fibrosis model by unilateral ureteral occlusion (UUO) described in Example 3.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the application can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Unless otherwise stated, any numerical value, such as a concentration or a concentration range described herein, are to be understood as being modified in all instances by the term "about." Thus, a numerical value typically includes ±10% of the recited value. For example, the recitation of "10-fold" includes 9-fold and 11-fold. As used herein, the use of a numerical range expressly includes all possible subranges, all individual numerical values within that range, including integers within such ranges and fractions of the values unless the context clearly indicates otherwise.

As used herein, "subject" means any animal, preferably a mammal, most preferably a human, to whom will be or has been treated by a method according to an embodiment of the application. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

The phrase "pharmaceutically acceptable salt(s)", as used herein, means those salts of a compound of interest that are safe and effective for topical use in mammals and that possess the desired biological activity. Pharmaceutically acceptable salts include salts of acidic or basic groups present in the specified compounds. Pharmaceutically acceptable acid addition salts include, but are not limited to, hydrochloride, hydrobromide, hydroiodide, nitrate, sulfate, bisulfate, phosphate, acid phosphate, isonicotinate, carbonate, bicarbonate, acetate, lactate, salicylate, citrate, tartrate, propionate, butyrate, pyruvate, oxalate, malonate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds used in the application can form pharmaceutically acceptable salts with various amino acids. Suitable base salts include, but are not limited to, aluminum, calcium, lithium, magnesium, potassium, sodium, zinc, bismuth, and diethanolamine salts. For a review on pharmaceutically acceptable salts see Berge et al., 66 *J. Pharm. Sci.* 1-19 (1977), incorporated herein by reference.

As used herein, the term "alkyl" means a saturated, monovalent, unbranched or branched hydrocarbon chain. An alkyl group can be unsubstituted or substituted with one or more suitable substituents. Examples of alkyl groups include, but are not limited to, methyl (Me), ethyl (Et), propyl (e.g., n-propyl, isopropyl), butyl (e.g., n-butyl, isobutyl, tert-butyl), and pentyl (e.g., n-pentyl, isopentyl, neopentyl), etc. An alkyl group can have a specified number of carbon atoms. When numbers appear in a subscript after the symbol "C", the subscript defines with more specificity the number of carbon atoms that a particular alkyl can contain. For example, "$C_1$ to $C_{10}$ alkyl" or "$C_{1-10}$ alkyl" is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having one to six carbon atoms.

The term "alkoxy" as used herein refers to an —O-alkyl group, wherein alkyl is as defined above. An alkoxy group is attached to the parent molecule through an oxygen atom. An alkoxy group can have a specified number of carbon atoms. For example, "$C_1$ to $C_{10}$ alkoxy" or "$C_{1-10}$ alkoxy" is intended to include $C_1$, $C_2$, $C_3$, $C_4$, $C_5$, $C_6$, $C_7$, $C_8$, $C_9$, and $C_{10}$ alkoxy groups. Additionally, for example, "$C_1$ to $C_6$ alkoxy" or "$C_{1-6}$ alkoxy" denotes alkoxy having 1 to 6 carbon atoms. Examples of alkoxy include, but are not limited to, methoxy, ethoxy, propoxy (e.g., n-propoxy, isopropoxy), butoxy (e.g., n-butoxy, isobutoxy, tert-butoxy), pentyloxy (e.g., n-pentyloxy, isopentyloxy, neopentyloxy), etc. An alkoxy group can be unsubstituted or substituted with one or more suitable substituents. Similarly, "alkylthio" or "thioalkoxy" represents an alkyl group as defined above attached through a sulfur bridge, for example, —S—methyl, —S-ethyl, etc. Representative examples of alkylthio include, but are not limited to, —$SCH_3$, —$SCH_2CH_3$, etc.

As used herein, the term "halogen" means fluorine, chlorine, bromine, or iodine. Correspondingly, the term "halo" means fluoro, chloro, bromo, and iodo.

"Haloalkyl" is intended to include both branched and straight-chain saturated aliphatic hydrocarbon groups substituted with one or more halogen atoms. Examples of haloalkyl include, but are not limited to, fluoromethyl, difluoromethyl, trifluoromethyl, chloromethyl, dichloromethyl, trichloromethyl, pentafluoroethyl, pentachloroethyl, 2,2,2-trifluoroethyl, heptafluoropropyl, and heptachloropropyl.

The terms "hydroxy" and "hydroxyl" can be used interchangeably, and refer to —OH.

The term "carboxy" refers to —COOH.

The term "cyano" refers to —CN.

The term "amino" refers to —$NH_2$. The term "alkylamino" refers to an amino group in which one or both of the hydrogen atoms attached to nitrogen is substituted with an alkyl group. For example, alkylamino includes methylamino (—$NHCH_3$), dimethylamino (—$N(CH_3)_2$), —$NHCH_2CH_3$, etc.

The term "aminoalkyl" as used herein is intended to include both branched and straight-chain saturated aliphatic hydrocarbon groups substituted with one or more amino groups. For example, "$C_{1-4}$ aminoalkyl" is intended to include $C_1$, $C_2$, $C_3$, and $C_4$ alkyl groups substituted with one or more amino groups. Representative examples of aminoalkyl groups include, but are not limited to, —CH$_2$NH$_2$, —CH$_2$CH$_2$NH$_2$, and —CH$_2$CH(NH$_2$)CH$_3$.

As used herein, "amide" refers to —C(O)N(R)$_2$, wherein each R is independently an alkyl group or a hydrogen. Examples of amides include, but are not limited to, —C(O)NH$_2$, —C(O)NHCH$_3$, and —C(O)N(CH$_3$)$_2$.

The terms "hydroxylalkyl" and "hydroxyalkyl" are used interchangeably, and refer to an alkyl group substituted with one or more hydroxyl groups. The alkyl can be a branched or straight-chain aliphatic hydrocarbon. Examples of hydroxylalkyl include, but are not limited to, hydroxylmethyl (—CH$_2$OH), hydroxylethyl (—CH$_2$CH$_2$OH), etc.

The term "aryl" as used herein is a group that contains any carbon-based aromatic group including, but not limited to, phenyl, naphthyl, anthracenyl, phenanthranyl, and the like. Aryl moieties are well known and described, for example, in Lewis, R. J., ed., Hawley's *Condensed Chemical Dictionary*, 13$^{th}$ Edition, John Wiley & Sons, Inc., New York (1997). An aryl group can be substituted or unsubstituted with one or more suitable substituents. An aryl group can be a single ring structure (i.e., monocyclic) or comprise multiple ring structures (i.e., polycyclic) that are fused ring structures. Preferably, an aryl group is a monocyclic aryl group for instance phenyl.

As used herein, the term "heteroaryl" includes stable monocyclic and polycyclic aromatic hydrocarbons that contain at least one heteroatom ring member such as sulfur, oxygen, or nitrogen. Heteroaryl can be monocyclic or polycyclic, e.g., bicyclic or tricyclic. Each ring of a heteroaryl group containing a heteroatom can contain one or two oxygen or sulfur atoms and/or from one to four nitrogen atoms provided that the total number of heteroatoms in each ring is four or less and each ring has at least one carbon atom. For bicyclic heteroaryl groups, the fused rings completing the bicyclic group can contain only carbon atoms and can be saturated, partially saturated, or unsaturated. Heteroaryl groups which are polycyclic, e.g., bicyclic or tricyclic must include at least one fully aromatic ring but the other fused ring or rings can be aromatic or non-aromatic. The heteroaryl group can be attached at any available nitrogen or carbon atom of any ring of the heteroaryl group. Preferably, the term "heteroaryl" refers to 5- or 6-membered monocyclic groups and 9- or 10-membered bicyclic groups which have at least one heteroatom (O, S, or N) in at least one of the rings, wherein the heteroatom-containing ring preferably has 1, 2, or 3 heteroatoms, more preferably 1 or 2 heteroatoms, selected from 0, S, and/or N. A heteroaryl group can be unsubstituted, or substituted with one or more suitable substituents. The nitrogen heteroatom(s) of a heteroaryl can be substituted or unsubstituted. The nitrogen and sulfur heteroatom(s) of a heteroaryl can optionally be oxidized (i.e., N→O and S(O)$_r$, wherein r is 0, 1 or 2).

Exemplary monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl. Exemplary bicyclic heteroaryl groups include, but are not limited to, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridinyl, furopyridinyl, dihydroisoindolyl, and tetrahydroquinolinyl.

In accordance with convention used in the art:

is used in structural formulas herein to depict the bond that is the point of attachment of the moiety or substituent to the core or backbone structure.

When a bond to a substituent is shown to cross a bond connecting two atoms in a ring, then such substituent can be bonded to any atom on the ring.

As referred to herein, the term "substituted" means that at least one hydrogen atom is replaced with a non-hydrogen group, provided that all normal valencies are maintained and that the substitution results in a stable compound. When a particular group is "substituted," that group can have one or more substituents, preferably from one to five substituents, more preferably from one to three substituents, most preferably from one to two substituents, independently selected from the list of substituents. The term "independently" when used in reference to substituents, means that when more than one of such substituents is possible, such substituents can be the same or different from each other. Examples of suitable substituents include, but are not limited to, alkyl, halogen, alkoxy, amide, alkythio, amine, alkylamine, aminoalkyl, hydroxyalkyl, hydroxyl, carboxyl, etc., such as C$_{1-4}$ alkyl, C$_{1-3}$ alkoxy, —OH, —COOH, —F, —C(O)NHCH$_3$, —C(O)N(CH$_3$)$_2$.

When any variable occurs more than one time in any constituent or formula for a compound, its definition at each occurrence is independent of its definition at every other occurrence. Thus, for example, if a group is shown to be substituted with 0-3R groups, then said group can be optionally substituted with up to three R groups, and at each occurrence, R is selected independently from the definition of R.

The terms "optional" or "optionally" mean that the event or circumstance described subsequently can, but need not, occur, and such a description includes the situation in which the event or circumstance does or does not occur. For example, "optionally substituted aryl" means that a substituent group can be, but need not be, present, and such a description includes the situation of the aryl group being substituted by a suitable substituent and the aryl group being not substituted by any substituent.

One skilled in the art will recognize that in certain embodiments compounds of the application can have one or more asymmetric carbon atoms in their structure. As used herein, any chemical formulas with bonds shown only as solid lines and not as solid wedged or hashed wedged bonds, or otherwise indicated as having a particular configuration (e.g., R or S) around one or more atoms, contemplates each possible stereoisomer, or mixture of two or more stereoisomers. In other words, if the stereochemistry of a structure is not specified, the structure is intended to encompass all individual stereoisomers and mixtures thereof. Stereoisomers includes enantiomers and diastereomers. Enantiomers are stereoisomers that are non-super-imposable mirror images of each other. A 1:1 mixture of a pair of enantiomers is a racemate or racemic mixture. Diastereomers (or diastereoisomers) are stereoisomers that are not enantiomers, i.e., they are not related as mirror images, and occur when two or more stereoisomers of a compound have different configurations at one or more of the equivalent stereocenters and are not mirror images of each other. Substituent groups (e.g., alkyl, heterocyclyl, etc.) can contain stereocenters in either the R or S configuration.

Thus, included within the scope of the invention are the stereochemically pure isomeric forms of the compounds of the invention (i.e., a single enantiomer or a single diastereomer) as well as mixtures thereof including their racemates. When a specific stereoisomer is identified, this means that the stereoisomer is substantially free, i.e., associated with less than 50%, preferably less than 20%, more preferably less than 5%, in particular less than 2% and most preferably less than 1% of the other stereoisomers. For example, when a compound is for instance specified as (R), this means that the compound is substantially free of the (S) isomer. Compounds of the application described herein can be used as racemic mixtures, enantiomerically or diastereomerically enriched mixtures, or as enantiomerically or diastereomerically pure individual stereoisomers.

Stereochemically pure isomeric forms can be obtained by techniques known in the art in view of the present disclosure. For example, diastereoisomers can be separated by physical separation methods such as fractional crystallization and chromatographic techniques, and enantiomers can be separated from each other by the selective crystallization of the diastereomeric salts with optically active acids or bases or by chiral chromatography. Pure stereoisomers can also be prepared synthetically from appropriate stereochemically pure starting materials, or by using stereoselective reactions.

Compounds of the application can also form tautomers. The term "tautomer" refers to compounds that are interchangeable forms of a particular compound structure and that vary in the displacement of hydrogen atoms and electrons. Tautomers are constitutional isomers of chemical compounds that readily interconvert, usually resulting in relocation of a proton (hydrogen). Thus, two structures can be in equilibrium through the movement of pi electrons and an atom (usually hydrogen). All tautomeric forms and mixtures of tautomers of the compounds of the application are including with the scope of the application.

Compounds of the application can exist in solvated and unsolvated forms. The term "solvate" means a physical association, e.g., by hydrogen bonding, of a compound of the application with one or more solvent molecules. The solvent molecules in the solvate can be present in a regular arrangement and/or a non-ordered arrangement. The solvate can comprise either a stoichiometric or nonstoichiometric amount of the solvent molecules. "Solvate" encompasses both solution-phase and isolable solvates. Compounds of the application can form solvates with water (i.e., hydrates) or common organic solvents. Exemplary solvates include, but are not limited to, hydrates, ethanolates, methanolates, and isopropanolates. Methods of solvation are generally known in the art.

Also included within the scope of the application are all isotopes of atoms occurring in the compounds of the application. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, the name of a compound is intended to encompass all possible existing isomeric forms (e.g., optical isomer, enantiomer, diastereomer, racemate or racemic mixture), tautomers, and pharmaceutically acceptable salts, of the compound.

Compounds

In a general aspect, the application relates to a compound of formula (I-b):

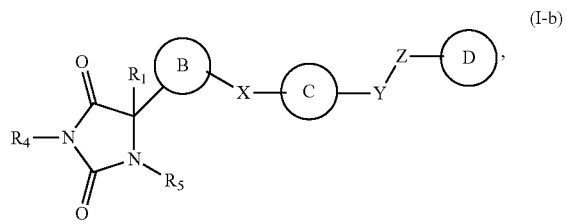

or a tautomer, stereoisomer, pharmaceutically acceptable salt, or solvate thereof, wherein:

ring B is an optionally substituted aryl or optionally substituted heteroaryl;

ring C is an optionally substituted aryl or optionally substituted heteoraryl;

ring D is an optionally substituted aryl or optionally substituted heteroaryl;

each of X, Y and Z is independently selected from the group consisting of $CH_2$, O, $NR_x$ and $S(O)_q$, wherein $R_x$ is hydrogen or alkyl;

$R_1$ is hydrogen or alkyl;

$R_4$ is hydrogen or alkyl;

$R_5$ is hydrogen; and q is 0, 1, or 2, provided that ring B is not furanyl.

In an embodiment, provided is a compound of formula (I):

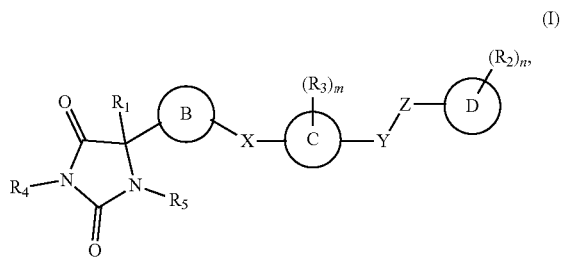

or a tautomer, stereoisomer, pharmaceutically acceptable salt, or solvate thereof, wherein:

ring B is an optionally substituted aryl or optionally substituted heteroaryl;

ring C is aryl or heteroaryl;

ring D is aryl or heteroaryl;

each of X, Y and Z is independently selected from the group consisting of O, $CH_2$, $NR_x$ and $S(O)_q$, wherein $R_x$ is hydrogen or alkyl;

$R_1$ is hydrogen or alkyl;

each $R_2$ is independently selected from the group consisting of hydrogen, alkyl, halo, hydroxyl, haloalkyl, alkoxy, alkylthio, amino, amide, alkylamino, aminoalkyl, cyano, hydroxyalkyl, $-(CH_2)_pC(O)OR_6$, and $-(CH_2)_pOC(O)R_6$;

each $R_3$ is independently selected from the group consisting of hydrogen, alkyl and halo;

$R_4$ is hydrogen or alkyl;

$R_5$ is hydrogen;

each R$_6$ is independently selected from the group consisting of hydrogen and alkyl, wherein the alkyl is unsubstituted or substituted with one or more groups independently selected from the group consisting of amino, hydroxyl, halo, and alkoxy;

m is 1, 2, 3, or 4;
n is 1, 2, 3, 4, or 5;
p is 0, 1, 2, 3, 4, or 5; and
q is 0, 1, or 2.

In an embodiment, provided is a compound of formula (I), or a tautomer, stereoisomer, pharmaceutically acceptable salt, or solvate thereof, wherein ring C is optionally substituted aryl, preferably optionally substituted phenyl.

In an embodiment, provided is a compound of formula (I), or a tautomer, stereoisomer, pharmaceutically acceptable salt, or solvate thereof, wherein ring C is optionally substituted heteroaryl, preferably optionally substituted pyridinyl.

In an embodiment, provided is a compound of formula (I), or a tautomer, stereoisomer, pharmaceutically acceptable salt, or solvate thereof, wherein m is 1, and R$_3$ is independently hydrogen, alkyl, or halo, preferably hydrogen, —CH$_3$, —F, or —Cl, more preferably H.

In an embodiment, provided is a compound of formula (I), or a tautomer, stereoisomer, pharmaceutically acceptable salt, or solvate thereof, wherein ring C is phenyl, m is 1, and R$_3$ is hydrogen.

In an embodiment, provided is a compound of formula (I), or a tautomer, stereoisomer, pharmaceutically acceptable salt, or solvate thereof, wherein ring C is phenyl, m is 1, and R$_3$ is fluoro.

In an embodiment, provided is a compound of formula (I), or a tautomer, stereoisomer, pharmaceutically acceptable salt, or solvate thereof, wherein ring C is phenyl, m is 1, and R$_3$ is methyl.

In an embodiment, provided is a compound of formula (I), or a tautomer, stereoisomer, pharmaceutically acceptable salt, or solvate thereof, wherein ring D is an optionally substituted aryl, preferably an optionally substituted phenyl.

In an embodiment, provided is a compound of formula (I), or a tautomer, stereoisomer, pharmaceutically acceptable salt, or solvate thereof, wherein ring D is an optionally substituted heteroaryl.

In an embodiment, provided is a compound of formula (I), or a tautomer, stereoisomer, pharmaceutically acceptable salt, or solvate thereof, wherein ring D is optionally substituted with 1, 2, 3, 4, or 5 substitutent groups, preferably 1 or 2 substituent groups, independently selected from the group consisting of alkyl, halo, haloalkyl, alkoxy, alkylthio, amino, amide, alkylamino, aminoalkyl, cyano, hydroxyalkyl, —(CH$_2$)$_p$C(O)OR$_6$, and —(CH$_2$)$_p$OC(O)R$_6$, wherein p is 0, 1, 2, 3, 4, or 5. The substituent group, if present, can be attached at any position of ring D. Preferably, ring D is substituted with one substituent group.

In an embodiment, provided is a compound of formula (I), or a tautomer, stereoisomer, pharmaceutically acceptable salt, or solvate thereof, wherein ring D is a monocyclic aryl or monocyclic heteroaryl group substituted with one substituent at the meta position, preferably phenyl or pyridinyl substituted at the meta position, relative to the bond to variable Z. Particularly preferred substituent groups for ring D include methyl (—CH$_3$), amide (—C(O)NH$_2$), methoxy (—OCH$_3$), hydroxyl (—OH), and hydroxylmethyl (—CH$_2$OH).

In a particular embodiment, ring D is phenyl.
In another particular embodiment ring D is pyridinyl.
In an embodiment, provided is a compound of formula (I), or a tautomer, stereoisomer, pharmaceutically acceptable salt, or solvate thereof, wherein n is 1 and R$_2$ is C$_{1-3}$ alkoxy (e.g., —OCH$_3$, —OCH$_2$CH$_2$CH$_3$, —OCH$_2$CH$_3$, —OCH(CH$_3$)$_2$), C$_{1-4}$ alkyl (e.g., —CH$_3$, —CH$_2$CH$_3$, —CH$_2$CH(CH$_3$)$_2$), —CH$_2$OH, —OH, —COOH, —C(O)NH$_2$, —C(O)NHCH$_3$, or —CH$_2$OC(O)CH(NH$_2$)CH(CH$_3$)$_2$, —C(O)NH$_2$, —C(O)NHCH$_3$. Preferably R$_2$ is —CH$_3$, —C(O)NH$_2$, —CH$_2$OH, —OCH$_3$, or OH.

In an embodiment, provided is a compound of formula (I), or a tautomer, stereoisomer, pharmaceutically acceptable salt, or solvate thereof, wherein ring D is:

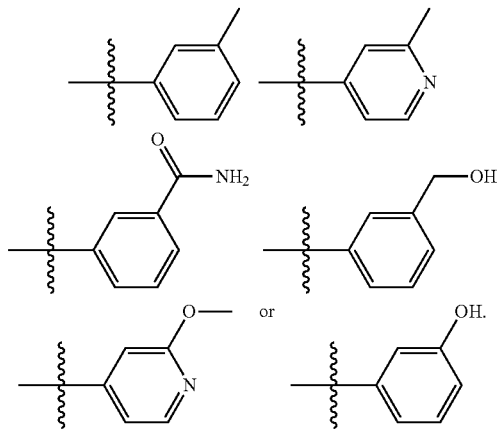

According to embodiments of the application, the chiral carbon atom of the hydantoin moiety can be unsubstituted (i.e., R$_1$ is hydrogen) or substituted. When substituted, the R$_1$ substituent is preferably alkyl. Preferred alkyl groups for substitution of the chiral carbon atom of the hydantoin moiety include C$_{1-2}$ alkyl groups, such as methyl and ethyl.

In an embodiment, provided is a compound of formula (I), or a tautomer, stereoisomer, pharmaceutically acceptable salt, or solvate thereof, wherein R$_1$ is hydrogen, —CH$_3$ or —CH$_2$CH$_3$.

In an embodiment, provided is a compound of formula (I), or a tautomer, stereoisomer, pharmaceutically acceptable salt, or solvate thereof, wherein R$_1$ is hydrogen.

Substitution of the nitrogen atoms of the hydantoin moiety is also possible. According to embodiments of the application, R$_4$ and R$_5$ are each independently hydrogen or alkyl. Preferred alkyl groups include methyl.

In an embodiment, provided is a compound of formula (I), or a tautomer, stereoisomer, pharmaceutically acceptable salt, or solvate thereof, wherein R$_4$ is hydrogen or —CH$_3$ and R$_5$ is —CH$_3$.

In an embodiment, provided is a compound of formula (I), or a tautomer, stereoisomer, pharmaceutically acceptable salt, or solvate thereof, wherein each of R$_4$ and R$_5$ is hydrogen.

According to embodiments of the application, each of X, Y, and Z is independently selected from the group consisting of O, NR$_x$, CH$_2$, and S(O)$_q$, wherein q is 0, 1, or 2 and R$_x$ is hydrogen or alkyl. As such, each of the linker units X, Y and Z is independently selected from O, S, S(O), SO$_2$, NH, N-alkyl, and CH$_2$. Preferably, each of X, Y, and Z is independently selected from S, S(O), S(O)$_2$, CH$_2$, and O, more preferably S, CH$_2$, and O.

In an embodiment, provided is a compound of formula (I), or a tautomer, stereoisomer, pharmaceutically acceptable salt, or solvate thereof, wherein X is O, Y is O, and Z is CH$_2$.

In an embodiment, provided is a compound of formula (I), or a tautomer, stereoisomer, pharmaceutically acceptable salt, or solvate thereof, wherein X is S, Y is S, and Z is $CH_2$.

In an embodiment, provided is a compound of formula (I), or a tautomer, stereoisomer, pharmaceutically acceptable salt, or solvate thereof, wherein X is O, Y is S, and Z is $CH_2$.

In an embodiment, provided is a compound of formula (I), or a tautomer, stereoisomer, pharmaceutically acceptable salt, or solvate thereof, wherein X is S, Y is O, and Z is $CH_2$.

In an embodiment, provided is a compound of formula (I), or a tautomer, stereoisomer, pharmaceutically acceptable salt, or solvate thereof, wherein Z is O, Y is $CH_2$, and X is S.

In an embodiment, provided is a compound of formula (I), or a tautomer, stereoisomer, pharmaceutically acceptable salt, or solvate thereof, wherein Z is S, Y is $CH_2$, and X is O.

In an embodiment, provided is a compound of formula (I), or a tautomer, stereoisomer, pharmaceutically acceptable salt, or solvate thereof, wherein X is S(O), Y is O, and Z is $CH_2$.

In an embodiment, provided is a compound of formula (I), or a tautomer, stereoisomer, pharmaceutically acceptable salt, or solvate thereof, wherein X is $S(O)_2$, Y is O, and Z is $CH_2$.

In an embodiment, provided is a compound of formula (I), or a tautomer, stereoisomer, pharmaceutically acceptable salt, or solvate thereof, wherein X is S, Y is NH, and Z is $CH_2$.

In an embodiment, provided is a compound of formula (I), or a tautomer, stereoisomer, pharmaceutically acceptable salt, or solvate thereof, wherein X is S, Y is $N(CH_3)$, and Z is $CH_2$.

In a preferred embodiment, provided is a compound of formula (I), or a tautomer, stereoisomer, pharmaceutically acceptable salt, or solvate thereof, wherein one of X and Y is S and the other is O.

In a more preferred embodiment, provided is a compound of formula (I) or a tautomer, stereoisomer, pharmaceutically acceptable salt, or solvate thereof, wherein X is S and Y is O.

In another preferred embodiment, provided is a compound of formula (I) or a tautomer, stereoisomer, pharmaceutically acceptable salt, or solvate thereof, wherein Z is $CH_2$.

In an embodiment, provided is a compound of formula (I), or a tautomer, stereoisomer, pharmaceutically acceptable salt, or solvate thereof, wherein ring B is an optionally substituted aryl, such as phenyl.

In an embodiment, provided is a compound of formula (I), or a tautomer, stereoisomer, pharmaceutically acceptable salt, or solvate thereof, wherein ring B is an optionally substituted heteroaryl. Preferably, ring B is an optionally substituted 5- or 6-membered heteroaryl having 1-2 heteroatoms selected from N, S, and O. In particular embodiments, ring B is a 5-membered heteroaryl ring, such as imidazolyl, thiophenyl, oxazolyl, or pyrazolyl. In other particular embodiments, ring B is a 6-membered heteroaryl, such as pyridinyl or pyridinyl N-oxide. Any positional or regioisomer of the heteroaryl ring can be used, meaning that the hydantoin moiety and X linker can be connected to the heteroaryl at any substitutable carbon atom on the heteroaryl ring. For example, when ring B is a 5-membered heteroaryl ring containing 1 heteroatom, the hydantoin moiety and X linker can be connected to the 5-membered heteroaryl ring in a 2, 3-substitution pattern, a 2, 4-substitution pattern, a 2, 5-substitution pattern, a 3, 4-substitution pattern, etc., relative to the heteroatom. As another illustrative example, when ring B is a 6-membered heteroaryl ring containing one heteroatom, the hydantoin moiety and X linker can be connected to the 6-membered heteroaryl ring in a 2, 3-substitution pattern, a 2, 4-substitution pattern, a 2, 5-substitution pattern, a 2, 6-substitution pattern, a 3, 4-substitution pattern, etc., relative to the heteroatom.

In some embodiments, provided is a compound of formula (I), or a tautomer, stereoisomer, pharmaceutically acceptable salt, or solvate thereof, wherein ring B is substituted. Ring B can be substituted on any substitutable carbon atom of an aryl or heteroaryl ring, or any substitutable heteroatom, e.g., nitrogen atom, of a heteroaryl ring. For example, ring B can be substituted with an alkyl group, e.g., methyl, including substitution with a methyl group for instance on a nitrogen atom of a heteroaryl ring, e.g., imidazolyl or pyrazolyl.

In some embodiments, provided is a compound of formula (I), or a tautomer, stereoisomer, pharmaceutically acceptable salt, or solvate thereof, wherein ring B is pyridinyl, pyrazolyl, or imidazolyl, wherein each of the pyridinyl, pyrazolyl, or imidazolyl is optionally substituted with —$CH_3$.

In an embodiment, provided is a compound of formula (I), or a tautomer, stereoisomer, pharmaceutically acceptable salt, or solvate thereof, wherein ring B is pyridinyl optionally substituted with —$CH_3$.

In an embodiment, provided is a compound of formula (I), or a tautomer, stereoisomer, pharmaceutically acceptable salt, or solvate thereof, wherein ring B is pyridinyl N-oxide.

In some embodiments, wherein ring B is pyridinyl, provided is a compound of formula (II):

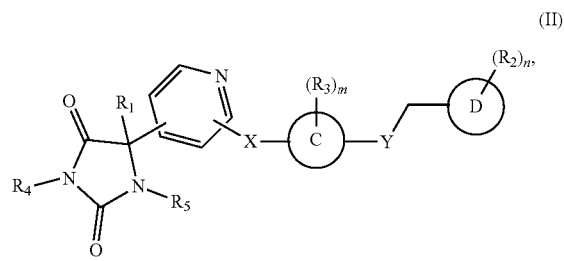

(II)

or a tautomer, stereoisomer, pharmaceutically acceptable salt, or solvate thereof, wherein each of the variables are as defined above for the compound of formula (I).

In certain embodiments, provided is a compound of formula (II), or a tautomer, stereoisomer, pharmaceutically acceptable salt, or solvate thereof, wherein:
ring C is phenyl or pyridinyl;
$R_1$ is hydrogen, —$CH_3$ or —$CH_2CH_3$;
$R_4$ is hydrogen or —$CH_3$;
$R_5$ is hydrogen or —$CH_3$;
X is S, S(O), or $SO_2$;
$R_3$ is hydrogen, —$CH_3$, —F, or —Cl;
Y is O, NH, $CH_2$, or —$NH_3$;
Z is $CH_2$;
ring D is phenyl or pyridinyl; and
$R_2$ is $C_{1-3}$ alkoxy, $C_{1-4}$ alkyl, —$CH_2OH$, —OH, —COOH, —$C(O)NH_2$, —$C(O)NHCH_3$, or —$CH_2OC(O)CH(NH_2)CH(CH_3)_2$;
m is 1; and
n is 1.

In particular embodiments, provided is a compound of formula (II-a), (II-b), (II-c), or (II-d):

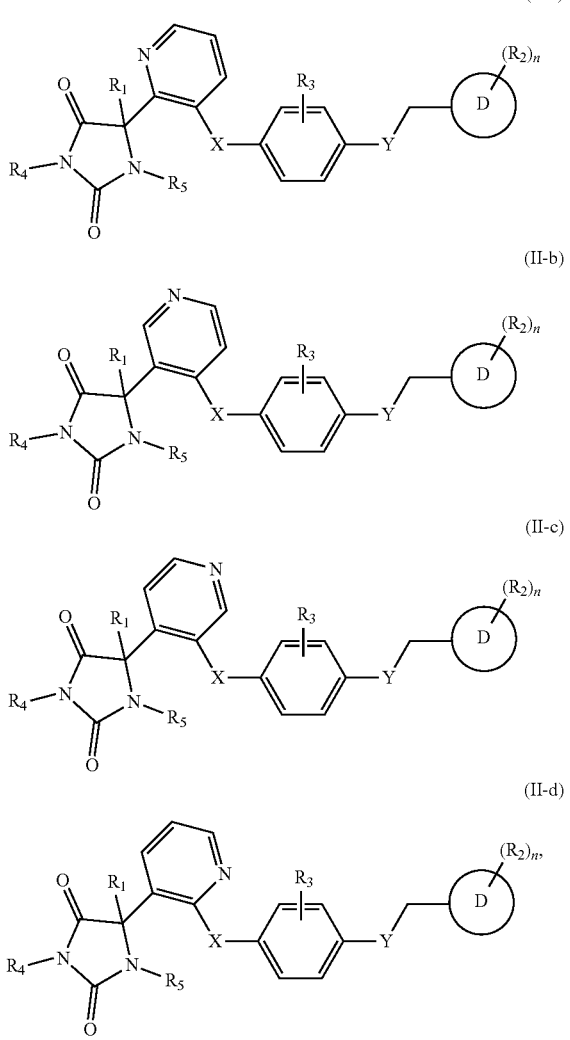

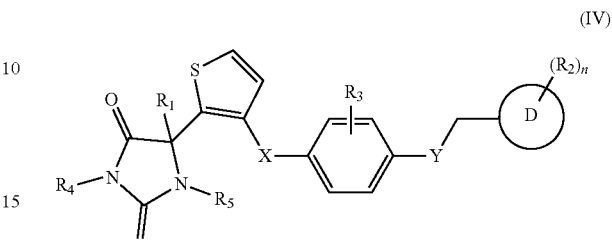

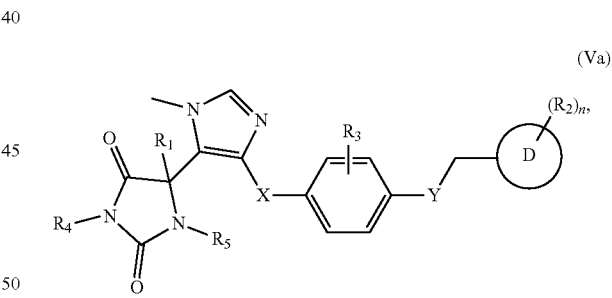

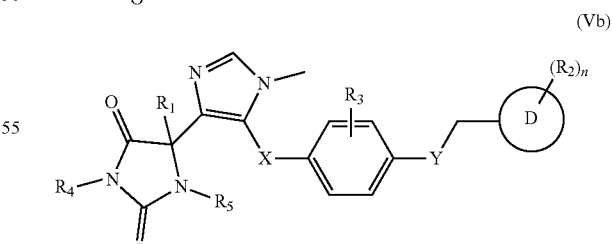

or a tautomer, stereoisomer, pharmaceutically acceptable salt, or solvate thereof, wherein each of the variables are as defined above for the compound of formula (I) or formula (II).

In certain embodiments, provided is a compound of formula formula (II-a), (II-b), (II-c), or (II-d), or a tautomer, stereoisomer, pharmaceutically acceptable salt, or solvate thereof, wherein:

$R_1$ is hydrogen, —$CH_3$ or —$CH_2CH_3$;
$R_4$ is hydrogen or —$CH_3$;
$R_5$ is hydrogen or —$CH_3$;
X is S, S(O), or $SO_2$;
$R_3$ is hydrogen, —$CH_3$, —F, or —Cl;
Y is O, NH, $CH_2$, or —$NH_3$;
Z is $CH_2$;
ring D is phenyl or pyridinyl; and
$R_2$ is $C_{1-3}$ alkoxy, $C_{1-4}$ alkyl, —$CH_2OH$, —OH, —COOH, —C(O)$NH_2$, —C(O)$NHCH_3$, or —$CH_2OC(O)CH(NH_2)CH(CH_3)_2$; and
n is 1.

In a preferred embodiment, wherein ring B is pyridinyl, provided is a compound of formula (II-b), or a tautomer, stereoisomer, pharmaceutically acceptable salt, or solvate thereof.

In an embodiment, provided is a compound of formula (I), or a tautomer, stereoisomer, pharmaceutically acceptable salt, or solvate thereof, wherein ring B is thiophenyl.

In some embodiments, wherein ring B is thiophenyl, provided is a compound of formula (IV):

or a tautomer, stereoisomer, pharmaceutically acceptable salt, or solvate thereof, wherein each of the variables are as defined above for the compound of formula (I).

In certain embodiments, provided is a compound of formula (IV), or a tautomer, stereoisomer, pharmaceutically acceptable salt, or solvate thereof, wherein:

each of $R_1$, $R_4$, and $R_5$ is hydrogen;
X is S;
Y is O;
Z is $CH_2$;
$R_3$ is hydrogen;
ring D is phenyl or pyridinyl; and
$R_2$ is —$CH_3$, —C(O)$NH_2$, —$CH_2OH$, —$OCH_3$, or —OH; and
n is 1.

In an embodiment, provided is a compound of formula (I), or a tautomer, stereoisomer, pharmaceutically acceptable salt, or solvate thereof, wherein ring B is imidazolyl.

In some embodiments, wherein ring B is imidazolyl, provided is a compound of formula (Va) or (Vb):

or a tautomer, stereoisomer, pharmaceutically acceptable salt, or solvate thereof, wherein each of the variables are as defined above for the compound of formula (I).

In certain embodiments, provided is a compound of formula (V), or a tautomer, stereoisomer, pharmaceutically acceptable salt, or solvate thereof, wherein:

each of $R_1$, $R_4$, and $R_5$ is hydrogen;
X is S;
Y is O;
Z is $CH_2$;
$R_3$ is hydrogen;
ring D is phenyl or pyridinyl; and
$R_2$ is —$CH_3$, —$C(O)NH_2$, —$CH_2OH$, —$OCH_3$, or —OH; and
n is 1.

In an embodiment, provided is a compound of formula (I), or a tautomer, stereoisomer, pharmaceutically acceptable salt, or solvate thereof, wherein ring B is pyrazolyl.

In some embodiments, wherein ring B is pyrazolyl, provided is a compound of formula (VI):

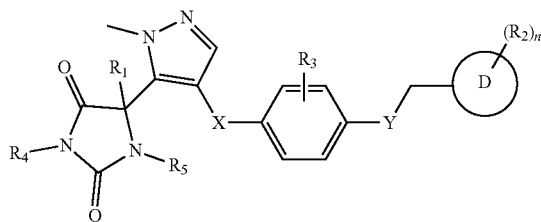

(VI)

or a tautomer, stereoisomer, pharmaceutically acceptable salt, or solvate thereof,
wherein each of the variables are as defined above for the compound of formula (I).

In certain embodiments, provided is a compound of formula (VI), or a tautomer, stereoisomer, pharmaceutically acceptable salt, or solvate thereof, wherein:
each of $R_1$, $R_4$, and $R_5$ is hydrogen;
X is S;
Y is O;
Z is $CH_2$;
$R_3$ is hydrogen;
ring D is phenyl or pyridinyl; and
$R_2$ is —$CH_3$, —$C(O)NH_2$, —$CH_2OH$, —$OCH_3$, or —OH; and
n is 1.

In an embodiment, provided is a compound of formula (I), or a tautomer, stereoisomer, pharmaceutically acceptable salt, or solvate thereof, wherein ring B is oxazolyl.

In some embodiments, wherein ring B is oxazolyl, provided is a compound of formula (VII):

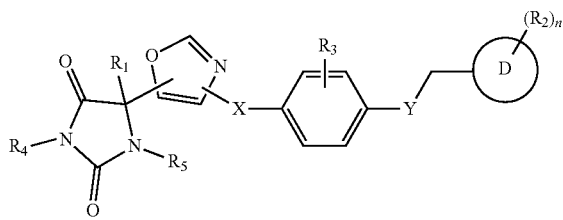

(VII)

or a tautomer, stereoisomer, pharmaceutically acceptable salt, or solvate thereof, wherein each of the variables are as defined above for the compound of formula (I).

In certain embodiments, provided is a compound of formula (VII), or a tautomer, stereoisomer, pharmaceutically acceptable salt, or solvate thereof, wherein:
each of $R_1$, $R_4$, and $R_5$ is hydrogen;
X is S;
Y is O;
Z is $CH_2$;
$R_3$ is hydrogen;
ring D is phenyl or pyridinyl; and
$R_2$ is —$CH_3$, —$C(O)NH_2$, —$CH_2OH$, —$OCH_3$, or —OH; and
n is 1.

In particular embodiments, wherein ring B is oxazolyl, provided is a compound of formula (VII-a) or a compound of formula (VII-b):

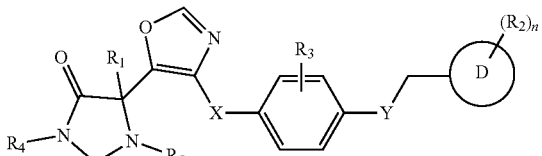

(VII-a)

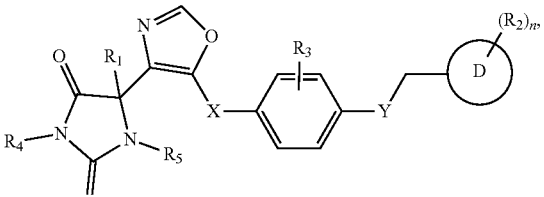

(VII-b)

or a tautomer, stereoisomer, pharmaceutically acceptable salt, or solvate thereof, wherein each of the variables are as defined above for the compound of formula (I) or formula (VII).

Compounds of particular interest include compounds of formula (I-a):

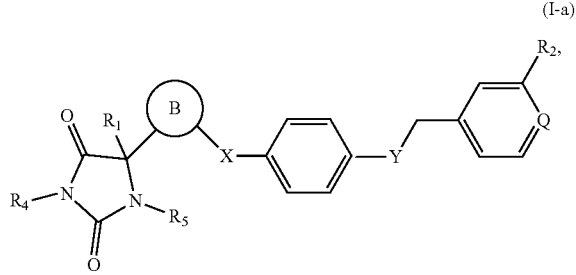

(I-a)

or a tautomer, stereoisomer, pharmaceutically acceptable salt, or solvate thereof, wherein Q is CH or N, and the rest of the variable groups are as defined above for the compound of formula (I).

In an embodiment, provided is a compound of formula (I-a) or a tautomer, stereoisomer, pharmaceutically acceptable salt, or solvate thereof, wherein Q is CH.

In an embodiment, provided is a compound of formula (I-a) or a tautomer, stereoisomer, pharmaceutically acceptable salt, or solvate thereof, wherein Q is N.

In an embodiment, provided is a compound of formula (I-a) or a tautomer, stereoisomer, pharmaceutically acceptable salt, or solvate thereof, wherein $R_2$ is alkyl, halogen, haloalkyl, alkoxy, alkylthio, amino, amide, alkylamino, aminoalkyl, cyano, hydroxyalkyl, —$(CH_2)_pC(O)OR_6$, and —$(CH_2)_pOC(O)R_6$, wherein p is 0, 1, 2, 3, 4, or 5.

In an embodiment, provided is a compound of formula (I-a) or a tautomer, stereoisomer, pharmaceutically acceptable salt, or solvate thereof, wherein $R_2$ is $C_{1-3}$ alkoxy (e.g., —$OCH_3$, —$OCH_2CH_2CH_3$, —$OCH_2CH_3$, —$OCH(CH_3)_2$), $C_{1-4}$ alkyl (e.g., —$CH_3$, —$CH_2CH_3$, —$CH_2CH(CH_3)_2$), —$CH_2OH$, —OH, —COOH, —$C(O)NH_2$, —$C(O)NHCH_3$, or —$CH_2OC(O)CH(NH_2)CH(CH_3)_2$, —$C(O)NH_2$, —$C(O)NHCH_3$. Preferably $R_2$ is —$CH_3$, —$C(O)NH_2$, —$CH_2OH$, —$OCH_3$, or —OH.

In an embodiment, provided is a compound of formula (I-a) or a tautomer, stereoisomer, pharmaceutically acceptable salt, or solvate thereof, wherein $R_1$ is hydrogen, —$CH_3$, or —$CH_2CH_3$. Preferably, $R_1$ is hydrogen.

In an embodiment, provided is a compound of formula (I-a) or a tautomer, stereoisomer, pharmaceutically acceptable salt, or solvate thereof, wherein $R_4$ is hydrogen.

In an embodiment, provided is a compound of formula (I-a) or a tautomer, stereoisomer, pharmaceutically acceptable salt, or solvate thereof, wherein $R_5$ is hydrogen or —$CH_3$.

In an embodiment, provided is a compound of formula (I-a) or a tautomer, stereoisomer, pharmaceutically acceptable salt, or solvate thereof, wherein each of $R_1$, $R_4$, and $R_5$ is hydrogen.

In an embodiment, provided is a compound of formula (I-a) or a tautomer, stereoisomer, pharmaceutically acceptable salt, or solvate thereof, wherein X is S, S(O), or $SO_2$.

In an embodiment, provided is a compound of formula (I-a) or a tautomer, stereoisomer, pharmaceutically acceptable salt, or solvate thereof, wherein Y is O, NH, $CH_2$, or $N(CH_3)$.

In an embodiment, provided is a compound of formula (I-a) or a tautomer, stereoisomer, pharmaceutically acceptable salt, or solvate thereof, wherein X is S and Y is O.

In an embodiment, provided is a compound of formula (I-a) or a tautomer, stereoisomer, pharmaceutically acceptable salt, or solvate thereof, wherein ring B is pyridinyl.

In an embodiment, provided is a compound of formula (I-a) or a tautomer, stereoisomer, pharmaceutically acceptable salt, or solvate thereof, wherein ring B is thiophenyl.

In an embodiment, provided is a compound of formula (I-a) or a tautomer, stereoisomer, pharmaceutically acceptable salt, or solvate thereof, wherein ring B is phenyl.

In an embodiment, provided is a compound of formula (I-a) or a tautomer, stereoisomer, pharmaceutically acceptable salt, or solvate thereof, wherein ring B is pyrazolyl.

In an embodiment, provided is a compound of formula (I-a) or a tautomer, stereoisomer, pharmaceutically acceptable salt, or solvate thereof, wherein ring B is imidazolyl.

In an embodiment, provided is a compound of formula (I-a) or a tautomer, stereoisomer, pharmaceutically acceptable salt, or solvate thereof, wherein ring B is oxazolyl.

In an embodiment, provided is a compound of formula (I-a), or a tautomer, stereoisomer, pharmaceutically acceptable salt, or solvate thereof, wherein:
ring B is pyridinyl;
Q is CH or N;
each of $R_1$, $R_4$ and $R_5$ is hydrogen;
$R_2$ is selected from the group consisting of alkyl, amide, hydroxyl, alkoxy, and hydroxylalkyl;
X is S; and
Y is O.

Exemplary compounds of the application include, but are not limited to, compounds listed in Table 1 below, and any tautomer, stereoisomer, pharmaceutically acceptable salt or solvate thereof. The MMP-12 $IC_{50}$ values were determined according to the assay described in Example 1 below. The $IC_{50}$ values are reported as follows: A=less than 10 nM, B=10 nM to 100 nM, C=100 nM to 1000 nM, D=greater than 1000 nM.

TABLE 1

| Compound ID | Structure | Analytical Data (LCMS, NMR, etc.) | MMP-12 $IC_{50}$ (nM) |
|---|---|---|---|
| TC1 | 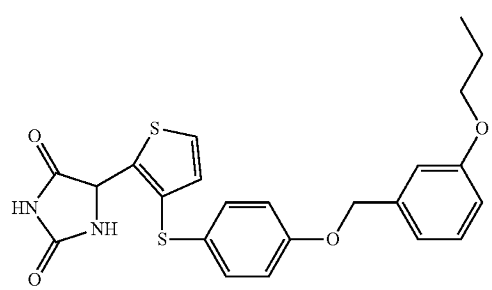 [SMILES: CCCOc1cccc(COc2ccc(Sc3ccsc3C3NC(=O)NC3=O)cc2)c1] | $^1$H-NMR (300 MHz CDCl$_3$) δ: 7.437 (d, J = 5.1 Hz, 1H), 7.304-7.226 (m, 3H), 6.953-6.834 (m, 6H), 5.755 (s, 1H), 5.033 (s, 2H), 3.923 (t, J = 6.5 Hz, 2H), 1.758 (tq, J = 7.8 Hz, 2H), 1.036 (t, J = 7.4 Hz, 3H); m/z (ESI+) 453.22 (M−); HPLC tR: 8.033 min. | C |
| TC2 | 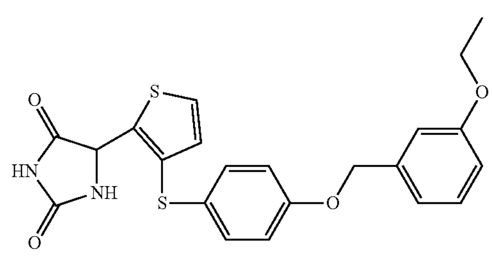 [SMILES: CCOc1cccc(COc2ccc(Sc3ccsc3C3NC(=O)NC3=O)cc2)c1] | $^1$H-NMR (300 MHz CDCl$_3$) δ: 7.431 (d, J = 5.4 Hz, 2H), 7.301-7.223 (m, 3H), 6.973-6.915 (m, 4H), 6.858-6.826 (m, 2H) 5.751 (s, 1H), 5.026 (s, 2H), 4.020 (q, J = 7.2 Hz, 2H), 1.371 (t, J = 7.2 Hz, 3H); m/z (ESI+) 439.16 (M−); HPLC tR: 6.066 min. | C |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| TC3 | 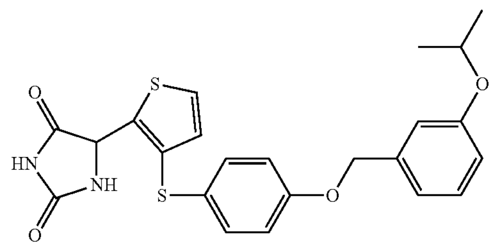 [SMILES: CC(C)Oc1cccc(COc2ccc(Sc3ccsc3C3NC(=O)NC3=O)cc2)c1] | $^1$H-NMR (300 MHz DMSO) δ: 7.435 (d, J = 5.4 Hz, 1H), 7.306-7.248 (m, 3H), 6.964-6.851 (m, 6H), 5.752 (s, 1H), 5.032 (s, 2H), 4.586 (qq, J = 6.0 Hz, 1H), 1.29 (d, J = 6.0 Hz, 6H); m/z (ESI+) 453.22 (M−); HPLC tR: 6.725 min. | C |
| TC4 | 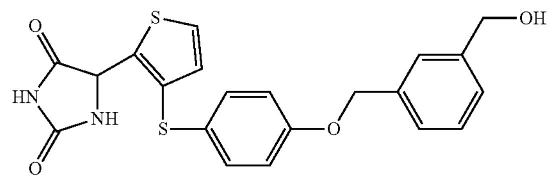 [SMILES: O=C1NC(=O)C(c2sccc2Sc2ccc(OCc3cccc(CO)c3)cc2)N1] | $^1$H-NMR (300 MHz DMSO) δ: 8.529 (bs, 1H), 7.574 (d, J = 5.1 Hz, 1H), 7.366-7.256 (m, 6H), 6.976 (d, J = 8.7 Hz, 2H) 6.860 (d, J = 5.1 Hz, H), 5.647 (s, 1H), 5.225-5.188 (m, 1H), 5.188-5.057 (m, 2H), 4.482 (d, J = 5.7 Hz, 2H); m/z (ESI+) 449.43 (M + Na)+; HPLC tR: 3.917 min. | A |
| TC5 | 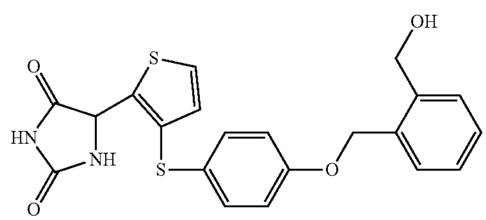 [SMILES: O=C1NC(=O)C(c2sccc2Sc2ccc(OCc3ccccc3CO)cc2)N1] | $^1$H-NMR (300 MHz DMSO) δ: 8.547 (bs, 1H), 7.595 (d, J = 5.1 Hz, 1H), 7.474-7.260 (m, 6H), 7.010-6.988 (m, 2H), 6.888 (d, J = 5.1 Hz, 1H), 5.556 (s, 1H), 5.198-5.130 (m, 2H), 4.585 (d, J = 5.1 Hz, 2H); m/z (ESI+) 449.16 (M + Na)+; HPLC tR: 3.436 min. | A |
| TC6 | 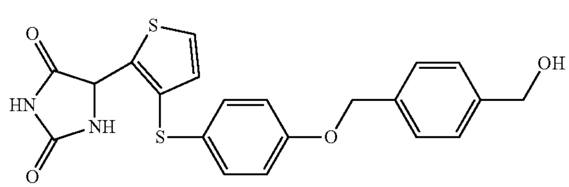 [SMILES: O=C1NC(=O)C(c2sccc2Sc2ccc(OCc3ccc(CO)cc3)cc2)N1] | $^1$H-NMR (300 MHz DMSO) δ: 10.942 (bs, 1H), 8.545 (s, 1H), 7.88 (d, J = 5.4 Hz, 1H), 7.392-7.267 (m, 6H), 6.981 (d, J = 8.7 Hz, 2H) 6.871 (d, J = 5.4 Hz, H), 5.663 (s, J = 1.2 Hz, 1H), 5.118 (t, J = 5.7 Hz, 1H), 5.065 (s, 2H), 4.486 (d, J = 6 Hz, 2H); m/z (ESI+) 449.17 (M + Na)+; HPLC tR: 6.435 min. | A |
| TC7 | 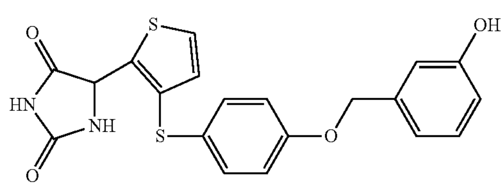 [SMILES: O=C1NC(=O)C(c2sccc2Sc2ccc(OCc3cccc(O)c3)cc2)N1] | $^1$H-NMR (300 MHz CDCl$_3$) δ: 7.418 (d, J = 5.4 Hz, 1H), 7.289-7.261 (m, 2H), 7.185-7.133 (m, 1H), 6.924-6.839 (m, 5H), 6.731-6.701 (m, 1H), 5.743 (s, 1H), 4.988 (s, 2H); m/z (ESI+) 412.00 (M+−); HPLC tR: 6.586 min. | A |
| TC8 | 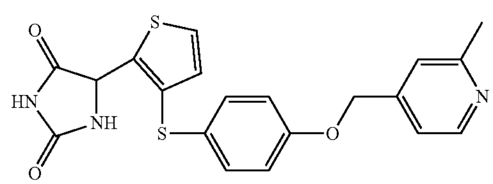 [SMILES: Cc1cc(COc2ccc(Sc3ccsc3C3NC(=O)NC3=O)cc2)ccn1] | $^1$H-NMR (300 MHz CDCl$_3$) δ: 10.935 (s, 1H), 8.532 (s, 1H), 8.403 (d, J = 5.4 Hz, 1H) 7.576 (d, J = 5.4 Hz, 1H), 7.286-7.178 (m, 4H), 6.973 (d, J = 8.7 Hz, 2H), 6.861 (d, J = 5.4 Hz, 1H), 5.698 (s, 1H), 5.298 (s, 2H), 2.482-2.443 (m, 3H); m/z (ESI+) 412.24 (M + Na)+; HPLC tR: 6.035 min. | A |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-1 | 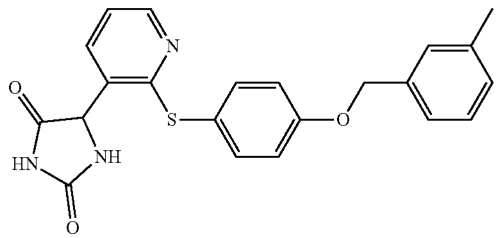 [SMILES: Cc1cccc(COc2ccc(Sc3ncccc3C3NC(=O)NC3=O)cc2)c1] | $^1$H NMR (400 MHz, CD$_3$OD) δ 8.297 (d, J = 5.2 Hz, 1H), 7.23 (d, J = 7.6 Hz, 1H), 7.385 (d, J = 11.2 Hz, 2H), 7.237 (dd, J = 7.6, 9.6 Hz, 4H), 7.137 (d, J = 6.8 Hz, 2H), 7.011 (d, J = 9.2 Hz, 1H), 5.66 (s, 2H), 4.872 (m, 2H), 2.347 (s, 3H); m/z (ESI+) (M + H)+ = 406.25; HPLC tR = 7.213 min. | B |
| PC-2 | 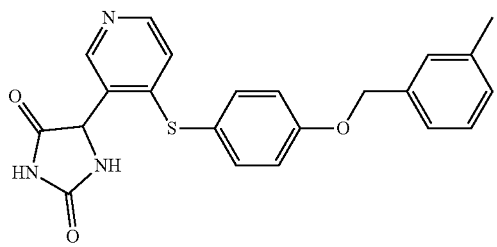 [SMILES: Cc1cccc(COc2ccc(Sc3ccncc3C3NC(=O)NC3=O)cc2)c1] | $^1$H NMR (400 MHz, CD$_3$OD) δ 8.672 (s, 1H), 8.396 (d, J = 6.4 Hz, 1H), 7.563 (d, J = 8.8 Hz, 2H), 7.281-7.148 (m, 7H), 5.809 (s, 2H), 5.145 (s, 2H), 2.358 (s, 3H); m/z (ESI+) (M + H)+ = 406.15; HPLC tR = 6.254 min. | B |
| PC-3 | 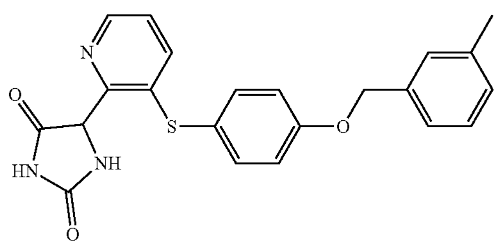 | $^1$H NMR (400 MHz, CD$_3$OD) δ 8.366 (dd, J = 0.8, 1.6 Hz, 1H), 7.475 (d, J = 9.2 Hz, 1H), 7.447 (d, J = 8.8 Hz, 2H), 7.279-7.218 (m, 4H), 7.143 (s, 1H), 7.052 (d, J = 9.2 Hz, 2H), 5.849 (s, 2H), 5.115 (s, 2H), 2.345 (s, 3H); m/z (ESI+) (M + H)+ = 406.15; HPLC tR = 7.317 min. | B |
| PC-4 | 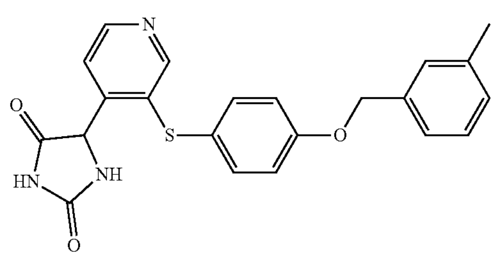 [SMILES: Cc1cccc(COc2ccc(Sc3cnccc3C3NC(=O)NC3=O)cc2)c1] | $^1$H NMR (400 MHz, CD$_3$OD) δ 7.431 (d, J = 8.8 Hz, 3H), 7.247-7.215 (m, 4H), 7.137 (d, J = 8.0 Hz, 2H), 7.040 (d, J = 8.8 Hz, 2H), 5.792 (s, 2H), 4.824 (s, 2H), 2.343 (s, 3H); m/z (ESI+) (M + H)+ = 406.1; HPLC tR = 6.553 min. | B |
| PC-5 | 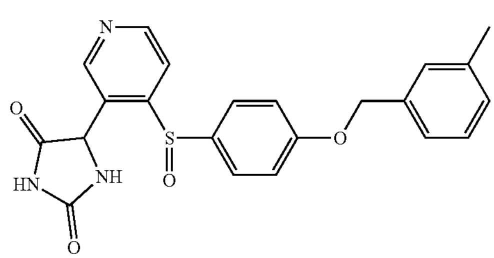 [SMILES: Cc1cccc(COc2ccc(S(=O)c3ccncc3C3NC(=O)NC3=O)cc2)c1] | $^1$H NMR (400 MHz, CD$_3$OD) δ 8.818 (d, J = 5.2 Hz, 1H), 8.654 (s, 1H), 7.989 (d, J = 4.8 Hz, 1H), 7.782 (d, J = 8.4 Hz, 2H), 7.260-7.120 (m, 6H), 5.789 (s, 1H), 5.155 (s, 2H), 2.331 (s, 3H); m/z (ESI+) (M − H)− = 420; HPLC tR = 6.378 min. | C |
| PC-6 | 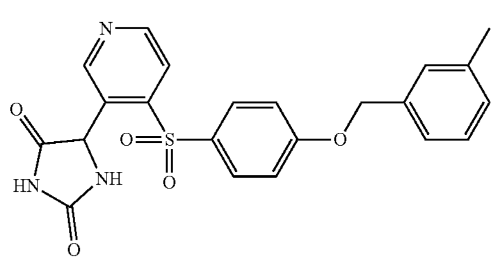 [SMILES: Cc1cccc(COc2ccc(S(=O)(=O)c3ccncc3C3NC(=O)NC3=O)cc2)c1] | $^1$H NMR (400 MHz, CD$_3$OD) δ 8.785 (d, J = 5.2 Hz, 1H), 8.690 (s, 1H), 7.955 (dd, J = 8.8, 5.2 Hz, 3H), 7.248 (s, 2H), 7.213 (d, J = 2.8 Hz, 3H), 7.182 (s, 1H), 6.345 (s, 1H), 5.141 (s, 2H), 2.335 (s, 3H); m/z (ESI+) (M − H)− = 436.1; HPLC tR = 6.544 min. | C |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-7 | 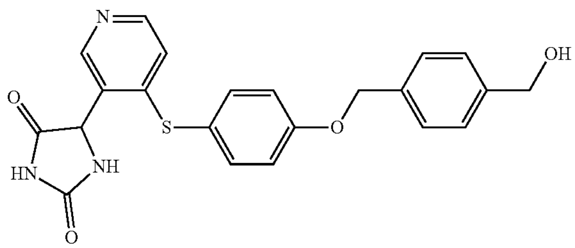 [SMILES: O=C1NC(=O)C(c2cnccc2Sc2ccc(OCc3ccc(CO)cc3)cc2)N1] | $^1$H NMR (400 MHz, CD$_3$OD) δ 8.33 (s, 1H), 8.19 (d, J = 5.9 Hz, 1H), 7.49-7.41 (m, 4H), 7.37 (d, J = 11.9 Hz, 2H), 7.12 (d, J = 8.7 Hz, 2H), 6.76 (s, 1H), 5.57 (s, 1H), 5.14 (s, 2H), 4.61 (s, 2H); m/z (ESI+) (M + H)+ = 422.10; HPLC tR = 5.271 min. | B |
| PC-8 | 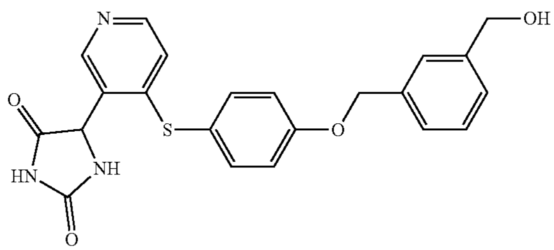 [SMILES: O=C1NC(=O)C(c2cnccc2Sc2ccc(OCc3cccc(CO)c3)cc2)N1] | $^1$H NMR (400 MHz, DMSO-d6) δ 11.03 (s, 1H), 8.37 (d, J = 12.2 Hz, 2H), 8.28 (s, 1H), 7.52-7.38 (m, 3H), 7.30 (d, J = 17.6 Hz, 3H), 7.16 (d, J = 7.1 Hz, 2H), 6.65 (s, 1H), 5.49 (s, 1H), 5.24 (s, 1H), 5.14 (s, 2H), 4.50 (s, 2H), 4.11 (s, 1H); m/z (ESI+) (M + H)+ = 422.15; HPLC tR = 5.282 min. | A |
| PC-9 | 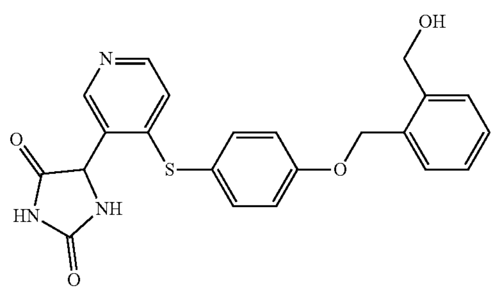 [SMILES: O=C1NC(=O)C(c2cnccc2Sc2ccc(OCc3ccccc3CO)cc2)N1] | $^1$H NMR (400 MHz, CD$_3$OD) δ 8.33 (s, 1H), 8.18 (s, 1H), 7.46 (d, J = 6.3 Hz, 4H), 7.37-7.27 (m, 2H), 7.15 (d, J = 8.7 Hz, 2H), 6.78 (d, J = 5.4 Hz, 1H), 5.57 (s, 1H), 5.24 (s, 2H), 4.73 (s, 2H); m/z (ESI+) (M + H)+ = 422.15; HPLC tR = 5.383 min. | B |
| PC-10 | 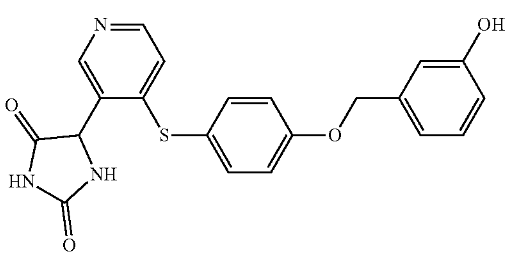 | $^1$H NMR (400 MHz, DMSO-d6) δ 9.47 (s, 1H), 8.36 (d, J = 7.9 Hz, 2H), 8.27 (s, 1H), 7.43 (d, J = 8.8 Hz, 2H), 7.20-7.09 (m, 3H), 6.84 (d, J = 11.9 Hz, 2H), 6.74-6.61 (m, 2H), 5.48 (s, 1H), 5.06 (s, 2H); m/z (ESI+) (M + H)+ = 408.10; HPLC tR = 5.309 min. | A |
| PC-11 | 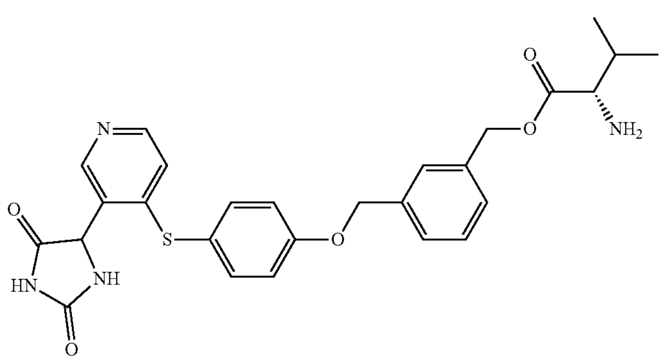 [SMILES: CC(C)[C@H](N)C(=O)OCc1cccc(COc2ccc(Sc3ccncc3C3NC(=O)NC3=O)cc2)c1] | $^1$H NMR (400 MHz, CD$_3$OD) δ 8.68 (s, 1H), 8.41 (s, 1H), 7.66-7.54 (m, 2H), 7.46 (d, J = 18.1 Hz, 2H), 7.25 (d, J = 9.0 Hz, 2H), 5.81 (s, 1H), 5.34 (dd, J = 29.1, 12.2 Hz, 2H), 5.21 (s, 2H), 3.98 (s, 1H), 3.85 (s, 1H), 2.99 (s, 1H), 2.86 (s, 1H), 2.29 (s, 1H), 2.03 (s, 1H), 1.29 (s, 3H), 1.03 (t, J = 14.5 Hz, 3H), 0.90 (s, 1H); m/z (ESI+) (M + H)+ = 521.25; HPLC tR = 5.165 min. | B |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-12 | 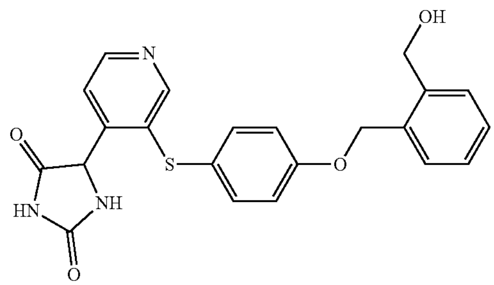 [SMILES: O=C1NC(=O)C(c2ccncc2Sc2ccc(OCc3ccccc3CO)cc2)N1] | $^1$H NMR (400 MHz, DMSO-d6) δ 10.99 (s, 1H), 8.46-8.34 (m, 2H), 8.27 (s, 1H), 7.50-7.19 (m, 7H), 7.04 (d, J = 8.9 Hz, 2H), 5.66 (s, 1H), 5.20-5.10 (m, 3H), 4.57 (d, J = 5.4 Hz, 2H); m/z (ESI+) (M + H)+ = 422.00; HPLC tR = 5.591 min. | A |
| PC-13 | 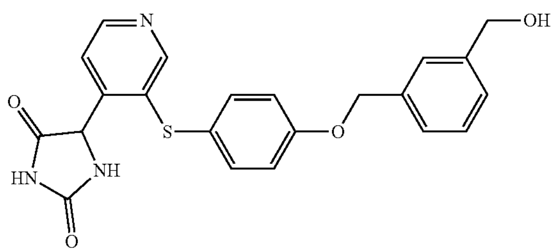 [SMILES: O=C1NC(=O)C(c2ccncc2Sc2ccc(OCc3cccc(CO)c3)cc2)N1] | $^1$H NMR (400 MHz, DMSO-d6) δ 11.00 (s, 1H), 8.46-8.36 (m, 2H), 8.27 (s, 1H), 7.38 (d, J = 8.8 Hz, 3H), 7.36-7.22 (m, 4H), 7.04 (d, J = 8.9 Hz, 2H), 5.66 (s, 1H), 5.20 (d, J = 5.7 Hz, 1H), 5.09 (s, 2H), 4.49 (d, J = 5.8 Hz, 2H); m/z (ESI+) (M + H)+ = 422.05; HPLC tR = 5.522 min. | A |
| PC-14 | 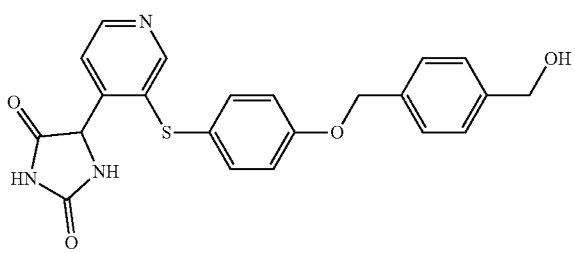 [SMILES: O=C1NC(=O)C(c2ccncc2Sc2ccc(OCc3ccc(CO)cc3)cc2)N1] | $^1$H NMR (400 MHz, DMSO-d6) δ 11.00 (s, 1H), 8.45-8.36 (m, 2H), 8.26 (s, 1H), 7.42-7.27 (m, 7H), 7.03 (d, J = 8.8 Hz, 2H), 5.66 (s, 1H), 5.18 (t, J = 5.7 Hz, 1H), 5.08 (s, 2H), 4.48 (d, J = 5.7 Hz, 2H); m/z (ESI+) (M + H)+ = 422.05; HPLC tR = 5.483 min. | B |
| PC-15 | 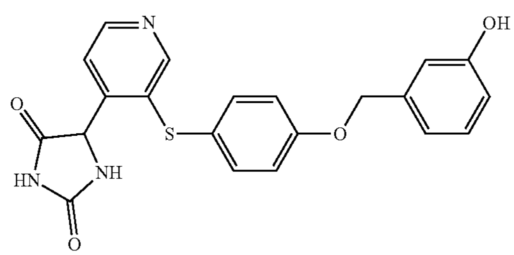 [SMILES: O=C1NC(=O)C(c2ccncc2Sc2ccc(OCc3cccc(O)c3)cc2)N1] | $^1$H NMR (400 MHz, DMSO-d6) δ 9.45 (s, 1H), 8.47-8.35 (m, 2H), 8.27 (s, 1H), 7.44-7.28 (m, 3H), 7.15 (t, J = 7.7 Hz, 1H), 7.06-6.96 (m, 2H), 6.82 (d, J = 8.0 Hz, 2H), 6.73-6.65 (m, 1H), 5.67 (s, 1H), 5.02 (s, 2H); m/z (ESI+) (M + H)+ = 408.10; HPLC tR = 5.607 min. | A |
| PC-16 | 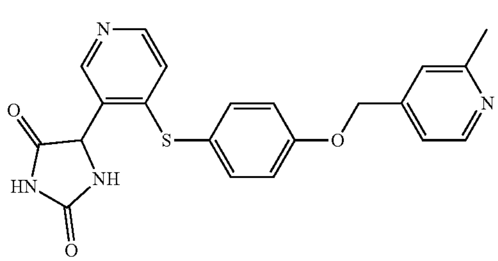 [SMILES: Cc1cc(COc2ccc(Sc3ccncc3C3NC(=O)NC3=O)cc2)ccn1] | $^1$H NMR (400 MHz, DMSO-d6) δ 11.04 (s, 1H), 8.41 (dd, J = 22.7, 9.8 Hz, 1H), 8.27 (d, J = 5.4 Hz, 3H), 7.46 (d, J = 8.7 Hz, 2H), 7.30 (s, 2H), 7.23 (d, J = 4.8 Hz, 1H), 7.15 (d, J = 8.8 Hz, 1H), 6.65 (d, J = 5.3 Hz, 1H), 5.74 (s, 1H), 5.49 (s, 2H), 2.46 (s, 3H); m/z (ESI+) (M − H)− = 407.15; HPLC tR = 3.792 min. | A |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-17 | 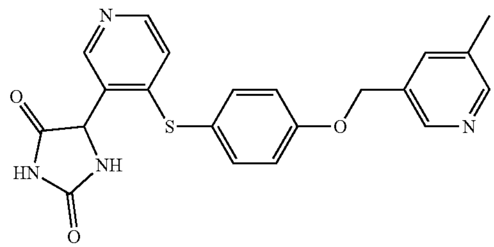 | $^1$H NMR (400 MHz, DMSO-d6) δ 11.09 (s, 1H), 8.82-8.30 (m, 5H), 8.21 (s, 1H), 7.51 (d, J = 8.7 Hz, 2H), 7.22 (d, J = 8.8 Hz, 2H), 6.80 (d, J = 5.7 Hz, 1H), 5.69 (s, 1H), 5.56 (s, 1H), 5.28 (s, 1H), 2.44 (s, 3H); m/z (ESI+) (M − H)− = 405.25; HPLC tR = 4.332 min. | C |
| PC-18 | 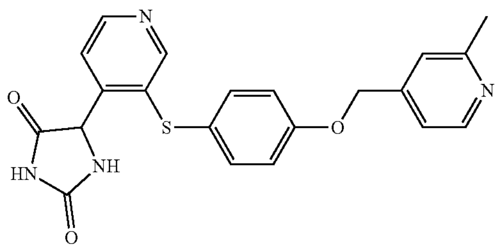 [SMILES: Cc1cc(COc2ccc(Sc3cnccc3C3NC(=O)NC3=O)cc2)ccn1] | $^1$H NMR (400 MHz, CD$_3$OD) δ 8.39 (d, J = 5.4 Hz, 3H), 8.25 (s, 1H), 7.42 (dd, J = 17.8, 10.4 Hz, 5H), 7.31 (d, J = 5.4 Hz, 1H), 7.05 (d, J = 8.6 Hz, 2H), 5.79 (s, 1H), 5.49 (s, 1H), 5.17 (s, 2H), 2.54 (s, 4H); m/z (ESI+) (M + H)+ = 407.15; HPLC tR = 5.028 min. | A |
| PC-19 | 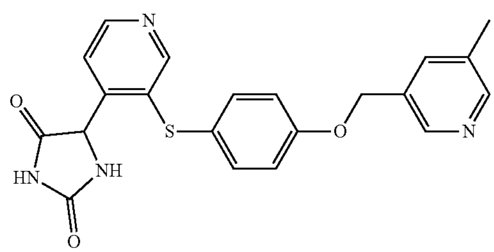 [SMILES: Cc1cncc(COc2ccc(Sc3cnccc3C3NC(=O)NC3=O)cc2)c1] | $^1$H NMR (400 MHz, CD$_3$OD) δ 8.38 (dd, J = 17.8, 12.6 Hz, 3H), 8.24 (s, 1H), 7.76 (s, 1H), 7.42 (t, J = 7.4 Hz, 3H), 7.05 (d, J = 8.8 Hz, 2H), 5.79 (s, 1H), 5.13 (s, 2H), 2.37 (d, J = 6.4 Hz, 4H); m/z (ESI+) (M + H)+ = 407.15; HPLC tR = 4.600 min. | C |
| PC-20 | 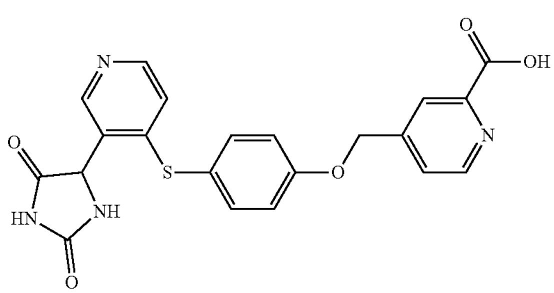 [SMILES: O=C1NC(=O)C(c2cnccc2Sc2ccc(OCc3ccnc(C(=O)O)c3)cc2)N1] | $^1$H NMR (400 MHz, DMSO-d6) δ 11.05 (s, 1H), 8.71 (d, J = 4.5 Hz, 1H), 8.36 (dd, J = 39.9, 8.9 Hz, 3H), 8.10 (s, 1H), 7.67 (s, 1H), 7.49 (d, J = 8.5 Hz, 2H), 7.20 (d, J = 8.5 Hz, 3H), 6.72 (d, J = 5.6 Hz, 1H), 5.52 (s, 1H), 5.34 (s, 2H); m/z (ESI+) (M + H)+ = 437.1; HPLC tR = 4.332 min. | D |
| PC-21 | 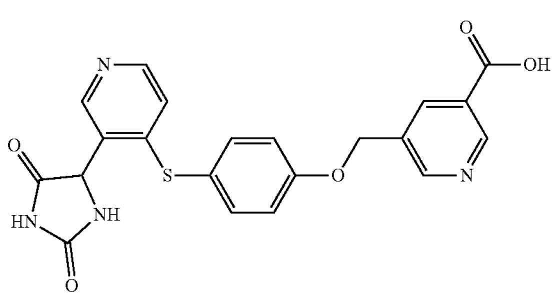 [SMILES: O=C1NC(=O)C(c2cnccc2Sc2ccc(OCc3cncc(C(=O)O)c3)cc2)N1] | $^1$H NMR (400 MHz, DMSO-d6) δ 11.10 (s, 1H), 8.97 (d, J = 56.5 Hz, 2H), 8.60-8.26 (m, 4H), 7.51 (d, J = 8.4 Hz, 2H), 7.23 (d, J = 8.5 Hz, 2H), 6.81 (d, J = 5.5 Hz, 1H), 5.57 (s, 1H), 5.31 (s, 2H); m/z (ESI+) (M + H)+ = 437.1; HPLC tR = 4.527 min. | D |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-22 | 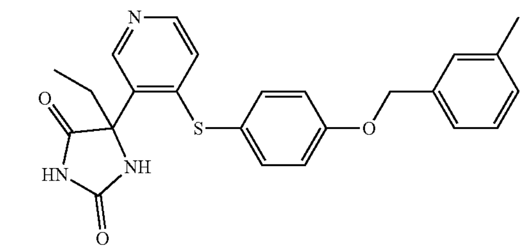 [SMILES: CCC1(c2cnccc2Sc2ccc(OCc3cccc(C)c3)cc2)NC(=O)NC1=O] | $^1$H NMR (400 MHz, DMSO-d6) δ 11.11 (s, 1H), 8.64-8.11 (m, 3H), 7.47-6.98 (m, 7H), 6.63 (s, 1H), 5.07 (s, 2H), 2.28 (d, J = 4.9 Hz, 3H), 2.26-2.18 (m, 2H), 0.92 (s, 3H); m/z (ESI+) (M + H)+ = 434.15; HPLC tR = 5.750 min. | A |
| PC-23 | 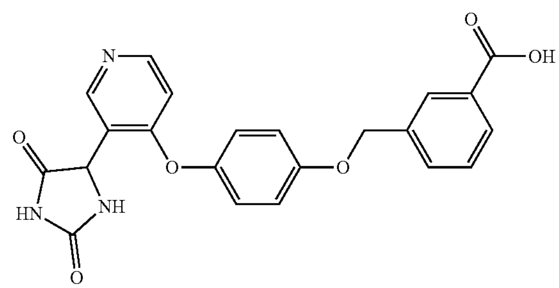 | $^1$H NMR (400 MHz, DMSO-d6) δ 10.82 (d, J = 0.8 Hz, 1H), 8.42 (dd, J = 29.8, 4.6 Hz, 2H), 8.21 (s, 1H), 8.00 (d, J = 1.7 Hz, 1H), 7.88 (d, J = 3.1 Hz, 1H), 7.67 (d, J = 2.7 Hz, 1H), 7.51 (d, J = 2.8 Hz, 1H), 7.17-6.91 (m, 4H), 6.62 (d, J = 1.5 Hz, 1H), 5.33 (d, J = 3.2 Hz, 1H), 5.17 (d, J = 1.9 Hz, 2H); m/z (ESI+) (M + H)+ = 420.15; HPLC tR = 6.453 min. | D |
| PC-24 | 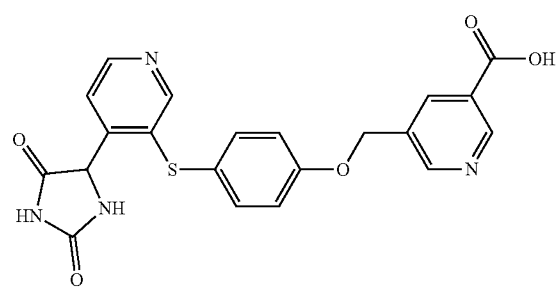 [SMILES: O=C1NC(=O)C(c2ccncc2Sc2ccc(OCc3cncc(C(=O)O)c3)cc2)N1] | $^1$H NMR (400 MHz, CD$_3$OD) δ 9.100 (s, 1H), 8.858 (s, 1H), 8.535 (s, 1H), 8.429 (d, J = 6.4 Hz, 1H), 8.256 (s, 1H), 7.498 (d, J = 11.6 Hz, 3H), 7.133 (d, J = 11.6 Hz, 2H), 5.835 (s, 1H), 5.237 (s, 3H); m/z (ESI+) (M + H)+ = 437.1; HPLC tR = 4.778 min. | D |
| PC-25 | 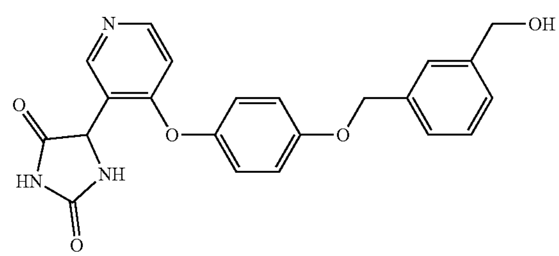 [SMILES: O=C1NC(=O)C(c2cnccc2Oc2ccc(OCc3cccc(CO)c3)cc2)N1] | $^1$H NMR (400 MHz, CD$_3$OD) δ 8.45 (s, 1H), 8.36 (d, J = 5.8 Hz, 1H), 7.46 (s, 1H), 7.34 (d, J = 11.5 Hz, 3H), 7.06 (q, J = 9.2 Hz, 4H), 6.71 (d, J = 5.8 Hz, 1H), 5.40 (s, 1H), 5.11 (s, 2H), 4.62 (s, 2H); m/z (ESI+) (M + H)+ = 406.25; HPLC tR = 5.024 min. | B |
| PC-26 | 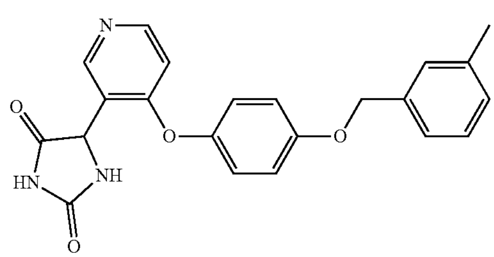 [SMILES: Cc1cccc(COc2ccc(Oc3ccncc3C3NC(=O)NC3=O)cc2)c1] | $^1$H NMR (400 MHz, CD$_3$OD) δ 8.45 (s, 1H), 8.36 (d, J = 5.8 Hz, 1H), 7.30-7.19 (m, 3H), 7.16-6.99 (m, 5H), 6.70 (d, J = 5.8 Hz, 1H), 5.40 (s, 1H), 5.06 (s, 2H), 2.35 (s, 3H); m/z (ESI+) (M + H)+ = 390.2; HPLC tR = 5.780 min. | B |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-27 | 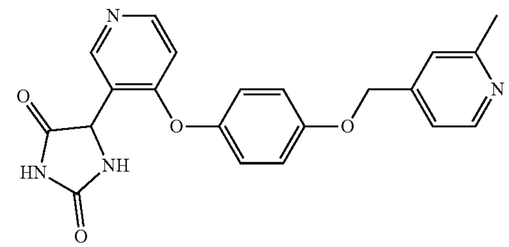 [SMILES: Cc1cc(COc2ccc(Oc3ccncc3C3NC(=O)NC3=O)cc2)ccn1] | $^1$H NMR (400 MHz, CD$_3$OD) δ 8.46 (s, 1H), 8.38 (dd, J = 9.4, 5.5 Hz, 2H), 7.42-7.28 (m, 2H), 7.13-7.03 (m, 4H), 6.72 (d, J = 5.8 Hz, 1H), 5.49 (s, 1H), 5.40 (s, 1H), 5.16 (s, 2H), 2.54 (s, 3H); m/z (ESI+) (M + H)+ = 391.3; HPLC tR = 3.846 min. | B |
| PC-28 | 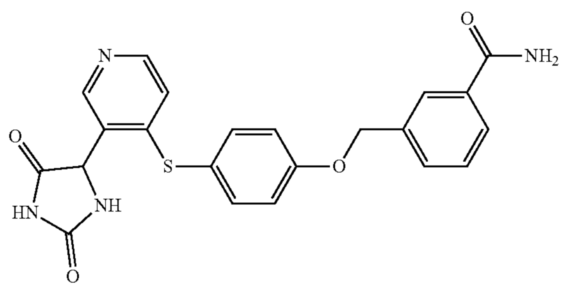 | $^1$H NMR (400 MHz, DMSO-d6) δ 11.01 (s, 1H), 8.37 (d, J = 5.1 Hz, 2H), 8.28 (d, J = 5.4 Hz, 1H), 7.98 (d, J = 12.2 Hz, 1H), 7.84 (d, J = 7.8 Hz, 2H), 7.61 (d, J = 7.5 Hz, 1H), 7.51-7.35 (m, 4H), 7.17 (d, J = 8.6 Hz, 2H), 6.66 (d, J = 5.3 Hz, 1H), 5.49 (s, 1H), 5.20 (s, 2H); m/z (ESI+) (M + H)+ = 435.15; HPLC tR = 4.567 min. | A |
| PC-29 | 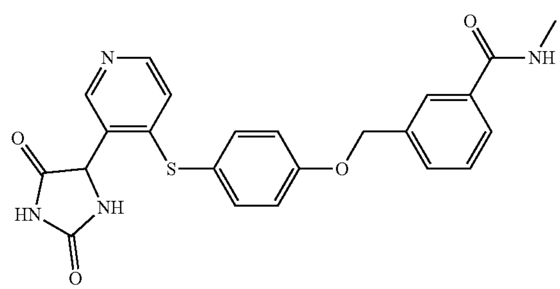 [SMILES: CNC(=O)c1cccc(COc2ccc(Sc3ccncc3C3NC(=O)NC3=O)cc2)c1] | $^1$H NMR (400 MHz, CDCl$_3$) δ 8.23 (s, 1H), 8.08 (d, J = 5.5 Hz, 1H), 7.79 (s, 1H), 7.64 (d, J = 7.7 Hz, 1H), 7.48 (d, J = 7.6 Hz, 1H), 7.39-7.34 (m, 4H), 6.96 (d, J = 8.5 Hz, 2H), 6.63 (d, J = 5.5 Hz, 1H), 5.40 (s, 1H), 5.05 (s, 3H), 2.87 (s, 3H); m/z (ESI+) (M + H)+ = 449.2; HPLC tR = 5.091 min. | B |
| PC-30 | 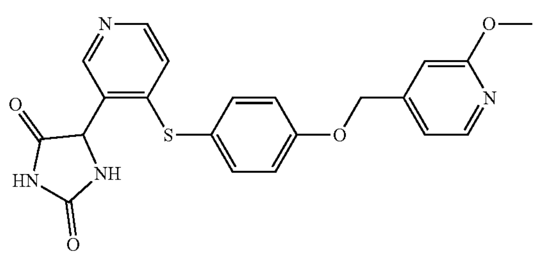 [SMILES: COc1cc(COc2ccc(Sc3ccncc3C3NC(=O)NC3=O)cc2)ccn1] | $^1$H NMR (400 MHz, DMSO-d6) δ 11.01 (s, 1H), 8.36 (d, J = 4.7 Hz, 2H), 8.28 (d, J = 5.3 Hz, 1H), 8.16 (d, J = 5.3 Hz, 1H), 7.46 (d, J = 8.4 Hz, 2H), 7.15 (d, J = 8.2 Hz, 2H), 7.03 (d, J = 5.1 Hz, 1H), 6.86 (s, 1H), 6.65 (d, J = 5.5 Hz, 1H), 5.49 (s, 1H), 5.19 (s, 2H), 3.84 (s, 3H); m/z (ESI+) (M + H)+ = 423.25; HPLC tR = 5.057 min. | B |
| PC-31 | 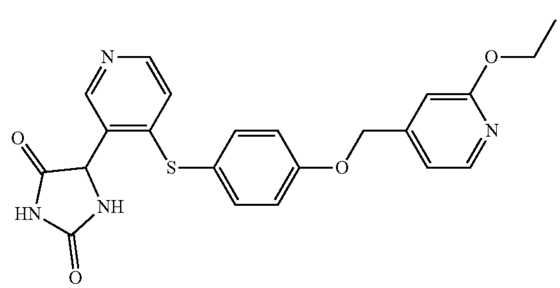 [SMILES: CCOc1cc(COc2ccc(Sc3ccncc3C3NC(=O)NC3=O)cc2)ccn1] | $^1$H NMR (400 MHz, DMSO-d6) δ 8.36 (d, J = 3.4 Hz, 2H), 8.28 (d, J = 5.4 Hz, 1H), 8.14 (d, J = 5.2 Hz, 1H), 7.46 (d, J = 8.2 Hz, 2H), 7.15 (d, J = 8.3 Hz, 2H), 7.00 (d, J = 5.3 Hz, 1H), 6.82 (s, 1H), 6.66 (d, J = 5.4 Hz, 1H), 5.49 (s, 1H), 5.18 (s, 2H), 4.29 (q, J = 7.0 Hz, 2H), 1.29 (dd, J = 7.4, 6.7 Hz, 3H); m/z (ESI+) (M + H)+ = 437.2; HPLC tR = 5.204 min. | B |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-32 | 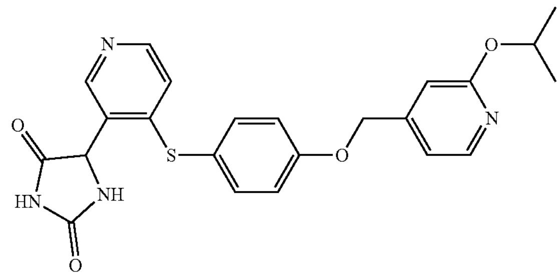 [SMILES: CC(C)Oc1cc(COc2ccc(Sc3ccncc3C3NC(=O)NC3=O)cc2)ccn1] | $^1$H NMR (400 MHz, DMSO-d6) δ 8.37 (d, J = 4.1 Hz, 2H), 8.27 (d, J = 5.4 Hz, 1H), 8.13 (d, J = 5.3 Hz, 1H), 7.46 (d, J = 8.6 Hz, 2H), 7.15 (d, J = 8.6 Hz, 2H), 6.98 (d, J = 5.1 Hz, 1H), 6.77 (s, 1H), 6.66 (d, J = 5.4 Hz, 1H), 5.49 (s, 1H), 5.23 (dt, J = 12.3, 6.1 Hz, 1H), 5.17 (s, 2H), 1.27 (d, J = 6.2 Hz, 6H); m/z (ESI+) (M + H)+ = 451.25; HPLC tR = 5.365 min. | B |
| PC-33 | 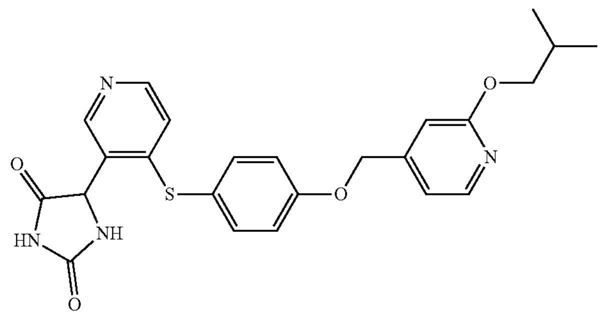 [SMILES: CC(C)COc1cc(COc2ccc(Sc3ccncc3C3NC(=O)NC3=O)cc2)ccn1] | $^1$H NMR (400 MHz, DMSO-d6) δ 10.97 (s, 1H), 8.36 (s, 2H), 8.27 (d, J = 5.4 Hz, 1H), 8.13 (d, J = 5.2 Hz, 1H), 7.46 (d, J = 8.8 Hz, 2H), 7.15 (d, J = 8.8 Hz, 2H), 7.01 (d, J = 5.1 Hz, 1H), 6.85 (s, 1H), 6.65 (d, J = 5.4 Hz, 1H), 5.49 (s, 1H), 5.18 (s, 2H), 4.02 (d, J = 6.7 Hz, 2H), 2.00 (dt, J = 13.4, 6.7 Hz, 1H), 0.94 (d, J = 6.7 Hz, 6H); m/z (ESI+) (M + H)+ = 465.25; HPLC tR = 5.690 min. | C |
| PC-34 | 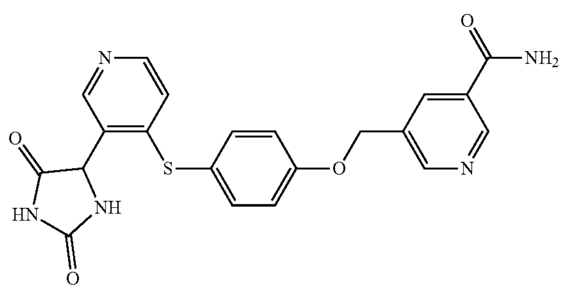 [SMILES: NC(=O)c1cncc(COc2ccc(Sc3ccncc3C3NC(=O)NC3=O)cc2)c1] | $^1$H NMR (400 MHz, DMSO-d6) δ 10.96 (s, 1H), 9.00 (d, J = 1.9 Hz, 1H), 8.81 (d, J = 1.8 Hz, 1H), 8.36 (s, 2H), 8.31-8.27 (m, 2H), 8.20 (s, 1H), 7.64 (s, 1H), 7.47 (d, J = 8.7 Hz, 2H), 7.20 (d, J = 8.8 Hz, 2H), 6.66 (d, J = 5.3 Hz, 1H), 5.49 (s, 1H), 5.26 (s, 2H); m/z (ESI+) (M + H)+ = 436.15; HPLC tR = 4.312 min. | B |
| PC-35 | 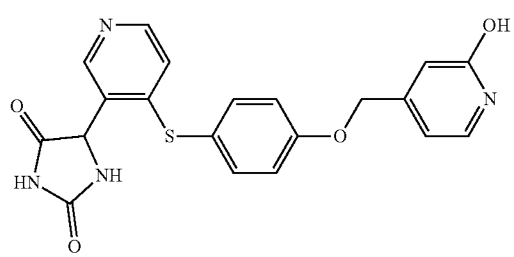 [SMILES: O=C1NC(=O)C(c2cnccc2Sc2ccc(OCc3ccnc(O)c3)cc2)N1] | $^1$H NMR (400 MHz, DMSO-d6) δ 11.04 (s, 1H), 8.37 (t, J = 22.6 Hz, 3H), 7.47 (d, J = 8.6 Hz, 2H), 7.37 (d, J = 6.7 Hz, 1H), 7.15 (d, J = 8.6 Hz, 2H), 6.72 (d, J = 5.3 Hz, 1H), 6.36 (s, 1H), 6.19 (d, J = 6.7 Hz, 1H), 5.52 (s, 1H), 5.04 (s, 2H); m/z (ESI+) (M + H)+ = 409; HPLC tR = 4.665 min. | C |
| PC-36 | 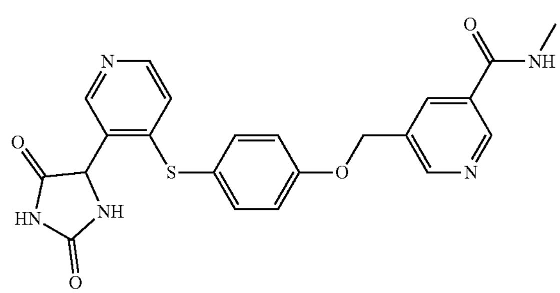 [SMILES: CNC(=O)c1cncc(COc2ccc(Sc3ccncc3C3NC(=O)NC3=O)cc2)c1] | $^1$H NMR (400 MHz, CD3OD) δ 8.94 (d, J = 2.1 Hz, 1H), 8.79 (d, J = 2.1 Hz, 1H), 8.35 (s, 2H), 8.20 (d, J = 5.5 Hz, 1H), 7.51 (s, 2H), 7.21 (s, 2H), 6.79 (d, J = 5.5 Hz, 1H), 5.58 (s, 1H), 5.28 (s, 2H), 2.95 (s, 3H); m/z (ESI+) (M + H)+ = 450.1; HPLC tR = 4.221 min. | C |

TABLE 1-continued

Exemplary Compounds of the Application

| Compound ID | Structure | Analytical Data (LCMS, NMR, etc.) | MMP-12 IC$_{50}$ (nM) |
| --- | --- | --- | --- |
| PC-37 | 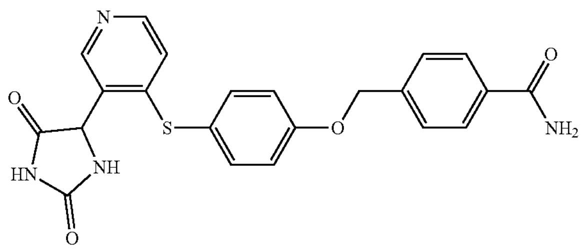 [SMILES: NC(=O)c1ccc(COc2ccc(Sc3ccncc3C3NC(=O)NC3=O)cc2)cc1] | $^1$H NMR (400 MHz, DMSO-d6) δ 8.36 (d, J = 4.4 Hz, 2H), 8.28 (d, J = 5.3 Hz, 1H), 7.97 (s, 1H), 7.89 (d, J = 7.8 Hz, 2H), 7.52 (d, J = 7.8 Hz, 2H), 7.45 (d, J = 8.2 Hz, 2H), 7.36 (s, 1H), 7.16 (d, J = 8.3 Hz, 2H), 6.65 (d, J = 5.6 Hz, 1H), 5.49 (s, 1H), 5.21 (s, 2H); m/z (ESI+) (M + H)+ = 435.1; HPLC tR = 5.069 min. | C |
| PC-38 | 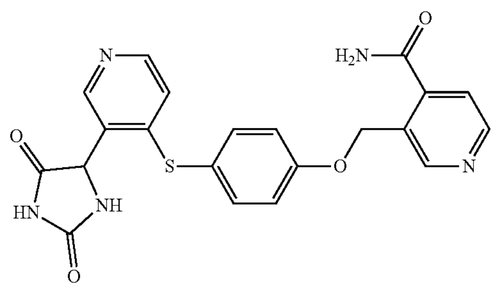 [SMILES: NC(=O)c1ccncc1COc1ccc(Sc2ccncc2C2NC(=O)NC2=O)cc1] | $^1$H NMR (400 MHz, DMSO-d6) δ 8.73 (s, 1H), 8.64 (d, J = 5.3 Hz, 1H), 8.31 (s, 1H), 8.23 (d, J = 5.4 Hz, 1H), 8.16 (s, 1H), 7.67 (s, 1H), 7.58 (d, J = 4.7 Hz, 1H), 7.45 (d, J = 8.5 Hz, 2H), 7.11 (d, J = 8.5 Hz, 3H), 6.63 (d, J = 5.1 Hz, 1H), 5.40 (s, 3H), 5.36 (s, 1H); m/z (ESI+) (M + H)+ = 436.10; HPLC tR = 4.842 min. | D |
| PC-39 | 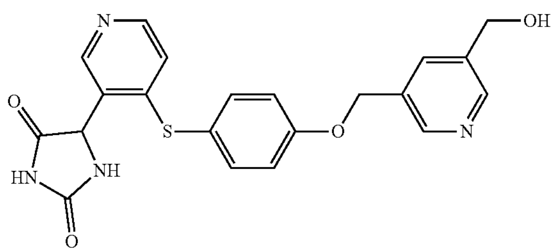 [SMILES: O=C1NC(=O)C(c2cnccc2Sc2ccc(OCc3cncc(CO)c3)cc2)N1] | $^1$H NMR (400 MHz, CD3OD) δ 8.54 (s, 1H), 8.50 (s, 1H), 8.35-8.31 (m, 1H), 8.20-8.15 (m, 1H), 7.94 (s, 1H), 7.52-7.45 (m, 2H), 7.20-7.13 (m, 2H), 6.77 (d, J = 5.5 Hz, 1H), 5.58-5.55 (m, 1H), 5.25-5.20 (m, 1H), 4.70-4.66 (m, 2H), 4.53 (s, 1H), 3.34-3.27 (m, 3H). m/z (ESI+) (M + H)+ = 423.20; HPLC tR = 1.472 min. | C |
| PC-40 | 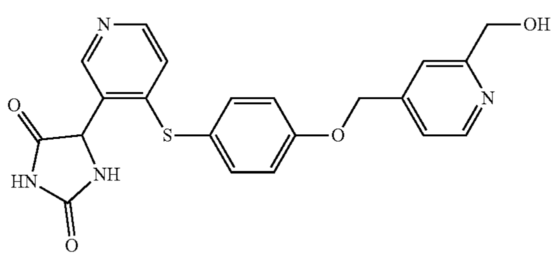 [SMILES: O=C1NC(=O)C(c2cnccc2Sc2ccc(OCc3ccnc(CO)c3)cc2)N1] | $^1$H NMR (400 MHz, CD3OD) δ 8.45 (d, J = 5.1 Hz, 1H), 8.33 (s, 1H), 8.18 (d, J = 5.5 Hz, 1H), 7.66 (s, 1H), 7.53-7.47 (m, 2H), 7.39 (d, J = 4.5 Hz, 1H), 7.15 (d, J = 8.9 Hz, 2H), 6.77 (d, J = 5.5 Hz, 1H), 5.56 (s, 1H), 5.25 (s, 2H), 4.70 (s, 2H). m/z (ESI+) (M + H)+ = 423.10; HPLC tR = 4.305 min. | A |
| PC-41 | 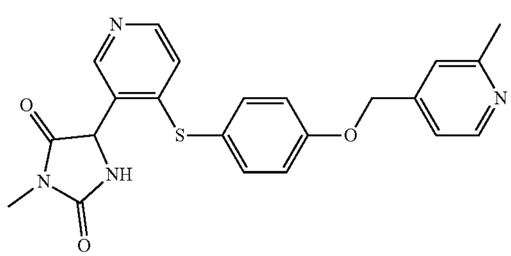 | $^1$H NMR (400 MHz, CDCl3) δ 8.50 (d, J = 5.1 Hz, 1H), 8.37 (s, 1H), 8.26 (d, J = 5.4 Hz, 1H), 7.45 (d, J = 8.5 Hz, 2H), 7.22 (s, 1H), 7.16 (d, J = 5.0 Hz, 1H), 7.02 (d, J = 8.4 Hz, 2H), 6.69 (d, J = 5.4 Hz, 1H), 6.48 (s, 1H), 5.45 (s, 1H), 5.08 (s, 2H), 3.11 (s, 3H), 2.58 (s, 3H). m/z (ESI+) (M + H)+ = 421.15; HPLC tR = 4.384 min. | C |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-42 | 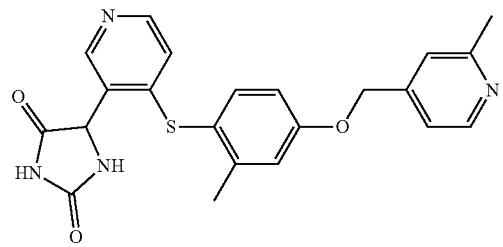 [SMILES: Cc1cc(COc2ccc(Sc3ccncc3C3NC(=O)NC3=O)c(C)c2)ccn1] | 1H NMR (400 MHz, CDCl3) δ 8.53 (d, J = 5.2 Hz, 1H), 8.42 (s, 1H), 8.25 (d, J = 5.6 Hz, 1H), 7.47 (m, 1H), 7.23 (s, 1H), 7.16 (m, 1H), 6.98 (m, 1H), 6.69 (m, 1H), 6.52 (m, 1H), 6.11 (m, 1 H), 5.54 (s, 1H), 5.08 (s, 2H), 2.60 (s, 3H), 2.28 (s, 3H). m/z (ESI+) (M + H)+ = 421.10; HPLC tR = 4.265 min. | B |
| PC-43 | 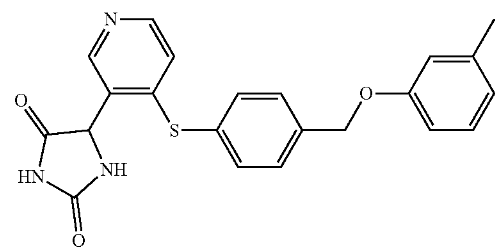 [SMILES: Cc1cccc(OCc2ccc(Sc3ccncc3C3NC(=O)NC3=O)cc2)c1] | $^1$H NMR (400 MHz, CD$_3$OD) δ 8.39 (s, 1H), 8.23 (d, J = 5.5 Hz, 1H), 7.61-7.53 (m, 6H), 7.14 (t, J = 7.9 Hz, 1H), 6.87 (d, J = 5.5 Hz, 1H), 6.79 (dd, J = 17.0, 9.6 Hz, 3H), 5.61 (s, 1H), 5.12 (s, 2H), 2.30 (s, 3H). m/z (ESI+) (M + H)+ = 406.10; HPLC tR = 5.862 min. | D |
| PC-44 | 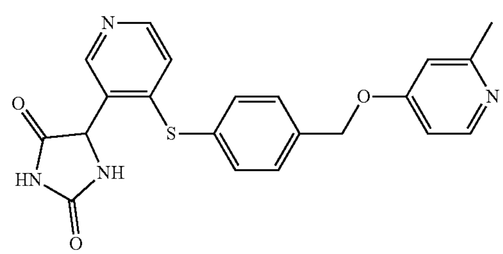 [SMILES: Cc1cc(OCc2ccc(Sc3ccncc3C3NC(=O)NC3=O)cc2)ccn1] | $^1$H NMR (400 MHz, DMSO-d6) δ 8.43 (d, J = 5.1 Hz, 1H), 8.32 (s, 1H), 8.23 (s, 1H), 7.47-7.40 (m, 2H), 7.30 (s, 1H), 7.23 (dd, J = 5.2, 1.6 Hz, 1H), 7.18-7.09 (m, 2H), 6.53 (s, 1H), 5.44 (s, 1H), 5.19 (d, J = 6.9 Hz, 2H), 2.46 (d, J = 2.2 Hz, 2H), 2.25 (d, J = 2.2 Hz, 3H). m/z (ESI+) (M + H)+ = 407.15; HPLC tR = 3.843 min. | B |
| PC-45 | 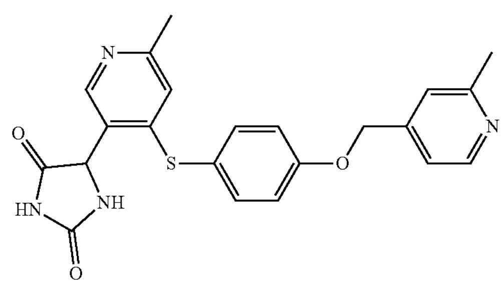 [SMILES: Cc1cc(COc2ccc(Sc3cc(C)ncc3C3NC(=O)NC3=O)cc2)ccn1] | $^1$H NMR (400 MHz, DMSO-d6) δ 8.43 (d, J = 5.1 Hz, 1H), 8.32 (s, 1H), 8.23 (s, 1H), 7.47-7.42 (m, 2H), 7.30 (s, 1H), 7.23 (d, J = 4.2 Hz, 1H), 7.18-7.11 (m, 2H), 6.53 (s, 1H), 5.44 (s, 1H), 5.19 (s, 2H), 2.46 (s, 3H), 2.25 (s, 3H). m/z (ESI+) (M + H)+ = 421.10; HPLC tR = 3.941 min. | B |
| PC-46 | 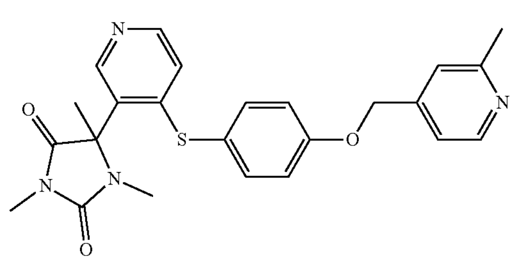 | $^1$H NMR (400 MHz, CDCl$_3$) δ 8.57 (s, 1H), 8.52 (d, J = 4.8 Hz, 1H), 8.26 (d, J = 5.6 Hz, 1H), 7.45 (m, 2H), 7.22 (s, 1H), 7.16 (m, 1H), 7.01 (d, J = 8.8 Hz, 2H), 6.66 (d, J = 5.6 Hz, 1H), 5.08 (s, 2H), 3.14 (s, 3H), 2.75 (s, 3H), 2.59 (s, 3H), 1.93 (s, 3H). m/z (ESI+) (M + H)+ = 449.15; HPLC tR = 4.478 min. | D |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-47 | 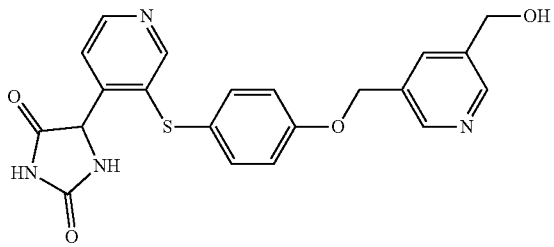 [SMILES: O=C1NC(=O)C(c2ccncc2Sc2ccc(OCc3cncc(CO)c3)cc2)N1] | $^1$H NMR (400 MHz, CD$_3$OD) δ 8.71 (m, 2H), 8.46-8.37 (m, 1H), 8.32 (s, 1H), 8.25 (s, 1H), 7.47 (d, J = 8.8 Hz, 3H), 7.10 (d, J = 8.8 Hz, 2H), 5.80 (s, 1H), 5.29 (s, 3H). m/z (ESI+) (M + H)+ = 423.20; HPLC tR = 4.554 min. | D |
| PC-48 | 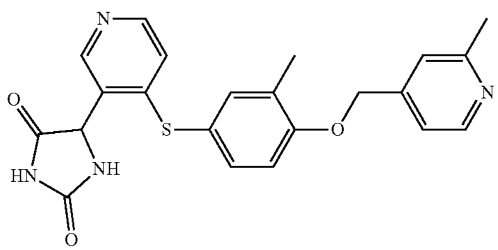 | $^1$H NMR (400 MHz, CD$_3$OD) δ 8.42 (d, J = 5.2 Hz, 1H), 8.33 (s, 1H), 8.19 (d, J = 5.6 Hz, 1H), 7.38 (m, 1 H), 7.36 (m, 3H), 7.07 (d, J = 9.2 Hz, 1H), 6.79 (d, J = 5.6 Hz, 1H), 5.57 (s, 1H), 5.23 (s, 2H), 2.56 (s, 3H), 2.32 (s, 3H); m/z (ESI+) (M + H)+ = 421.15; HPLC tR = 5.222 min. | A |
| PC-49 | 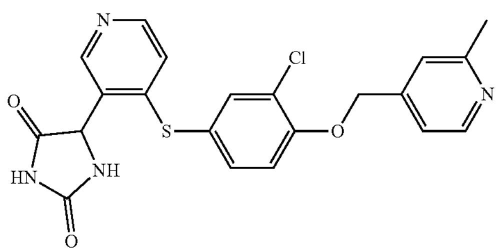 [SMILES: Cc1cc(COc2ccc(Sc3ccncc3C3NC(=O)NC3=O)cc2Cl)ccn1] | $^1$H NMR (400 MHz, CD$_3$OD) δ 8.42 (d, J = 5.2 Hz, 1H), 8.37 (s, 1H), 8.24 (d, J = 5.6 Hz, 1H), 7.64 (m, 1 H), 7.38-7.25 (m, 4H), 6.83 (d, J = 5.6 Hz, 1H), 5.54 (s, 1H), 5.30 (s, 2H), 2.56 (s, 3H); m/z (ESI+) (M + H)+ = 441.10; HPLC tR = 4.186 min. | B |
| PC-50 | 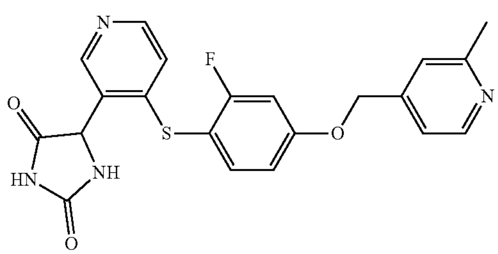 | $^1$H NMR (400 MHz, DMSO) δ 11.04 (s, 1H), 8.46-8.41 (m, 2H), 8.39 (s, 1H), 8.29 (d, J = 5.3 Hz, 1H), 7.55 (t, J = 8.6 Hz, 1H), 7.30 (s, 1H), 7.26-7.15 (m, 2H), 7.06-7.00 (m, 1H), 6.64 (d, J = 5.3 Hz, 1H), 5.53 (s, 1H), 5.21 (s, 2H), 2.47 (s, 3H); m/z (ESI+) (M + H)+ = 425.10; HPLC tR = 4.416 min. | A |
| PC-51 | 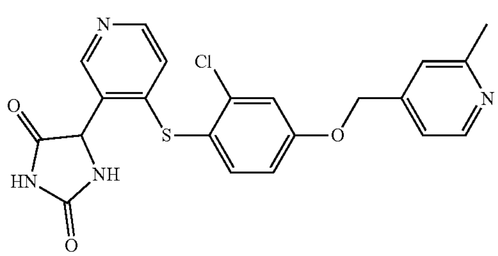 [SMILES: Cc1cc(COc2ccc(Sc3ccncc3C3NC(=O)NC3=O)c(Cl)c2)ccn1] | $^1$H NMR (400 MHz, DMSO) δ 11.04 (s, 1H), 8.45 (d, J = 5.6 Hz, 2H), 8.40 (s, 1H), 8.29 (d, J = 5.3 Hz, 1H), 7.63 (d, J = 8.7 Hz, 1H), 7.41 (d, J = 2.7 Hz, 1H), 7.30 (s, 1H), 7.23 (d, J = 5.0 Hz, 1H), 7.14 (dd, J = 8.7, 2.7 Hz, 1H), 6.58 (d, J = 5.3 Hz, 1H), 5.53 (d, J = 1.1 Hz, 1H), 5.22 (s, 2H), 2.50-2.48 (m, 3H); m/z (ESI+) (M + H)+ = 441.20; HPLC tR = 7.101 min. | A |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-52 | 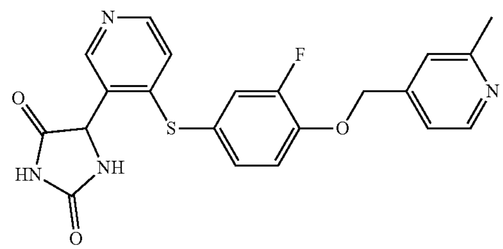 | $^1$H NMR (400 MHz, DMSO) δ 8.45 (d, J = 5.0 Hz, 1H), 8.39 (s, 2H), 8.31 (d, J = 5.3 Hz, 1H), 7.45 (d, J = 10.1 Hz, 1H), 7.32 (t, J = 8.6 Hz, 3H), 7.23 (d, J = 4.2 Hz, 1H), 6.78 (d, J = 5.2 Hz, 1H), 5.50 (s, 1H), 5.26 (s, 2H), 2.47 (s, 4H); m/z (ESI+) (M + H)+ = 425.20; HPLC tR = 6.742 min. | B |
| PC-53 | 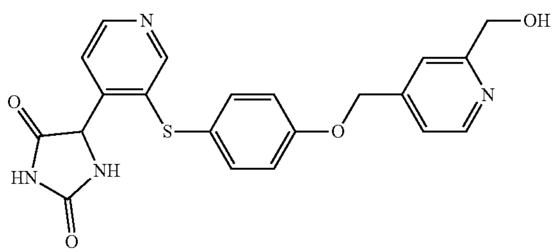 [SMILES: O=C1NC(=O)C(c2ccncc2Sc2ccc(OCc3ccnc(CO)c3)cc2)N1] | $^1$H NMR (400 MHz, CD$_3$OD) δ 8.66-8.64 (m, 1H), 8.41-8.39 (m, 1H), 8.24-8.23 (m, 1H), 8.02-8.01 (m, 1H), 7.94-7.91 (m, 1H), 7.43 (m, 3H), 7.11-7.08 (m, 2H), 5.78-5.78 (m, 1H), 5.43-5.42 (m, 2H), 4.82-4.82 (m, 2H); m/z (ESI+) (M + H)+ = 423.05; HPLC tR = 4.514 min. | B |
| PC-54 | 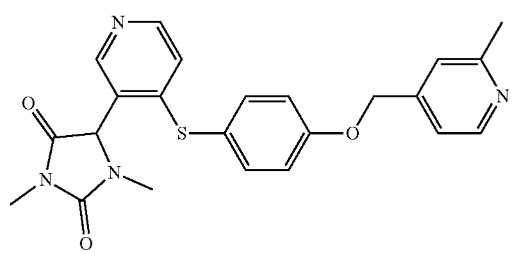 | $^1$H NMR (400 MHz, CD$_3$OD) δ 8.69 (d, J = 6.2 Hz, 1H), 8.49 (s, 1H), 8.32 (d, J = 5.8 Hz, 1H), 8.01 (s, 1H), 7.94 (d, J = 5.4 Hz, 1H), 7.55 (s, 2H), 7.27 (d, J = 8.8 Hz, 2H), 6.94 (d, J = 5.6 Hz, 1H), 5.48 (s, 3H), 3.08 (s, 3H), 2.90 (s, 3H), 2.81 (s, 3H); m/z (ESI+) (M + H)+ = 435.10; HPLC tR = 4.199 min. | D |
| PC-55 | 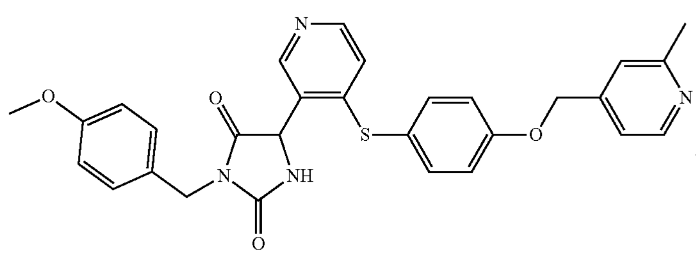 | $^1$H NMR (400 MHz, CDCl$_3$) δ 8.52 (d, J = 5.2 Hz, 1H), 8.31 (s, 1H), 8.24 (d, J = 5.4 Hz, 1H), 7.37 (dd, J = 11.8, 8.6 Hz, 4H), 7.24 (s, 1H), 7.18 (d, J = 4.9 Hz, 1H), 6.99 (d, J = 8.7 Hz, 2H), 6.76 (d, J = 8.6 Hz, 2H), 6.66 (d, J = 5.4 Hz, 1H), 6.19 (s, 1H), 5.40 (s, 1H), 5.09 (s, 2H), 4.68 (s, 2H), 3.70 (s, 3H), 2.60 (s, 3H); m/z (ESI+) (M + H)+ = 527.20; HPLC tR = 5.118 min. | C |
| PC-56 | 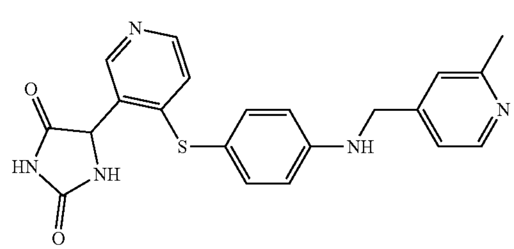 [SMILES: Cc1cc(CNc2ccc(Sc3ccncc3C3NC(=O)NC3=O)cc2)ccn1] | $^1$H NMR (400 MHz, CD$_3$OD) δ: 8.309 (d, J = 5.2 Hz, 1H), 8.262 (s, 1H), 8.149 (d, J = 5.2 Hz, 1H), 7.281-7.225 (m, 4H), 6.756 (d, J = 5.6 Hz, 1H), 6.669 (d, J = 8.8 Hz, 2H), 5.517 (s, 1H), 4.393 (s, 2H), 2.487 (s, 3H); m/z (ESI+) (M + H)+ = 406.30, (M − H)− = 404.20; HPLC tR = 4.831 min. | B |

… 51 …

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-57 | 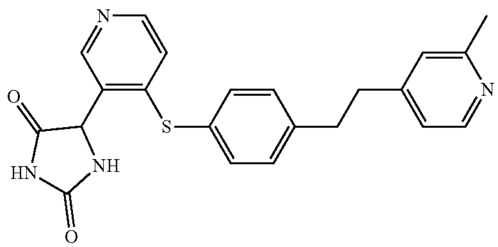 [SMILES: Cc1cc(CCc2ccc(Sc3ccncc3C3NC(=O)NC3=O)cc2)ccn1] | ¹H-NMR (400 MHz DMSO) δ: 10.997 (s, 1H), 8.369 (s, 2H), 8.281 (d, J = 5.2 Hz, 2H), 7.399-7.326 (m, 4H), 7.082 (s, 1H), 7.017 (d, J = 5.2 Hz, 1H), 6.665 (d, J = 5.2 Hz, 1H), 5.486 (s, 1H), 2.917-2.846 (m, 4H), 2.378 (s, 3H); m/z (ESI+) (M + H)+ = 405.25; HPLC tR = 3.645 min. | B |
| PC-58 | 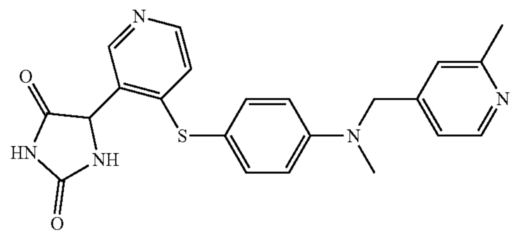 [SMILES: Cc1cc(CN(C)c2ccc(Sc3ccncc3C3NC(=O)NC3=O)cc2)ccn1] | ¹H NMR (400 MHz, CD$_3$OD) δ: 8.577-8.545 (m, 2H), 8.319 (s, 1H), 7.741-7.686 (m, 2H), 7.393 (s, 2H), 7.100 (s, 1H), 6.873 (s, 2H), 5.703 (s, 1H), 4.923-4.868 (m, 2H), 3.232 (s, 3H), 2.752 (s, 3H); m/z (ESI+) (M + H)+ = 420.25; HPLC tR = 3.637 min. | B |
| PC-59 | 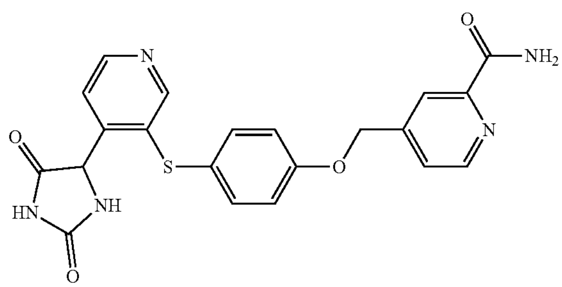 [SMILES: NC(=O)c1cc(COc2ccc(Sc3cnccc3C3NC(=O)NC3=O)cc2)ccn1] | ¹H NMR (400 MHz, CD$_3$OD) δ: 8.607 (d, J = 5.2 Hz, 1H), 8.376 (d, J = 5.2 Hz, 1H), 8.247 (s, 1H), 8.173 (s, 1H), 7.837 (s, 1H), 7.604-7.596 (m, 1H), 7.430 (d, J = 9.2 Hz, 2H), 7.398 (d, J = 5.2 Hz, 1H), 7.058 (d, J = 8.8 Hz, 2H), 5.772 (s, 1H), 5.447 (s, 1H), 5.237 (s, 2H); m/z (ESI+) (M + H)+ = 436.25, (M − H) 434.20; HPLC tR = 4.762 min. | C |
| PC-60 | 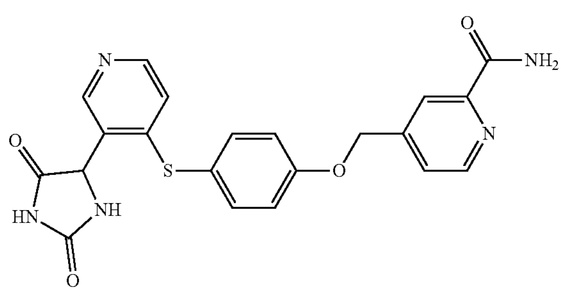 [SMILES: NC(=O)c1cc(COc2ccc(Sc3ccncc3C3NC(=O)NC3=O)cc2)ccn1] | ¹H-NMR (400 MHz DMSO) δ: 10.980 (s, 1H), 8.625 (d, J = 4.8 Hz, 1H), 8.345 (s, 1H), 8.269 (d, J = 5.2 Hz, 1H), 8.107 (s, 1H), 8.078 (s, 1H), 7.646 (s, 1H), 7.624 (d, J = 5.2 Hz, 1H), 7.466 (d, J = 8.8 Hz, 2H), 7.176 (d, J = 8.8 Hz, 2H), 6.654 (d, J = 5.2 Hz, 1H), 5.472 (s, 1H), 5.326 (s, 1H); m/z (ESI+) (M + H)+ = 436.25, (M − H)− = 434.15; HPLC tR = 4.966 min. | B |
| PC-61 | 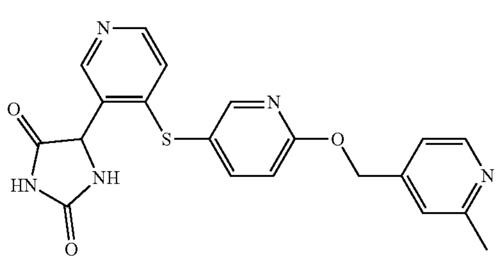 [SMILES: Cc1cc(COc2ccc(Sc3ccncc3C3NC(=O)NC3=O)cn2)ccn1] | ¹H NMR (400 MHz, CD$_3$OD) δ: 8.581 (d, J = 6.4 Hz, 1H), 8.310 (d, J = 5.6 Hz, 1H), 8.238 (s, 1H), 7.730 (s, 1H), 7.715 (s, 1H), 7.393 (d, J = 5.6 Hz, 1H), 6.927 (s, 1H), 5.094 (d, J = 17.2 Hz, 1H), 4.784 (d, J = 17.2 Hz, 1H), 2.77 (s, 3H); m/z (ESI+) (M + H)+ = 408.25, (M − H)− = 406.20; HPLC tR = 2.054 min. | C |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| PC-62 | 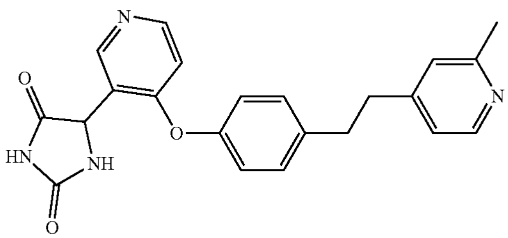 [SMILES: Cc1cc(CCc2ccc(Oc3ccncc3C3NC(=O)NC3=O)cc2)ccn1] | $^1$H NMR (400 MHz, CDCl$_3$) δ: 8.475 (s, 1H), 8.417 (d, J = 5.6 Hz, 1H), 8.352 (d, J = 4.8 Hz, 1H), 7.165 (d, J = 8.4 Hz, 2H), 6.977 (d, J = 8.4 Hz, 3H), 6.886 (d, J = 5.2 Hz, 1H), 6.595 (d, J = 5.6 Hz, 1H), 6.087 (s, 1H), 5.346 (s, 1H), 2.916-2.859 (m, 4H), 2.512 (s, 3H); m/z (ESI+) (M + H)+ = 389.25; HPLC tR = 3.522 min. | C |
| PC-63 | 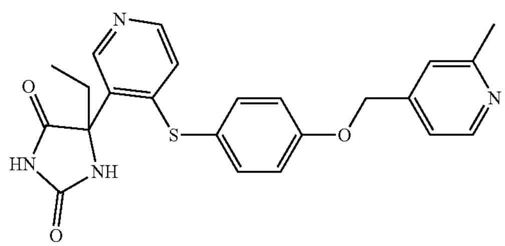 [SMILES: CCC1(c2cnccc2Sc2ccc(OCc3ccnc(C)c3)cc2)NC(=O)NC1=O] | $^1$H NMR (400 MHz, CDCl$_3$) δ: 9.146 (bs, 1H), 8.674 (s, 1H), 8.515 (d, J = 5.2 Hz, 1H), 8.227 (d, J = 5.2 Hz, 1H), 7.421 (d, J = 8.8 Hz, 2H), 7.219 (s, 1H), 7.162 (d, J = 4.4 Hz, 1H), 7.017 (d, J = 8.8 Hz, 2H), 6.696 (d, J = 5.2 Hz, 1H), 6.662 (s, 1H), 5.074 (s, 1H), 2.584 (s, 3H), 2.480-2.426 (m, 1H), 2.343-2.289 (m, 1H), 1.057 (t, J = 7.2 Hz, 3H); m/z (ESI+) (M + H)+ = 435, (M − H)− = 430; HPLC tR = 3.674 min. | A |
| PC-64 | 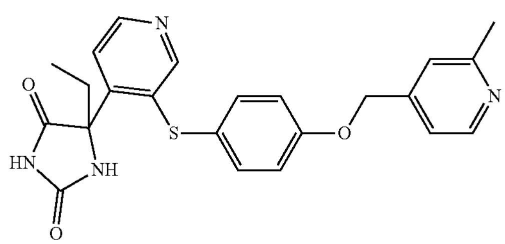 [SMILES: CCC1(c2ccncc2Sc2ccc(OCc3ccnc(C)c3)cc2)NC(=O)NC1=O] | $^1$H NMR (400 MHz, CDCl$_3$) δ: 8.753 (bs, 1H), 8.502 (d, J = 5.2 Hz, 1H), 8.402 (d, J = 5.6 Hz, 1H), 8.327 (s, 1H), 7.605 (d, J = 5.2 Hz, 2H), 7.295 (d, J = 8.8 Hz, 2H), 7.207 (s, 1H), 7.148 (d, J = 4.8 Hz, 1H), 6.930 (d, J = 8.8 Hz, 2H), 5.036 (s, 2H), 2.583 (s, 3H), 2.296-2.163 (m, 2H), 1.011 (t, J = 7.2 Hz, 3H); m/z (ESI+) (M + H)+ = 435.30, (M − H)− = 433.30; HPLC tR = 3.924 min. | A |
| OC-1 | 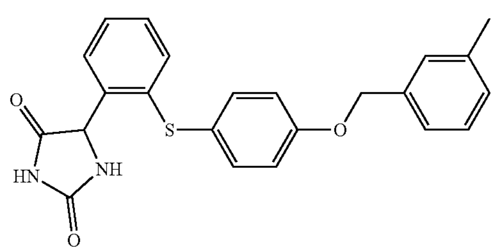 [SMILES: Cc1cccc(COc2ccc(Sc3ccccc3C3NC(=O)NC3=O)cc2)c1] | $^1$H NMR (400 MHz, CD$_3$OD) δ 7.321 (d, J = 9.2 Hz, 3H), 7.260-7.181 (m, 6H), 7.131 (s, 1H), 6.971 (d, J = 8.8 Hz, 2H), 5.738 (s, 2H), 5.030 (s, 2H), 2.338 (s, 3H); m/z (ESI+) (M + H)+ = 405.1; HPLC tR = 7.747 min. | B |
| OC-2 | 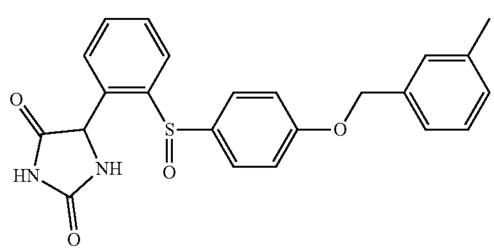 [SMILES: Cc1cccc(COc2ccc(S(=O)c3ccccc3C3NC(=O)NC3=O)cc2)c1] | $^1$H NMR (400 MHz, CD$_3$OD) δ 8.007 (d, J = 7.2 Hz, 1H), 7.777-7.749 (m, 1H), 7.656-7.581 (m, 2H), 7.531 (dd, J = 7.6, 9.2 Hz, 2H), 7.479 (d, J = 7.2 Hz, 1H), 7.235 (m, 2H), 7.198 (s, 1H), 7.151-7.079 (m, 3H), 5.648 (s, 1 H), 5.078 (s, 2 H), 2.329 (s, 3H); m/z (ESI+) (M + H)+ = 421.1; HPLC tR = 6.849 min. | C |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| OC-3 | 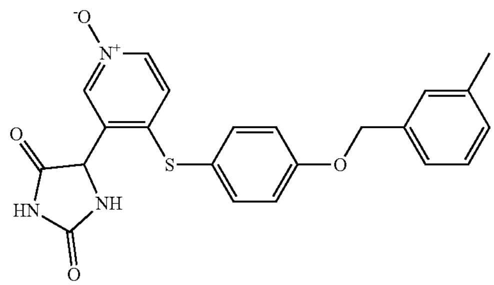 | $^1$H NMR (400 MHz, CD$_3$OD) δ 8.886 (s, 1H), 8.189 (d, J = 4 Hz, 1H), 7.424 (d, J = 8.8 Hz, 2H), 7.268 (d, J = 10.0 Hz, 3H), 7.154-7.103 (m, 3H), 6.769 (d, J = 5.6 Hz, 1H), 5.096 (s, 2H), 2.355 (s, 3H); m/z (ESI+) (M + H)+ = 422.2; HPLC tR = 5.706 min. | B |
| OC-4 | 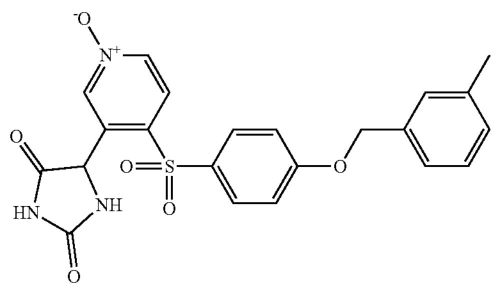 | $^1$H NMR (400 MHz, CD$_3$OD) δ 8.378 (d, J = 6.8 Hz, 1H), 8.328 (s, 1H), 8.097 (d, J = 6.8 Hz, 1H), 7.995 (d, J = 9.2 Hz, 2H), 7.251-7.134 (m, 6H), 6.370 (s, 1H), 5.148 (s, 2H), 2.339 (s, 3H); m/z (ESI+) (M − H)− = 452.25; HPLC tR = 6.255 min. | D |
| OC-5 | 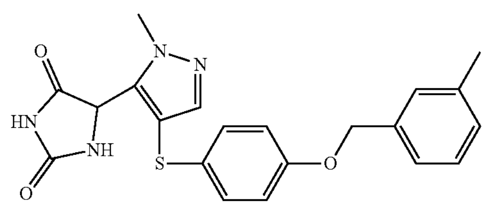 [SMILES: Cc1cccc(COc2ccc(Sc3cnn(C)c3C3NC(=O)NC3=O)cc2)c1] | $^1$H NMR (400 MHz, CDCl$_3$) δ 7.53 (s, 1H), 7.24 (dd, J = 13.2, 4.1 Hz, 1H), 7.18 (d, J = 7.2 Hz, 2H), 7.12 (s, 1H), 7.08-7.04 (m, 2H), 6.87-6.77 (m, 2H), 6.50 (s, 1H), 5.49 (d, J = 0.5 Hz, 1H), 4.93 (s, 2H), 3.83 (s, 3H), 2.33 (s, 3H); m/z (ESI+) (M − H)− = 407.15; HPLC tR = 7.094 min. | B |
| OC-6 | 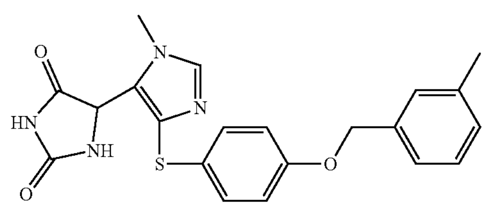 [SMILES: Cc1cccc(COc2ccc(Sc3ncn(C)c3C3NC(=O)NC3=O)cc2)c1] | $^1$H NMR (400 MHz, CD$_3$OD) δ 7.73 (s, 1H), 7.24-7.19 (m, 4H), 7.16 (d, J = 7.9 Hz, 1H), 7.10 (d, J = 7.7 Hz, 1H), 6.89-6.85 (m, 2H), 5.67 (s, 1H), 4.98 (s, 2H), 3.67 (s, 3H), 2.32 (s, 3H); m/z (ESI+) (M + H)+ = 409.1; HPLC tR = 8.891 min. | B |
| OC-7 | 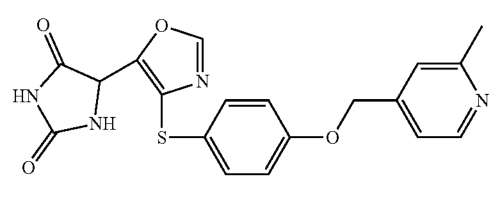 [SMILES: Cc1cc(COc2ccc(Sc3ncoc3C3NC(=O)NC3=O)cc2)ccn1] | $^1$H NMR (400 MHz, CD$_3$OD) δ 8.35 (d, J = 5.3 Hz, 1H), 8.23 (s, 1H), 7.39 (d, J = 8.9 Hz, 2H), 7.34 (s, 1H), 7.27 (d, J = 5.1 Hz, 1H), 6.94 (d, J = 8.9 Hz, 2H), 5.11 (s, 2H), 2.51 (s, 3H); m/z (ESI+) (M + H)+ = 397.25; HPLC tR = 4.881 min. | A |
| OC-8 | 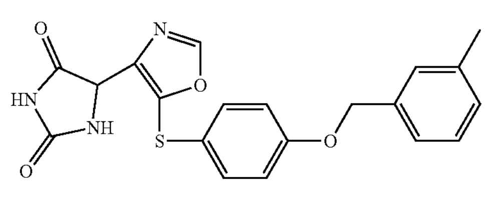 | $^1$H-NMR (300 MHz CDCl$_3$) δ: 7.683 (s, 1H), 7.509 (d, J = 8.7 Hz, 2H), 7.288-7.193 (m, 6H), 5.076 (s, 1H), 5.018 (s, 2H), 1.563 (s, 3H); m/z (ESI+) 412.23 (M + Na)+; HPLC tR: 5.234 min. | D |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| OC-9 | 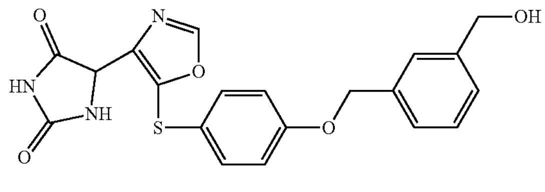 [SMILES: O=C1NC(=O)C(c2ncoc2Sc2ccc(OCc3cccc(CO)c3)cc2)N1] | $^1$H-NMR (300 MHz CDCl$_3$) δ: 7.684 (s, 1H), 7.534 (d, J = 8.4 Hz, 2H), 7.438-7.348 (m, 4H), 6.997 n (d, J = 8.4 Hz, 2H), 5.085 (s, 2H), 4.800 (bs, 1H), 4.726-4.711 (m, 2H); m/z (ESI+) 418.19 (M + Na)+; HPLC tR: 5.485 min. | D |
| OC-10 | 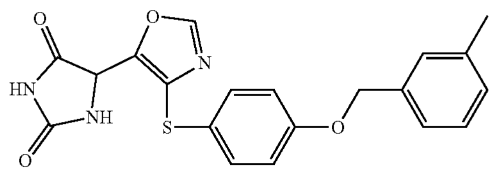 | $^1$H-NMR (300 MHz CDCl$_3$) δ: 7.683 (s, 1H), 7.509 (d, J = 8.7 Hz, 2H), 7.288-7.193 (m, 6H), 5.076 (s, 1H), 5.018 (s, 2H), 1.563 (s, 3H); m/z (ESI+) 412.23 (M + Na)+; HPLC tR: 5.234 min. | B |
| OC-11 | 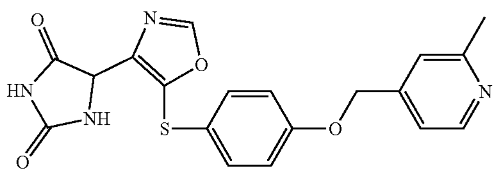 [SMILES: Cc1cc(COc2ccc(Sc3ocnc3C3NC(=O)NC3=O)cc2)ccn1] | $^1$H NMR (400 MHz, CD$_3$OD) δ 8.38 (d, J = 5.1 Hz, 1H), 7.95 (s, 1H), 7.54 (d, J = 8.9 Hz, 2H), 7.38 (s, 1H), 7.30 (d, J = 4.9 Hz, 1H), 7.06 (d, J = 8.8 Hz, 2H), 5.17 (s, 2H), 5.14 (s, 1H), 2.53 (s, 3H); m/z (ESI+) (M + H)+ = 397.10; HPLC tR = 4.623 min. | D |
| OC-12 | 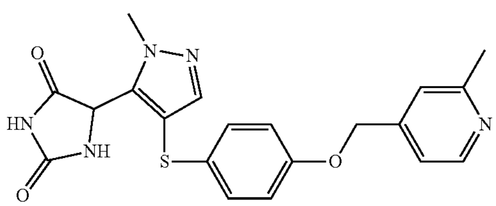 [SMILES: Cc1cc(COc2ccc(Sc3cnn(C)c3C3NC(=O)NC3=O)cc2)ccn1] | $^1$H NMR (400 MHz, CD$_3$OD) δ: 8.337 (d, J = 5.2 Hz, 1H), 7.491 (s, 1H), 7.402 (s, 1H), 7.287 (s, 1H), 7.224 (d, J = 4.8 Hz, 1H), 7.136 (d, J = 8.8 Hz, 2H), 6.854 (d, J = 9.2 Hz, 2H), 5.601 (s, 1H), 5.401 (s, 1H), 5.043 (s, 2H), 3.867 (s, 3H), 2.501 (s, 3H); m/z (ESI+) (M + H)+ = 410.20, (M − H)− = 408.20; HPLC tR = 4.468 min. | A |
| OC-13 | 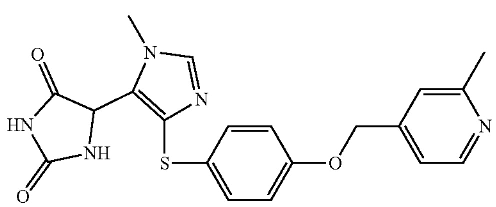 [SMILES: Cc1cc(COc2ccc(Sc3ncn(C)c3C3NC(=O)NC3=O)cc2)ccn1] | $^1$H-NMR (400 MHz DMSO) δ: 11.013 (s, 1H), 8.390 (d, J = 5.2 Hz, 1H), 8.197 (s, 1H), 7.729 (s, 1H), 7.233 (s, 1H), 7.163 (d, J = 8.8 Hz, 3H), 6.892 (d, J = 8.8 Hz, 2H), 5.511 (s, 1H), 5.064 (s, 2H), 3.521 (s, 3H), 2.427 (s, 3H); m/z (ESI+) (M + H)+ = 410.25, (M − H)− = 408.15; HPLC tR = 5.139 min. | A |
| OC-14 | 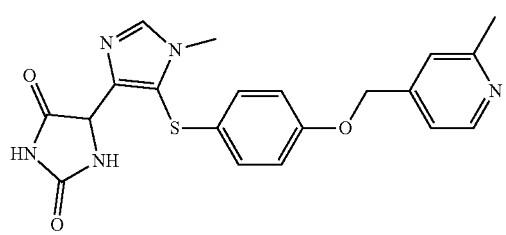 [SMILES: Cc1cc(COc2ccc(Sc3c(C4NC(=O)NC4=O)ncn3C)cc2)ccn1] | $^1$H-NMR (400 MHz DMSO) δ: 10.699 (s, 1H), 8.395 (d, J = 5.2 Hz, 1H), 8.127 (s, 1H), 7.851 (s, 1H), 7.238 (s, 1H), 7.187 (d, J = 8.8 Hz, 2H), 6.950 (d, J = 8.8 Hz, 2H), 5.160 (s, 1H), 5.077 (s, 2H), 3.423 (s, 3H), 2.428 (s, 3H); m/z (ESI+) (M + H)+ = 410.20; HPLC tR = 4.608 min. | B |

Compounds of the application can be prepared by any number of processes as described generally below and more specifically illustrated by the exemplary examples. which follow herein. For example, compounds of the application can by prepared according to any one of General Schemes 1 to 9. In particular, compounds in which X is S, Y is O and Z is CH$_2$ can be prepared as shown in General Schemes 1-4 and 9; compounds in which each of X and Y is O and Z is CH$_2$ can be prepared as shown in General Scheme 5; compounds in which X is S, Y is CH$_2$ and Z is O can be prepared as shown in General Scheme 6; compounds in which X is S, Y is NH and Z is CH$_2$ can be prepared as shown in General Scheme 7; and compounds in which X is S and each of Y and Z is CH$_2$ can be prepared as shown in General Scheme 8.

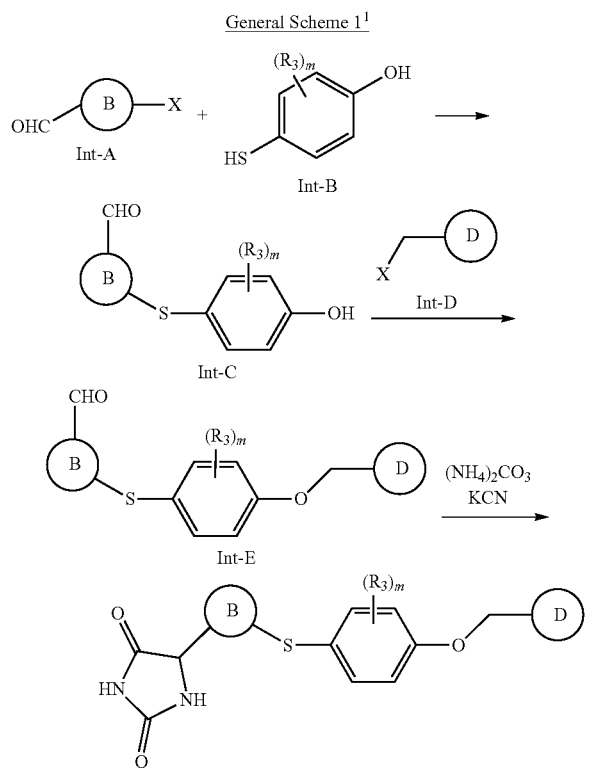

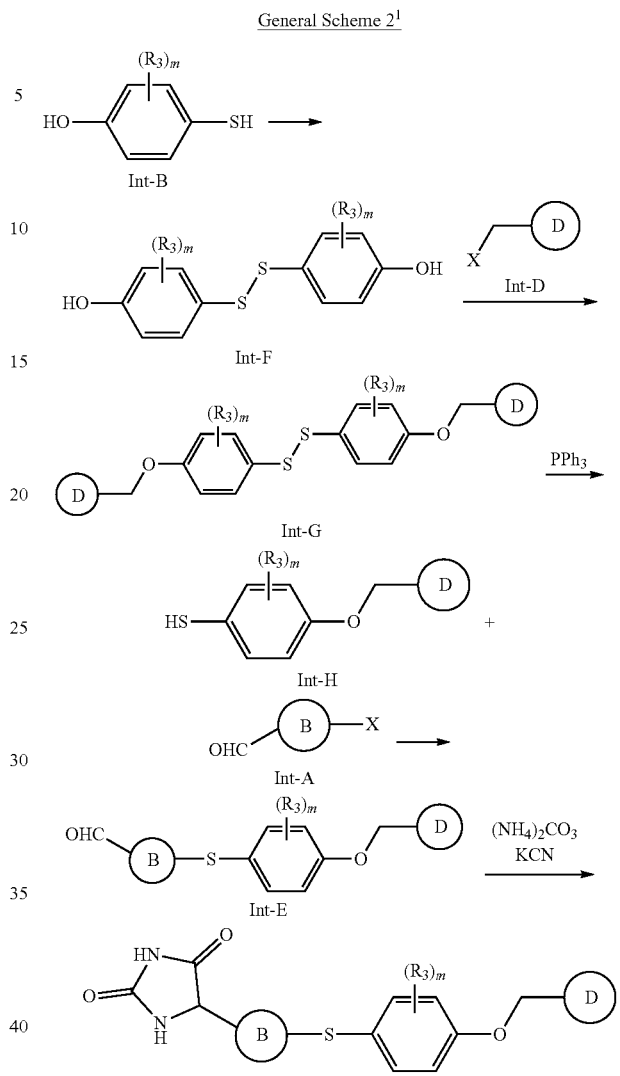

[1]X is halo; ring D is optionally substituted aryl or heteroaryl; R$_3$ is independently selected from hydrogen alkyl, and halo; m is an integer of 1 to 4; ring B is optionally substituted aryl or heteroaryl A solution of Int-A and Int-B in an organic solvent is prepared and sodium hydroxide is added to the solution to form a reaction mixture. The reaction mixture is stirred overnight then mixed with water and an organic solvent and extracted. The organic layer is dried and evaporated under high vacuum and the residue is purified by column chromatography to Int-C. Int-C is then mixed with Int-D and potassium carbonate in an organic solvent and the reaction is monitored by thin layer chromatography (TLC). Once formation of Int-E is confirmed by TLC, the reaction mixture is extracted, and the organic layer dried and evaporated under high vacuum. The residue is purified by column chromatography to obtain Int-E. Int-E is then reacted with (NH$_4$)$_2$CO$_3$ and potassium cyanide (KCN) in aqueous alcohol overnight. The reaction mixture is evaporated to remove the solvent and then extracted. The organic layer is dried and evaporated, and the residue purified by column chromatography to obtain compounds according to embodiments of the application.

[1]X is halo; ring D is optionally substituted aryl or heteroaryl; R$_3$ is independently selected from hydrogen alkyl, and halo; m is an integer of 1 to 4; ring B is optionally substituted aryl or heteroaryl A mixture of Int-B in DMSO is stirred overnight with heating under nitrogen atmosphere. Then the mixture is diluted with water and extracted. The organic layer is washed with brine, dried, filtered and concentrated to give Int-F. A mixture of Int-F, Int-D and potassium carbonate is stirred with heating under nitrogen atmosphere. The mixture is diluted with water and extracted. The organic layer is washed with brine, dried, filtered, concentrated and purified by column chromatography to give Int-G. Triphenyphosphine, tetra-n-butylammonium bromide (TBAB) and dilute hydrochloric acid is added to Int-G in an organic solvent to form a mixture that is stirred at room temperature. The mixture is concentrated and the residue purified by column chromatography to give Int-H. Int-H is reacted with Int-A and potassium carbonate and the mixture is stirred overnight with heating under nitrogen atmosphere. The mixture is concentrated under vacuum and purified by prep-TLC to give Int-E. Int-E is then reacted with (NH$_4$)$_2$CO$_3$ and potassium cyanide (KCN) in aqueous alcohol overnight. The reaction mixture is evaporated to remove the solvent and General Scheme 3[1]

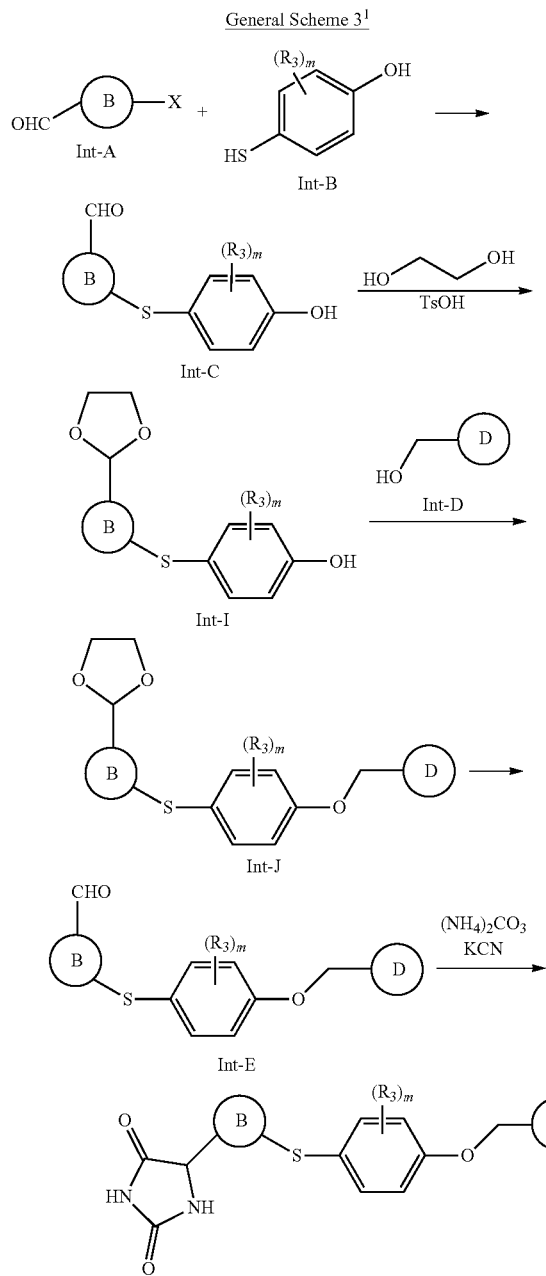

[1]X is halo; ring D is optionally substituted aryl or heteroaryl; $R_3$ is independently selected from hydrogen alkyl, and halo; m is an integer of 1 to 4; ring B is optionally substituted aryl or heteroaryl A solution of Int-A and Int-B in an organic solvent is prepared and sodium hydroxide is added to the solution to form a reaction mixture. The reaction mixture is stirred overnight then mixed with water and an organic solvent and extracted. The organic layer is dried and evaporated under high vacuum and the residue is purified by column chromatography to give Int-C. Ethane-1,2-diol and TsOH are added to a mixture of Int-C in organic solvent and the mixture is heated under reflux under nitrogen atmosphere. The mixture is concentrated under reduced pressure and the residue purified by column chromatograph to give Int-I. Int-I is reacted with Int-D, triphenylphosphine, and diethyl azodicarboxylate (DEAD) at room temperature under stirring. The reaction is quenched with water and extracted. The organic layer is dried, concentrated under reduced pressure, and the residue is purified by column chromatography to give Int-J. A mixture of Int-J in acid is stirred under heating. The reaction mixture is cooled to room temperature and concentrated under reduced pressure. The residue is added with saturated sodium bicarbonate and extracted. The organic layer is washed, dried, and concentrated under reduced pressure to give Int-E. Int-E is then reacted with $(NH_4)_2CO_3$ and potassium cyanide (KCN) in aqueous alcohol overnight. The reaction mixture is evaporated to remove the solvent and then extracted. The organic layer is dried and evaporated, and the residue purified by column chromatography to obtain compounds according to embodiments of the application.

General Scheme 4[1]

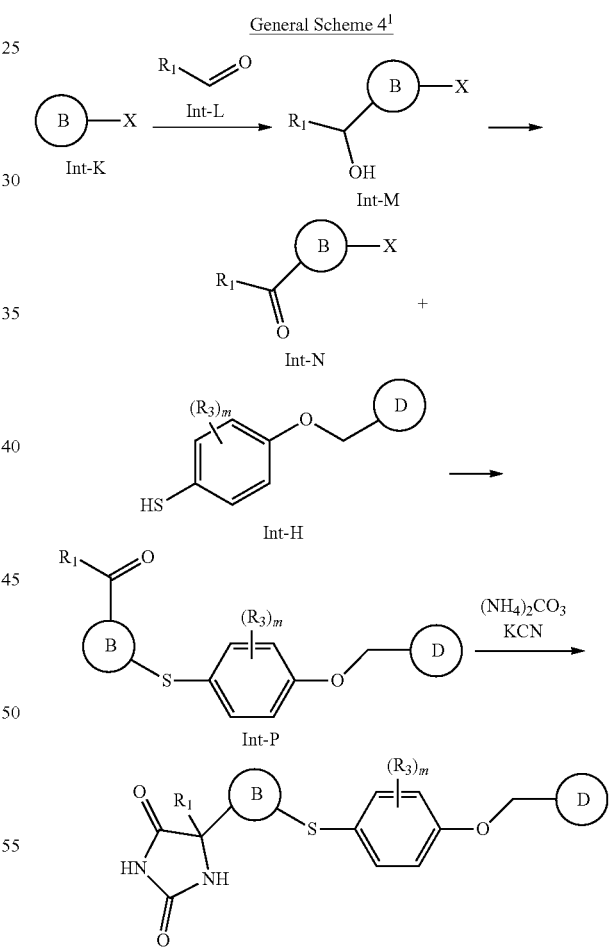

[1]X is halo; ring D is optionally substituted aryl or heteroaryl; $R_3$ is independently selected from hydrogen alkyl, and halo; m is an integer of 1 to 4; ring B is optionally substituted aryl or heteroaryl; $R_1$ is alkyl LDA is added to a mixture of Int-K at −78° C. under nitrogen atmosphere and the mixture is stirred for 1 hour. Then, Int-L is added dropwise and the mixture is stirred for 1 hour. The reaction is quenched with a saturated aqueous solution of ammonium chloride and extracted. The organic layer is washed, dried, concentrated under vacuum and the residue purified by column chromatography to give Int-M. Int-M is oxidized to give Int-N. Pd(dba)$_2$ is added to a mixture of Int-N, Int-H (prepared as described above in General Scheme 2), DPPF and DIEA. The mixture is stirred under heating, then filtered and extracted. The organic phase is dried, concentrated under reduced pressure and the residue purified by column chromatograph to provide Int-P. Int-P is then reacted with (NH$_4$)$_2$CO$_3$ and potassium cyanide (KCN) in aqueous alcohol overnight. The reaction mixture is evaporated to remove the solvent and then extracted. The organic layer is dried and evaporated, and the residue purified by column chromatography to obtain compounds according to embodiments of the application.

fied by column chromatography to give Int-S. Int-S is then reacted with (NH$_4$)$_2$CO$_3$ and potassium cyanide (KCN) in aqueous alcohol overnight. The reaction mixture is evaporated to remove the solvent and then extracted. The organic layer is dried and evaporated, and the residue purified by column chromatography to obtain compounds according to embodiments of the application.

General Scheme 6[1]

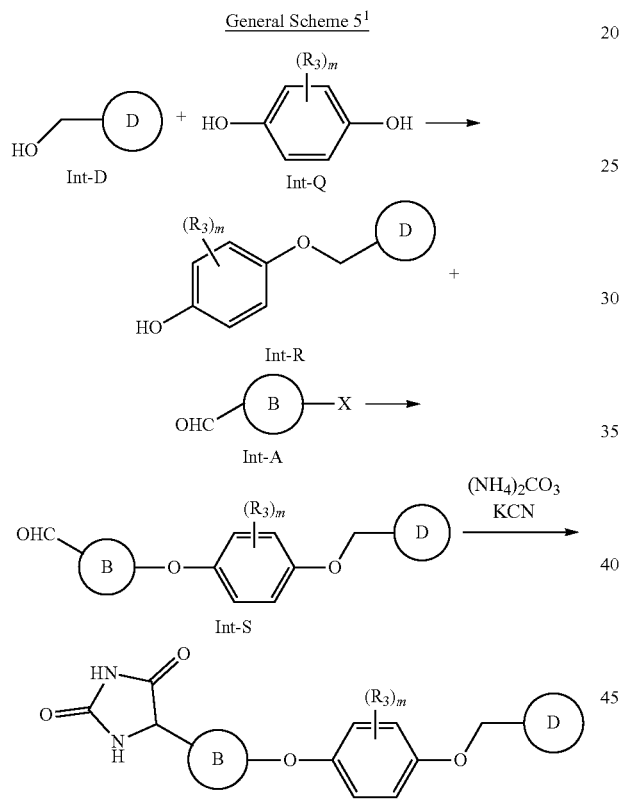

General Scheme 5[1]

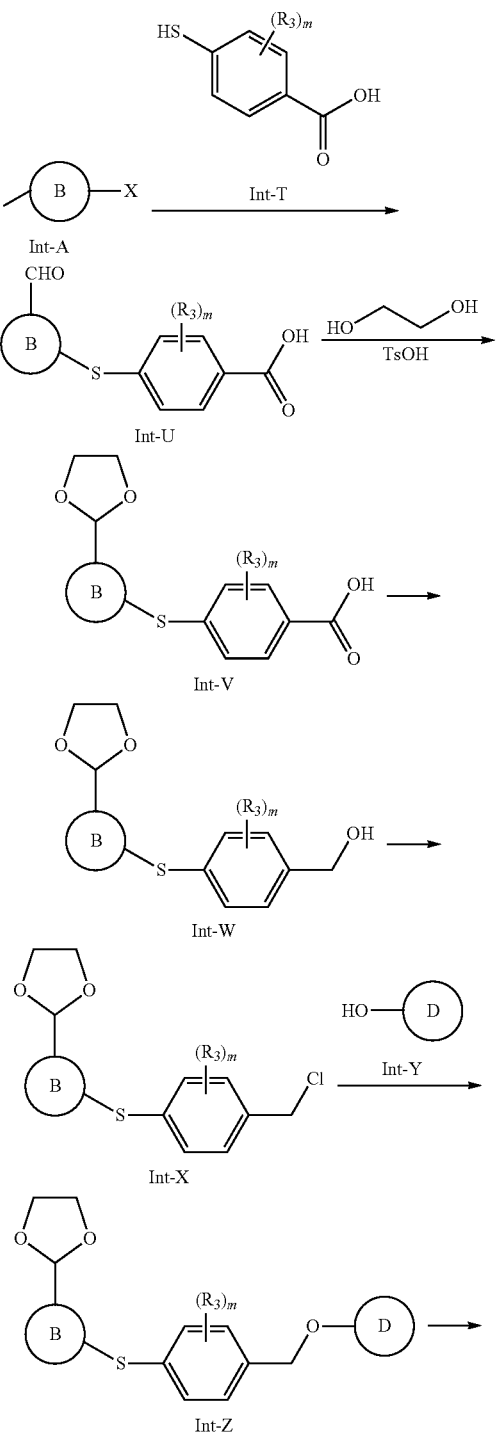

[1]X is halo; ring D is optionally substituted aryl or heteroaryl; R$_3$ is independently selected from hydrogen alkyl, and halo; m is an integer of 1 to 4; ring B is optionally substituted aryl or heteroaryl To a solution of Int-D in organic solvent, Int-Q, triphenylphosphine, and DEAD are added at 0°. The mixture is warmed to room temperature and stirred. Then the mixture is quenched with water and extracted. The organic layer is washed, dried, concentrated under vacuum and the residue purified by column chromatography to give Int-R. To a solution of Int-R in organic solvent, Int-A and potassium carbonate are added. The mixture is stirred under heating then hydrochloric acid is added to adjust the pH to 6-7. The mixture is extracted and the organic layer is washed, dried, concentrated under reduced pressure, and the residue puri- -continued

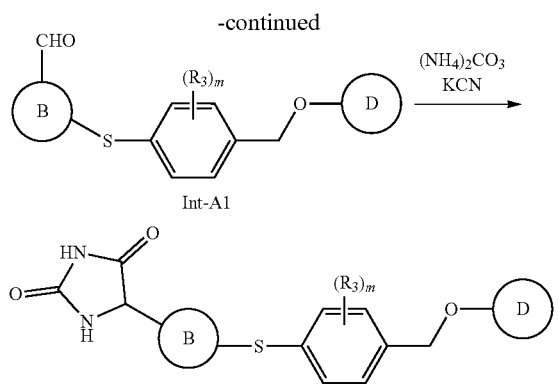

[1]X is halo; ring D is optionally substituted aryl or heteroaryl; $R_3$ is independently selected from hydrogen alkyl, and halo; m is an integer of 1 to 4; ring B is optionally substituted aryl or heteroaryl To a solution of Int-A in organic solvent, Int-T and potassium carbonate are added at room temperature under nitrogen atmosphere. The mixture is stirred at room temperature and after TLC analysis of the mixture shows conversion to the desired product, the mixture is diluted with water, extracted, and the organic layer is washed, dried, concentrated under reduced pressure, and the residue purified by column chromatography to obtain Int-U. TsOH is added to a solution of Int-U in organic solvent. After several minutes of stirring, a solution of ethane-1,2-diol in organic solvent is added dropwise. The mixture is stirred under heating and then poured over saturated sodium bicarbonate solution and extracted. The organic phase is dried, concentrated under reduced pressure and purified by column chromatography to obtain Int-V. Int-V is reduced with LAH and the reaction is quenched, extracted and the organic layer dried and concentrated under reduced pressure. The residue is purified by column chromatography to give Int-Y. $SOCl_2$ is added to a mixture of Int-Y in organic solvent at 0° C. After stirring for several hours, the pH is adjusted to pH 7 and the mixture is extracted. The organic layer is dried, concentrated under reduced pressure and the residue purified by column chromatography to give Int-X. Int-X is reacted with Int-Y and potassium carbonate at room temperature under nitrogen atmosphere. The mixture is diluted with water and extracted, and the organic layer is washed, dried, concentrated under reduced pressure, and the residue purified by column chromatography to provide Int-Z. A mixture of Int-Z in acid is stirred under heating. The reaction mixture is cooled to room temperature and concentrated under reduced pressure. The residue is added with saturated sodium bicarbonate and extracted. The organic layer is washed, dried, and concentrated under reduced pressure to give Int-A1. Int-A1 is then reacted with $(NH_4)_2CO_3$ and potassium cyanide (KCN) in aqueous alcohol overnight. The reaction mixture is evaporated to remove the solvent and then extracted. The organic layer is dried and evaporated, and the residue purified by column chromatography to obtain compounds according to embodiments of the application.

General Scheme 7[1]

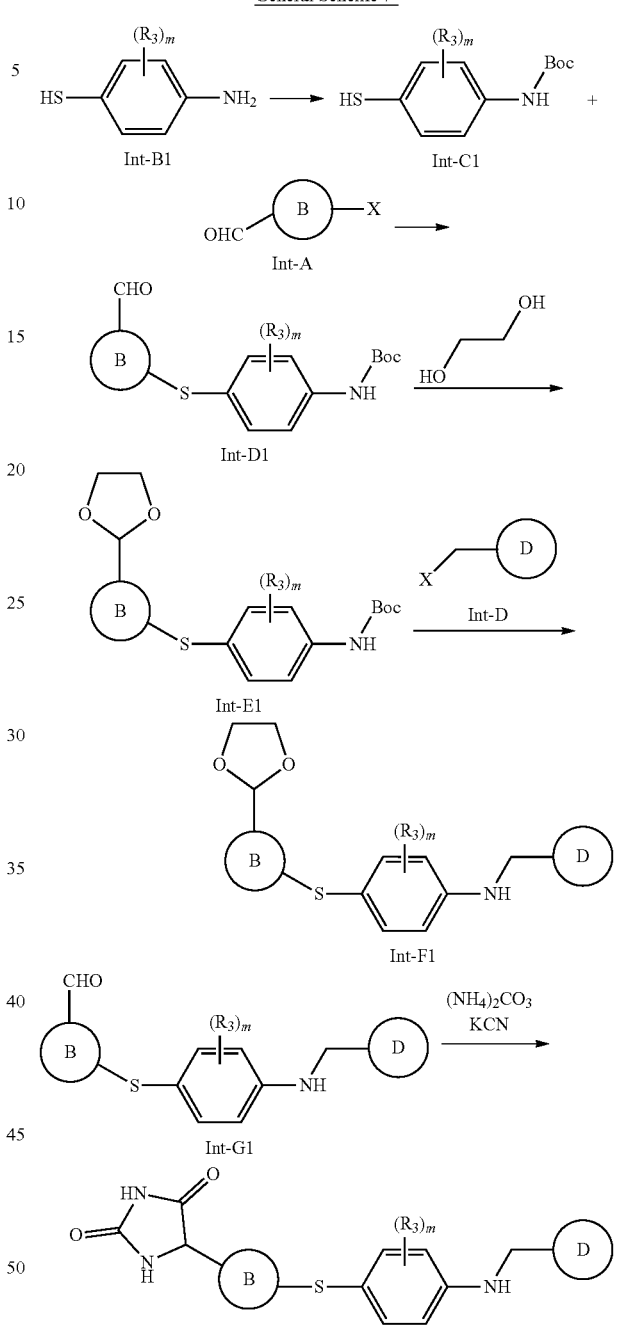

[1]X is halo; ring D is optionally substituted aryl or heteroaryl; $R_3$ is independently selected from hydrogen alkyl, and halo; m is an integer of 1 to 4; ring B is optionally substituted aryl or heteroaryl Triethylamine and DMAP are added to a solution of Int-B1 and $BOC_2O$ in organic solvent and the mixture is stirred at room temperature. The mixture is quenched, extracted, and the organic phase washed, dried, concentrated under reduced pressure and the residue purified by column chromatography to obtain Int-C1. Int-C1 is reacted with Int-A and potassium carbonate at room temperature. The mixture is diluted with water, extracted, and the organic phase washed, dried, concentrated under reduced pressure and the residue purified by column chromatography to obtain Int-D1. TsOH is added to a stirred solution of Int-D1 in organic solvent. After several minutes of stirring, a solution of ethane-1,2-diol in organic solvent is added dropwise. The mixture is stirred under heating and then poured over saturated sodium bicarbonate solution and extracted. The organic phase is dried, concentrated under reduced pressure and purified by column chromatography to obtain Int-E1. Sodium hydride is added to a solution of Int-E1 and Int-D. The mixture is diluted with water and extracted, and the organic layer is washed, dried, concentrated under reduced pressure, and the residue purified by column chromatography to provide Int-F1. A mixture of Int-F1 in acid is stirred under heating. The reaction mixture is cooled to room temperature and concentrated under reduced pressure. The residue is added with saturated sodium bicarbonate and extracted. The organic layer is washed, dried, and concentrated under reduced pressure to give Int-G1. Int-G1 is then reacted with $(NH_4)_2CO_3$ and potassium cyanide (KCN) in aqueous alcohol overnight. The reaction mixture is evaporated to remove the solvent and then extracted. The organic layer is dried and evaporated, and the residue purified by column chromatography to obtain compounds according to embodiments of the application.

General Scheme 8[1]

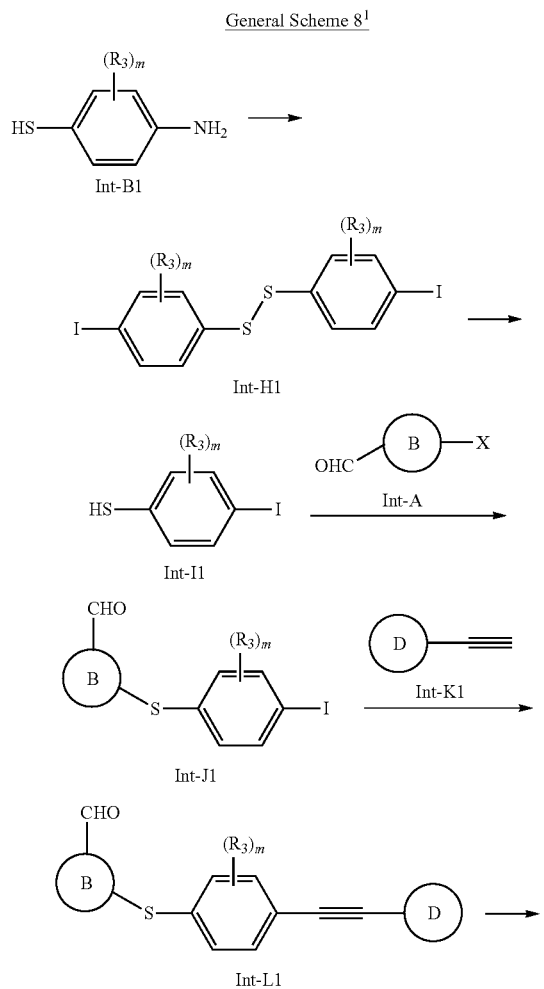

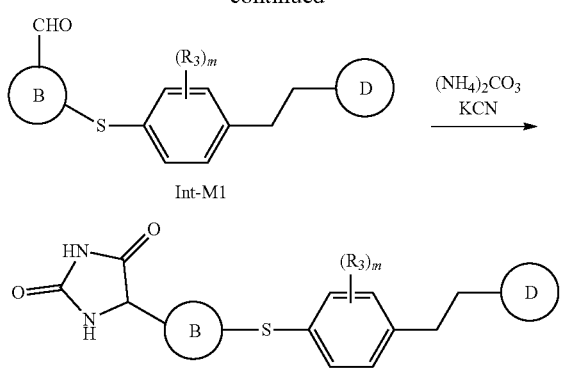

[1]X is halo; ring D is optionally substituted aryl or heteroaryl; $R_3$ is independently selected from hydrogen alkyl, and halo; m is an integer of 1 to 4; ring B is optionally substituted aryl or heteroaryl Hydrochloric acid (HCl), sulfuric acid ($H_2SO_4$) and $NaNO_2$ are successively added to a solution of Int-B1 at 0° C. and the mixture is stirred. Then, urea is added. After stirring for several minutes, a solution of KI in water is added dropwise and the mixture is stirred at 0° C. The mixture is extracted, the organic layer is dried and evaporated, and the residue purified by column chromatography to obtain Int-H1. A mixture of Int-H1 in alcohol is stirred at room temperature for several hours, then the mixture is concentrated under reduced pressure, extracted and purified by column chromatography to obtain Int-I1. Int-A and potassium carbonate are added to a solution of Int-I1 and the mixture is stirred at room temperature. Then, water is added and the mixture is extracted. The organic layer is dried and evaporated, and the residue purified by column chromatography to obtain Int-J1. To a solution of Int-J1 and Int-K1 in triethylamine is added palladium complex suitable for palladium-catalyzed coupling reactions and CuI under nitrogen atmosphere. The mixture is stirred at room temperature and then quenched with saturated ammonium chloride solution. The mixture is extracted, and the organic layer is washed, dried, and concentrated under reduced pressure to give Int-L1. Pd/C is added to a solution of Int-L1 in alcohol and the mixture is stirred under hydrogen atmosphere at room temperature. The mixture is filtered, and the filtrate is concentrated to give Int-M1. Int-M1 is then reacted with $(NH_4)_2CO_3$ and potassium cyanide (KCN) in aqueous alcohol overnight. The reaction mixture is evaporated to remove the solvent and then extracted. The organic layer is dried and evaporated, and the residue purified by column chromatography to obtain compounds according to embodiments of the application.

General Scheme 9[1]

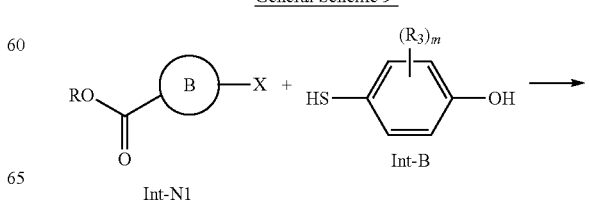

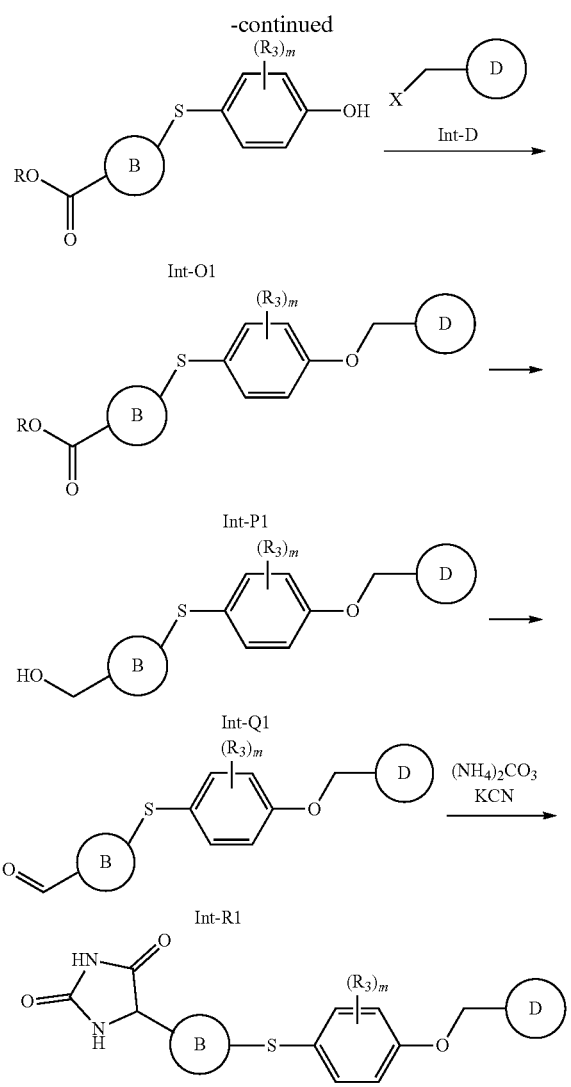

[1] X is halo; ring D is optionally substituted aryl or heteroaryl; $R_3$ is independently selected from hydrogen alkyl, and halo; m is an integer of 1 to 4; ring B is optionally substituted aryl or heteroaryl; R is alkyl To a solution of Int-N1, sodium hydroxide and Int-B are added and the mixture is stirred overnight. The reaction mixture is extracted, the organic layer is dried, and the residue purified by flash chromatography to give Int-O1. To a solution of Int-O1, potassium carbonate and Int-D are added and the mixture is stirred at room temperature. The mixture is extracted, the organic layer washed, dried, concentrated under reduced pressure, and the residue purified by column chromatography to give Int-P1. To a solution of Int-P1 in anhydrous solvent is added DIBAL-H at 0° C. The mixture is quenched, extracted, the organic layer washed, dried, concentrated under reduced pressure, and the residue purified by column chromatography to give Int-Q1. Int-Q1 is oxidized to give Int-$R_1$. Int-$R_1$ is then reacted with $(NH_4)_2CO_3$ and potassium cyanide (KCN) in aqueous alcohol overnight. The reaction mixture is evaporated to remove the solvent and then extracted. The organic layer is dried and evaporated, and the residue purified by column chromatography to obtain compounds according to embodiments of the application.

Nitrogen atoms of the hydantoin moiety of compounds of the application can be alkylated by reacting compounds prepared according to any one of the above General Schemes with sodium hydride and alkyl iodide (e.g., $CH_3I$). Compounds in which one of X, Y, and Z is S(O) or $SO_2$ can be prepared by reacting compounds prepared according to any one of the above General Schemes within m-CPBA.

Pharmaceutically acceptable salts of compounds of the application can be synthesized from the parent compound containing an acidic or basic moiety by conventional chemical methods. Generally, such salts can be prepared by reacting the free acid or base forms of these compounds with a stoichiometric amount of the appropriate acid or base in water or in an organic solvent, or in a mixture of the two. Examples of suitable organic solvents include, but are not limited to, ether, ethyl acetate, ethanol, isopropanol, or acetonitrile.

Compositions

Another aspect of the application relates to a pharmaceutical composition comprising a compound of the application as described herein, or a tautomer, stereoisomer, pharmaceutically acceptable salt, or solvate thereof.

Compositions of the application can also comprise a pharmaceutically acceptable carrier. A pharmaceutically acceptable carrier is non-toxic and should not interfere with the efficacy of the active ingredient. Pharmaceutically acceptable carriers can include one or more excipients such as binders, disintegrants, swelling agents, suspending agents, emulsifying agents, wetting agents, lubricants, flavorants, sweeteners, preservatives, dyes, solubilizers and coatings. The precise nature of the carrier or other material can depend on the route of administration, e.g., intramuscular, intradermal, subcutaneous, oral, intravenous, cutaneous, intramucosal (e.g., gut), intranasal or intraperitoneal routes. For liquid injectable preparations, for example, suspensions and solutions, suitable carriers and additives include water, glycols, oils, alcohols, preservatives, coloring agents and the like. For solid oral preparations, for example, powders, capsules, caplets, gelcaps and tablets, suitable carriers and additives include starches, sugars, diluents, granulating agents, lubricants, binders, disintegrating agents and the like. For nasal sprays/inhalant mixtures, the aqueous solution/suspension can comprise water, glycols, oils, emollients, stabilizers, wetting agents, preservatives, aromatics, flavors, and the like as suitable carriers and additives.

Compositions of the application can be formulated in any matter suitable for administration to a subject to facilitate administration and improve efficacy, including, but not limited to, oral (enteral) administration and parenteral injections. The parenteral injections include intravenous injection or infusion, subcutaneous injection, intradermal injection, and intramuscular injection. Compositions of the application can also be formulated for other routes of administration including transmucosal, ocular, rectal, long acting implantation, sublingual administration, under the tongue, from oral mucosa bypassing the portal circulation, inhalation, or intranasal.

In particular embodiments, compositions are formulated for oral administration.

Yet another aspect of the application relates to a method of preparing a pharmaceutical composition comprising combining a compound of the application or a tautomer, stereoisomer, pharmaceutically acceptable salt, or solvate thereof, with at least one pharmaceutically acceptable carrier. Pharmaceutical compositions can be prepared by any method known in the art in view of the present disclosure, and one of ordinary skill in the art will be familiar with such techniques used to prepare pharmaceutical compositions. For example, a pharmaceutical composition according to the application can be prepared by mixing a compound of the application with one or more pharmaceutically acceptable carriers according to conventional pharmaceutical compounding techniques, including but not limited to, conventional admixing, dissolving, granulating, emulsifying, encapsulating, entrapping or lyophilizing processes.

Methods of Use

The application also provides methods of inhibiting a matrix metalloproteinase (MMP), and treating diseases mediated by MMPs using the compounds of the application and pharmaceutical compositions of the application.

Matrix metalloproteinases (MMPs), also known as matrixins, are a group of enzymes that in concert are responsible for the degradation of most extracellular matrix proteins during organogenesis, growth and normal tissue turnover. MMPs are calcium-dependent zinc-containing endopeptidases, and belong to a larger family of proteases known as the metzincin superfamily. MMPs are capable of degrading extracellular matrix proteins, but can also process a number of bioactive molecules, and known to be involved in, e.g., cleavage of cell surface receptors, release of apoptotic ligands, and chemokine/cytokine inactivation. MMPs are also thought to play a major role in cell behaviors such as cell proliferation, migration (adhesion/dispersion), differentiation, angiogenesis, apoptosis, and host defense. The MMPs are inhibited by specific endogenous tissue inhibitor of metalloproteinases (TIMPs), which comprise a family of four protease inhibitors: TIMP-1, TIMP-2, TIMP-3, and TIMP-4. Examples of MMPs include, but are not limited to, MMP-1 (Interstitial collagenase), MMP-2 (gelatinase-A), MMP-3 (stromelysin 1), MMP-7 (matrilysin), MMP-8 (neutrophil collagenase), MMP-9 (gelatinase-B), MMP-10 (stromelysin 2), MMP-11 (stromelysin 3), MMP-12 (macrophage elastase), MMP-13 (collagenase 3), MMP-14 (MT1-MMP), etc.

In a preferred embodiment, compounds of the application are capable of inhibiting microphage elastase (MMP-12) and/or treating diseases mediated by MMP-12. MMP-12, also known as macrophage metalloelastase (MME) or macrophage elastase (ME), is encoded by the MMP12 gene in humans. In other embodiments, compounds of the application are capable of selectively inhibiting MMP-12. The terms "selective," "selectivity," and "selectively" when used with reference to binding or inhibiting the activity of a particular MMP, mean that a compound binds or inhibits the activity of a particular MMP to a greater extent than said compound binds or inhibits the activity of other MMPs. For example, a compound that has selectivity for MMP-12 inhibits the activity of MMP-12 to a greater extent than other MMPs, e.g., MMP-1, MMP-2, MMP-3, MMP-7, MMP-8, MMP-9, MMP-10, MMP-13, MMP-14, etc.

According to embodiments of the application, a compound that is selective for MMP-12 inhibits the activity of MMP-12 by at least about 10-fold, 100-fold, or 1000-fold greater than one or more other MMPs, and preferably inhibits the activity of MMP-12 by at least about 1000-fold greater than at least one other MMP, such as MMP-1 or MMP-7.

The application also provides methods of treating a disease mediated by MMP-12. According to embodiments of the invention, a method of treating a disease mediated by MMP-12 comprises administering to the subject a therapeutically effective amount of a compound of the application or a tautomer, stereoisomer, pharmaceutically acceptable salt, or solvate thereof, or a pharmaceutical composition of the application.

As used herein, the terms "treat," "treating," and "treatment" are all intended to refer to an amelioration or reversal of at least one measurable physical parameter related to a disease mediated by MMP-12, which is not necessarily discernible in the subject, but can be discernible in the subject. The terms "treat," "treating," and "treatment," can also refer to causing regression, preventing the progression, or at least slowing down the progression of a disease mediated by MMP-12. In a particular embodiment, "treat," "treating," and "treatment" refer to an alleviation, prevention of the development or onset, or reduction in the duration of one or more symptoms associated with a disease mediated by MMP-12. In a particular embodiment, "treat," "treating," and "treatment" refer to prevention of the recurrence of a disease mediated by MMP-12. In a particular embodiment, "treat," "treating," and "treatment" refer to an increase in the survival of a subject having a disease mediated by MMP-12. In a particular embodiment, "treat," "treating," and "treatment" refer to elimination of a disease mediated by MMP-12 in the subject.

As used herein, "a therapeutically effective amount" means an amount of a composition or compound that elicits a biological or medicinal response in a tissue system or subject that is being sought by a researcher, veterinarian, medical doctor or other conditions, which can include alleviation of the symptoms of the disease or disorder being treated. A therapeutically effective amount can vary depending upon a variety of factors, such as the physical condition of the subject, age, weight, health, etc.; and the particular disease to be treated. A therapeutically effective amount can readily be determined by one of ordinary skill in the art in view of the present disclosure.

In particular embodiments of the application, a therapeutically effective amount refers to the amount of a composition or compound of the application which is sufficient to inhibit MMP-12 or treat a disease mediated by MMP-12. Diseases mediated by MMP-12 that can be treated according to the methods of the application include, but are not limited to, asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

EMBODIMENTS

Embodiment 1 is a compound of formula (I-b):

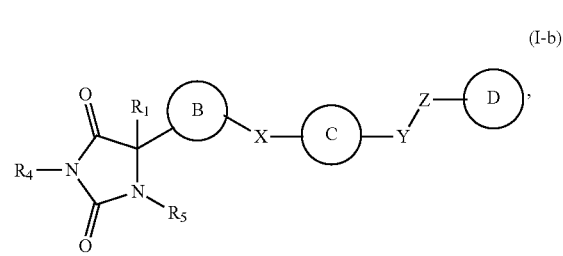

or a tautomer, stereoisomer, pharmaceutically acceptable salt, or solvate thereof, wherein:
ring B is an optionally substituted aryl or optionally substituted heteroaryl;
ring C is an optionally substituted aryl or optionally substituted heteoraryl;
ring D is an optionally substituted aryl or optionally substituted heteroaryl;
each of X, Y and Z is independently selected from the group consisting of $CH_2$, O, $NR_x$ and $S(O)_q$, wherein $R_x$ is hydrogen or alkyl;
$R_1$ is hydrogen or alkyl;
$R_4$ is hydrogen or alkyl;
$R_5$ is hydrogen; and
q is 0, 1, or 2,
provided that ring B is not furanyl.

Embodiment 2 is a compound of formula (I):

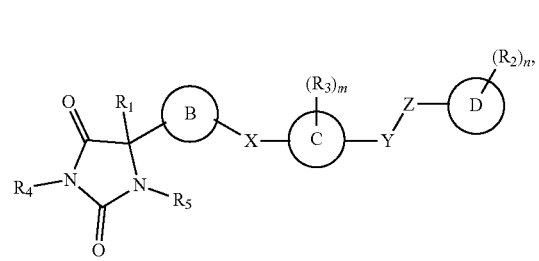

(I)

or a tautomer, stereoisomer, pharmaceutically acceptable salt, or solvate thereof,
wherein:
ring B is an optionally substituted aryl or optionally substituted heteroaryl;
ring C is aryl or heteroaryl;
ring D is aryl or heteroaryl;
each of X, Y, and Z is independently selected from the group consisting of O, $CH_2$, $NR_x$, and $S(O)_q$, wherein $R_x$, is hydrogen or alkyl;
$R_1$ is hydrogen or alkyl;
each $R_2$ is independently selected from the group consisting of hydrogen, alkyl, halogen, hydroxyl, haloalkyl, alkoxy, alkylthio, amine, amide, alkylamine, aminoalkyl, cyano, hydroxyalkyl, —$(CH_2)_pC(O)OR_6$, and —$(CH_2)_pOC(O)R_6$;
each $R_3$ is independently selected from the group consisting of hydrogen, alkyl and halogen;
$R_4$ is hydrogen or alkyl;
$R_5$ is hydrogen;
each $R_6$ is independently selected from the group consisting of hydrogen and alkyl, wherein the alkyl is unsubstituted or substituted with one or more groups independently selected from the group consisting of amine, hydroxyl, halogen, and alkoxy;
m is 1, 2, 3, or 4;
n is 1, 2, 3, 4, or 5;
p is 0, 1, 2, 3, 4, or 5; and
q is 0, 1, or 2
provided that ring B is not furanyl.

Embodiment 3 is the compound of embodiment 1 or embodiment 2, wherein ring B is a five or six membered monocyclic heteroaryl having 1-2 heteroatoms independently selected from N, S, and O.

Embodiment 4 is the compound of any one of embodiments 1-3, wherein ring B is pyridinyl, thiophenyl, imidazolyl, pyrazolyl, or oxazolyl.

Embodiment 5 is the compound of embodiment 4, wherein ring B is pyridinyl.

Embodiment 6 is the compound of embodiment 5, wherein the compound is a compound of formula (II):

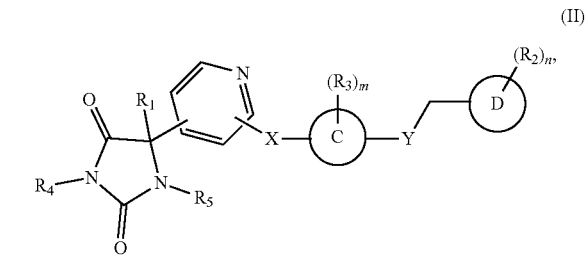

(II)

or a tautomer, stereoisomer, pharmaceutically acceptable salt, or solvate thereof,
wherein each of the variables is as defined in the compound of formula (I).

Embodiment 7 is the compound of embodiment 5, wherein the compound is a compound of formula (II-a), (II-b), (II-c), or (II-d):

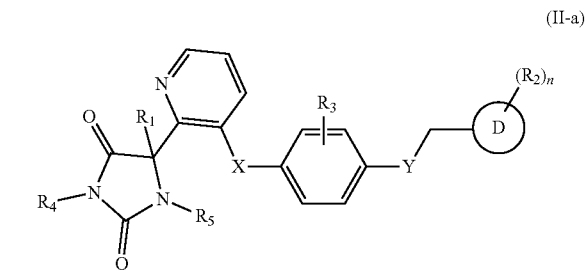

(II-a)

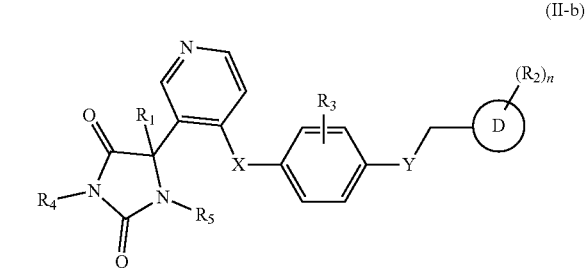

(II-b)

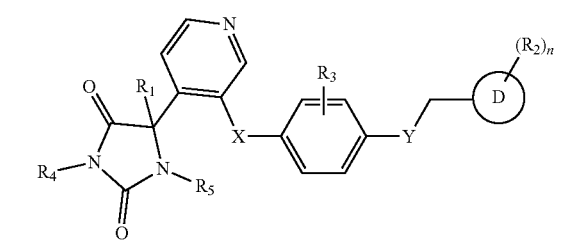

(II-c)

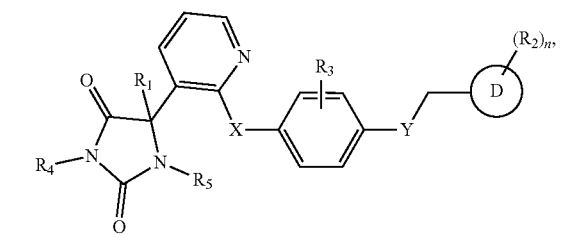

(II-d)

or a tautomer, stereoisomer, pharmaceutically acceptable salt, or solvate thereof, wherein each of the variables is as defined in the compound of formula (I).

Embodiment 8 is the compound of embodiment 4, wherein ring B is thiophenyl.

Embodiment 9 is the compound of embodiment 8, wherein the compound is a compound of formula (IV):

(IV)

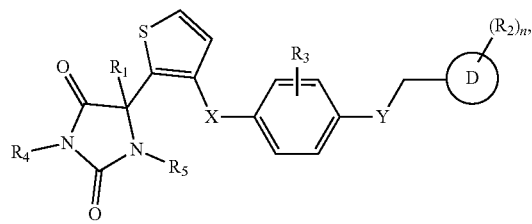

or a tautomer, stereoisomer, pharmaceutically acceptable salt, or solvate thereof, wherein each of the variables is as defined in the compound of formula (I).

Embodiment 10 is the compound of embodiment 4, wherein ring B is imidazolyl.

Embodiment 11 is the compound of embodiment 10, wherein the compound is a compound of formula (Va) or (Vb):

(Va)

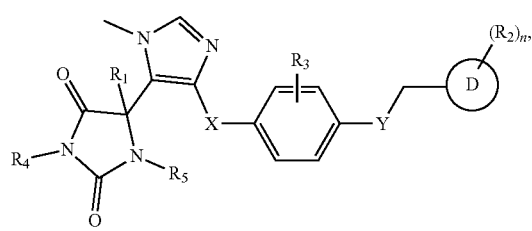

(Vb)

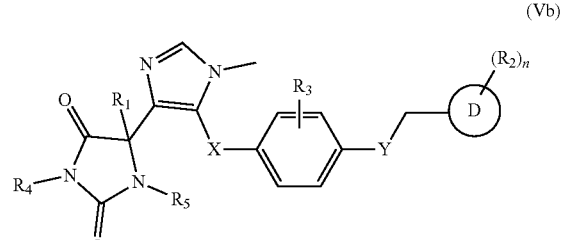

or a tautomer, stereoisomer, pharmaceutically acceptable salt, or solvate thereof, wherein each of the variables is as defined in the compound of formula (I).

Embodiment 12 is the compound of embodiment 4, wherein ring B is pyrazolyl.

Embodiment 13 is the compound of embodiment 12, wherein the compound is a compound of formula (VI):

(VI)

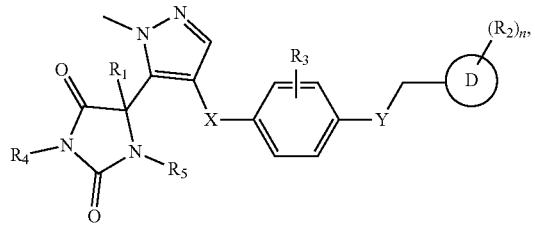

or a tautomer, stereoisomer, pharmaceutically acceptable salt, or solvate thereof, wherein each of the variables is as defined in the compound of formula (I).

Embodiment 14 is the compound of embodiment 4, wherein ring B is oxazolyl.

Embodiment 15 is the compound of embodiment 14, wherein the compound is a compound of formula (VII):

(VII)

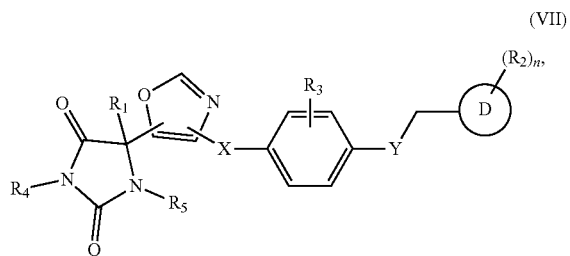

or a tautomer, stereoisomer, pharmaceutically acceptable salt, or solvate thereof, wherein each of the variables is as defined in the compound of formula (I).

Embodiment 16 is the compound of embodiment 15, wherein the compound is a compound of formula (VII-a) or (VII-b):

(VII-a)

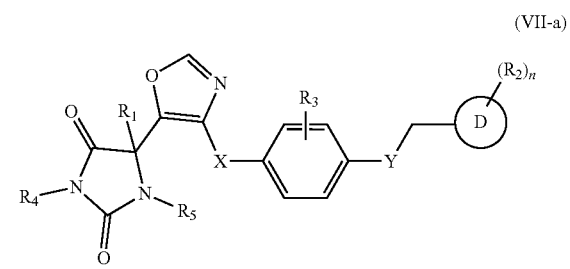

(VII-b)

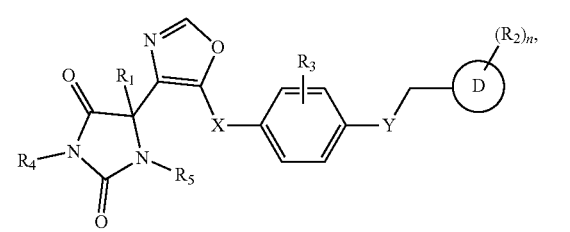

or a tautomer, stereoisomer, pharmaceutically acceptable salt, or solvate thereof, wherein each of the variables is as defined in the compound of formula (I).

Embodiment 17 is the compound of any one of embodiments 1 to 6, wherein ring C is phenyl.

Embodiment 18 is the compound of any one of embodiments 1 to 6, wherein ring C is pyridinyl.

Embodiment 19 is the compound of any one of embodiments 2 to 18, wherein $R_3$ is selected from the group consisting of hydrogen, methyl, fluoro, and chloro.

Embodiment 20 is the compound of any one of embodiments 1 to 19, wherein ring D is pyridinyl or phenyl.

Embodiment 21 is the compound of any one of embodiments 2 to 20, wherein $R_2$ is selected from the group consisting of methyl, —$CH_2OH$, hydroxyl, —OC(O)CH($NH_2$)CH($CH_3$)$_2$, —COOH, —$CH_2OC(O)CH(NH_2)CH(CH_3)_2$, —C(O)$NH_2$, —C(O)NH($CH_3$), and $C_{1-4}$alkoxy.

Embodiment 22 is the compound of any one of embodiments 1 to 21, wherein ring D is:

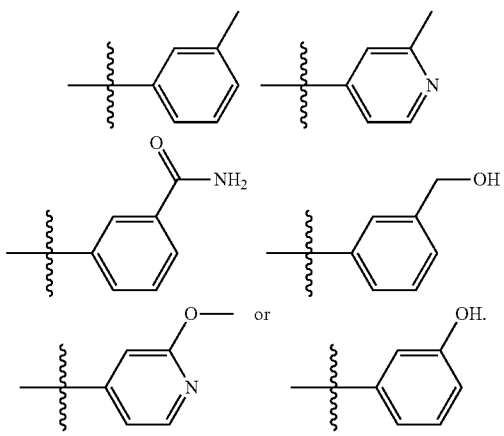

Embodiment 23 is the compound of any one of embodiments 1 to 22, wherein $R_4$ is hydrogen.

Embodiment 24 is the compound of any one of embodiments 1 to 22, wherein $R_4$ is alkyl.

Embodiment 25 is the compound of embodiment 24, wherein $R_4$ is methyl.

Embodiment 26 is the compound of any one of embodiments 1 to 25, wherein $R_5$ is methyl.

Embodiment 27 is the compound of any one of embodiments 1 to 25, wherein $R_5$ is hydrogen.

Embodiment 28 is the compound of any one of embodiments 1 to 27, wherein $R_1$ is a $C_{1-4}$ alkyl.

Embodiment 29 is the compound of embodiment 28, wherein $R_1$ is methyl or ethyl.

Embodiment 30 is the compound of any one of embodiments 1 to 27, wherein $R_1$ is hydrogen.

Embodiment 31 is the compound of any one of embodiments 1 to 30, wherein X is S, Y is O, and Z is $CH_2$.

Embodiment 32 is a compound of formula (I-a):

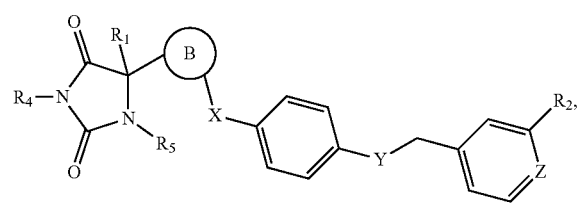

(I-a)

or a tautomer, stereoisomer, pharmaceutically acceptable salt, or solvate thereof, wherein:
  ring B is 5- or -6-membered heteroaryl;
  Z is CH or N;
  each of $R_1$ and $R_4$ is alkyl or hydrogen;
  $R_5$ is hydrogen;
  $R_2$ is selected from the group consisting of alkyl, amide, hydroxyl, alkoxy, and hydroxylalkyl; and
  X and Y are each independently selected from S and O.

Embodiment 33 is the compound of embodiment 32, wherein ring B is pyridinyl, thiophenyl, imidazolyl, pyrazolyl, or oxazolyl.

Embodiment 34 is the compound of embodiment 32 or embodiment 33, wherein $R_1$ is hydrogen.

Embodiment 35 is the compound of embodiment 32 or embodiment 33, wherein $R_1$ is $C_{1-4}$ alkyl.

Embodiment 36 is the compound of embodiment 35, wherein $R_1$ is methyl or ethyl.

Embodiment 37 is the compound of any one of embodiments 32 to 36, wherein $R_4$ is hydrogen.

Embodiment 38 is a pharmaceutical composition comprising the compound of any one of embodiments 1-37, and at least one pharmaceutically acceptable carrier.

Embodiment 39 is a method of inhibiting macrophage elastase (MMP-12) in a subject in need thereof, the method comprising administering to the subject the pharmaceutical composition of embodiment 38.

Embodiment 40 is a method of treating a disease mediated by macrophage elastase (MMP-12) in a subject in need thereof, the method comprising administering to the subject the pharmaceutical composition of embodiment 38.

Embodiment 41 is the method of embodiment 40, wherein the disease is selected from the group consisting of asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

Embodiment 42 is the compound of any one of embodiments 1-37, or the pharmaceutical composition of embodiment 38 for use in inhibiting macrophage elastase (MMP-12).

Embodiment 43 is the compound of any one of embodiments 1-37, or the pharmaceutical composition of embodiment 38 for use treating a disease mediated by macrophage elastase (MMP-12).

Embodiment 44 is the compound or composition for use of embodiment 43, wherein the disease is selected from the group consisting of asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

Embodiment 45 is use of the compound of any one of embodiments 1-37, or the pharmaceutical composition of embodiment 38 in the manufacture of a medicament for inhibiting macrophage elastase (MMP-12).

Embodiment 46 is use of the compound of any one of embodiments 1-37, or the pharmaceutical composition of embodiment 38 in the manufacture of a medicament for treating a disease mediated by macrophage elastase (MMP-12).

Embodiment 47 is use of embodiment 46, wherein wherein the disease is selected from the group consisting of asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

Embodiment 48 is a method of preparing the pharmaceutical composition of embodiment 38, comprising combining the compound or a pharmaceutically acceptable salt thereof with at least one pharmaceutically acceptable carrier.

EXAMPLES

The following examples of the application are to further illustrate the nature of the application. It should be understood that the following examples do not limit the application and the scope of the application is to be determined by the appended claims.

Methods of Synthesis

Unless indicated otherwise, the abbreviations for chemical reagents and synthesis conditions have their ordinary meaning known in the art as follows:

"LDA" refers to lithium diisopropyl amide;
"EA" refers to ethyl acetate;
"PE" refers to petroleum ether;
"r.t." and "rt" refer to room temperature;
"THF" refers to tetrahydrofuran;
"DEAD" refers to diethyl azodicarboxylate;
"TBAB" refers to tetrabutylammonium bromide;
"DCM" refers to dichloromethane;
"HOBT" refers to hydroxybenzotriazole;
"LAH" refers to lithium aluminum hydride;
"TLC" refers to thin layer chromatography;
"Prep-TLC" refers to preparatory thin layer chromatography;
"TMS-I" refers to trimethylsilyl iodide;
"Hex" refers to hexanes;
"DMF" refers to dimethylformamide;
"h" refers to hours;
"EDCI" refers to 1-Ethyl-3-(3-dimethylaminopropyl)carbodiimide;
"DMAP" refers to 4-Dimethylaminopyridine;
"Prep-HPLC" refers to preparative high performance liquid chromatography;
"DHP" refers to dihydropyran;
"DPPF" refers to 1,1'-Bis(diphenylphosphino)ferrocene; and
"DIEA" refers to diisopropylethylamine.

Preparation of Key Intermediate TI-1 for the Synthesis of Compounds TC-1, TC-2, TC-3, TC-4, TC-5, TC-6, TC-7 and TC-8.

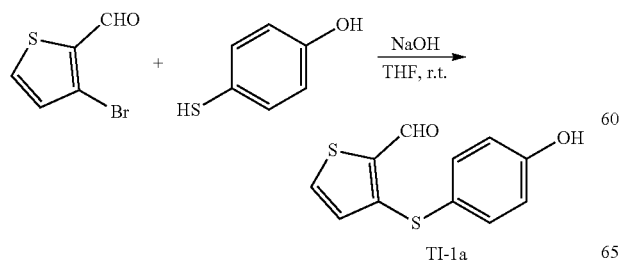

To a solution of 3-bromothiophene-2-carbaldehyde (10 g, 52.5 mmol) and 4-mercaptophenol (6.3 g, 50 mmol) in THF (255 mL) was added NaOH (0.06 g, 1.5 mmol). The reaction mixture was stirred overnight at rt. The residue was added with water and EA, and extracted with EA twice. The combined organic layer was dried with MgSO₄, and evaporated under high vacuum to give a yellow solid. The residue was purified by flash chromatography with DCM/MeOH (DCM/MeOH=1:50) to give TI-1a as a light yellow solid (9.2 g, 75%).

Synthesis of Compounds TC-1, TC-2, TC-3, TC-4, TC-5, and TC-6:

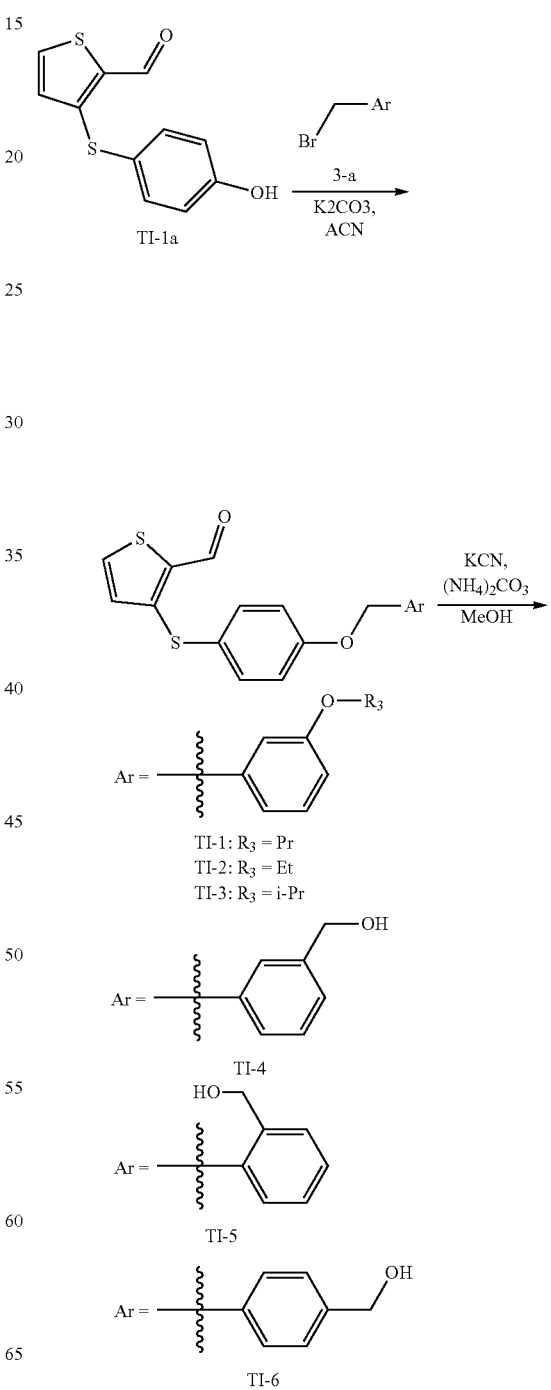

-continued

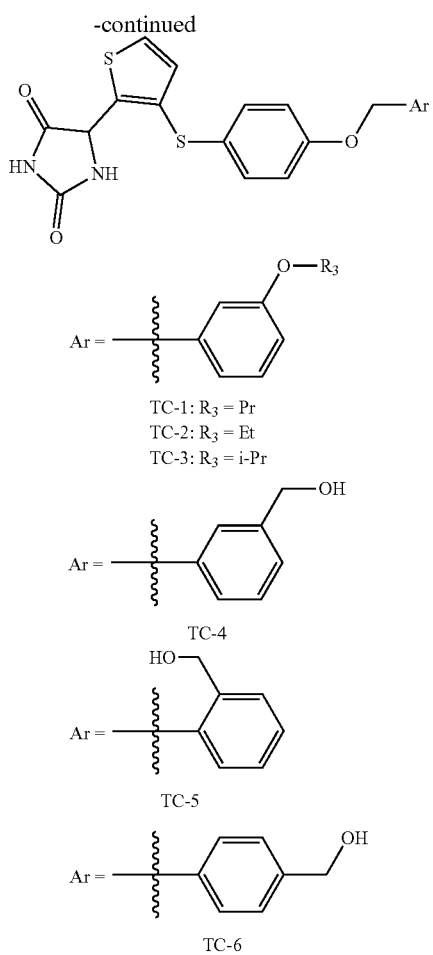

TC-1: R₃ = Pr
TC-2: R₃ = Et
TC-3: R₃ = i-Pr

TC-4

TC-5

TC-6

A solution of 3-a (0.2 g, 1.65 mmol), TI-1a (0.40 g, 1.7 mmol), and K₂CO₃ (0.7 g) in ACN was stirred at r.t. overnight. The reaction was monitored by TLC (EA/Hex=2/7), to determine when the benzyl bromide spot was disappeared. The reaction mixture was added with EA and water, and extracted EA twice. The combined organic layer was dried with MgSO₄. The residue was purified by flash chromatography with EA/Hexane (EA/Hexane=1:3) to give intermediate TI-1 as a light yellow solid (0.41 g, 55%). Intermediates TI-2, TI-3, TI-4, TI-5 and TI-6 were synthesized according to the same procedure except that the starting material 3-12 was replaced with 344, 345, 346 or 347, accordingly.

To a solution of TM (0.42 g, 1.18 mmol) in EtOH/H₂O (10 mL/5 mL) was added (NH₄)₂CO₃ (1.71 g, 17.8 mmol) and KCN (0.15 g, 0.98 mmol). The reaction mixture was stirred at r.t. overnight. The solution was evaporated to remove most of the solvent. The mixture was added with water and then extracted with EA twice. The organic layers were combined, dried with MgSO₄ and evaporated. The residue was purified by flash chromatography with EA/Hexane (EA/Hexane=1:1) to give TC-1 as a light yellow solid (0.28 g, 38%). Compounds TI-2, TI-3, TI-4, TI-5 and TI-6 were synthesized using the same procedure except that intermediate TI-1 was replaced with intermediates TI-2, TI-3, TI-4, TI-5 or TI-6, accordingly.

Preparation of Compound TC-7:

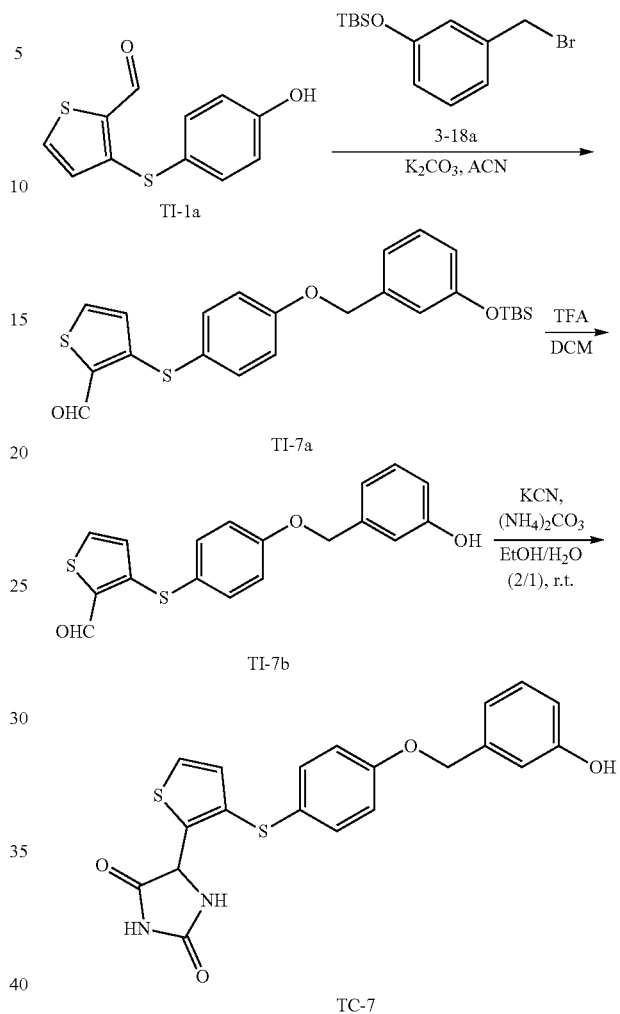

A solution of 3-18a (0.23 g, 0.76 mmol), TI-1a (0.15 g, 0.64 mmol), and K₂CO₃ (0.35 g, 2.56 mmol) in ACN (4 mL) was stirred at r.t. overnight. The reaction mixture was added with water and EA, and extracted with EA twice. The combined organic layer was dried with MgSO₄, and evaporated under high vacuum. The residue was purified by flash chromatography with EA/Hex (EA/Hex=1:10 to 1:4) to yield TI-7a as a yellow solid (0.17 g, 50%)

To a solution of TI-7a (1.03 g) in DCM (25 mL) was added TFA (1 mL) dropwise at r.t. The reaction mixture was stirred overnight, then the solvent and TFA were removed to obtain a brown oil. The brown oil was added with NaHCO₃ and MeOH. Then the solvent was removed again. The residue was purified by flash chromatography with EA/Hex (EA/Hex=1:4) to yield TI-7b as a white solid (0.14 g).

To a solution of TI-1b (0.14 g, 0.41 mmol) in EtOH/H₂O (5 mL/2.5 mL) was added (NH₄)₂CO₃ (0.24 g, 2.46 mmol) and KCN (32 mg, 0.41 mmol). The reaction mixture was stirred at r.t. overnight. The solution was evaporated to remove most of the solvent. The mixture was added with water and EA, and then extracted with EA twice. The organic layers were combined, dried with MgSO₄ and evaporated under high vacuum. The residue was purified by flash chromatography with DCM/MeOH (DCM/MeOH=20:1) to yield TC-7 as an oily compound (51 mg).

Preparation of Compound TC-8:

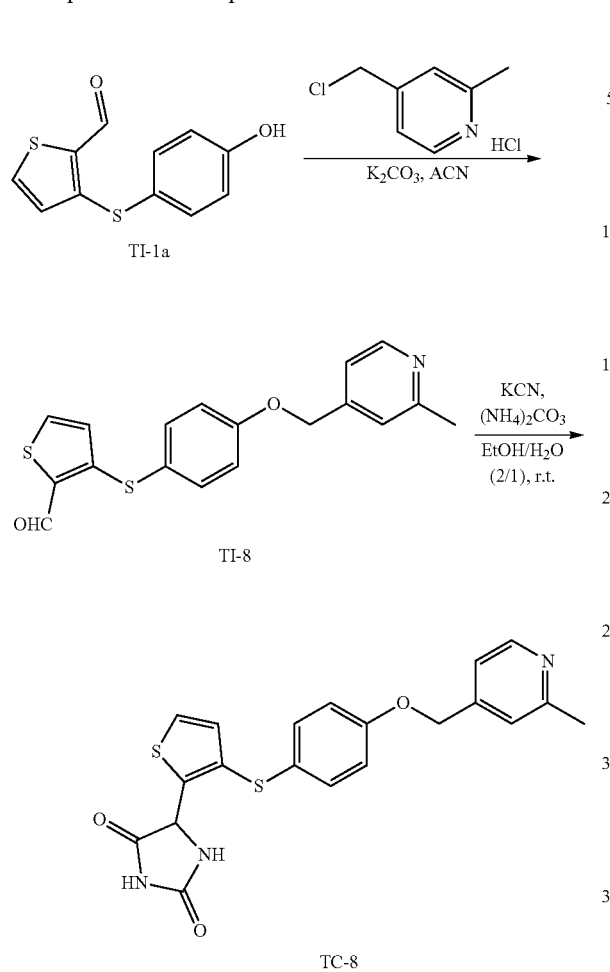

A solution of TI-1a (0.9 g, 3.81 mmol, 1 eq.), 4-Chloromethyl-2-methylpyridine (mg, 1.19 mmol, 1 eq.), and $K_2CO_3$ (1.58 g, 3 eq.) in 70 ml of ACN was stirred and heated to 50° C. The mixture was monitored by TLC. The solvent was removed by rotary evaporator. The residue was added with EA and water, and the water layer was quenched with EA two times. The crude product was purified with silica gel (DCM/EA=1/4) to yield TI-8 as a pale-yellow solid (1.02 g, 76%).

To a solution of TI-8 (200 mg, 0.4 mmol, 1 eq.), KCN (0.057 mg, 1.5 eq.) and ammonium carbonate (0.844 g, 15 eq.) in 10 ml of EtOH/D.I. water (2/1) was added to the mixture. The mixture was monitored by TLC. The solvent was removed by rotary evaporator. The residue was added with EA and water, and the water layer was quenched with EA two times. The crude product was purified on silica gel (DCM/MeOH=30/2) to yield TC-8 as a yellow solid (45 mg, 18%).

General Scheme: Preparation of Intermediate 4a-1

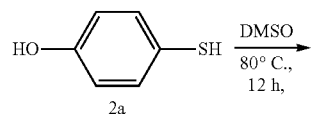

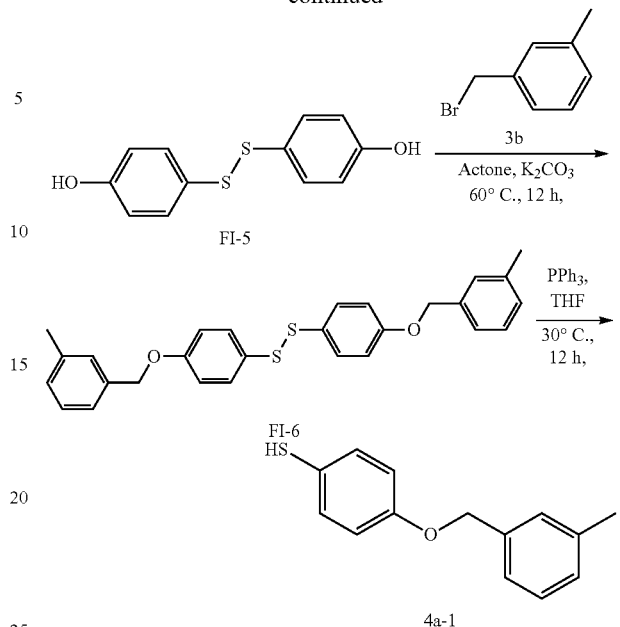

Synthesis of Intermediate FI-5:
A mixture of compound 2a (68 g, 538.9 mmol, 1.0 eq) in DMSO (500 mL) was stirred at 80° C. overnight under nitrogen atmosphere. Then the mixture was diluted with $H_2O$ (1000 mL) and extracted with ethyl acetate. The organic layer was washed with brine, dried over $Na_2SO_4$, filtered and concentrated to give compound FI-5 (67 g, 99%).

Synthesis of Intermediate FI-6:
A mixture of compound FI-5 (5 g, 19.97 mmol, 1.0 eq), compound 3b (7.39 g, 39.95 mmol, 2 eq) and $K_2CO_3$ (11.04 g, 79.89 mmol, 4.0 eq) in acetone (100 mL) was stirred at 60° C. for 4 h under nitrogen atmosphere. Then the mixture was diluted with $H_2O$ (1000 mL) and extracted with ethyl acetate. The organic layer was washed with brine, dried over $Na_2SO_4$, filtered and concentrated. The residue was purified by column chromatography on a silica gel (PE/EA, 10:1) to give compound FI-6 (8.7 g, 97%).

Synthesis of Compound 4a-1:
To a mixture of compound FI-6 (10.7 g, 23.33 mmol, 1.0 eq) in THF (100 mL) was added $PPh_3$ (6.11 g, 23.33 mmol, 1 eq), TBAB (15.04 g, 46.66 mmol, 2 eq) and 5% HCl (5 mL). The mixture was stirred at rt for 12 h under nitrogen atmosphere. Then the mixture was concentrated. The residue was purified by column chromatography on a silica gel (PE/EA, 2:1) to give compound 4a-1 (6.6 g, 56%).

Preparation of Compound PC-1:

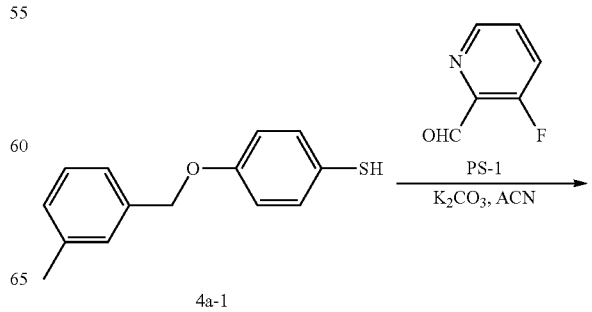

85

-continued

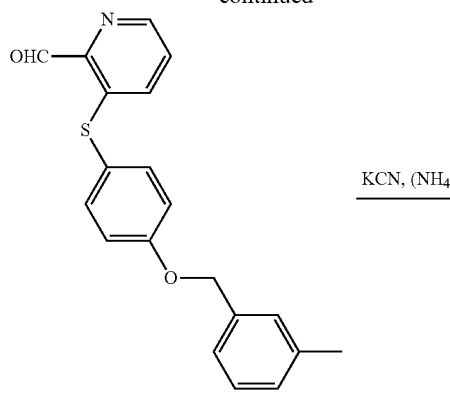

PI-1

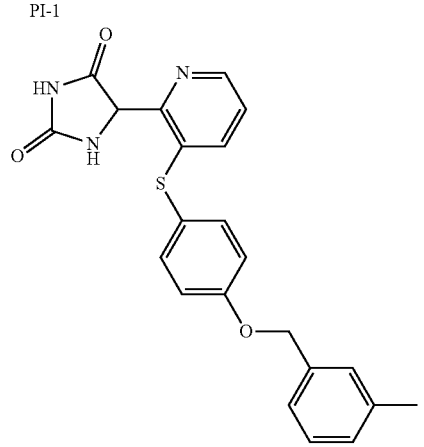

PC-1

To a mixture of compound 4a-1 (0.5 g, 2.17 mmol, 1.0 eq) in ACN (15 mL) was added compound 2-chloronicotinaldehyde (0.307 g, 2.17 mmol, 1.0 eq) and K₂CO₃ (0.906 g, 6.52 mmol, 3.0 eq). The mixture was stirred at 85° C. overnight under nitrogen atmosphere. Then the mixture was concentrated under vacuum. The residue was purified by Prep-TLC to give compound PI-1 (500 mg, 69%).

To a mixture of compound PI-1 (450 mg, 1.34 mmol, 1.0 eq) in MeOH (30 mL) was added KCN (174 mg, 2.68 mmol, 2.0 eq) and (NH₄)₂CO₃ (516 mg, 5.3 mmol, 4.0 eq). The mixture was stirred at 40° C. overnight under nitrogen atmosphere. Then the mixture was concentrated in vacuum. The residue was purified by Prep-TLC to give compound PC-1 (44 mg, 10%).

Preparation of Compounds PC-2, PC-3 and PC-4:

86

-continued

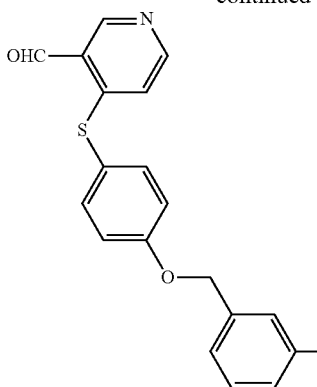

PI-2

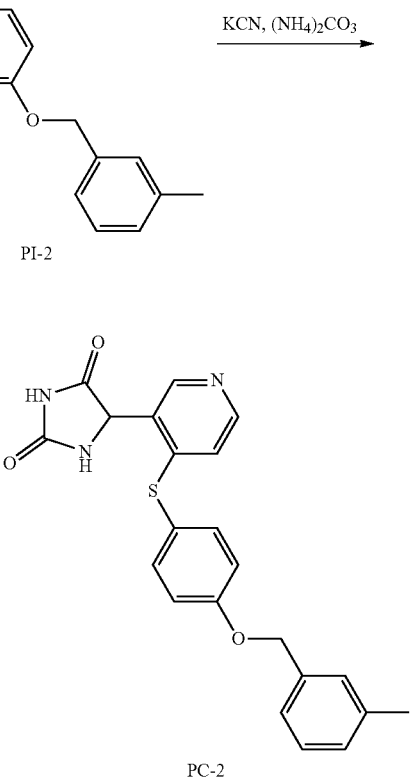

PC-2

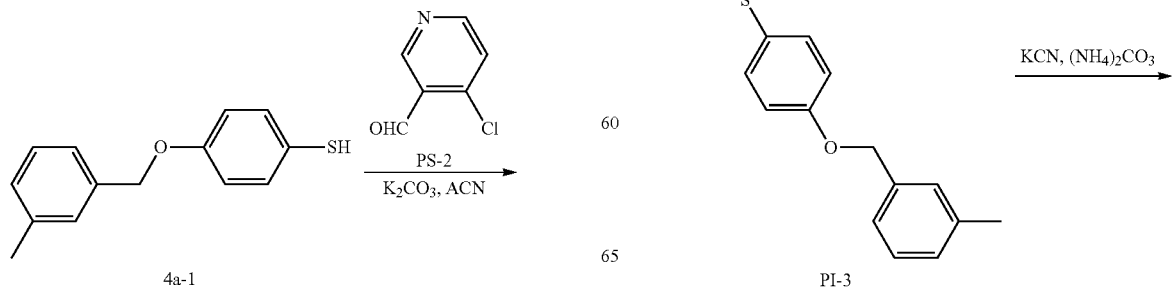

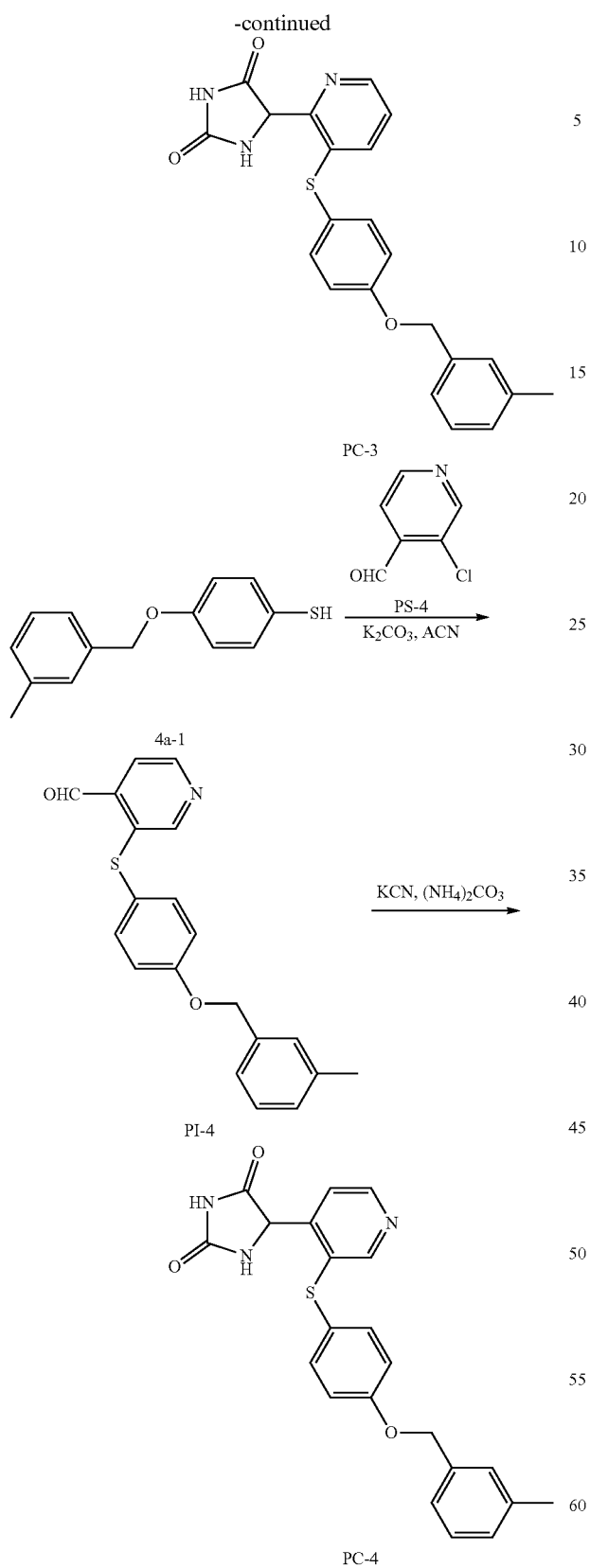

replaced with 4-chloro-nicotinaldehyde PS-2, 3-fluoropicolinaldehyde PS-3, or 3-chloro isonicotinaldehyde PS-4, accordingly.

Preparation of Key Intermediate PI-a.1

To a mixture of 4-chloronicotinaldehyde (2.2 g, 15.54 mmol, 1.0 eq) and 4-mercaptophenol (2.94 g, 23.31 mmol, 1.5 eq) in THF (20 mL) was added NaH (1.24 g, 31.08 mmol, 2.0 eq) at 0° C. and the mixture was stirred at rt overnight under nitrogen atmosphere. Then the mixture was concentrated to half solvent and then 2.0 N HCl was added to adjust the pH=6, and filtered to give compound PI-a.1 (950 mg, 26%), which was used in the next step without further purification.

Preparation of Compounds PC-7, PC-8 and PC-9:

Compounds PC-2, PC-3, and PC-4 were synthesized using the same procedure as the synthesis of PC-1 except that the starting material 2-chloronicotinaldehyde PS-1 was

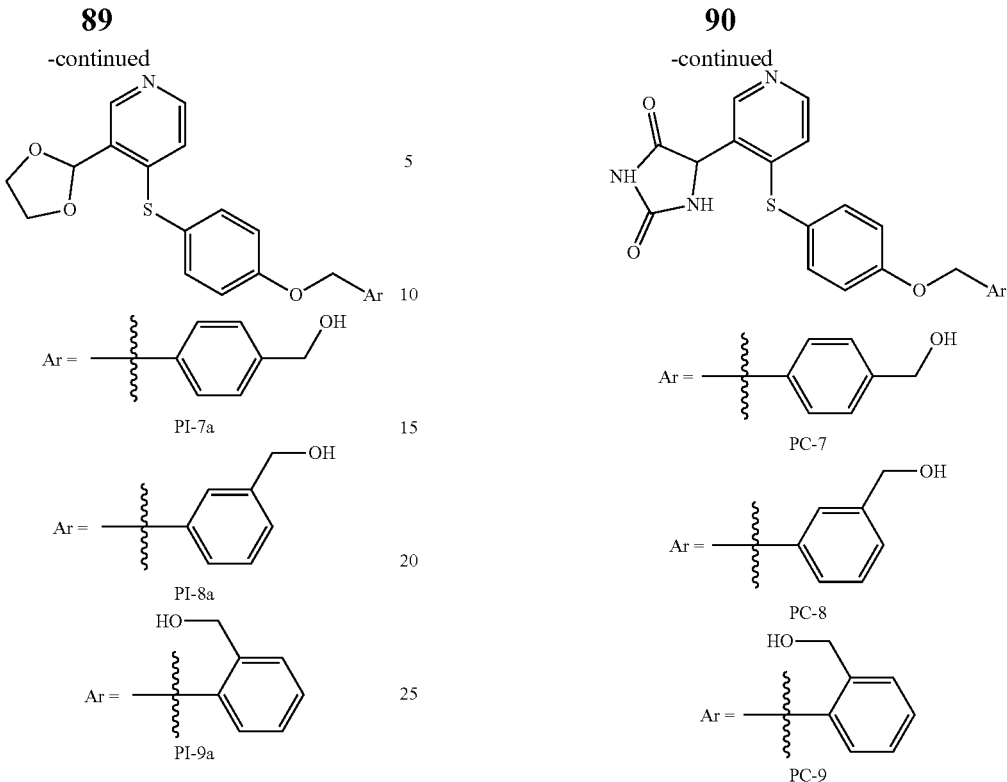

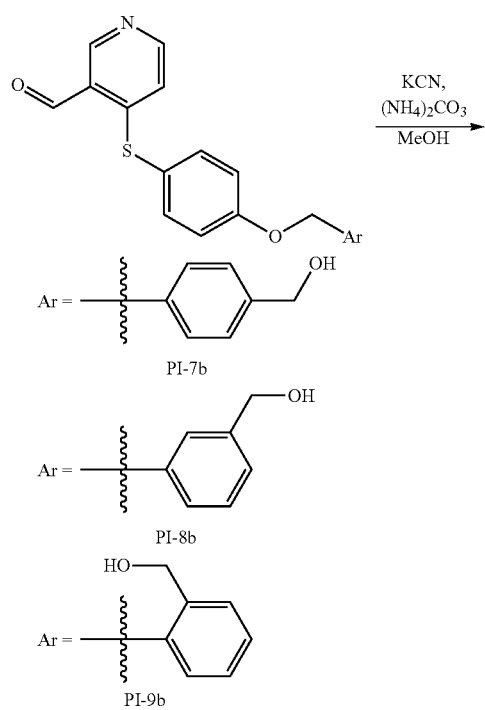

To a mixture of compound PI-a.1 (3.0 g, 12.99 mmol, 1.0 eq) in toluene (100 mL) was successively added ethane-1,2-diol (1.6 g, 260 mmol, 20 eq) and TsOH (0.112 g, 0.65 mmol, 0.05 eq). The mixture was heated under reflux for 12 h under nitrogen atmosphere. Then the mixture was concentrated under reduced pressure. The residue was purified by column chromatography on silica gel (PE/EA, 2:1) to give compound PI-b.1 (2.9 g, 82%).

To a solution of compound PI-b.1 (200 mg, 0.727 mmol, 1.0 eq) in THF (10 mL) was successively added 1,4-phenylenedimethanol (50 mg, 3.64 mmol, 5.0 eq), PPh₃ (381 mg, 1.454 mmol, 2.0 eq) and DEAD (253 mg, 1.454 mmol, 2.0 eq) at 0° C. The mixture was allowed to warm to room temperature and stirred for 16 h. Then the mixture was quenched with H₂O (10 mL) and extracted with ethyl acetate (2×10 mL). The combined organic layers were dried over anhydrous Na₂SO₄ and concentrated under reduced pressure. The residue was purified by column chromatography on silica gel to give compound PI-7a (200 mg, 70%).

A mixture of compound PI-7a (140 mg, 0.354 mmol, 1.0 eq) in HCl/THF (2.0 M, 3 mL/3 mL) was stirred at 70° C. for 3 h. The reaction mixture was cooled to room temperature and concentrated under reduced pressure. The residue was added with saturated NaHCO₃ solution to adjust the pH=8 and extracted with ethyl acetate. The organic layer was washed with brine, dried over anhydrous Na₂SO₄ and concentrated under reduced pressure to give compound PI-7b (130 mg, 100%), which was used in the next step without further purification.

To a mixture of compound PI-7b (150 mg, 0.427 mmol, 1.0 eq) in MeOH (5 mL) was added KCN (55 mg, 0.854 mmol, 2.0 eq) and (NH₄)₂CO₃ (164 mg, 1.71 mmol, 4.0 eq). The mixture was stirred at room temperature for 12 h. Then the mixture was diluted with water and extracted with ethyl acetate. The organic phase was dried over anhydrous Na₂SO₄ and concentrated under reduced pressure. The residue was purified by Prep-TLC to give compound PC-7 (38 mg, 21%) as a white solid.

Compounds PC-8 and PC-9 were synthesized by the same procedure except that 1,4-phenylenedimethanol was replaced with 1,3-phenylenedimethanol or 1,2-phenylenedimethanol accordingly.

Preparation of Compound PC-10:

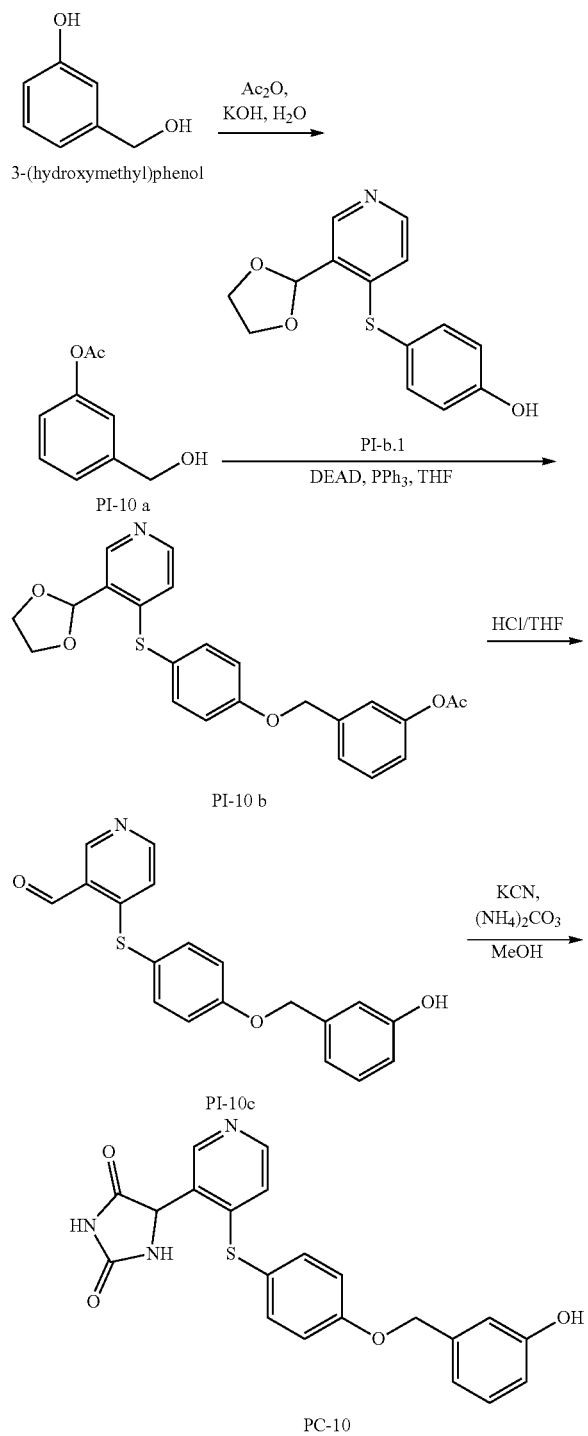

A mixture of 3-(hydroxymethyl)phenol (180 mL, 1.9 mol, 4.0 eq) in Ac$_2$O (360 mL, 9.54 mol, 21.2 eq) was stirred at 60° C. for 1 h under nitrogen atmosphere. The reaction mixture was cooled to room temperature, then KOH (42.3 g, 0.45 mol, 1.0 eq) was added. Then the mixture was stirred at room temperature for 16 h. After the mixture was extracted with EA (3×150 mL) and water, the combined organic layers were washed with H$_2$O (3×100 mL) and saturated NaHCO$_3$ solution (2×100 mL), dried over Na$_2$SO$_4$ and concentrated under reduced pressure to give compound PI-10a (60 g, 26%).

To a solution of compound PI-b.1 (300 mg, 1.09 mmol, 1.0 eq) in THF (10 mL) was successively added compound PI-10a (905 mg, 5.45 mmol, 5.0 eq), PPh$_3$ (572 mg, 2.18 mmol, 2.0 eq) and DEAD (380 mg, 2.18 mmol, 2.0 eq) at 0° C. The mixture was allowed to warm to room temperature and stirred for 16 h. Then the mixture was quenched with H$_2$O (10 mL) and extracted with ethyl acetate (2×10 mL). The combined organic layers were dried over anhydrous Na$_2$SO$_4$ and concentrated under reduced pressure. The residue was purified by column chromatography on a silica gel to give compound PI-10b (200 mg, 44%).

A mixture of compound PI-10b (200 mg, 0.473 mmol, 1.0 eq) in HCl/THF (2.0 M, 3 mL/3 mL) was stirred at 70° C. for 3 h. The reaction mixture was cooled to room temperature and concentrated under reduced pressure. The residue was added with saturated NaHCO$_3$ solution to adjust the pH=8 and extracted with ethyl acetate. The organic layer was washed with brine, dried over anhydrous Na$_2$SO$_4$ and concentrated under reduced pressure to give compound PI-10c (150 mg, 91%), which was used in the next step without further purification.

To a mixture of compound PI-10c (150 mg, 0.427 mmol, 1.0 eq) in MeOH (5 mL) was added KCN (55 mg, 0.854 mmol, 2.0 eq) and (NH$_4$)$_2$CO$_3$ (164 mg, 1.71 mmol, 4.0 eq). The mixture was stirred at room temperature for 12 h. Then the mixture was diluted with water and extracted with ethyl acetate. The organic phase was dried over anhydrous Na$_2$SO$_4$ and concentrated under reduced pressure. The residue was purified by Prep-TLC to give compound PC-10 (55 mg, 30%) as a white solid.

Preparation of Compound PC-11:

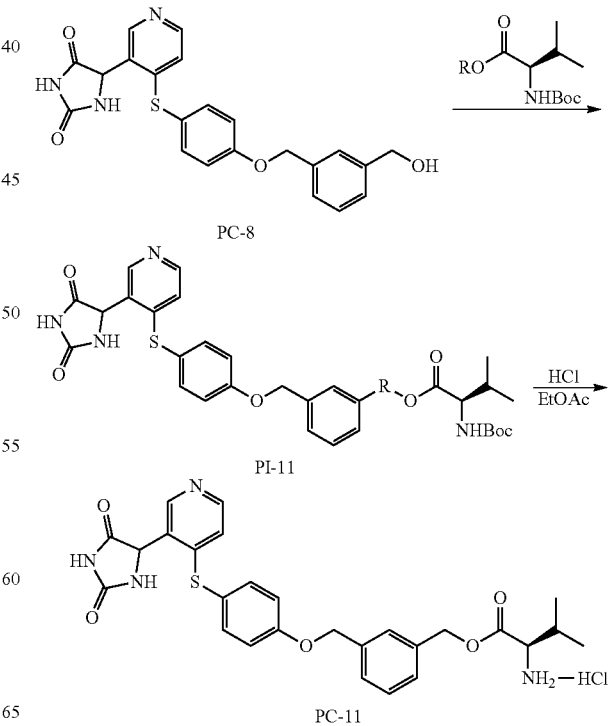

To a solution of compound PC-8 (1.0 g, 2.37 mmol, 1.0 eq) in DCM (50 mL) was successively added (tert-butoxycarbonyl)-D-valine (1.02 g, 2.61 mol, 1.1 eq), EDCI (0.53 g, 2.84 mol, 1.2 eq) and DMAP (0.056 g, 0.47 mol, 0.2 eq). The mixture was stirred at 25° C. for 24 h. Then the mixture was concentrated under reduced pressure. The residue was purified by column chromatography on silica gel (DCM/MeOH, 10:1) to give compound PI-11 (496 mg, 35%) as a yellow solid.

To a solution of compound PI-11 (0.5 g, 0.8 mmol, 1.0 eq) in EA (20 mL) was added HCl (4.5 M in EA, 20 mL). The mixture was stirred at room temperature for 12 h. Then the mixture was concentrated under reduced pressure to give PC-11 (430 mg, 96%) as a white solid.

Preparation of Key Intermediate PI-a.2.

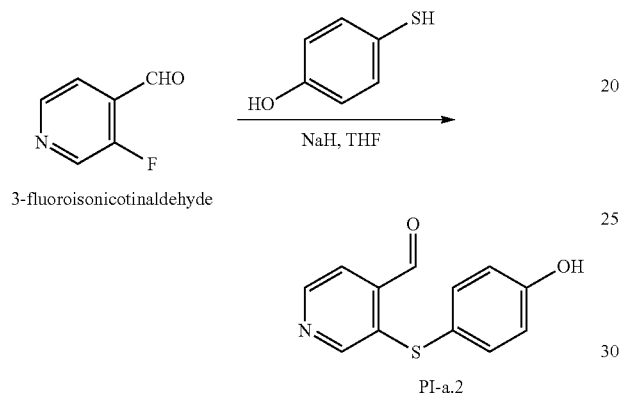

To a mixture of 3-fluoroisonicotinaldehyde (2.9 g, 23.2 mmol, 1.0 eq) in DMF (150 mL) was successively added 4-mercaptophenol (5.85 g, 46.4 mmol, 2.0 eq) and K$_2$CO$_3$ (12.8 g, 92.8 mmol, 4.0 eq). The mixture was stirred at room temperature for 16 h under nitrogen atmosphere. Then 3 M HCl was added to adjust the pH=6 to 7. The mixture was extracted with EA and the organic layer was washed with brine, dried over Na$_2$SO$_4$, concentrated under reduced pressure. The residue was purified by column chromatography on a silica gel to give compound PI-a.2 (1.6 g, 30%).

Preparation of Compounds PC-12, PC-13 and PC-14:

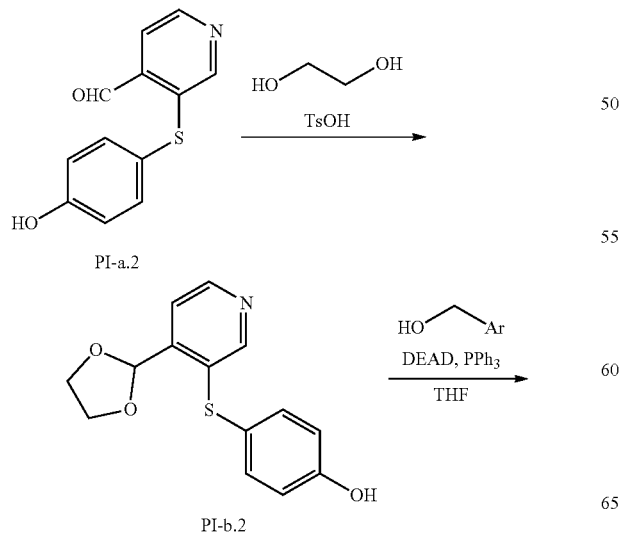

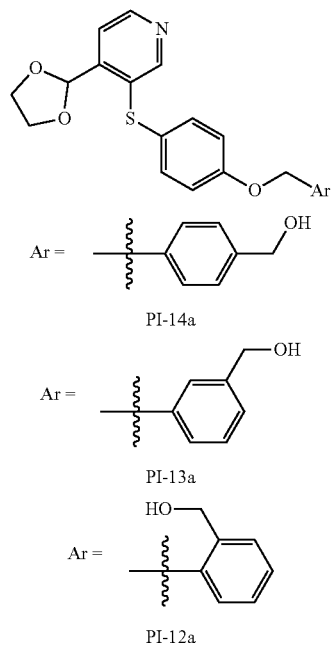

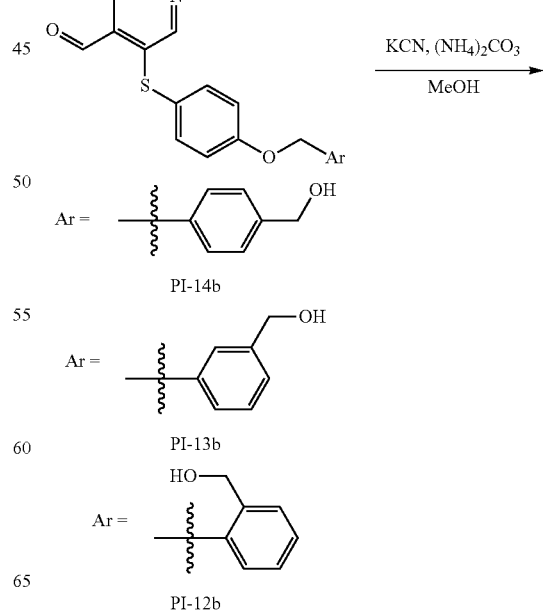

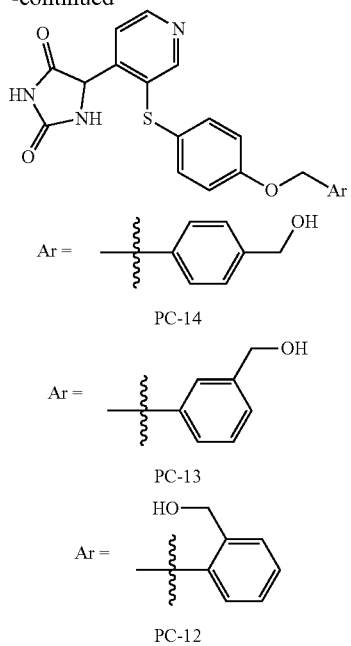

PC-14

PC-13

PC-12

To a mixture of compound PI-a.2 (2.3 g, 9.96 mmol, 1.0 eq) in toluene (100 mL) was successively added ethane-1,2-diol (1.2 g, 19.9 mmol, 20 eq) and TsOH (86 mg, 0.498 mmol, 0.05 eq). The mixture was heated under reflux for 12 h under nitrogen atmosphere. Then the mixture was concentrated under reduced pressure. The residue was purified by column chromatography on silica gel to give compound PI-b.2 (2.2 g, 81%).

To a solution of compound PI-b.2 (1.5 g, 5.45 mmol, 1.0 eq) in THF (50 mL) was successively added 1,4-phenylenedimethanol (2.63 g, 19 mmol, 3.5 eq), PPh$_3$ (2.86 g, 10.9 mmol, 2.0 eq) and DEAD (1.9 g, 10.9 mmol, 2.0 eq) at 0° C. The mixture was allowed to warm to room temperature and stirred for 16 h. Then the mixture was quenched with H$_2$O (50 mL) and extracted with ethyl acetate (2×50 mL). The combined organic layers were dried over anhydrous Na$_2$SO$_4$ and concentrated under reduced pressure. The residue was purified by column chromatography on silica gel to give compound PI-14a (1.5 g, 70%).

A mixture of compound PI-14a (500 mg, 1.266 mmol, 1.0 eq) in HCl/THF (3.0 M, 35 mL/35 mL) was stirred at 70° C. for 12 h. The reaction mixture was cooled to room temperature and concentrated under reduced pressure. The residue was added with saturated NaHCO$_3$ solution to adjust the pH=8 and extracted with ethyl acetate. The organic layer was washed with brine, dried over anhydrous Na$_2$SO$_4$ and concentrated under reduced pressure. The residue was purified by silica gel chromatography to give compound PI-14b (280 mg, 63%).

To a mixture of compound PI-14b (150 mg, 0.427 mmol, 1.0 eq) in EtOH (5 mL) and H$_2$O (2.5 mL) was added KCN (42 mg, 0.641 mmol, 1.5 eq) and (NH$_4$)$_2$CO$_3$ (410 mg, 4.27 mmol, 10.0 eq). The mixture was stirred at 50° C. for 5 h. Then the mixture was diluted with water and extracted with ethyl acetate. The organic phase was dried over anhydrous Na$_2$SO$_4$ and concentrated under reduced pressure. The residue was purified by Prep-TLC to give compound PC-14 (70 mg, 25%) as a white solid.

Compounds PC-12 and PC-13 were synthesized by the same procedure except that 1,2-phenylenedimethanol was replaced with 1,3-phenylenedimethanol or 1,4-phenylenedimethanol, accordingly.

Preparation of Compound PC-15:

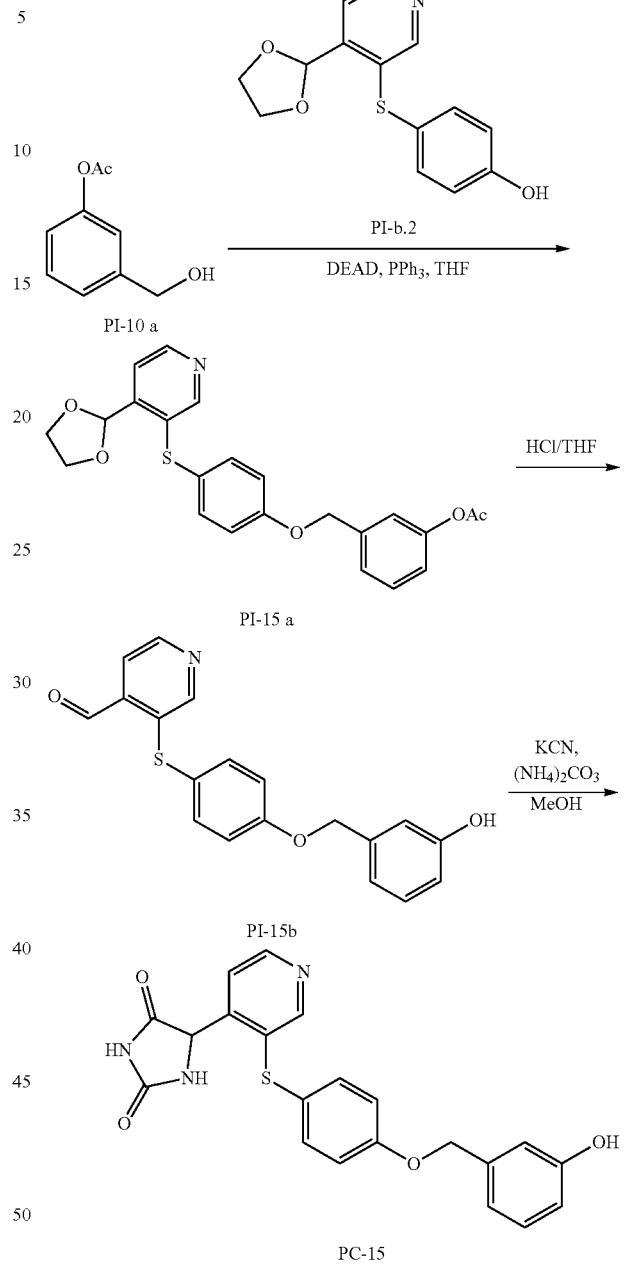

To a solution of compound PI-b.2 (500 mg, 1.82 mmol, 1.0 eq) in THF (20 mL) was successively added compound PI-10a (1.1 g, 6.37 mmol, 3.5 eq), PPh$_3$ (954 mg, 3.64 mmol, 2.0 eq) and DEAD (634 mg, 3.64 mmol, 2.0 eq) at 0° C. The mixture was allowed to warm to room temperature and stirred for 16 h. Then the mixture was quenched with H$_2$O (10 mL) and extracted with ethyl acetate (2×10 mL). The combined organic layers were dried over anhydrous Na$_2$SO$_4$ and concentrated under reduced pressure. The residue was purified by column chromatography on silica gel to give compound PI-15a (460 mg, 60%).

A mixture of compound PI-15a (1 g, 2.364 mmol, 1.0 eq) in HCl/THF (3.0 M, 25 mL/25 mL) was stirred at 70° C. for 16 h. The reaction mixture was cooled to room temperature and concentrated under reduced pressure. The residue was added with saturated NaHCO$_3$ solution to adjust the pH=8 and extracted with ethyl acetate. The organic layer was washed with brine, dried over anhydrous Na$_2$SO$_4$ and concentrated under reduced pressure. The residue was purified by silica gel chromatography to give compound PI-15b (200 mg, 25%).

To a mixture of compound PI-15b (200 mg, 0.593 mmol, 1.0 eq) in EtOH (6 mL) and H$_2$O (6 mL) was added KCN (58 mg, 0.89 mmol, 1.5 eq) and (NH$_4$)$_2$CO$_3$ (570 mg, 5.93 mmol, 10.0 eq). The mixture was stirred at 50° C. for 4 h. Then the mixture was diluted with water and extracted with ethyl acetate. The organic phase was dried over anhydrous Na$_2$SO$_4$ and concentrated under reduced pressure. The residue was purified by Prep-HPLC to give compound PC-15 (58 mg, 24%) as a white solid.

Preparation of Compounds PC-16 and PC-17:

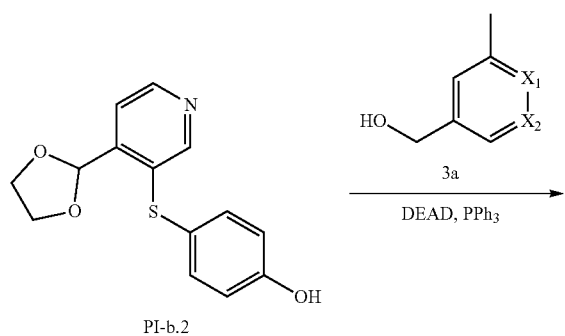

PI-b.2

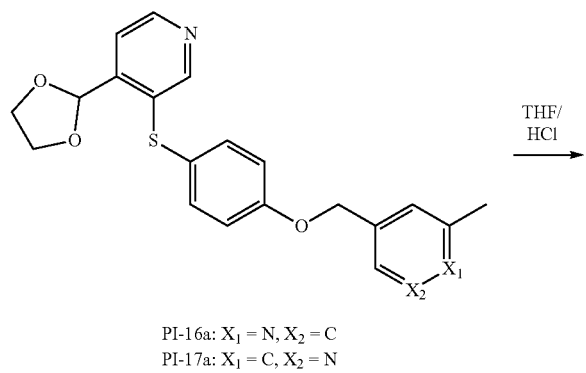

PI-16a: X$_1$ = N, X$_2$ = C
PI-17a: X$_1$ = C, X$_2$ = N

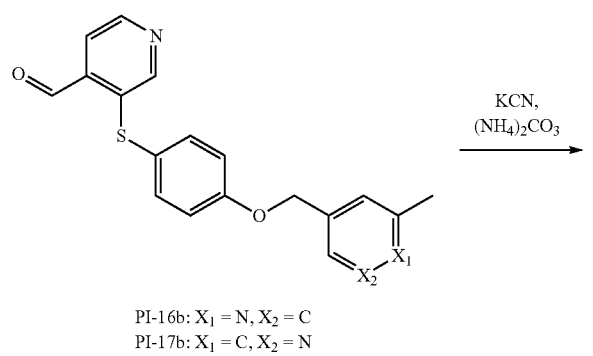

PI-16b: X$_1$ = N, X$_2$ = C
PI-17b: X$_1$ = C, X$_2$ = N

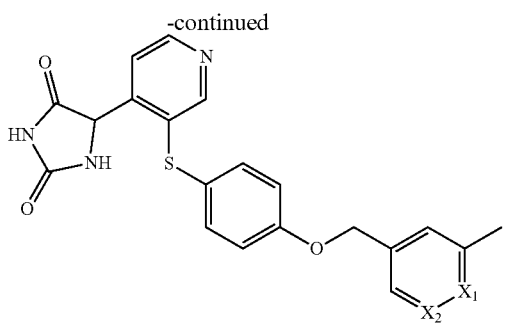

PC-16: X$_1$ = N, X$_2$ = C
PC-17: X$_1$ = C, X$_2$ = N

To a solution of compound PI-b.2 (1.2 g, 4.363 mmol, 1.0 eq) in THF (20 mL) was successively added (2-methylpyridin-4-yl)methanol (2.68 g, 21.8 mmol, 5.0 eq), PPh$_3$ (2.29 g, 8.73 mmol, 2.0 eq) and DEAD (1.5 g, 8.73 mmol, 2.0 eq) at 0° C. The mixture was allowed to warm to room temperature and stirred for 16 h. Then the mixture was quenched with H$_2$O (50 mL) and extracted with ethyl acetate (2×50 mL). The combined organic layers were dried over anhydrous Na$_2$SO$_4$ and concentrated under reduced pressure. The residue was purified by column chromatography on silica gel to give compound PI-16a (1.4 g, 84%).

A mixture of compound PI-16a (1.4 g, 3.684 mmol, 1.0 eq) in HCl/THF (2.0 M, 30 mL/30 mL) was stirred at 70° C. for 3 h. The reaction mixture was cooled to room temperature and concentrated under reduced pressure. The residue was added with saturated NaHCO$_3$ solution to adjust the pH=8 and extracted with ethyl acetate. The organic layer was washed with brine, dried over anhydrous Na$_2$SO$_4$ and concentrated under reduced pressure to give compound PI-16b (760 mg, 61%), which was used in the next step without further purification.

To a mixture of compound PI-16b (760 mg, 2.262 mmol, 1.0 eq) in MeOH (10 mL) was added KCN (294 mg, 4.524 mmol, 2.0 eq) and (NH$_4$)$_2$CO$_3$ (869 mg, 9.048 mmol, 4.0 eq). The mixture was stirred at room temperature for 12 h. Then the mixture was diluted with water and extracted with ethyl acetate. The organic phase was dried over anhydrous Na$_2$SO$_4$ and concentrated under reduced pressure. The residue was purified by silica gel chromatography to give compound PC-16 (130 mg, 14%) as a white solid.

Compound PC-17 was synthesized by the same procedure as the synthesis of compound PC-16 except that (2-methylpyridin-4-yl)methanol was replaced with (5-methylpyridin-3-yl)methanol.

Preparation of Compounds PC-18 and PC-19:

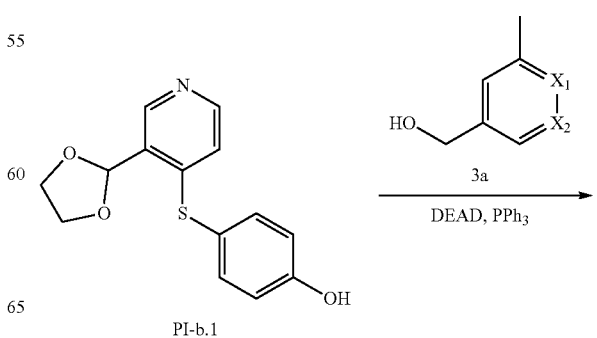

PI-b.1

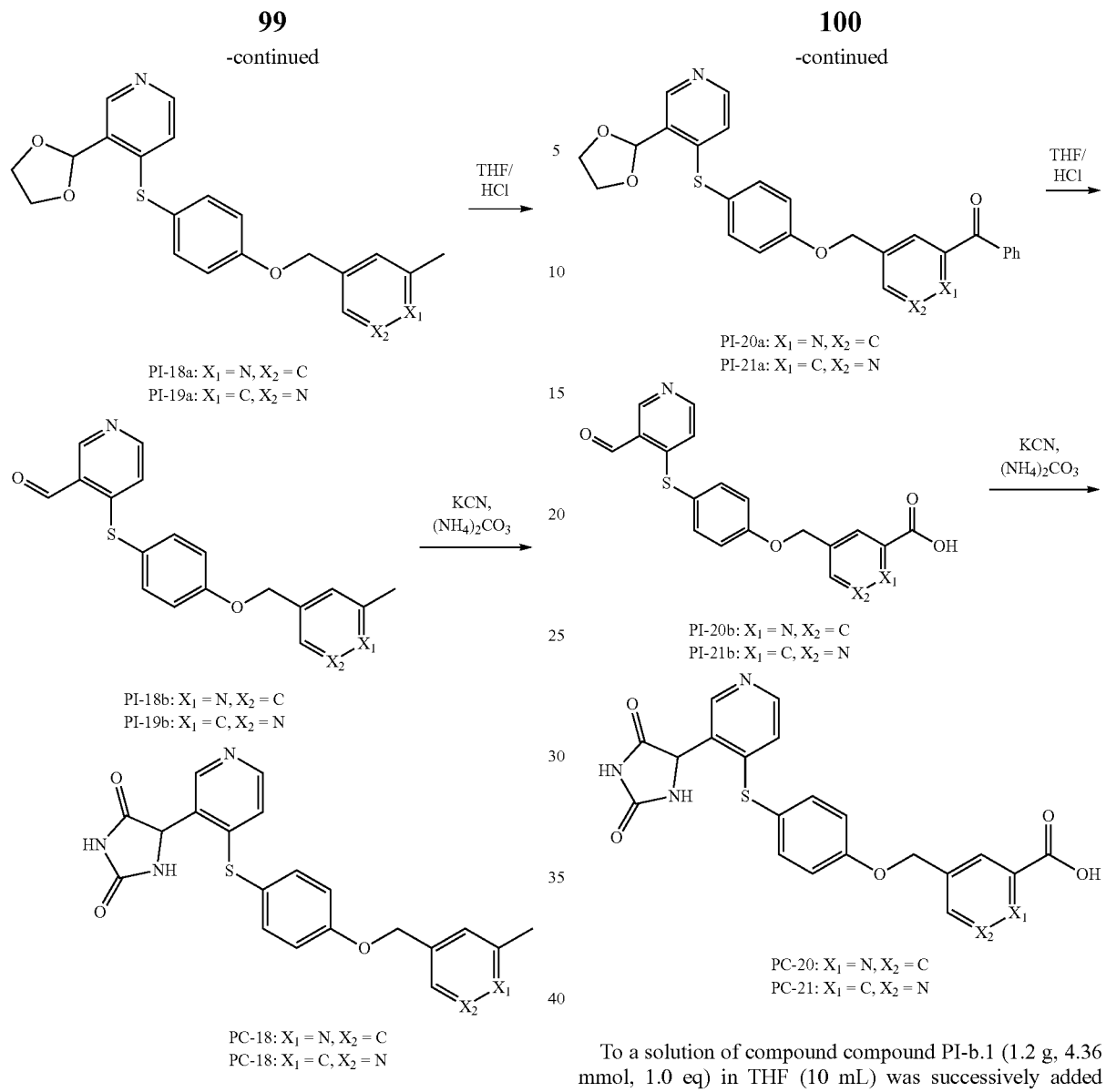

Compounds PC-18 and PC-19 were synthesized by the same procedure as the synthesis of PC-16 except that PI-b.2 was replaced with PI-b.1 as starting material.

Preparation of Compounds PC-20 and PC-21:

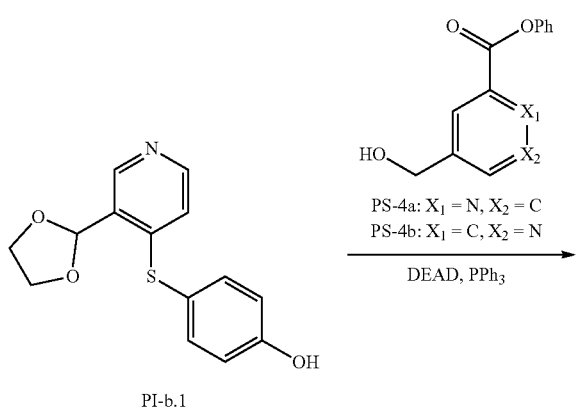

To a solution of compound compound PI-b.1 (1.2 g, 4.36 mmol, 1.0 eq) in THF (10 mL) was successively added compound PS-4a (2.0 g, 8.73 mmol, 2.0 eq), PPh$_3$ (3.4 g, 13.0 mmol, 3.0 eq) and DEAD (2.3 g, 13.0 mmol, 3.0 eq) at 0° C. The mixture was allowed to warm to room temperature and stirred for 20 h. Then the mixture was quenched with H$_2$O (100 mL) and extracted with ethyl acetate (2×100 mL). The combined organic layers were dried over anhydrous Na$_2$SO$_4$ and concentrated under reduced pressure. The residue was purified by column chromatography on silica gel (PE/EA, 1:1) to give compound PI-20a (2.0 g, 95%) as a white solid.

A mixture of compound PI-20a (500 mg, 1.02 mmol, 1.0 eq) and HCl (3 M in H$_2$O, 10 mL) in THF (15 mL) was stirred at 70° C. for 12 h. The reaction mixture was cooled to room temperature and concentrated under reduced pressure. The residue was added with saturated NaHCO$_3$ solution to adjust the pH=8 and filtered to give compound PI-20b (400 mg, 100%), which was used in the next step without further purification.

To a solution of compound PI-20b (220 mg, 0.601 mmol, 1.0 eq) and KCN (117 mg, 1.803 mmol, 3.0 eq) in EtOH (12 mL) and H$_2$O (6 mL) was added (NH$_4$)$_2$CO$_3$ (577 mg, 6.01 mmol, 10.0 eq). The mixture was stirred at 50° C. for 5 h. The mixture was added with 0.5 M HCl to adjust the pH=1~2 and stirred for 10 min. Then saturated NaHCO$_3$ solution was added to adjust the pH=6 to 7. The mixture was stirred for 1 h and filtered. The residue was purified by Prep-HPLC to give PC-20 (160 mg, 61.3%) as a white solid.

Preparation of Intermediates of PS-4a and PS-4b:

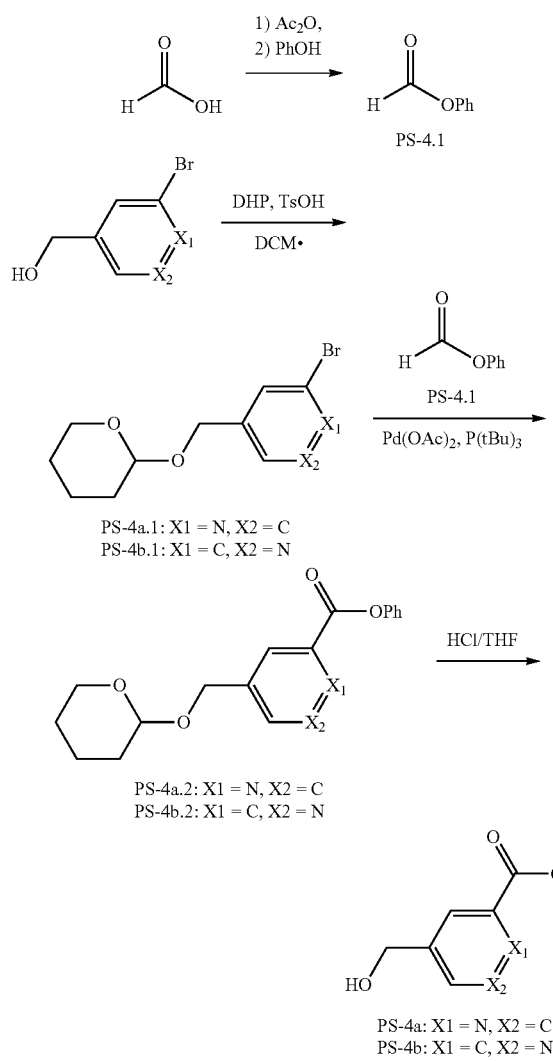

A mixture of formic acid (180 mL, 1.9 mol, 4.0 eq) in Ac$_2$O (360 mL, 9.54 mol, 21.2 eq) was stirred at 60° C. for 1 h under nitrogen atmosphere. The reaction mixture was cooled to room temperature, then PhOH (42.3 g, 0.45 mol, 1.0 eq) and NaHCO$_3$ (76.5 g, 0.91 mol, 2.0 eq) were added. Then the mixture was stirred at room temperature for 16 h. After the mixture was extracted with EA (3×150 mL) and water, the combined organic layers were washed with H$_2$O (3×100 mL) and saturated NaHCO$_3$ solution (2×100 mL), dried over Na$_2$SO$_4$ and concentrated under reduced pressure to give compound PS-4.1 (60 g, 26%).

To a mixture of (2-bromopyridin-4-yl)methanol (25 g, 133.69 mmol, 1.0 eq) and DHP (22.46 g, 267.38 mmol, 2.0 eq) in DCM (290 mL) was added TsOH (2.23 g, 13.37 mmol, 0.1 eq). The mixture was stirred at room temperature for 15 h. TLC analysis of the reaction mixture showed full conversion to the desired product. Then the mixture was diluted with H$_2$O (100 mL) and extracted with dichloromethane. The organic layer was washed with brine (100 mL), dried over anhydrous Na$_2$SO$_4$ and concentrated under reduced pressure. The residue was purified by column chromatography on silica gel (PE/EA, 4:1) to give compound PS-4a.1 (34.1 g, 94.1%).

To a mixture of compound PS-4a.1 (30 g, 110.7 mmol, 1.0 eq), compound PS-4.1 (33.7 g, 276.75 mmol, 2.5 eq), Et$_3$N (28 g, 276.75 mmol, 2.5 eq) and P(t-Bu)$_3$HBF$_4$ (3.85 g, 13.284 mmol, 0.12 eq) in ACN (700 mL) was added Pd(OAc)$_2$ (743.9 mg, 3.321 mmol, 0.03 eq) under nitrogen atmosphere. The mixture was stirred at 80° C. for 15 h. Then the mixture was filtered and the filtrate was concentrated under reduced pressure. The residue was purified by column chromatography on silica gel (PE/EA, 1:1) to give compound PS-4a.2 (11 g, 32%).

A mixture of compound PS-4a.2 (25 g, 79.8 mmol, 1.0 eq) and HCl (2 M in H$_2$O, 55 mL) in THF (55 mL) was stirred at room temperature for 3 h. TLC analysis of the reaction mixture showed full conversion to the desired product. Then the mixture was dried over Na$_2$SO$_4$ and concentrated under reduced pressure. The residue was purified by column chromatography on a silica gel (PE/EA, 2:1) to give compound PS-4a (8 g, 44%).

The intermediate PS-4b was prepared by the same procedure of synthesizing PS-4a except that (2-bromopyridin-4-yl)methanol was replaced with (5-bromopyridin-3-yl)methanol as starting material.

Preparation of Compound PC22:

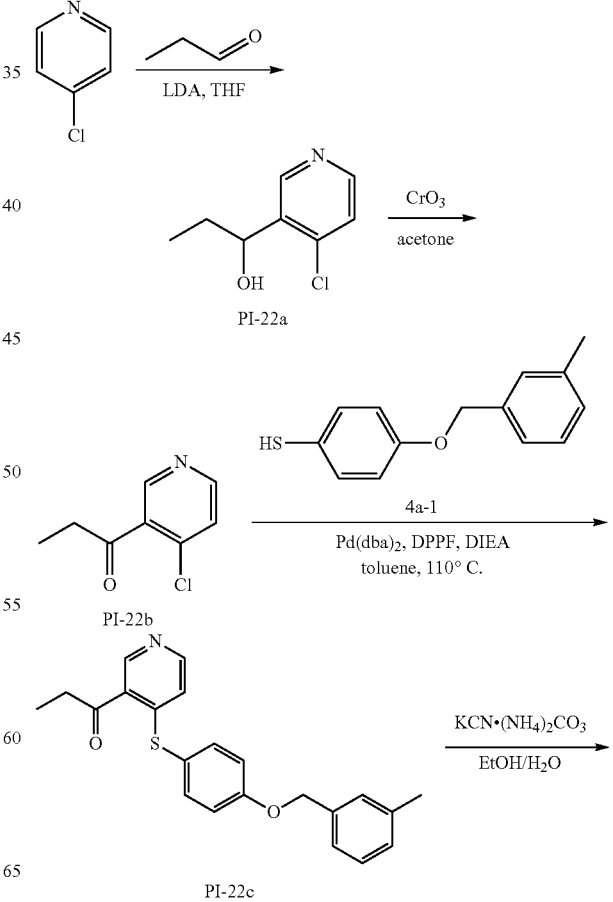

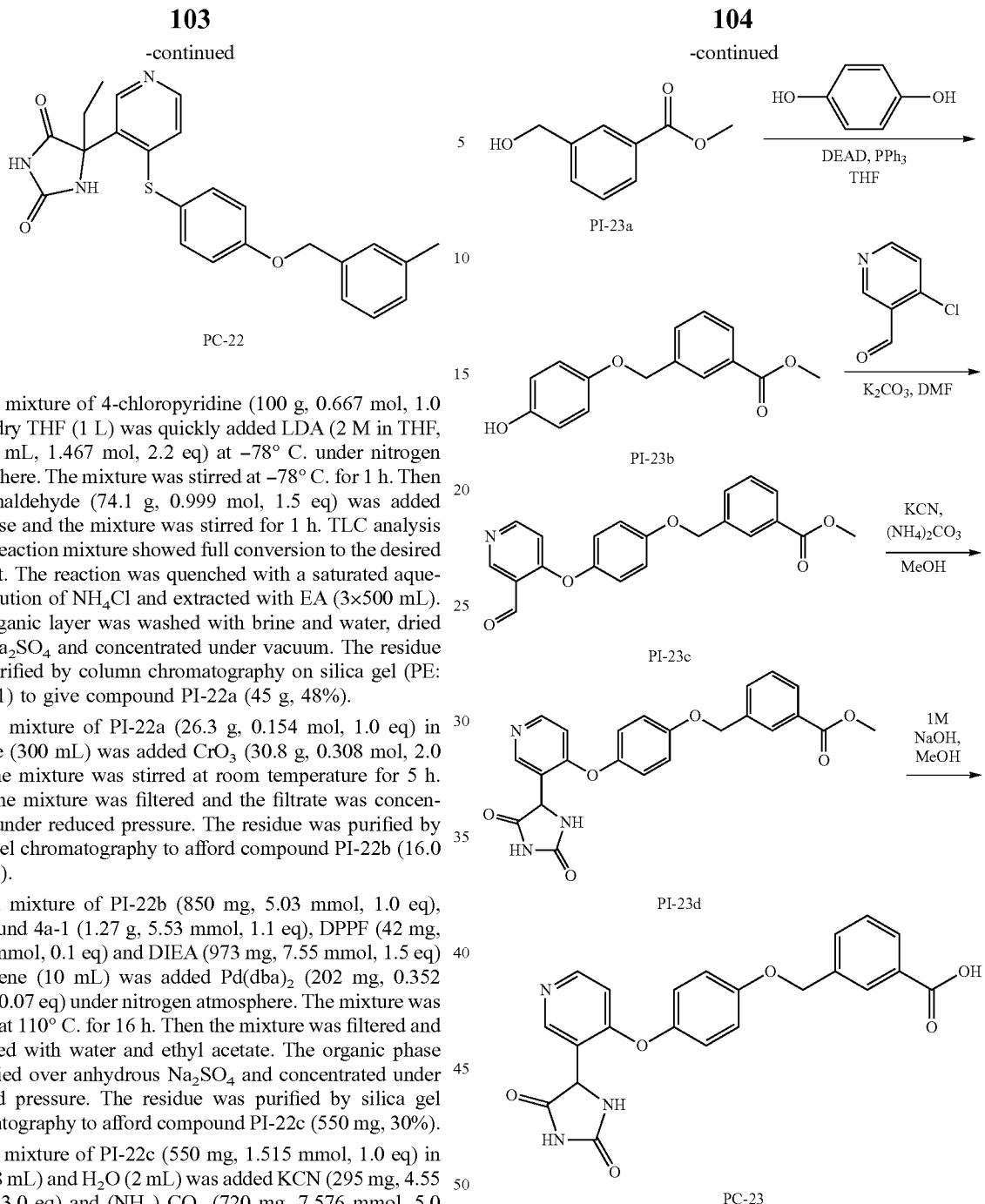

To a mixture of 4-chloropyridine (100 g, 0.667 mol, 1.0 eq) in dry THF (1 L) was quickly added LDA (2 M in THF, 733.26 mL, 1.467 mol, 2.2 eq) at −78° C. under nitrogen atmosphere. The mixture was stirred at −78° C. for 1 h. Then propionaldehyde (74.1 g, 0.999 mol, 1.5 eq) was added dropwise and the mixture was stirred for 1 h. TLC analysis of the reaction mixture showed full conversion to the desired product. The reaction was quenched with a saturated aqueous solution of NH$_4$Cl and extracted with EA (3×500 mL). The organic layer was washed with brine and water, dried over Na$_2$SO$_4$ and concentrated under vacuum. The residue was purified by column chromatography on silica gel (PE:EA, 3:1) to give compound PI-22a (45 g, 48%).

To a mixture of PI-22a (26.3 g, 0.154 mol, 1.0 eq) in acetone (300 mL) was added CrO$_3$ (30.8 g, 0.308 mol, 2.0 eq). The mixture was stirred at room temperature for 5 h. Then the mixture was filtered and the filtrate was concentrated under reduced pressure. The residue was purified by silica gel chromatography to afford compound PI-22b (16.0 g, 62%).

To a mixture of PI-22b (850 mg, 5.03 mmol, 1.0 eq), compound 4a-1 (1.27 g, 5.53 mmol, 1.1 eq), DPPF (42 mg, 0.503 mmol, 0.1 eq) and DIEA (973 mg, 7.55 mmol, 1.5 eq) in toluene (10 mL) was added Pd(dba)$_2$ (202 mg, 0.352 mmol, 0.07 eq) under nitrogen atmosphere. The mixture was stirred at 110° C. for 16 h. Then the mixture was filtered and extracted with water and ethyl acetate. The organic phase was dried over anhydrous Na$_2$SO$_4$ and concentrated under reduced pressure. The residue was purified by silica gel chromatography to afford compound PI-22c (550 mg, 30%).

To a mixture of PI-22c (550 mg, 1.515 mmol, 1.0 eq) in Et$_0$H (8 mL) and H$_2$O (2 mL) was added KCN (295 mg, 4.55 mmol, 3.0 eq) and (NH$_4$)$_2$CO$_3$ (720 mg, 7.576 mmol, 5.0 eq). The mixture was stirred at 50° C. for 3 d. Then the mixture was diluted with water and extracted with ethyl acetate. The organic phase was dried over anhydrous Na$_2$SO$_4$ and concentrated under reduced pressure. The residue was purified by silica gel chromatography to give compound PC-22 (50 mg, 7%) as a white solid.

Preparation of Compound PC-23:

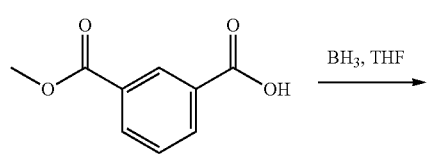

To a mixture of 3-(methoxycarbonyl)benzoic acid (5 g, 27.78 mmol, 1.0 eq) in dry THF (20 mL) was added BH$_3$/THF (1 M in THF, 55 mL, 55.5 mmol, 2.0 eq) at 0° C. The mixture was stirred at 30° C. for 16 h under nitrogen atmosphere. Then the mixture was diluted with water and extracted with ethyl acetate. The organic layer was washed with brine, dried over anhydrous Na$_2$SO$_4$ and concentrated under reduced pressure. The residue was purified by column chromatography on silica gel to give compound PI-23a (4.2 g, 91%).

To a solution of PI-23a (4.1 g, 24.7 mmol, 1.0 eq) in THF (100 mL) was successively added 1,4-hydroquinone (5.4 g, 49.4 mmol, 2.0 eq), PPh$_3$ (13.0 g, 49.4 mmol, 2.0 eq) and DEAD (8.6 g, 49.4 mmol, 2.0 eq) at 0° C. The mixture was allowed to warm to room temperature and stirred for 16 h.

Then the mixture was quenched with H₂O (100 mL) and extracted with ethyl acetate (2×100 mL). The combined organic layers were dried over anhydrous Na₂SO₄ and concentrated under reduced pressure. The residue was purified by column chromatography on a silica gel (PE/EA, 2:1) to give compound PI-23b (2.1 g, 33%).

To a solution of compound PI-23b (2.1 g, 8.14 mmol, 1.0 eq) in DMF (15 mL) were added 4-chloronicotinaldehyde (1.73 g, 12.2 mmol, 1.5 eq) and K₂CO₃ (2.25 g, 16.28 mmol, 2.0 eq). The mixture was stirred at 80° C. for 4 h under nitrogen atmosphere. Then 3 M HCl was added to adjust the pH=6 to 7. The mixture was extracted with EA and the organic layer was washed with brine, dried over Na₂SO₄, concentrated under reduced pressure. The residue was purified by column chromatography on a silica gel (PE/EA, 3:1) to give compound PI-23c (900 mg, 31%).

To a mixture of compound PI-23c (200 mg, 0.551 mmol, 1.0 eq) in MeOH (5 mL) was added KCN (72 mg, 1.1 mmol, 2.0 eq) and (NH₄)₂CO₃ (211 mg, 2.2 mmol, 4.0 eq). The mixture was stirred at room temperature for 12 h. Then the mixture was diluted with water and extracted with ethyl acetate. The organic phase was dried over anhydrous Na₂SO₄ and concentrated under reduced pressure. The residue was purified by Prep-TLC to give compound PI-23d (100 mg, 42%).

To a mixture of PI-23d (100 mg, 0.23 mmol, 1.0 eq) in MeOH (5 mL) was added NaOH (80 mg, 2.0 mmol, 10.0 eq). The mixture was stirred at room temperature for 3 h. The mixture was concentrated to halve the solvent and then 1 N HCl was added to adjust the pH=5. The mixture was filtered to give PC-23 (47 mg, 48%).

Preparation of Compound PC-24:

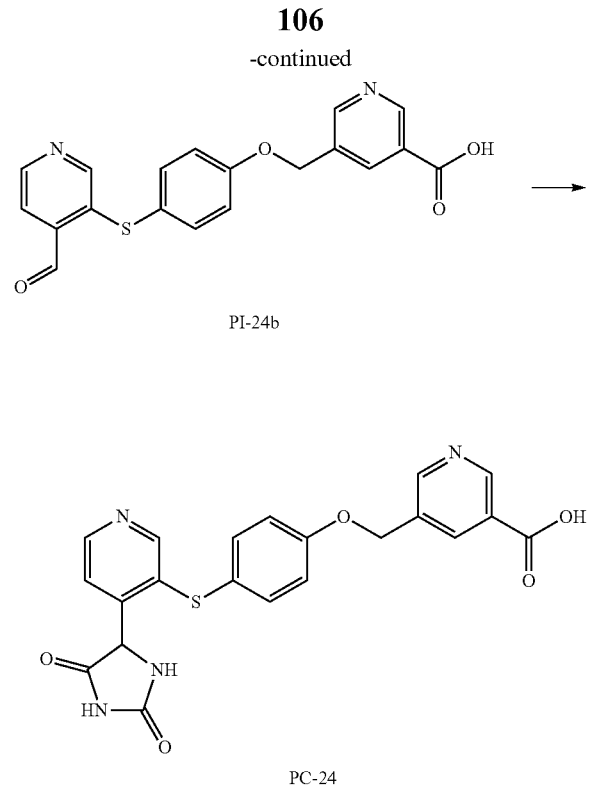

Compound PC-24 was synthesized by the same procedure as the synthesis of PC-22 except that the starting material PI-b.1 was replaced with PI-b.2.

Preparation of Compound PC-25:

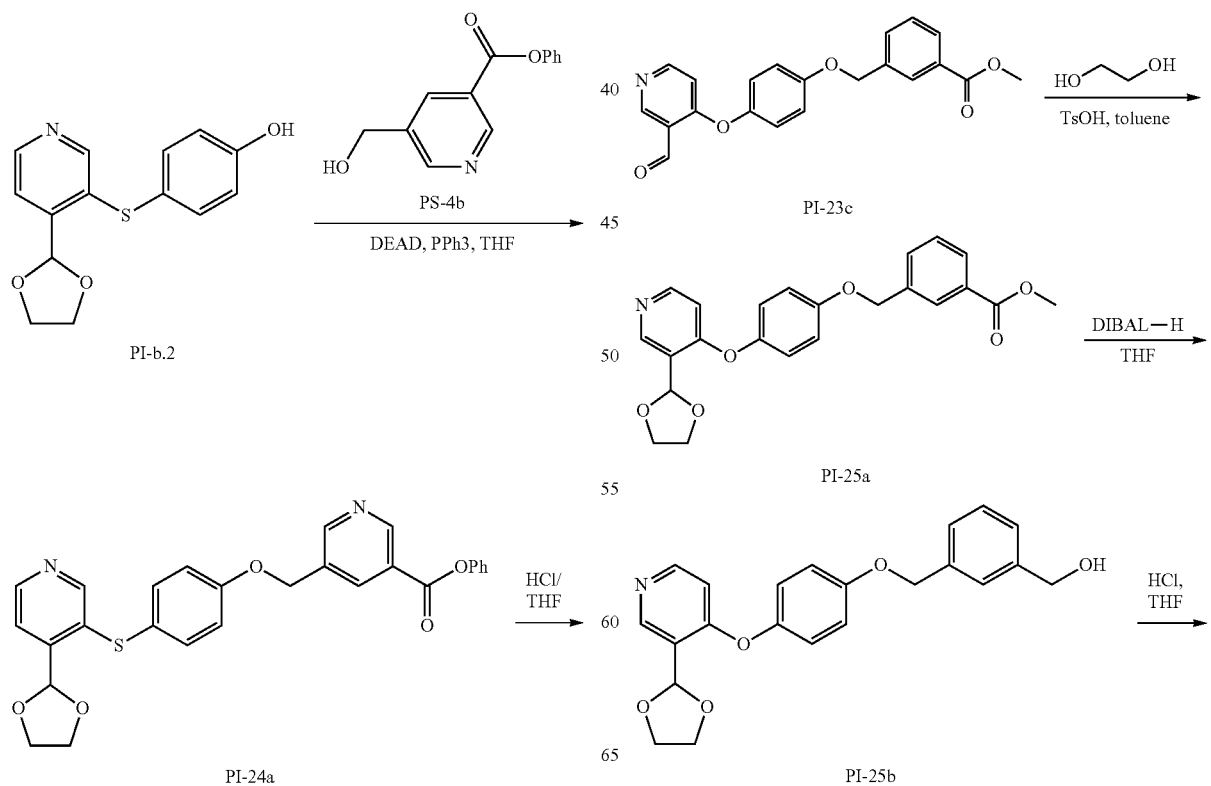

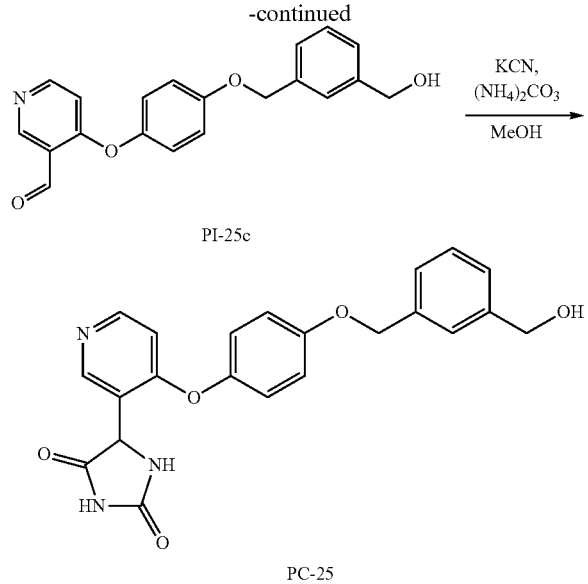

PI-25c

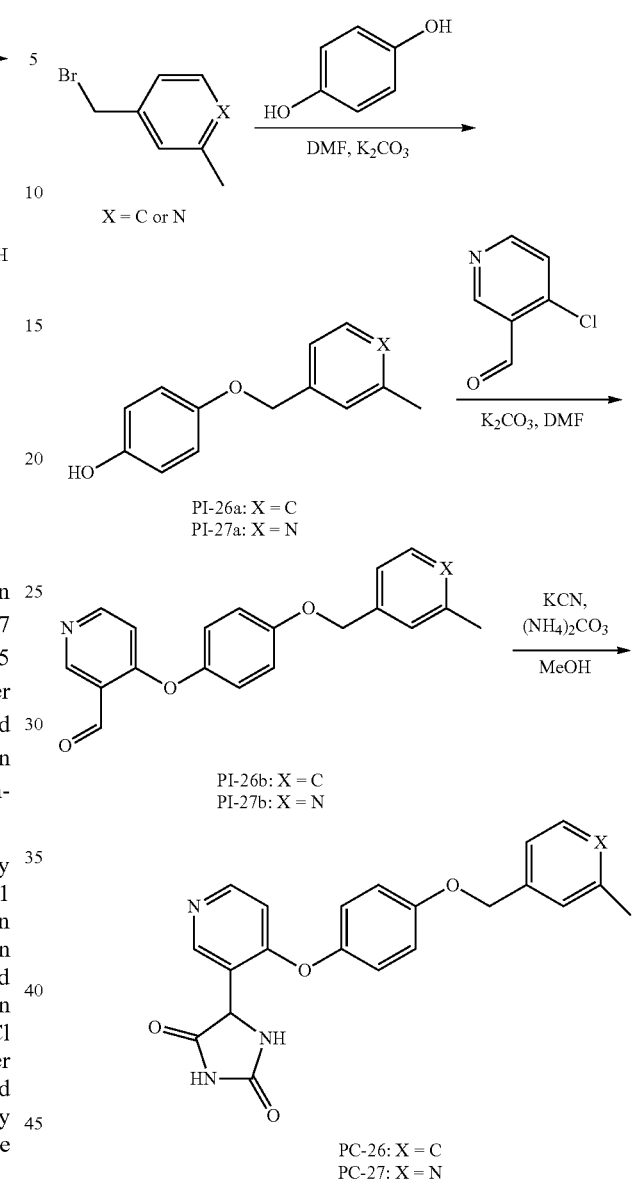

Preparation of Compounds PC-26 and PC-27:

To a mixture of PI-23c (2.4 g, 6.61 mmol, 1.0 eq) in toluene (40 mL) was successively added ethane-1,2-diol (3.7 g, 60 mmol, 10 eq) and TsOH (56.5 mg, 0.33 mmol, 0.05 eq). The mixture was heated under reflux for 12 h under nitrogen atmosphere. Then the mixture was concentrated under reduced pressure. The residue was purified by column chromatography on silica gel (PE/EA, 2:1) to give compound PI-25a (2.3 g, 85%).

To a mixture of PI-25a (2.3 g, 25.65 mmol, 1.0 eq) in dry THF (100 mL) was added DIBAL-H (1.0 M in toluene, 14.1 mL, 14.1 mmol, 2.5 eq) dropwise at 0° C. under nitrogen atmosphere. The mixture was stirred at 0° C. for 1 h. Then $Na_2SO_4·10H_2O$ (6.6 g, 20.5 mmol, 0.8 eq) was added dropwise and the mixture was stirred for 0.5 h. The reaction was quenched with a saturated aqueous solution of $NH_4Cl$ and extracted with EtOAc (3×100 mL). The organic layer was washed with brine and water, dried over $Na_2SO_4$ and concentrated under vacuum. The residue was purified by column chromatography on silica gel (PE:EA, 3:1) to give compound PI-25b (1.1 g, 51%).

A mixture of PI-25b (1.1 g, 2.902 mmol, 1.0 eq) in HCl/THF (2.0 M, 20 mL/20 mL) was stirred at 70° C. for 3 h. The reaction mixture was cooled to room temperature and concentrated under reduced pressure. The residue was added with saturated $NaHCO_3$ solution to adjust the pH=8 and extracted with ethyl acetate. The organic layer was washed with brine, dried over anhydrous $Na_2SO_4$ and concentrated under reduced pressure to give compound PI-25c (1.0 g, 100%), which was used in the next step without further purification.

To a mixture of compound PI-25c (1.0 g, 2.98 mmol, 1.0 eq) in MeOH (20 mL) was added KCN (38 mg, 5.96 mmol, 2.0 eq) and $(NH_4)_2CO_3$ (1.14 g, 11.92 mmol, 4.0 eq). The mixture was stirred at room temperature for 12 h. Then the mixture was diluted with water and extracted with ethyl acetate. The organic phase was dried over anhydrous $Na_2SO_4$ and concentrated under reduced pressure. The residue was purified by Prep-TLC to give compound PC-25 (215 mg, 18%) as a white solid.

To a mixture of 1-(bromomethyl)-3-methylbenzene (5.0 g, 27 mmol, 1.0 eq) in DMF (150 mL) was successively added 1,4-hydroquinone (5.94 g, 54 mmol, 2.0 eq) and $K_2CO_3$ (14.9 g, 108 mmol, 4.0 eq). The mixture was stirred at 80° C. for 3 h under nitrogen atmosphere. Then 3 M HCl was added to adjust the pH=6 to 7. The mixture was extracted with EA and the organic layer was washed with brine, dried over $Na_2SO_4$, and concentrated under reduced pressure. The residue was purified by column chromatography on silica gel (PE/EA, 3:1) to give compound PI-26a (2.6 g, 45%).

To a mixture of PI-26a (1.0 g, 4.67 mmol, 1.0 eq) in DMF (15 mL) was successively added 4-chloronicotinaldehyde (0.99 g, 7 mmol, 1.5 eq) and $K_2CO_3$ (1.5 g, 9.34 mmol, 2.0 eq). The mixture was stirred at 80° C. for 3.5 h under nitrogen atmosphere. TLC analysis of the reaction mixture showed full conversion to the desired product. Then the mixture was diluted with $H_2O$ (100 mL) and extracted with EA (3×100 mL). The combined organic layers were washed with a saturated aqueous solution of $NH_4Cl$ (3×100 mL), brine, dried over anhydrous Na$_2$SO$_4$ and concentrated under reduced pressure. The residue was purified by column chromatography on silica gel (PE/EA, 1:1) to give compound PI-26b (480 mg, 32%).

To a solution of compound PI-26b (480 mg, 1.5 mmol, 1.0 eq) in MeOH (10 mL) was added (NH$_4$)$_2$CO$_3$ (578 mg, 6.01 mmol, 4.0 eq) and KCN (195 mg, 3 mmol, 2.0 eq). The mixture was stirred at 45° C. for 16 h. The reaction was added with 3 M HCl to adjust the pH=1 to 2 and stirred at room temperature for 1 h, then a saturated aqueous solution of NaHCO$_3$ was added to adjust the pH=6 to 7 and extracted with ethyl acetate. The organic layer was washed with brine, dried over anhydrous Na$_2$SO$_4$ and concentrated under reduced pressure. The residue was purified by Prep-TLC to give PC-26 (208.1 mg, 44%) as a white solid. Compound PC-27 was synthesized in the same fashion expect that the starting material 1-(bromomethyl)-3-methylbenzene was replaced with 4-(bromomethyl)-2-methylpyridine.

Preparation of Compounds PC-28 and PC-29:

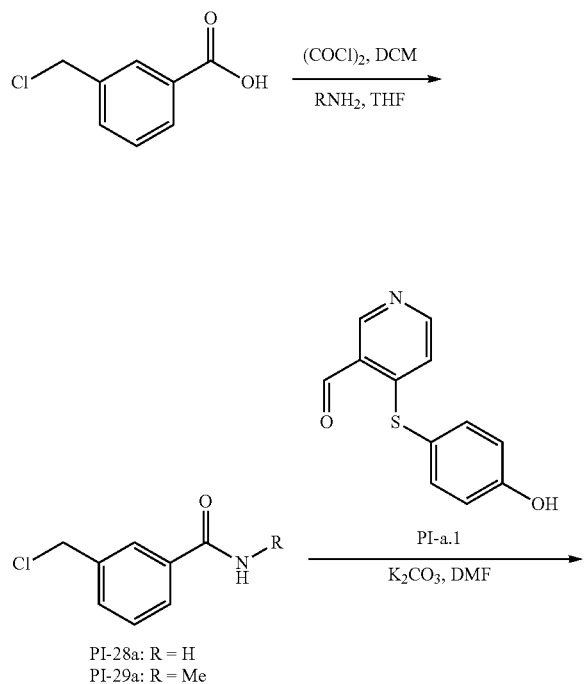

PI-28a: R = H
PI-29a: R = Me

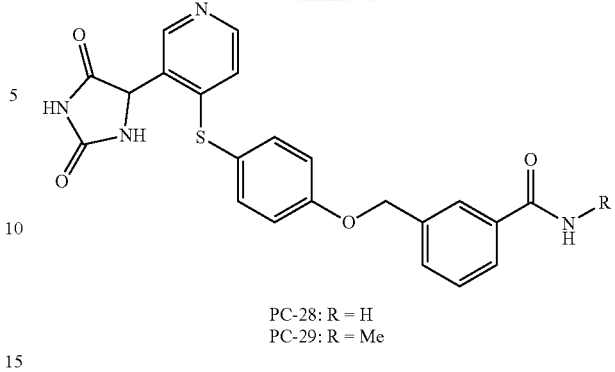

PC-28: R = H
PC-29: R = Me

To a mixture of 3-(chloromethyl)benzoic acid (1.7 g, 9.965 mmol, 1.0 eq) in DCM (50 mL) was added (COCl)$_2$ (1.7 mL, 19.931 mmol, 2.0 eq) drop wise at 0° C. The mixture was stirred for 1 h while the solution became clarified. Then the mixture was concentrated under reduced pressure. To a mixture of the residue in DCM was added a solution of NH$_3$ in THF at −10° C. The mixture was stirred for 0.5 h and then concentrated under reduced pressure to give compound PI-28a (1.3 g, 77%)

To a mixture of compound PI-28a (1.0 g, 5.92 mmol, 1.0 eq) in DMF (50 mL) was successively added compound PI-a.1 (1.36 g, 5.92 mmol, 1.0 eq) and K$_2$CO$_3$ (2.45 g, 17.76 mmol, 3.0 eq). The mixture was stirred at room temperature for 16 h under nitrogen atmosphere. Then 3 M HCl was added to adjust the pH=6 to 7. The mixture was extracted with EA and the organic layer was washed with brine, dried over Na$_2$SO$_4$, and concentrated under reduced pressure. The residue was purified by column chromatography on silica gel to give compound PI-28b (850 mg, 40%).

To a mixture of compound PI-28b (850 mg, 2.33 mmol, 1.0 eq) in MeOH (10 mL) was added KCN (303 mg, 4.66 mmol, 2.0 eq) and (NH$_4$)$_2$CO$_3$ (904 mg, 9.33 mmol, 4.0 eq). The mixture was stirred at 45° C. for 16 h. Then the mixture was diluted with water and extracted with ethyl acetate. The organic phase was dried over anhydrous Na$_2$SO$_4$ and concentrated under reduced pressure. The residue was purified by Prep-TLC to give compound PC-28 (500 mg, 49%) as a white solid.

Compound PC-29 was synthesized in the same procedure except that NH$_3$ was replaced with MeNH$_2$.

Preparation of Compounds PC-30, PC-31, PC-32 and PC-33:

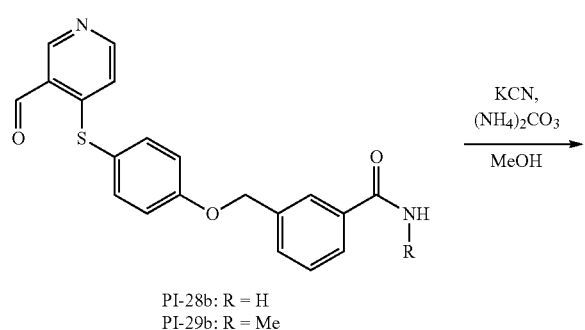

PI-28b: R = H
PI-29b: R = Me

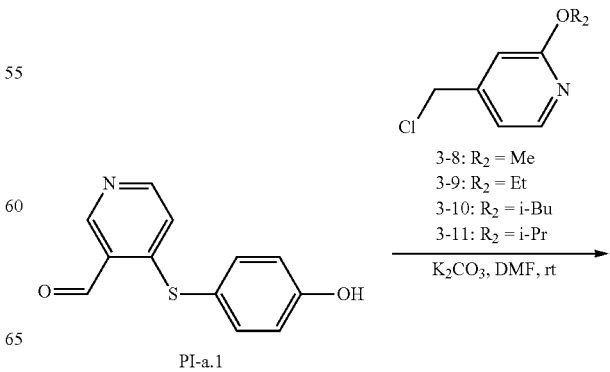

PI-a.1

3-8: R$_2$ = Me
3-9: R$_2$ = Et
3-10: R$_2$ = i-Bu
3-11: R$_2$ = i-Pr

-continued

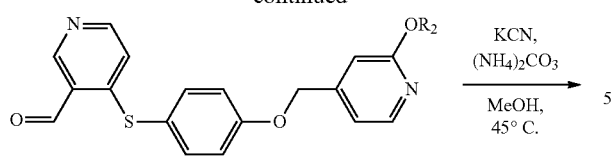

PI-30: R₂ = Me
PI-31: R₂ = Et
PI-32: R₂ = i-Pr
PI-33: R₂ = i-Bu

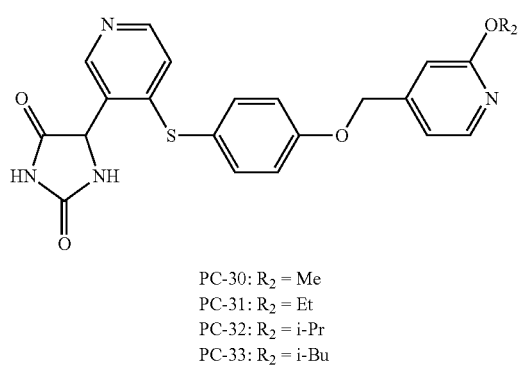

PC-30: R₂ = Me
PC-31: R₂ = Et
PC-32: R₂ = i-Pr
PC-33: R₂ = i-Bu

To a mixture of compound 3-8 (750 mg, 3.876 mmol, 1.0 eq) in DMF (15 mL) was successively added compound PI-a.1 (895 mg, 3.876 mmol, 1.0 eq) and K₂CO₃ (2.14 g, 15.5 mmol, 4.0 eq). The mixture was stirred at room temperature for 16 h under nitrogen atmosphere. Then 3 M HCl was added to adjust the pH=6 to 7. The mixture was extracted with EA and the organic layer was washed with brine, dried over Na₂SO₄, and concentrated under reduced pressure. The residue was purified by column chromatography on a silica gel (PE/EA, 1:1) to give compound PI-30 (610 mg, 36%).

To a solution of compound PI-30 (500 mg, 1.419 mmol, 1.0 eq) in MeOH (6 mL) was added (NH₄)₂CO₃ (545 mg, 5.676 mmol, 4.0 eq) and KCN (185 mg, 2.838 mmol, 2.0 eq). The mixture was stirred at 45° C. for 16 h. The reaction was added with 3 M HCl to adjust the pH=1 to 2 and stirred at room temperature for 1 h, then a saturated aqueous solution of NaHCO₃ was added to adjust the pH=6 to 7 and extracted with ethyl acetate. The organic layer was washed with brine, dried over anhydrous Na₂SO₄ and concentrated under reduced pressure. The residue was purified by Prep-TLC to give PC-30 (350 mg, 58%) as a white solid. Compounds PC-31, PC-32 and PC-33 were synthesized in the same fashion except intermediate 3-8 was replaced with 3-9, 3-11, and 3-10, accordingly.

Preparation of Compounds PC-34 and PC-36:

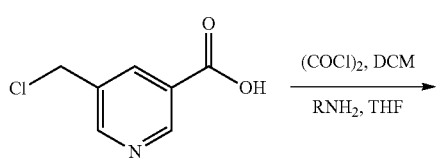

-continued

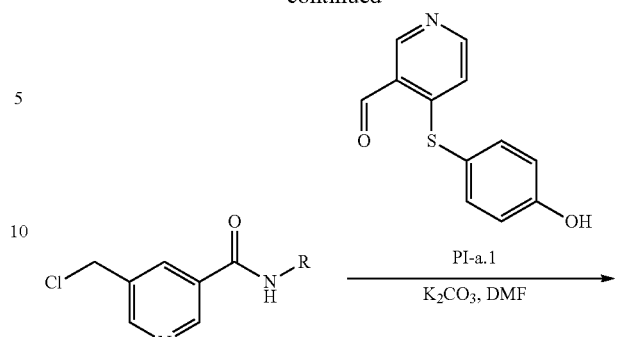

PI-34a: R = H
PI-36a: R = Me

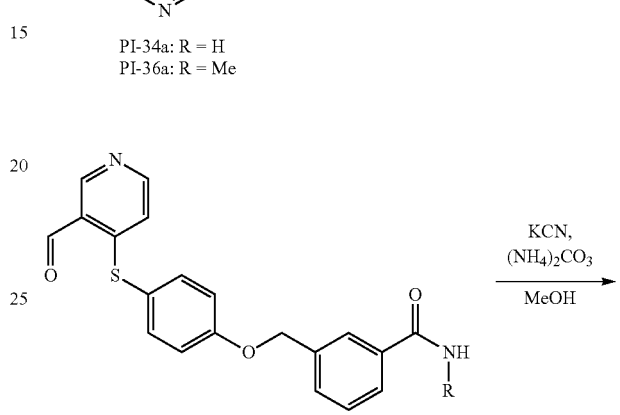

PI-34b: R = H
PI-36b: R = Me

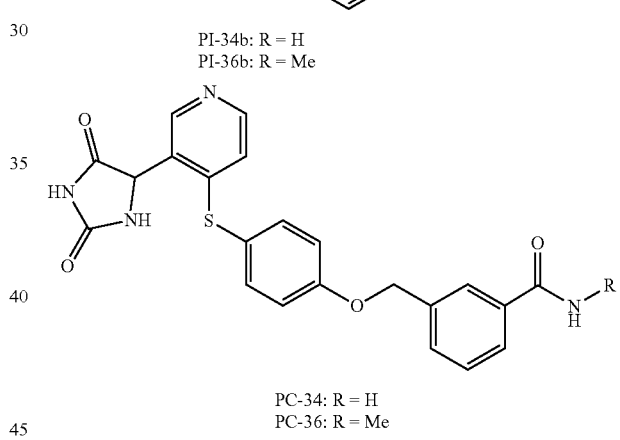

PC-34: R = H
PC-36: R = Me

Compounds PC-34 and PC-36 were synthesized according to the same procedure as the synthesis of compounds PC-28 and PC-29 except that starting material 3-(chloromethyl)benzoic acid was replaced with 5-(chloromethyl)nicotinic acid.

Preparation of Compound PC-35:

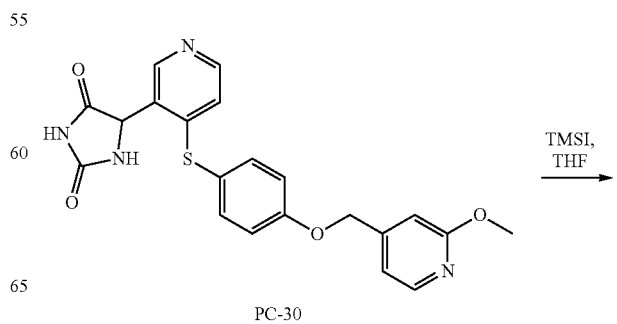

PC-30

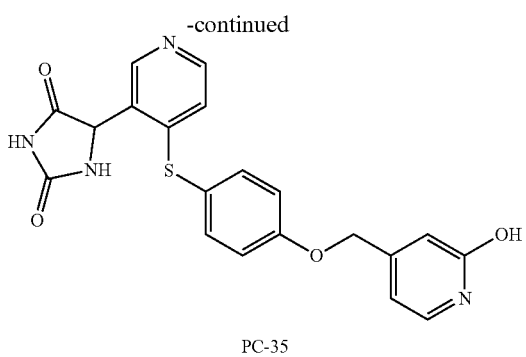

PC-35

To a solution of compound PC-30 (400 mg, 0.95 mmol, 1.0 eq) in CHCl₃ (30 mL) was added TMS-I (1.35 mL, 9.5 mmol, 10.0 eq). The mixture was stirred at 55° C. for 16 h. The reaction mixture was cooled to room temperature and concentrated under reduced pressure. The residue was purified by prep-TLC (EA:MeOH, 10:1) to provide compound PC-35 (350 mg, 90%) as a white solid.

Preparation of Compound PC-37:

Compound PC-37 was synthesized according to the same procedure as the synthesis of compound PC-28 except that the intermediate PC-28a was replaced with FI-18a.

Preparation of Compound PC-38:

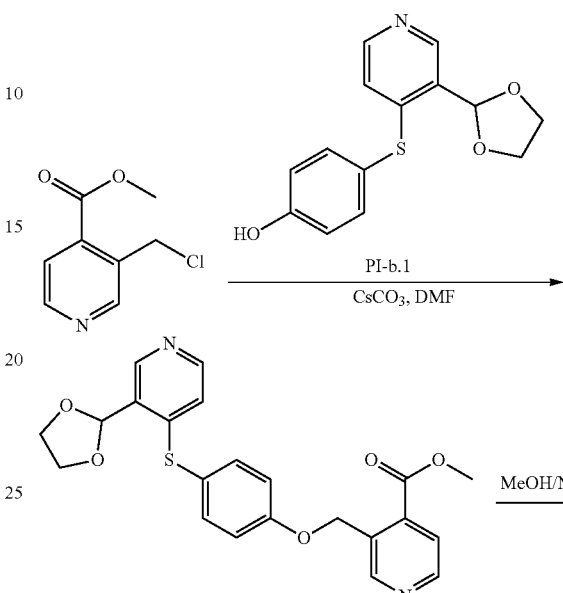

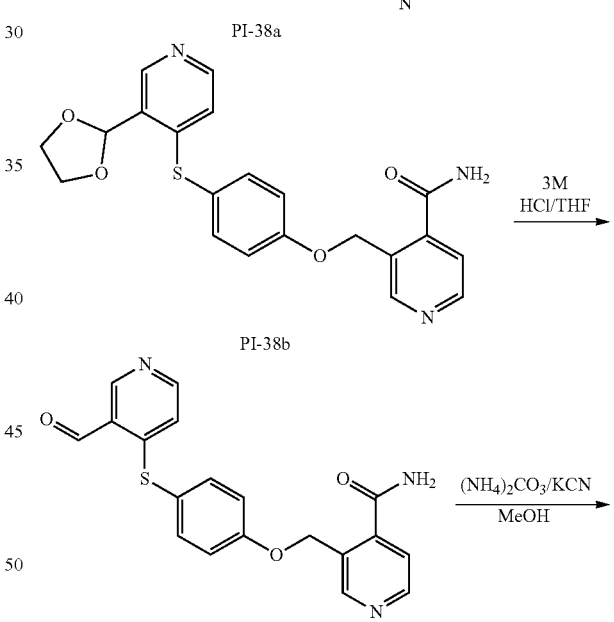

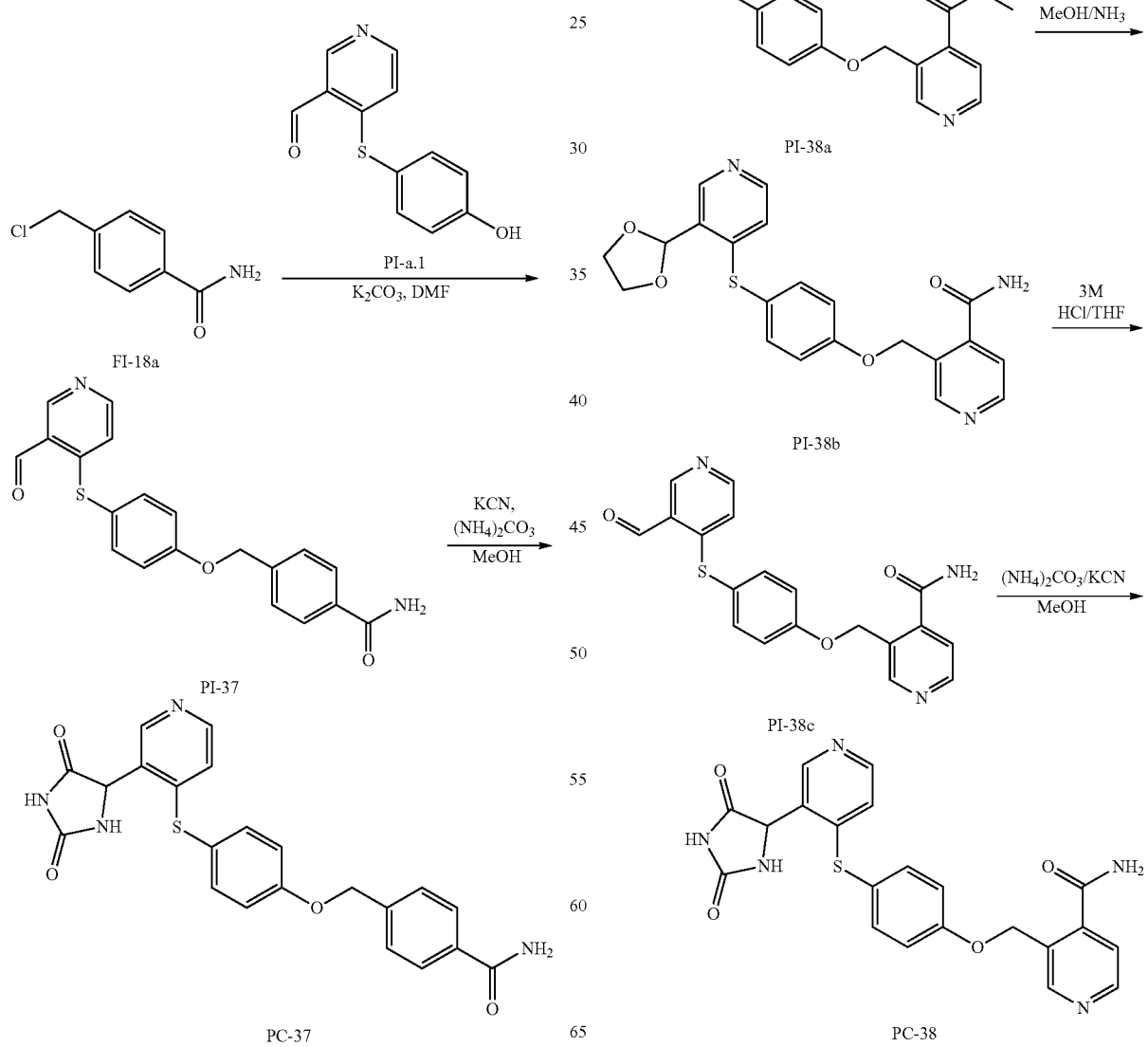

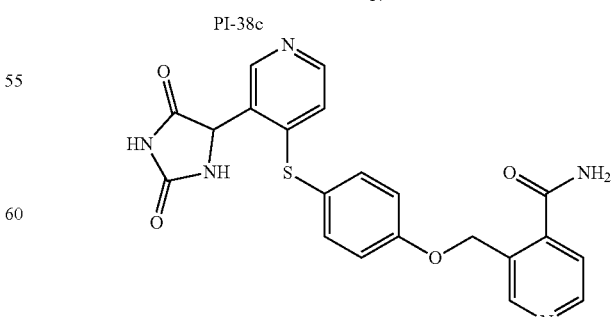

To a mixture of methyl 3-(chloromethyl)isonicotinate (800 mg, 4.32 mmol, 1.0 eq) in DMF (10 mL) was successively added compound PI-b.1 (1.19 g, 4.32 mmol, 1.0 eq) and $CsCO_3$ (4.23 g, 12.97 mmol, 3.0 eq). The mixture was stirred at room temperature for 16 h under nitrogen atmosphere. TLC analysis of the reaction mixture showed full conversion to the desired product. Then the mixture was diluted with $H_2O$ (50 mL) and extracted with EA (3×50 mL). The combined organic layers were washed with a saturated aqueous solution of $NH_4Cl$ (3×50 mL), brine, dried over anhydrous $Na_2SO_4$ and concentrated under reduced pressure. The residue was purified by column chromatography on a silica gel to give compound PI-38a (300 mg, 16%).

A solution of compound PI-38a (300 mg, 0.708 mmol, 1.0 eq) in MeOH (10 mL) was purged with $NH_3$ gas for 10 min at −78° C. The flask was sealed and the mixture was stirred at room temperature for 16 h. TLC analysis of the reaction mixture showed full conversion to the desired product. The mixture was concentrated under reduced pressure and the residue was purified by silica gel chromatography to afford compound PI-38b (180 mg, 62%).

A mixture of compound PI-38b (180 mg, 0.440 mmol, 1.0 eq) in HCl/THF (3.0 M, 2 mL/2 mL) was stirred at 70° C. for 3 h. The reaction mixture was cooled to room temperature and concentrated under reduced pressure. The residue was added with saturated $NaHCO_3$ solution to adjust the pH=8 and extracted with ethyl acetate. The organic layer was washed with brine, dried over anhydrous $Na_2SO_4$ and concentrated under reduced pressure. The residue was purified by prep-TLC to give compound PI-38c (100 mg, 62%).

To a solution of compound PI-38c (90 mg, 0.247 mmol, 1.0 eq) in MeOH (5 mL) was added $(NH_4)_2CO_3$ (94 mg, 0.986 mmol, 4.0 eq) and KCN (32 mg, 0.493 mmol, 2.0 eq). The mixture was stirred at 45° C. for 16 h. The reaction was added with 3 M HCl to adjust the pH=1 to 2 and stirred at room temperature for 1 h, then a saturated aqueous solution of $NaHCO_3$ was added to adjust the pH=6 to 7 and extracted with ethyl acetate. The organic layer was washed with brine, dried over anhydrous $Na_2SO_4$ and concentrated under reduced pressure. The residue was purified by Prep-TLC to give PC-38 (55 mg, 51%) as a white solid.

Preparation of Compounds PC-39 and PC-40:

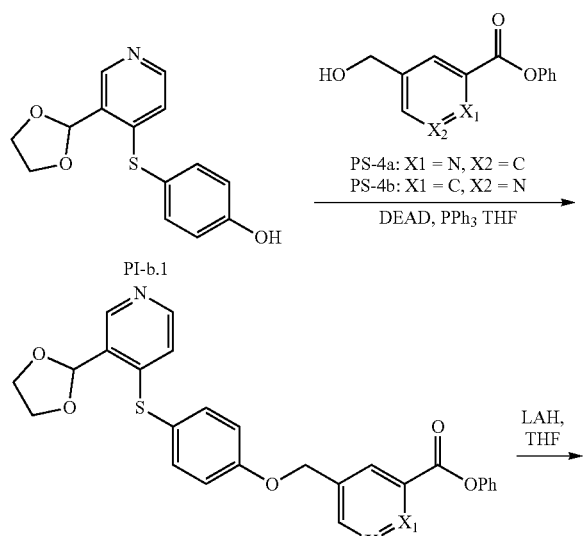
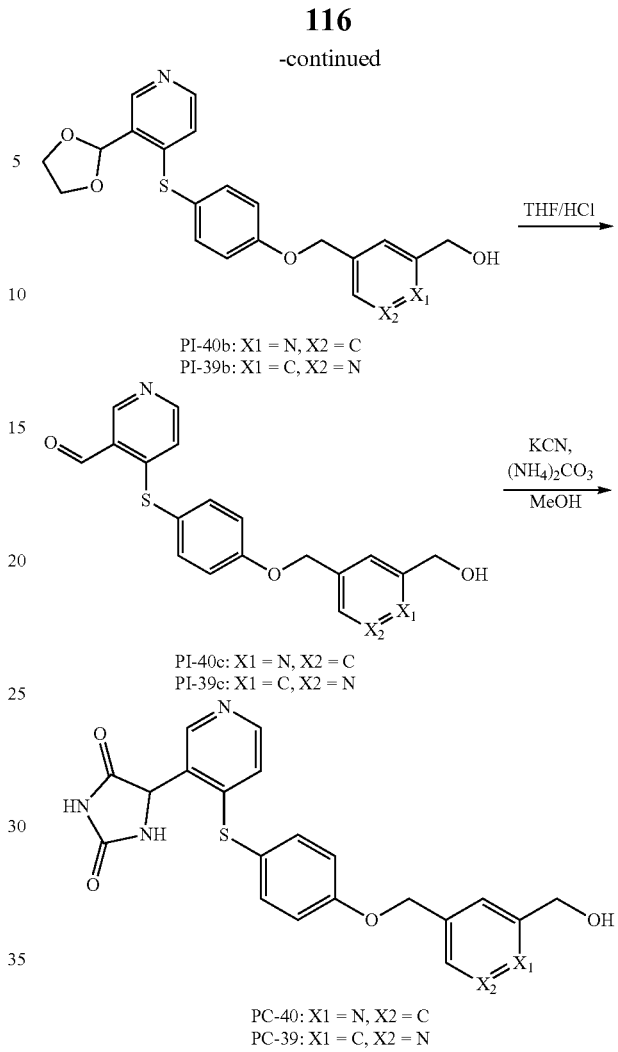

To a solution of compound PI-b.1 (738 mg, 2.68 mmol, 1.0 eq) in THF (20 mL) was successively added compound PS-4b (615 mg, 2.68 mmol, 1.0 eq), $PPh_3$ (1.4 g, 5.37 mmol, 2.0 eq) and DEAD (934 mg, 5.37 mmol, 2.0 eq) at 0° C. The mixture was allowed to warm to room temperature and stirred for 16 h. Then the mixture was quenched with $H_2O$ (50 mL) and extracted with ethyl acetate (2×50 mL). The combined organic layers were dried over anhydrous $Na_2SO_4$ and concentrated under reduced pressure. The residue was purified by column chromatography on a silica gel to give compound PI-39a (490 mg, 37%).

To a mixture of compound PI-39a (300 mg, 0.617 mmol, 1.0 eq) in dry THF (10 mL) was quickly added LAH (47 mg, 1.23 mmol, 2.0 eq) at 0° C. under nitrogen atmosphere. The mixture was stirred at 0° C. for 1 h. TLC analysis of the reaction mixture showed full conversion to the desired product. The reaction was quenched with $Na_2SO_4·10H_2O$ (159 mg, 0.494 mmol, 0.8 eq) and the mixture was stirred for 0.5 h. Then the mixture was filtered, and the organic layer was concentrated under vacuum. The residue was purified by prep-TLC to give compound PI-39b (150 mg, 61%).

A mixture of compound PI-39b (150 mg, 0.379 mmol, 1.0 eq) in HCl/THF (3.0 M, 4 mL/4 mL) was stirred at 70° C. for 16 h. The reaction mixture was cooled to room temperature and concentrated under reduced pressure. The residue was added with saturated $NaHCO_3$ solution to adjust the pH=8 and extracted with ethyl acetate. The organic layer was washed with brine, dried over anhydrous Na$_2$SO$_4$ and concentrated under reduced pressure. The residue was purified by prep-TLC to give compound PI-39c (110 mg, 82%).

To a solution of compound PI-39c (110 mg, 0.313 mmol, 1.0 eq) in MeOH (5 mL) was added (NH$_4$)$_2$CO$_3$ (120 mg, 1.25 mmol, 4.0 eq) and KCN (40 mg, 0.625 mmol, 2.0 eq). The mixture was stirred at 45° C. for 16 h. The reaction was added with 3 M HCl to adjust the pH=1 to 2 and stirred at room temperature for 1 h, then a saturated aqueous solution of NaHCO$_3$ was added to adjust the pH=6 to 7 and extracted with ethyl acetate. The organic layer was washed with brine, dried over anhydrous Na$_2$SO$_4$ and concentrated under reduced pressure. The residue was purified by prep-TLC to give compound PC-39 (49 mg, 37%) as a white solid.

Compound PC-40 was synthesized by the same procedure except that PS-4b was replaced with PS-4a.

Preparation of Compounds PC-41, PC-46, PC-54, and PC-55

To a stirred solution of compound PC-41 (100 mg, 0.238 mmol, 1.0 eq) in DMF (2 mL) was added NaH (12 mg, 0.476 mmol, 2.0 eq) at 0° C. After 10 min, CH$_3$I (68 mg, 0.476 mmol, 2.0 eq) was added. After additional stirring at 0° C. for 0.5 h, the mixture was allowed to warm to room temperature and stirred for 12 h. The reaction mixture was quenched with water and extracted with EA (3×50 mL). The combined organic phases were dried over anhydrous Na$_2$SO$_4$ and concentrated under reduced pressure. The residue was purified by prep-TLC to afford compound PC-46 (40 mg, 37%) as a yellow solid.

To a stirred solution of compound PC-41 (300 mg, 0.714 mmol, 1.0 eq) in DMF (5 mL) was added NaH (17 mg, 0.714 mmol, 1.0 eq) at 0° C. After 10 min, CH$_3$I (101 mg, 0.714 mmol, 1.0 eq) was added. After additional stirring at 0° C. for 0.5 h, the mixture was allowed to warm to room temperature and stirred for 12 h. The reaction mixture was quenched with water and extracted with EA (3×50 mL). The combined organic phases were dried over anhydrous

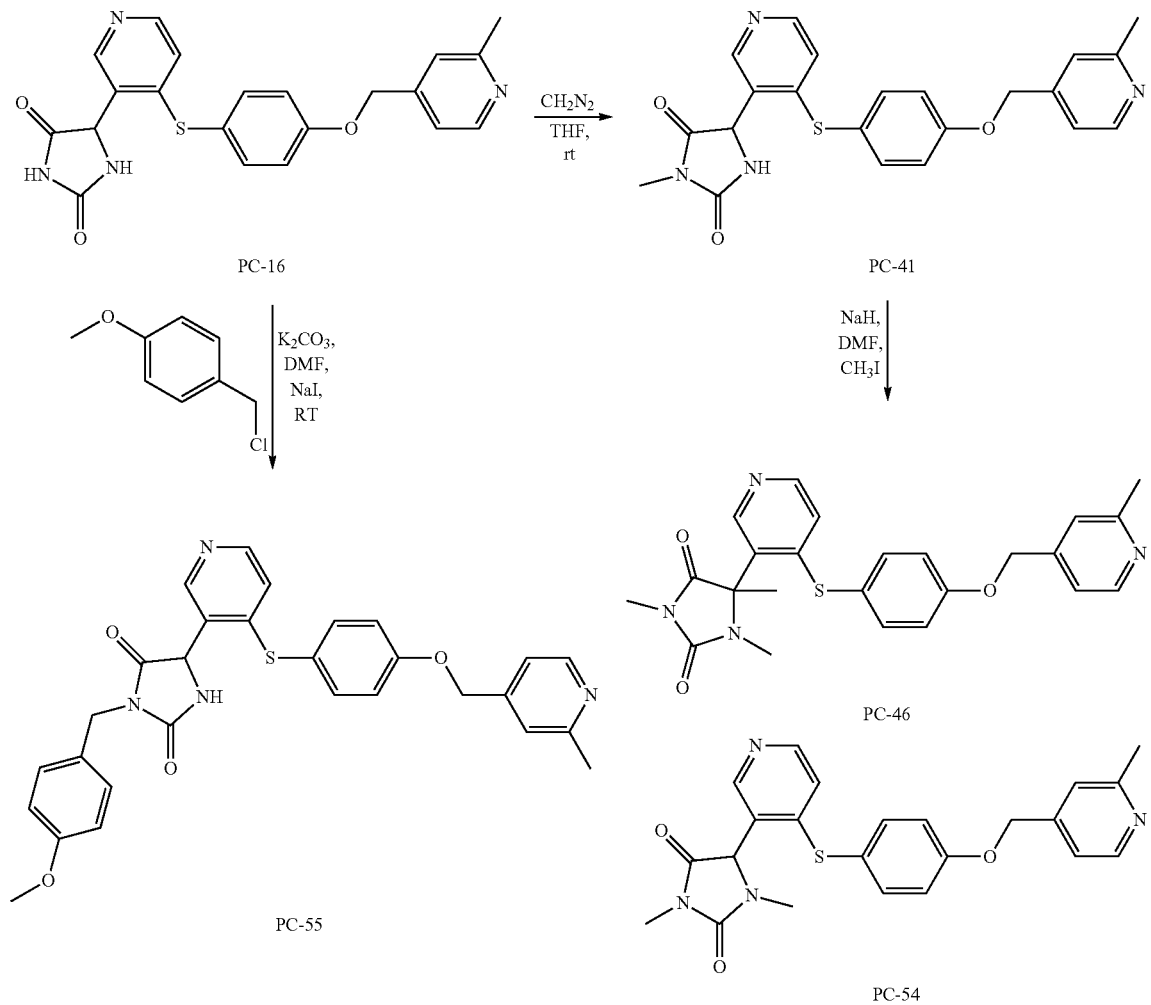

To a mixture of compound PC-16 (250 mg, 0.616 mmol, 1.0 eq) in THF (2 mL) was added CH$_2$N$_2$ (1 M in ether, 3 mL, 3.08 mmol, 5.0 eq). The mixture was stirred at room temperature for 3 h. Then the mixture was concentrated under reduced pressure to give compound PC-41 (80 mg, 30%) as a white solid.

Na$_2$SO$_4$ and concentrated under reduced pressure. The residue was purified by prep-TLC to afford compound PC-54 (45 mg, 14%) as a white solid.

To a solution of compound PC-16 (1 g, 2.46 mmol, 1.0 eq) and 1-(chloromethyl)-4-methoxybenzene (461 mg, 2.96 mmol, 1.2 eq) in DMF (10 mL) was added NaI (369 mg, 2.46 mol, 1.0 eq) and K$_2$CO$_3$ (679 mg, 4.92 mmol, 2.0 eq). The mixture was stirred at room temperature for 16 h. LCMS analysis of the reaction mixture showed full conversion to the desired product. Then the mixture was diluted with water and extracted with DCM. The organic layer was dried over anhydrous Na$_2$SO$_4$ and concentrated under reduced pressure. The residue was purified by silica gel chromatography to afford compound PC-55 (130 mg, 34%) as a pink solid.

Preparation of Compounds PC-42, PC-50 and PC-51:

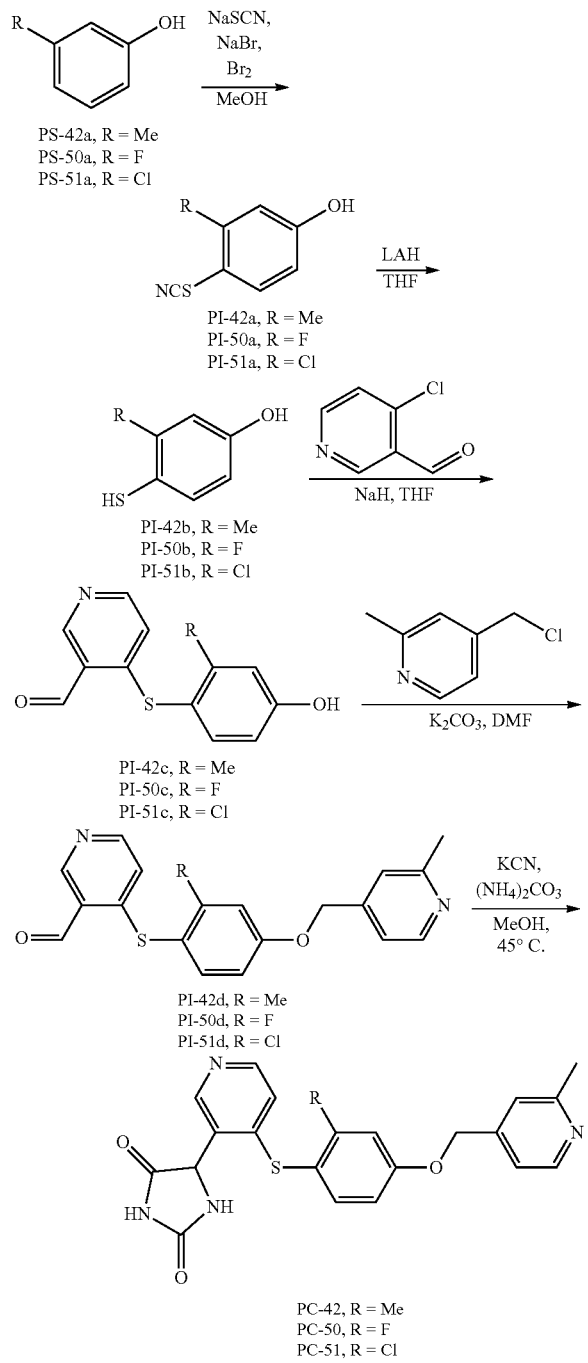

To a mixture of m-cresol (10 g, 92.5 mmol, 1.0 eq) and NaSCN (22.5 g, 277.6 mmol, 3.0 eq) in MeOH (100 mL) was dropwise added a solution of NaBr (9.5 g, 92.5 mmol, 1.0 eq) and Br$_2$ (5.7 mL, 111 mmol, 1.2 eq) in MeOH (100 mL). The mixture was stirred at rt for 14 h. TLC analysis of the reaction mixture showed full conversion to the desired product. The reaction was added with water and extracted with EA (3×100 mL). The organic layer was washed with brine and water, dried over Na$_2$SO$_4$ and concentrated under vacuum. The residue was purified by column chromatography on silica gel to give compound PI-42a (5 g, 33%).

To a mixture of compound PI-42a (5.0 g, 30.3 mmol, 1.0 eq) in dry THF (50 mL) was quickly added LAH (1.72 g, 45.5 mmol, 1.5 eq) at 0° C. under nitrogen atmosphere. The mixture was stirred at rt for 3 h. TLC analysis of the reaction mixture showed full conversion to the desired product. The reaction was quenched with Na$_2$SO$_4$·10H$_2$O and stirred at 0° C. for 0.5 h. Then the mixture was filtered, and the organic layer concentrated under vacuum. The residue was purified by silica gel chromatography to give compound PI-42b (2.9 g, 68%).

To a stirred solution of compound PI-42b (1.0 g, 7.1 mmol, 1.5 eq) in THF (10 mL) was added NaH (170.4 mg, 7.1 mmol, 1.5 eq) at 0° C. After 30 min, 4-chloronicotinaldehyde (667.4 mg, 4.73 mmol, 1.0 eq) was added at 0° C. The mixture was allowed to warm to room temperature and stirred for 16 h. The reaction mixture was quenched with water and extracted with EA (3×10 mL). The combined organic phases were dried over anhydrous Na$_2$SO$_4$ and concentrated under reduced pressure. The residue was purified by silica gel chromatography to afford compound PI-42c (1.2 g, 100%).

To a mixture of compound PI-42c (200 mg, 0.82 mmol, 1.0 eq) and 4-(chloromethyl)-2-methylpyridine (130 mg, 0.902 mmol, 1.1 eq) in DMF (2 mL) was successively added K$_2$CO$_3$ (340 mg, 2.46 mmol, 3.0 eq). The mixture was stirred at 50° C. for 3 h under nitrogen atmosphere. TLC analysis of the reaction mixture showed full conversion to the desired product. Then the mixture was poured into water and extracted with EA (3×5 mL). The combined organic layers were washed with brine, dried over anhydrous Na$_2$SO$_4$ and concentrated under reduced pressure. The residue was purified by column chromatography on silica gel to give compound PI-42d (150 mg, 52%).

To a solution of compound PI-42d (190 mg, 0.54 mmol, 1.0 eq) in MeOH (2 mL) was added (NH$_4$)$_2$CO$_3$ (208.45 mg, 2.17 mmol, 4.0 eq) and KCN (70.2 mg, 1.08 mmol, 2.0 eq). The mixture was stirred at 45° C. for 16 h. The reaction was added with 3 M HCl to adjust the pH=1 to 2 and stirred at room temperature for 1 h, then a saturated aqueous solution of NaHCO$_3$ was added to adjust the pH=6 to 7 and extracted with ethyl acetate. The organic layer was washed with brine, dried over anhydrous Na$_2$SO$_4$ and concentrated under reduced pressure. The residue was purified by Prep-TLC to give compound PC-42 (200 mg, 88%) as a white solid. Compounds PC-50 and PC-51 were synthesized in the same fashion except that the starting material m-cresol was replaced with 3-fluorophenol and 3-chlorophenol, accordingly.

Preparation of Compounds PC-48, PC-49 and PC-52:

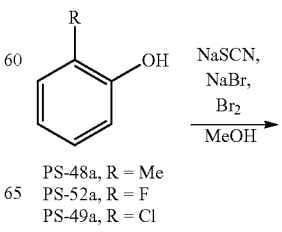

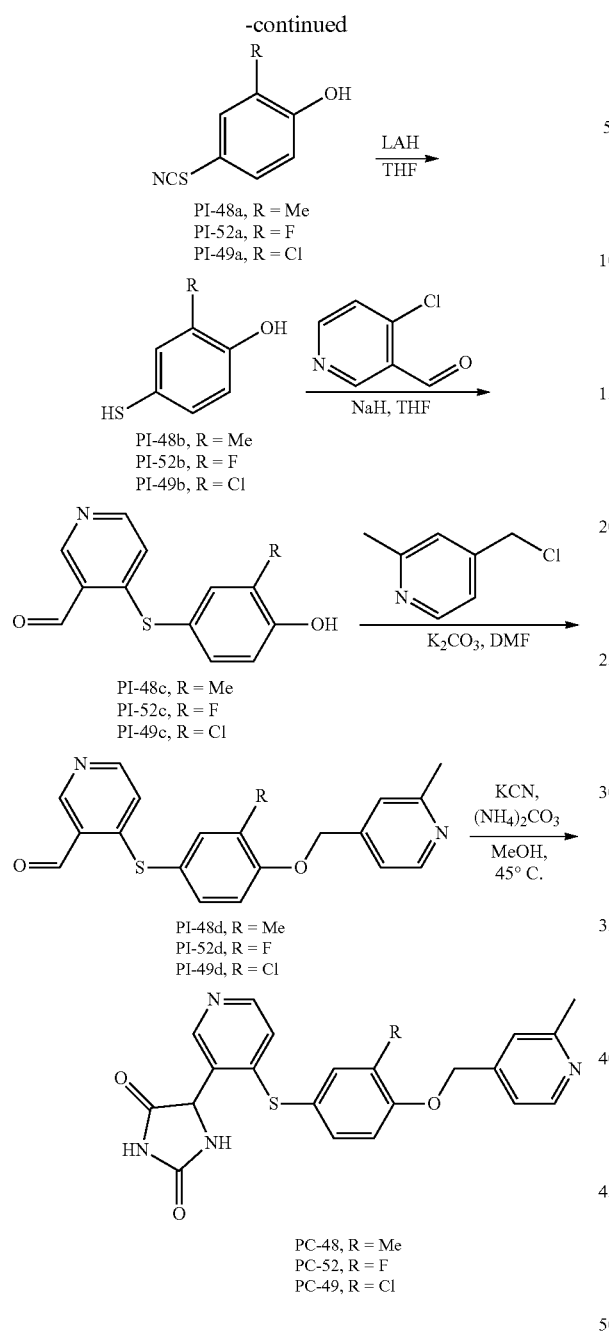
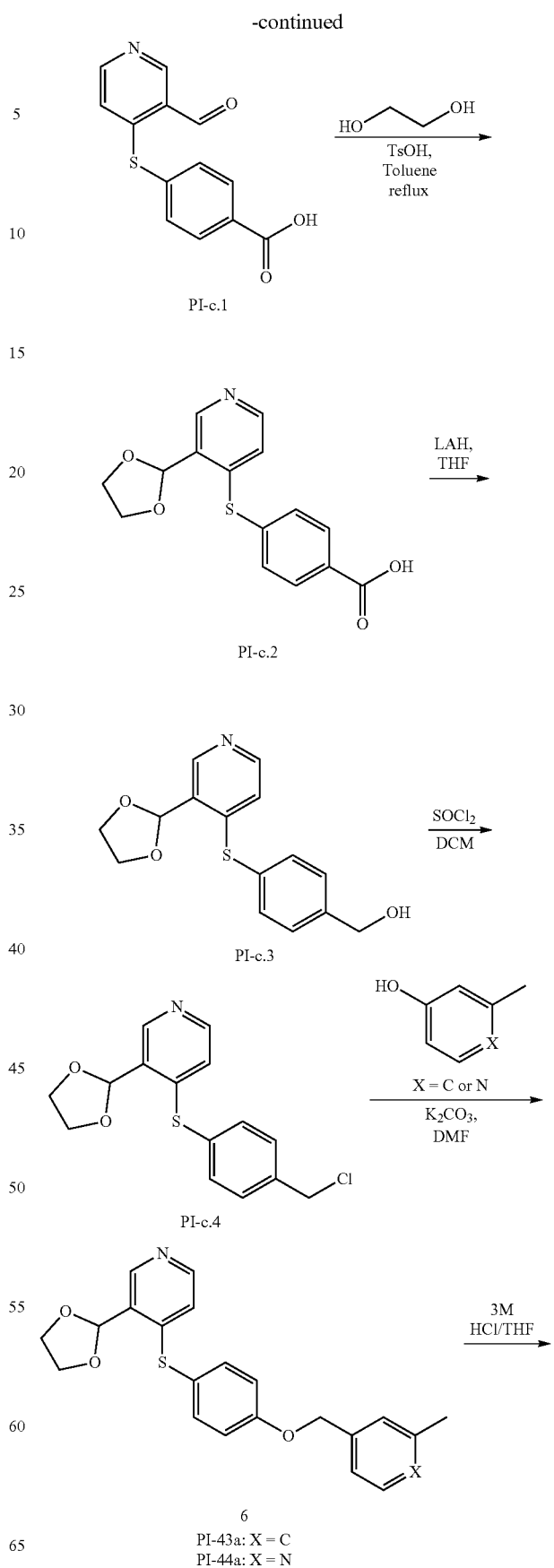
Compounds PC-48, PC-49 and PC-52 were synthesized by the same procedure as the synthesis of PC-42 except that the starting material m-cresol was replaced with o-cresol, 2-chlorophenol and 2-fluorophenol, accordingly.
Preparation of Compounds PC-43 and PC-44:
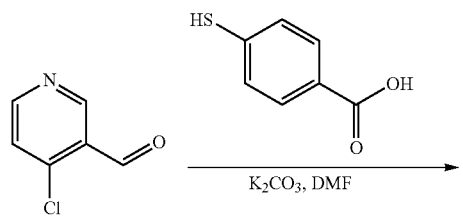

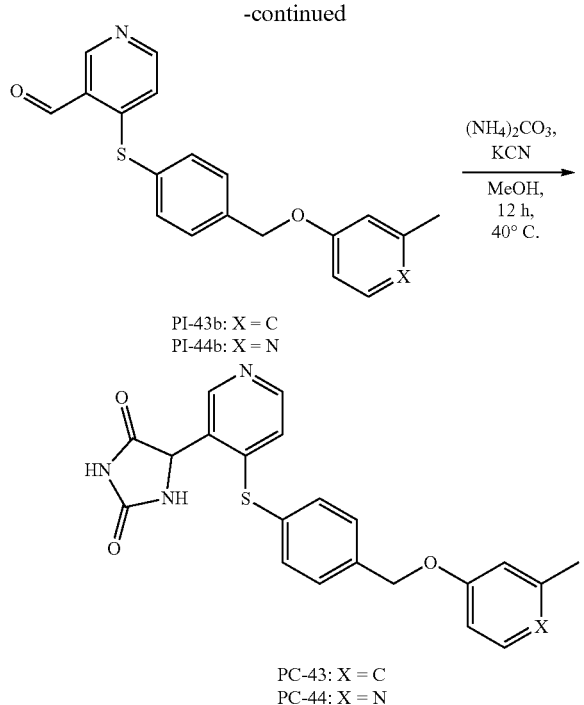

PI-43b: X = C
PI-44b: X = N

PC-43: X = C
PC-44: X = N

To a solution of 4-chloronicotinaldehyde (10 g, 70.92 mmol, 1.0 eq) in DMF (100 mL) was added 4-mercaptobenzoic acid (13.1 g, 85.11 mmol, 1.2 eq) and $K_2CO_3$ (29.4 g, 0.213 mol, 3.0 eq) at room temperature under nitrogen atmosphere. The mixture was stirred at room temperature for 16 h. TLC analysis of the reaction mixture showed full conversion to the desired product. Then the mixture was diluted with water and extracted with ethyl acetate. The organic layer was washed with brine, dried over anhydrous $Na_2SO_4$ and concentrated under reduced pressure. The residue was purified by silica gel chromatography to afford PI-c.1 (11 g, 59%).

To a stirred solution of PI-c.1 (11 g, 42.47 mmol, 1.0 eq) in THF (100 mL) was added TsOH (731 mg, 4.25 mmol, 0.1 eq). After 10 min, ethane-1,2-diol (13.1 g, 0.212 mol, 5.0 eq) in THF (50 mL) was added drop wise. The mixture was stirred at 110° C. for 16 h. The reaction mixture was poured over saturated $NaHCO_3$ solution (160 mL) and extracted with EA (3×100 mL). The combined organic phases were dried over anhydrous $Na_2SO_4$ and concentrated under reduced pressure. The residue was purified by silica gel chromatography to afford PI-c.2 (8 g, 62%).

To a mixture of PI-c.2 (8 g, 26.40 mmol, 1.0 eq) in dry THF (100 mL) was quickly added LAH (2 g, 52.81 mmol, 2.0 eq) at 0° C. under nitrogen atmosphere. The mixture was stirred at 0° C. for 1 h. TLC analysis of the reaction mixture showed full conversion to the desired product. The reaction was quenched with $Na_2SO_4 \cdot 10H_2O$ (6.8 g, 21.12 mmol, 0.8 eq) and the mixture was stirred for 0.5 h. The mixture is extracted and then the organic layer was dried over anhydrous $Na_2SO_4$ and concentrated under reduced pressure. The residue was purified by silica gel chromatography to give PI-c.3 (4 g, 52%).

To a mixture of PI-c.3 (1 g, 3.46 mmol, 1.0 eq) in DCM (10 mL) was added $SOCl_2$ (824 mg, 6.92 mmol, 2.0 eq) at 0° C. under nitrogen atmosphere. The mixture was stirred at 0° C. for 4 h. TLC analysis of the reaction mixture showed full conversion to the desired product. The reaction was added with $NaHCO_3$ (aq.) to adjust the pH>7 and extracted with DCM. Then the organic layer was dried over anhydrous $Na_2SO_4$ and concentrated under reduced pressure. The residue was purified by silica gel chromatography to give PI-c.4 (1 g, 94%).

To a solution of compound PI-c.4 (500 mg, 1.63 mmol, 1.0 eq) in DMF (5 mL) was added m-cresol (211 mg, 1.95 mmol, 1.2 eq) and $K_2CO_3$ (675 mg, 4.89 mmol, 3.0 eq) at room temperature under nitrogen atmosphere. The mixture was stirred at room temperature for 16 h. TLC analysis of the reaction mixture showed full conversion to the desired product. Then the mixture was diluted with water and extracted with ethyl acetate. The organic layer was washed with brine, dried over anhydrous $Na_2SO_4$ and concentrated under reduced pressure. The residue was purified by silica gel chromatography to afford compound PI-43a (230 mg, 37%).

A mixture of PI-43a (230 mg, 0.607 mmol, 1.0 eq) in HCl/THF (3.0 M, 2 mL/2 mL) was stirred at 70° C. for 14 h. The reaction mixture was cooled to room temperature and concentrated under reduced pressure. The residue was added with saturated $NaHCO_3$ solution to adjust the pH=8 and extracted with ethyl acetate. The organic layer was washed with brine, dried over anhydrous $Na_2SO_4$ and concentrated under reduced pressure. The residue was purified by silica gel chromatography to give PI-43b (150 mg, 73%).

To a solution of PI-43b (150 mg, 0.448 mmol, 1.0 eq) in MeOH (3 mL) was added $(NH_4)_2CO_3$ (172 mg, 1.79 mmol, 4.0 eq) and KCN (58 mg, 0.896 mmol, 2.0 eq). The mixture was stirred at 40° C. for 12 h. The reaction was added with 3 M HCl to adjust the pH=1 to 2 and stirred at room temperature for 1 h, then a saturated aqueous solution of $NaHCO_3$ was added to adjust the pH=6 to 7 and extracted with ethyl acetate. The organic layer was washed with brine, dried over anhydrous $Na_2SO_4$ and concentrated under reduced pressure. The residue was purified by prep-TLC to give compound PC-43 (40 mg, 22%) as a white solid.

Compound PC-44 was synthesized in the same fashion except that m-cresol was replaced with 2-methylpyridin-4-ol.

Preparation of Compound PC-45:

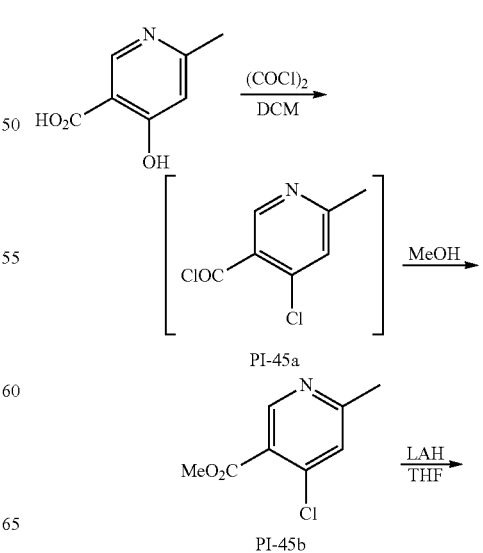

PI-45a

PI-45b

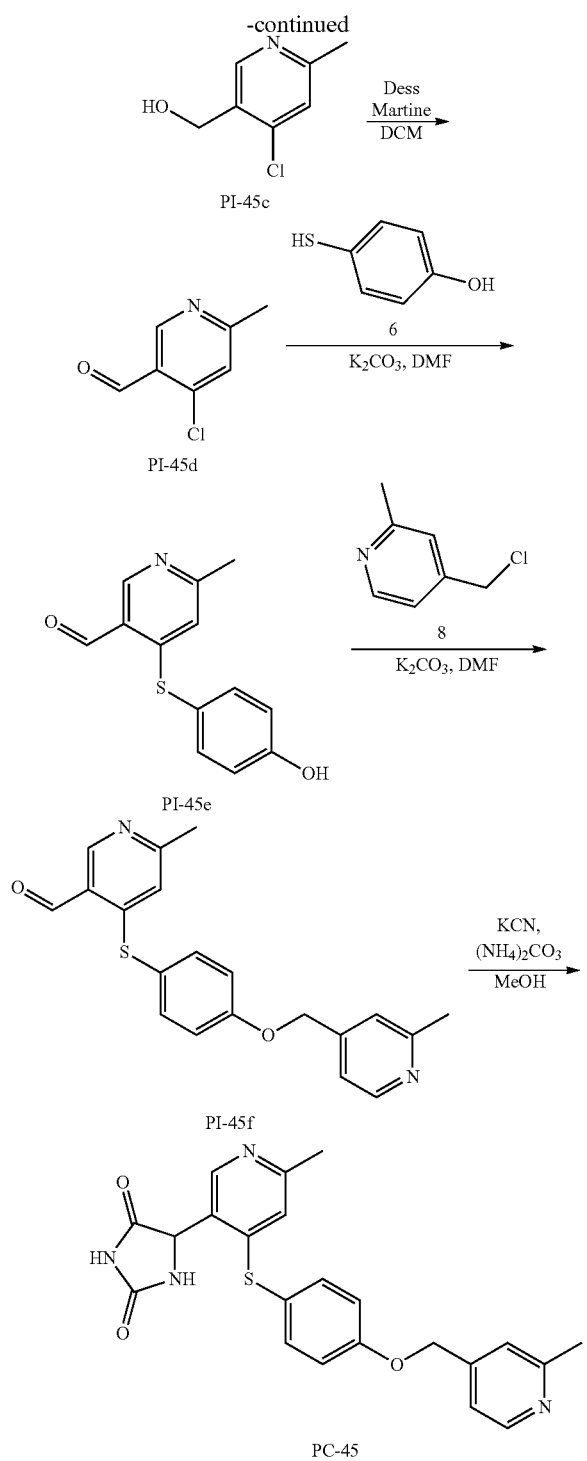

trated under vacuum. The residue was purified by silica gel chromatography to give crude PI-45b (12 g, 100%).

To a mixture of PI-45b (12.0 g, 64.86 mmol, 1.0 eq) in dry THF (100 mL) was quickly added LAH (3.69 g, 97.3 mmol, 1.5 eq) at 0° C. under nitrogen atmosphere. The mixture was stirred at rt for 3 h. TLC analysis of the reaction mixture showed full conversion to the desired product. The reaction was quenched with $Na_2SO_4·10H_2O$ and stirred at 0° C. for 0.5 h. Then the mixture was filtered, and the organic layer concentrated under vacuum. The residue was purified by silica gel chromatography to give PI-45c (6.0 g, 59%).

To a stirred solution of PI-45c (6.0 g, 38.2 mmol, 1.0 eq) in DCM (60 mL) was added Dess-Martin periodinane (32.4 g, 76.4 mmol, 2.0 eq). The mixture was stirred at rt for 16 h. The reaction mixture was quenched with water and extracted with EA (3×60 mL). The combined organic phases were dried over anhydrous $Na_2SO_4$ and concentrated under reduced pressure. The residue was purified by silica gel chromatography to afford PI-45d (2.3 g, 39%).

To a mixture of PI-45d (2.3 g, 14.8 mmol, 1.0 eq) and 4-mercaptophenol (2.06 g, 16.3 mmol, 1.1 eq) in DMF (25 mL) was successively added $K_2CO_3$ (6.14 g, 44.4 mmol, 3.0 eq). The mixture was stirred at 50° C. for 3 h under nitrogen atmosphere. TLC analysis of the reaction mixture showed full conversion to the desired product. Then the mixture was poured into water and extracted with EA (3×30 mL). The combined organic layers were washed with brine, dried over anhydrous $Na_2SO_4$ and concentrated under reduced pressure. The residue was purified by column chromatography on a silica gel to give PI-45e (1.6 g, 44%).

To a mixture of PI-45e (1.0 g, 4.08 mmol, 1.0 eq) and 4-(chloromethyl)-2-methylpyridine (633 mg, 4.48 mmol, 1.1 eq) in DMF (10 mL) was successively added $K_2CO_3$ (1.69 g, 12.24 mmol, 3.0 eq). The mixture was stirred at 50° C. for 3 h under nitrogen atmosphere. TLC analysis of the reaction mixture showed full conversion to the desired product. Then the mixture was poured into water and extracted with EA (3×10 mL). The combined organic layers were washed with brine, dried over anhydrous $Na_2SO_4$ and concentrated under reduced pressure. The residue was purified by column chromatography on silica gel to give PI-45f (700 mg, 49%).

To a solution of PI-45f (700 mg, 2.0 mmol, 1.0 eq) in MeOH (1 mL) was added $(NH_4)_2CO_3$ (767.8 mg, 8.0 mmol, 4.0 eq) and KCN (260 mg, 4.0 mmol, 2.0 eq). The mixture was stirred at 45° C. for 16 h. The reaction was added with 3 M HCl to adjust the pH=1 to 2 and stirred at room temperature for 1 h, then a saturated aqueous solution of $NaHCO_3$ was added to adjust the pH=6 to 7 and extracted with ethyl acetate. The organic layer was washed with brine, dried over anhydrous $Na_2SO_4$ and concentrated under reduced pressure. The residue was purified by Prep-TLC to give PC-45 (512 mg, 61%) as a white solid.

Preparation of Compounds PC-47 and PC-53:

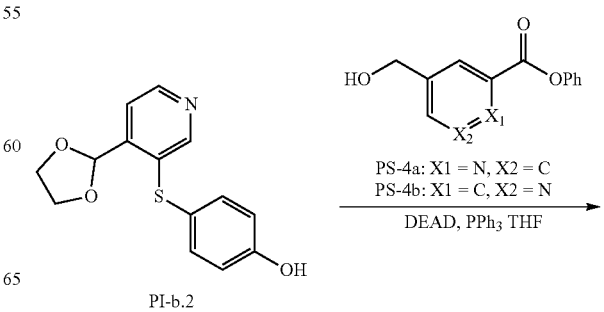

To a mixture of 4-hydroxy-6-methylnicotinic acid (10 g, 65.4 mmol, 1.0 eq) in DCM (100 mL), a solution of $(COCl)_2$ (12.35 g, 98.1 mmol, 1.5 eq) was added dropwise at 0° C. The mixture was stirred for 12 h. TLC analysis of the reaction mixture showed full conversion to the desired product. The reaction was dried over $Na_2SO_4$ and concentrated under vacuum to give crude PI-45a (10 g, crude).

A mixture of PI-45a (10 g, 52.9 mmol, 1.0 eq) in MeOH (100 mL) was stirred at rt for 2 h. TLC analysis of the reaction mixture showed full conversion to the desired product. The reaction was dried over $Na_2SO_4$ and concen- 127
-continued
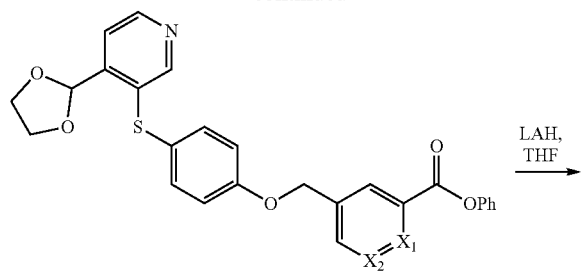
PI-47a: X1 = N, X2 = C
PI-53a: X1 = C, X2 = N
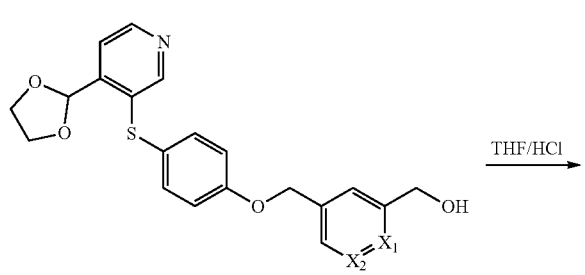
PI-47b: X1 = N, X2 = C
PI-53b: X1 = C, X2 = N
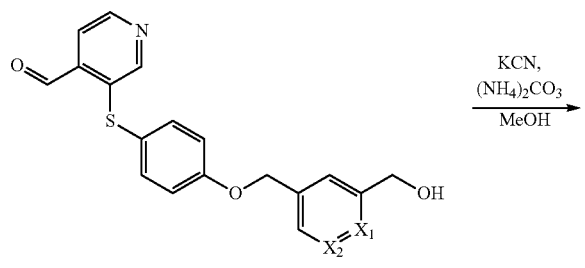
PI-47c: X1 = N, X2 = C
PI-53c: X1 = C, X2 = N
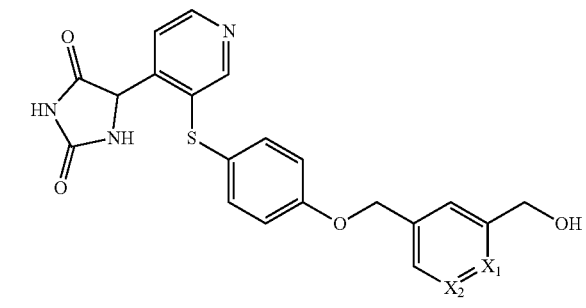
PC-47: X1 = N, X2 = C
PC-53: X1 = C, X2 = N
Compounds PC-47 and PC-53 were synthesized by the same procedure as the synthesis of PC-39 and PC-40 except that the starting material PI-b.1 was replaced with PI-b.2.
Preparation of Compound PC-56:
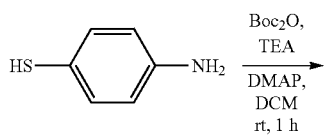
128
-continued
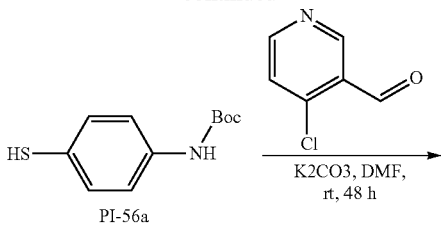
PI-56a
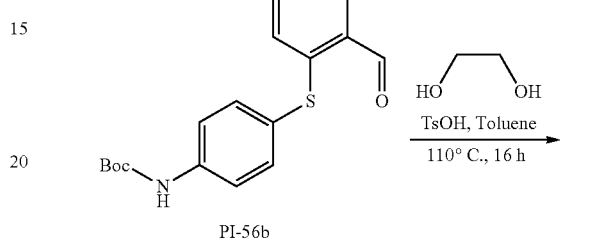
PI-56b
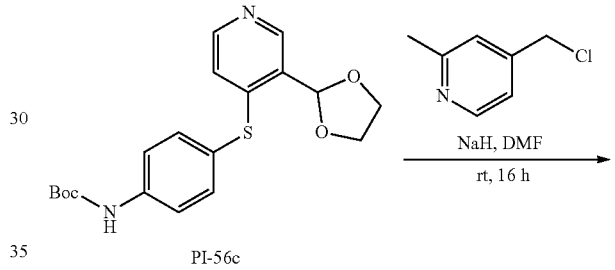
PI-56c
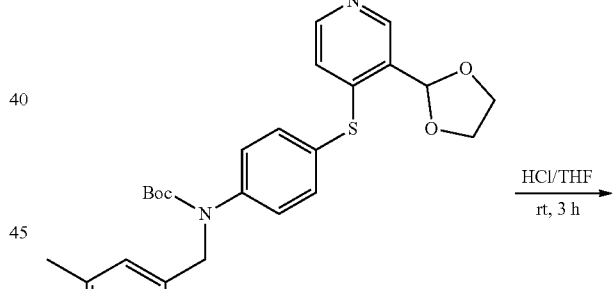
PI-56d
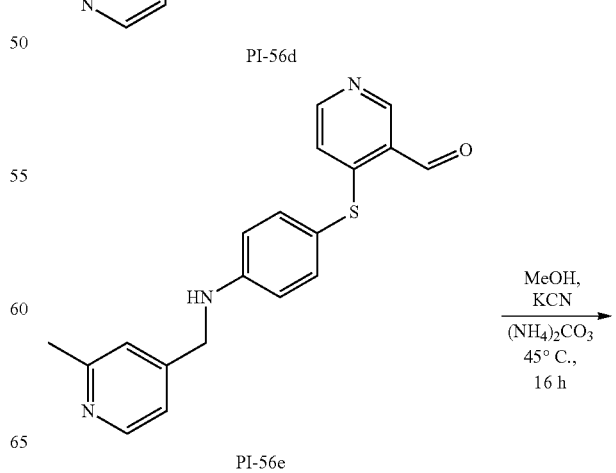
PI-56e -continued

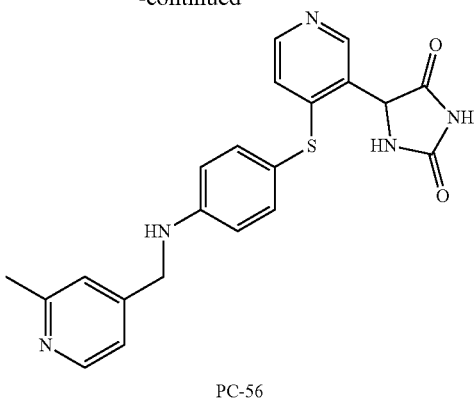

PC-56

To a solution of 4-aminothiophenol (16 g, 127.8 mmol, 1.0 eq) and Boc₂O (55.2 g, 255.6 mmol, 2.0 eq) in DCM (200 mL) was added TEA (25.8 g, 255.6 mmol, 2.0 eq) and DMAP (1.56 g, 12.78 mmol, 0.05 eq) at −0° C. The mixture was stirred at room temperature for 16 h under nitrogen atmosphere. Then the mixture was quenched with saturated NH₄Cl solution. The mixture was extracted with ethyl acetate. The combined organic phases were washed with brine, dried over anhydrous Na₂SO₄ and concentrated under reduced pressure. The residue was purified by silica gel chromatography to afford PI-56a (8.1 g, 28%).

To a solution of PI-56a (5 g, 22.19 mmol, 1.0 eq) in DMF (40 mL) was added 4-chloronicotinaldehyde (3.14 g, 22.19 mmol, 1.0 eq) and K₂CO₃ (9.12 g, 66.57 mmol, 3.0 eq) at room temperature under nitrogen atmosphere. The mixture was stirred at room temperature for 16 h. TLC analysis of the reaction mixture showed full conversion to the desired product. Then the mixture was diluted with water and extracted with ethyl acetate. The organic layer was washed with brine, dried over anhydrous Na₂SO₄ and concentrated under reduced pressure. The residue was purified by silica gel chromatography to afford PI-56b (1.4 g, 19%).

To a mixture of PI-56b (0.6 g, 1.82 mmol, 1.0 eq) in toluene (50 mL) was successively added ethane-1,2-diol (2.25 g, 36.3 mmol, 20 eq) and TsOH (0.02 g, 0.09 mmol, 0.05 eq). The mixture was heated under reflux for 12 h under nitrogen atmosphere. Then the mixture was concentrated under reduced pressure. The residue was purified by column chromatography on a silica gel to give PI-56c (0.25 g, 36%).

To a solution of PI-56c (0.2 g, 0.53 mmol, 1.0 eq) in DMF (5 mL) was added compound 4-(chloromethyl)-2-methylpyridine (0.09 g, 0.64 mmol, 1.2 eq) and NaH (14 mg, 0.58 mmol, 1.1 eq, 60%) at room temperature under nitrogen atmosphere. The mixture was stirred at room temperature for 16 h. TLC analysis of the reaction mixture showed full conversion to the desired product. Then the mixture was diluted with water and extracted with ethyl acetate. The organic layer was washed with brine, dried over anhydrous Na₂SO₄ and concentrated under reduced pressure. The residue was purified by silica gel chromatography to afford PI-56d (0.13 g, 51%).

A mixture of PI-56d (250 mg, 0.52 mmol, 1.0 eq) in HCl/THF (2.0 M, 3 mL/3 mL) was stirred at room temperature for 5 h. The reaction mixture was concentrated under reduced pressure. The residue was added with saturated NaHCO₃ solution to adjust pH=8 and extracted with ethyl acetate. The organic layer was washed with brine, dried over anhydrous Na₂SO₄ and concentrated under reduced pressure. The residue was purified by silica gel chromatography to afford PI-56e (110 mg, 63%).

To a solution of PI-56e (110 mg, 0.33 mmol, 1.0 eq) in MeOH (3 mL) was added (NH₄)₂CO₃ (126 mg, 1.31 mmol, 4.0 eq) and KCN (43 mg, 0.66 mmol, 2.0 eq). The mixture was stirred at 45° C. for 16 h. The reaction was added with 3 M HCl to adjust pH=1~2 and stirred at room temperature for 1 h, then saturated aqueous of NaHCO₃ was added to adjust pH=7~8 and extracted with ethyl acetate. The organic layer was washed with brine, dried over anhydrous Na₂SO₄ and concentrated under reduced pressure. The residue was purified by prep-TLC to give PC-56 (50 mg, 37%) as a white solid.

Preparation of Compound PC-57:

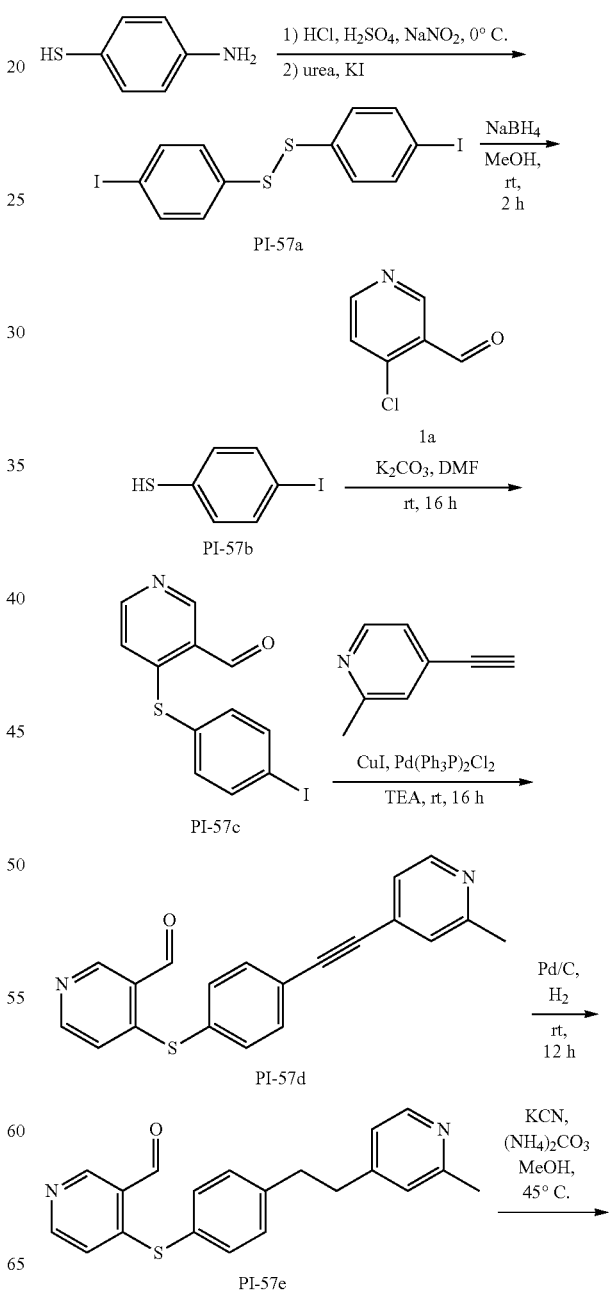

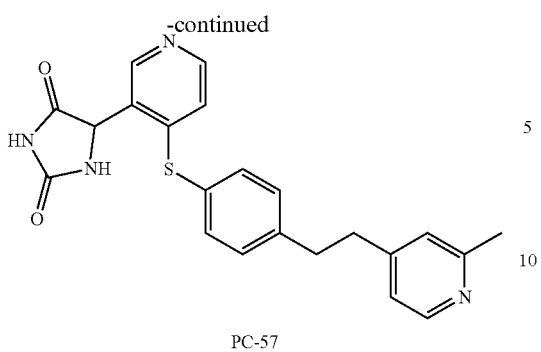

PC-57

To a solution of 4-aminothiophenol (10 g, 79.87 mmol, 1.0 eq) in H₂O (80 mL) was successively added HCl (80 mL), H₂SO₄ (30 mL) and NaNO₂ (6.6 g, 95.84 mmol, 1.2 eq) at 0° C. The mixture was stirred at 0° C. for 0.5 h. Then urea (0.46 g, 7.99 mmol, 0.1 eq) was added. After 15 min, the solution of KI (26.5 g, 159.74 mmol, 2.0 eq) in H₂O (1.5 L) was drop wise added at 0° C. The mixture was stirred at 0° C. for 5 h. Then the mixture was extracted with ethyl acetate. The organic layer was washed with brine, dried over anhydrous Na₂SO₄ and concentrated under reduced pressure. The residue was purified by silica gel chromatography to afford PI-57a (7.3 g, 39%).

A mixture of PI-57a (1.8 g, 3.83 mmol, 1.0 eq) in MeOH (40 mL) was stirred at room temperature for 2 h. The reaction mixture was concentrated under reduced pressure. The residue was diluted with ethyl acetate (50 mL) and washed with water, and brine. The organic layer was dried over anhydrous Na₂SO₄ and concentrated under reduced pressure. The residue was purified by silica gel chromatography to afford PI-57b (0.9 g, 50%).

To a solution of PI-57b (230 mg, 1 mmol, 1.0 eq) in DMF (10 mL) was added 4-chloronicotinaldehyde (140 mg, 1 mmol, 1.0 eq) and K₂CO₃ (276 mg, 2 mmol, 2.0 eq). The mixture was stirred at room temperature for 16 h. Then water (30 mL) was added and extracted with ethyl acetate (20 mL×3). The organic layer was washed with brine, dried over anhydrous Na₂SO₄ and concentrated under reduced pressure. The residue was purified by silica gel chromatography to afford PI-57c (0.3 g, 88%).

To a solution of PI-57c (1 g, 2.9 mmol, 1.0 eq) and 4-ethynyl-2-methylpyridine (0.41 g, 3.5 mmol, 1.2 eq) in TEA (1.19 g, 0.29 mmol, 0.1 eq) was added Pd(Ph₃P)₂Cl₂ (0.21 g, 0.29 mmol, 0.1 eq) and CuI (0.06 g, 0.29 mmol, 0.1 eq) under nitrogen atmosphere. The mixture was stirred at room temperature for 16 h under nitrogen atmosphere. Then the mixture was quenched with saturated NH₄Cl solution. The mixture was extracted with ethyl acetate. The combined organic phases were washed with brine, dried over anhydrous Na₂SO₄ and concentrated under reduced pressure. The residue was purified by silica gel chromatography to afford PI-57d (0.8 g, 83%).

To a solution of PI-57d (0.2 g, 0.61 mmol, 1.0 eq) in methanol (10 mL) was added Pd/C (20 mg). The mixture was stirred under hydrogen atmosphere (20 psi) at room temperature for 16 h. The mixture was filtered, and the filtrate was concentrated to give PI-57e (170 mg, 84%) without further purification.

To a solution of PI-57e (180 mg, 0.54 mmol, 1.0 eq) in MeOH (5 mL) was added (NH₄)₂CO₃ (206 mg, 2.15 mmol, 4.0 eq) and KCN (70 mg, 1.08 mmol, 2.0 eq). The mixture was stirred at 45° C. for 16 h. The reaction was added with 3 M HCl to adjust pH=1~2 and stirred at room temperature for 1 h, then saturated aqueous of NaHCO₃ was added to adjust pH=7~8 and extracted with ethyl acetate. The organic layer was washed with brine, dried over anhydrous Na₂SO₄ and concentrated under reduced pressure. The residue was purified by prep-TLC to give PC-57 (60 mg, 27%) as a yellow solid.

Preparation of Compound PC-58:

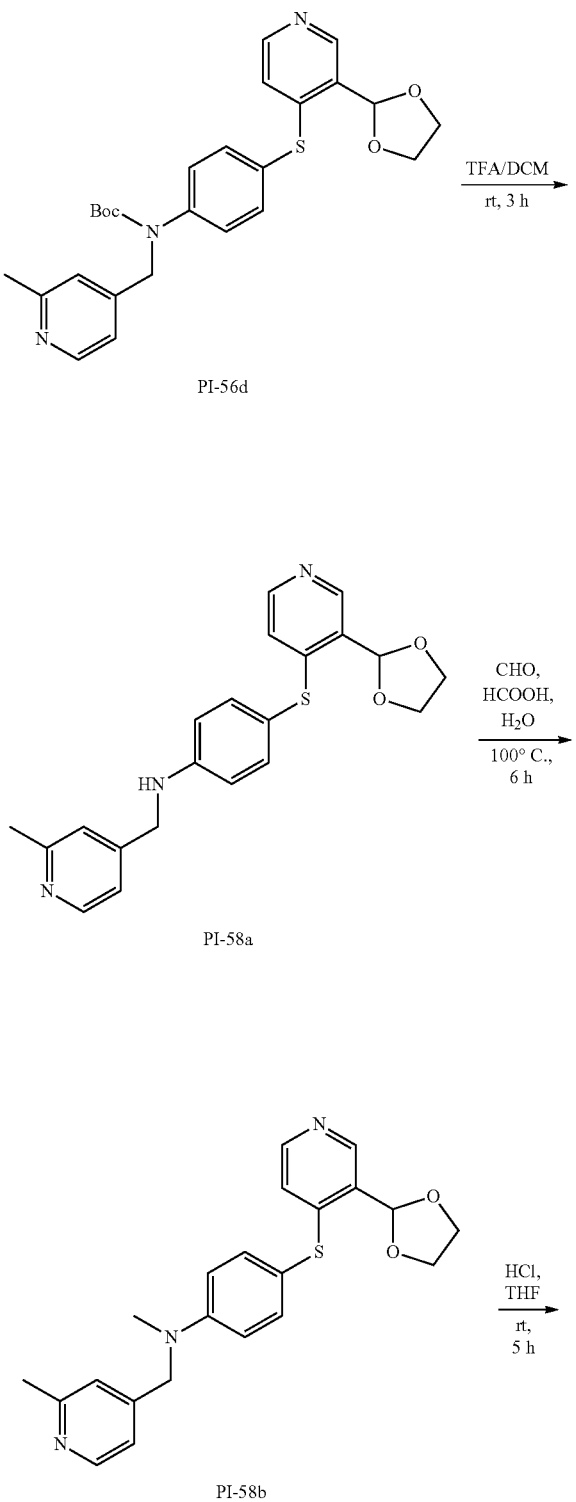

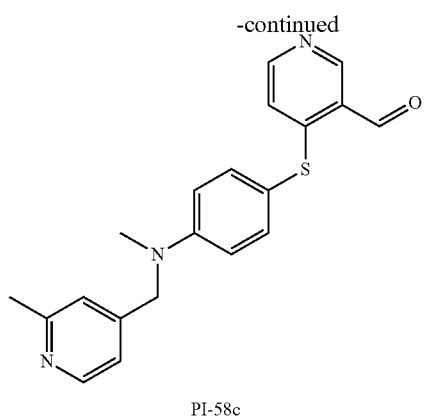

PI-58c

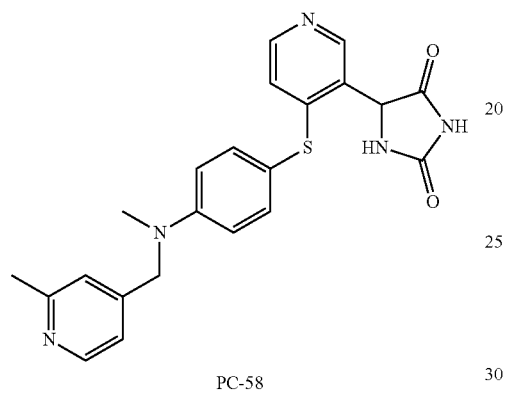

PC-58

A mixture of PI-56d (400 mg, 0.83 mmol, 1.0 eq) in TFA/DCM (1 mL/3 mL) was stirred at room temperature for 3 h. The reaction mixture was concentrated under reduced pressure. The residue was added saturated NaHCO$_3$ solution to adjust pH=8 and extracted with ethyl acetate. The organic layer was washed with brine, dried over anhydrous Na$_2$SO$_4$ and concentrated under reduced pressure to give PI-58a (350 mg, 100%), which was used in the next step without further purification.

A mixture of PI-58a (360 mg, 0.95 mmol, 1.0 eq) in formic acid (80%, 3 ml) and formaldehyde solution (40%, 1 ml) was prepared. The mixture was heated at 100° C. for 6 hours. The reaction mixture was cooled to room temperature and concentrated under reduced pressure. The residue was added with saturated NaHCO$_3$ solution to adjust pH=8 and extracted with ethyl acetate. The organic layer was washed with brine, dried over anhydrous Na$_2$SO$_4$ and concentrated under reduced pressure. The residue was purified by silica gel chromatography to afford PI-58b (210 mg, 56%).

A mixture of PI-58b (210 mg, 0.53 mmol, 1.0 eq) in HCl/THF (2.0 M, 3 mL/3 mL) was stirred at room temperature for 5 h. The reaction mixture was concentrated under reduced pressure. The residue was added with saturated NaHCO$_3$ solution to adjust pH=8 and extracted with ethyl acetate. The organic layer was washed with brine, dried over anhydrous Na$_2$SO$_4$ and concentrated under reduced pressure to give PI-58c (160 mg, 86%), which was used in the next step without further purification.

To a solution of PI-58c (180 mg, 0.52 mmol, 1.0 eq) in MeOH (3 mL) was added (NH$_4$)$_2$CO$_3$ (198 mg, 2.06 mmol, 4.0 eq) and KCN (67 mg, 1.03 mmol, 2.0 eq). The mixture was stirred at 45° C. for 16 h. The reaction was added with 3 M HCl to adjust pH=1~2 and stirred at room temperature for 1 h, then a saturated aqueous solution of NaHCO$_3$ was added to adjust pH=7~8 and extracted with ethyl acetate. The organic layer was washed with brine, dried over anhydrous Na$_2$SO$_4$ and concentrated under reduced pressure. The residue was purified by silica gel chromatography to give PC-58 (118 mg, 54%) as a yellow solid.

Preparation of Compound PC-59:

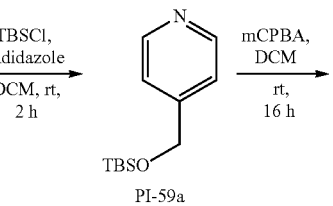

PI-59a

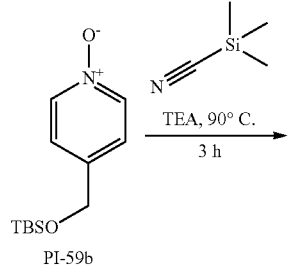

PI-59b

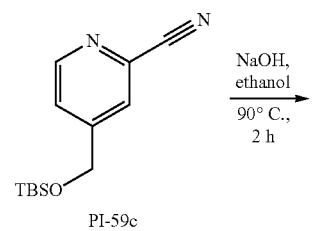

PI-59c

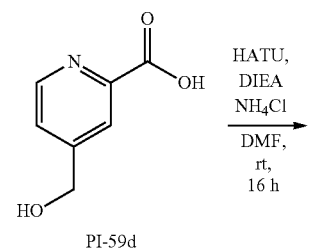

PI-59d

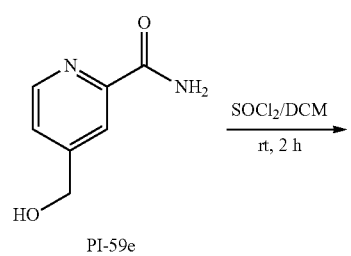

PI-59e

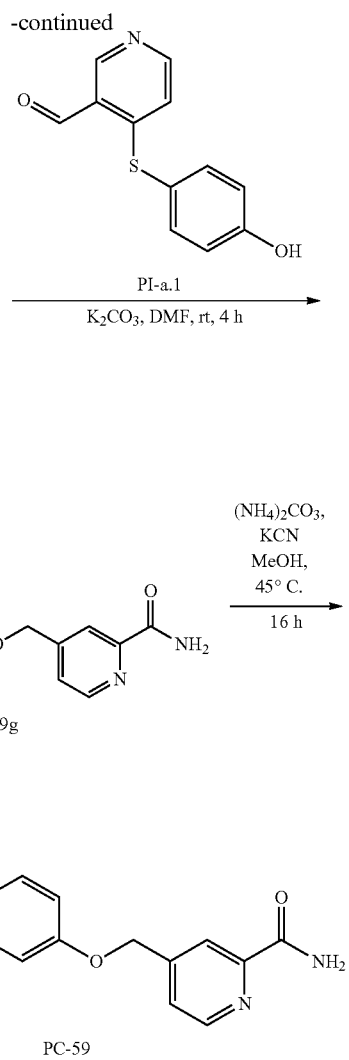

To a solution of compound 4-Pyridinemethanol (5 g, 45.82 mmol, 1.0 eq) and imidazole (7.97 g, 137.45 mmol, 3.0 eq) in DCM (100 mL) was added TBSCl (13.8 g, 91.64 mmol, 2.0 eq) at 0° C. The mixture was stirred at room temperature for 2 h. Then the mixture was quenched with saturated NH₄Cl solution (100 mL). The mixture was extracted with ethyl acetate (50 mL×3). The combined organic phases were washed with brine, dried over anhydrous Na₂SO₄ and concentrated under reduced pressure. The residue was purified by silica gel chromatography to afford compound PI-59a (7.2 g, 70%).

To a solution of compound PI-59a (10 g, 44.76 mmol, 1.0 eq) in DCM (150 mL) was added m-CPBA (11.58 g, 67.14 mmol, 1.5 eq) at room temperature. The mixture was stirred at room temperature for 16 h. TLC analysis of the reaction mixture showed full conversion to the desired product. Then the mixture was quenched with saturated aqueous of sodium sulfite. The organic layer was washed with brine, dried over anhydrous Na₂SO₄ and concentrated under reduced pressure. The residue was purified by silica gel chromatography to afford compound PI-59b (8.1 g, 75%).

To a mixture of compound PI-59b (10.3 g, 43.4 mmol, 1.0 eq) in TEA (40 mL) was added trimethylsilyl cyanide (13 g, 130.4 mmol, 3 eq). The mixture was heated at 90° C. for 3 h under nitrogen atmosphere. Then the mixture was concentrated under reduced pressure. The residue was purified by silica gel chromatography to give PI-59c (5.1 g, 47%).

To a solution of PI-59c (5.1 g, 20.53 mmol, 1.0 eq) in ethanol/H₂O (100/17 mL) was added NaOH (6.9 g, 172.5 mmol, 8.4 eq). The mixture was stirred at 90° C. for 2 h. Then the mixture was cooled to room temperature and diluted with water (100 mL) and extracted with ethyl acetate. The aqueous layer was acidified to pH=4-5 and extracted with ethyl acetate. The organic layer was washed with brine, dried over anhydrous Na₂SO₄ and concentrated under reduced pressure. The residue was purified by silica gel chromatography to afford PI-59d (3.2 g, 99%).

To a solution of PI-59d (2.2 g, 14.36 mmol, 1.0 eq) in DMF (100 mL) was successively added NH₄Cl (1.54 g, 28.73 mmol, 2.0 eq), HATU (5.46 g, 14.36 mmol, 1.0 eq) and DIEA (5.57 g, 43.08 mmol, 3.0 eq). The mixture was stirred at room temperature for 16 h. The reaction mixture was diluted with ethyl acetate (200 mL) and washed with brine, water, dried over anhydrous Na₂SO₄ and concentrated under reduced pressure. The residue was purified by silica gel chromatography to afford PI-59e (0.6 g, 27%).

To a mixture of PI-59e (0.53 g, 3.48 mmol, 1.0 eq) in DCM (50 mL) was added SOCl₂ (0.83 g, 6.96 mmol, 2.0 eq) drop wise at 0° C. under nitrogen atmosphere. The mixture was stirred at room temperature for 2 h. The reaction mixture was diluted with DCM (50 mL) and washed with saturated aqueous of NaHCO₃, brine, dried over anhydrous Na₂SO₄ and concentrated under reduced pressure to afford PI-59f (0.47 g, 79%).

To a solution of PI-59f (470 mg, 2.75 mmol, 1.0 eq) in DMF (20 mL) was added PI-a.1 (636 mg, 2.75 mmol, 1.0 eq) and K₂CO₃ (759 mg, 5.5 mmol, 2 eq). The mixture was stirred at room temperature for 4 h. Then the mixture was diluted with water (50 mL) and extracted with ethyl acetate (30 mL×3). The organic layer was washed with brine, dried over anhydrous Na₂SO₄ and concentrated under reduced pressure. The residue was purified by silica gel chromatography to afford PI-59 g (210 mg, 21%).

To a solution of PI-59 g (400 mg, 1.09 mmol, 1.0 eq) in MeOH (7 mL) was added (NH₄)₂CO₃ (419 mg, 4.38 mmol, 4.0 eq) and KCN (141 mg, 2.19 mmol, 2.0 eq). The mixture was stirred at 45° C. for 16 h. The reaction was added 3 M HCl to adjust pH=1~2 and stirred at room temperature for 1 h, then a saturated aqueous solution of NaHCO₃ was added to adjust pH=7~8 and extracted with ethyl acetate. The organic layer was washed with brine, dried over anhydrous Na₂SO₄ and concentrated under reduced pressure. The residue was purified by silica gel chromatography to give PC-59 (52 mg, 11%) as a white solid.

Preparation of Compound PC-60:

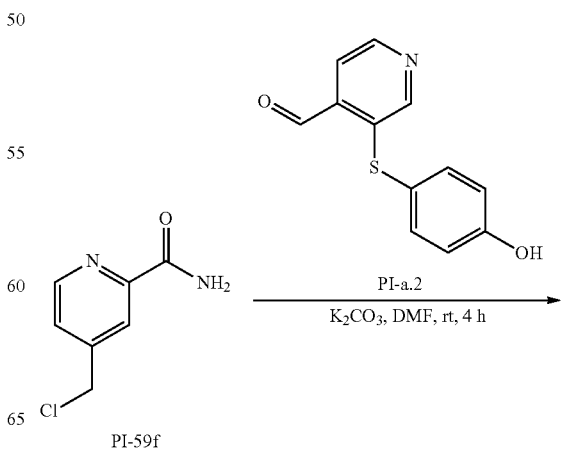

-continued

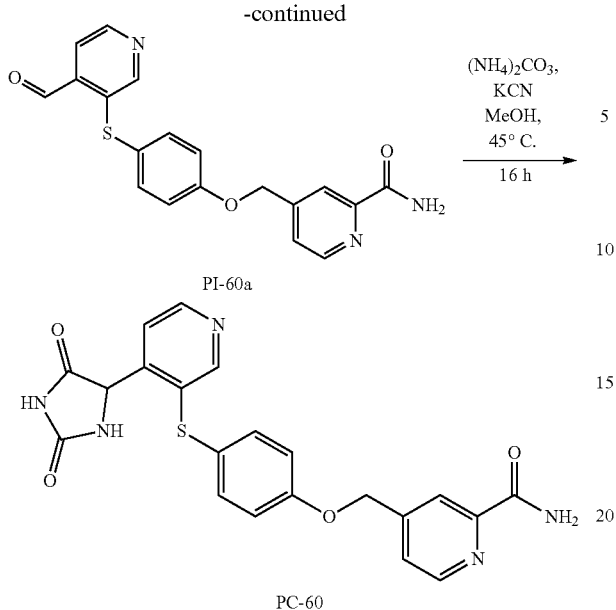

To a solution of PI-59f (470 mg, 2.75 mmol, 1.0 eq) in DMF (20 mL) was added PI-a.2 (636 mg, 2.75 mmol, 1.0 eq) and K₂CO₃ (759 mg, 5.5 mmol, 2 eq). The mixture was stirred at room temperature for 4 h. Then the mixture was diluted with water (50 mL) and extracted with ethyl acetate (30 mL×3). The organic layer was washed with brine, dried over anhydrous Na₂SO₄ and concentrated under reduced pressure. The residue was purified by silica gel chromatography to afford PI-60a (230 mg, 23%).

To a solution of PI-60a (230 mg, 0.63 mmol, 1.0 eq) in MeOH (6 mL) was added (NH₄)₂CO₃ (241 mg, 2.51 mmol, 4.0 eq) and KCN (81 mg, 1.26 mmol, 2.0 eq). The mixture was stirred at 45° C. for 16 h. The reaction was added 3 M HCl to adjust pH=1~2 and stirred at room temperature for 1 h, then a saturated aqueous solution of NaHCO₃ was added to adjust pH=7~8 and extracted with ethyl acetate. The organic layer was washed with brine, dried over anhydrous Na₂SO₄ and concentrated under reduced pressure. The residue was purified by silica gel chromatography to give PC-60 (53 mg, 19%) as a yellow solid.

Preparation of Compound PC-61:

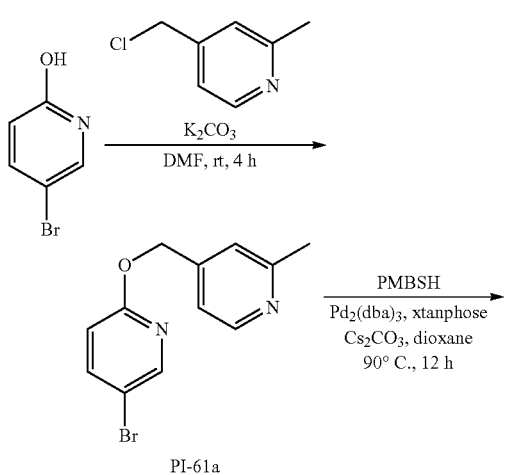

-continued

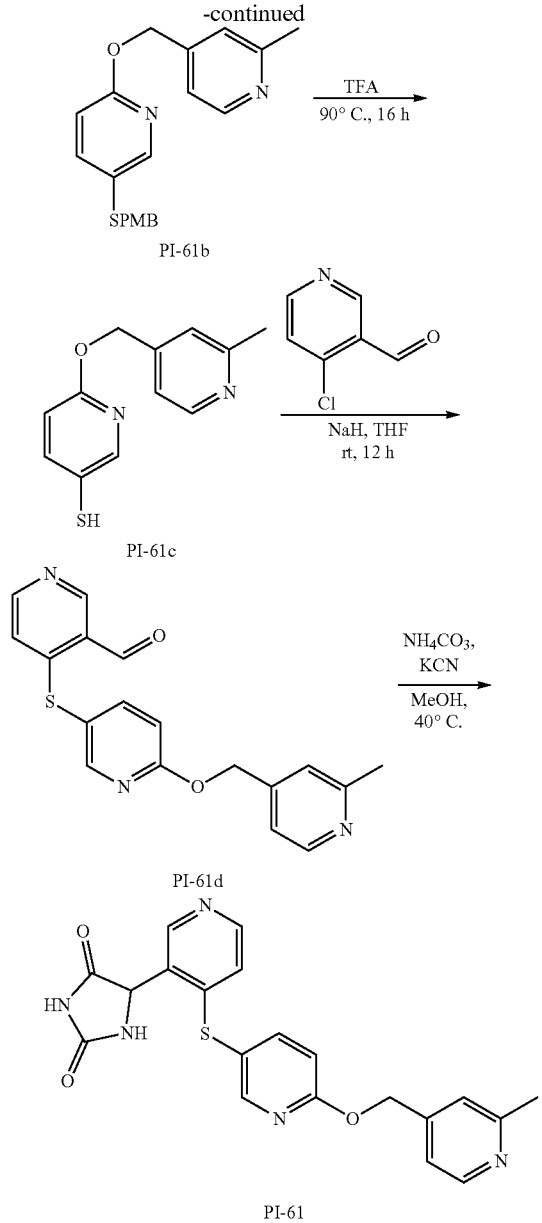

To a solution of 5-Bromo-2-hydroxypyridine (5 g, 28.74 mmol, 1.0 eq) in DMF (100 mL) was added 4-(chloromethyl)-2-methylpyridine (4.07 g, 28.74 mmol, 1.0 eq) and K₂CO₃ (7.93 g, 57.47 mmol, 2 eq). The mixture was stirred at room temperature for 4 h. Then the mixture was diluted with water (200 mL) and extracted with ethyl acetate (100 mL×3). The organic layer was washed with brine, dried over anhydrous Na₂SO₄ and concentrated under reduced pressure. The residue was purified by silica gel chromatography to afford PI-61a (4.1 g, 51%).

To a mixture of PI-61a (1 g, 3.58 mmol, 1.0 eq), 4-Methoxy-α-toluenethiol (607 mg, 3.94 mmol, 1.1 eq), xantphose (207 mg, 0.36 mmol, 0.1 eq) and Cs₂CO₃ (1.75 g, 5.37 mmol, 1.5 eq) in dioxane (30 mL) was added Pd₂(dba)₃ (230 mg, 0.25 mmol, 0.07 eq) under nitrogen atmosphere. The mixture was stirred at 90° C. for 12 h. Then the mixture was filtered and extracted with water (50 mL) and ethyl acetate (30 mL×3). The organic phase was dried over anhydrous Na₂SO₄ and concentrated under reduced pressure. The residue was purified by silica gel chromatography to afford PI-61b (0.8 g, 63%).

PI-61b (1 g, 2.83 mmol, 1.0 eq) was dissolved in TFA (20 mL) and stirred at 90° C. for 16 h under nitrogen atmosphere. Then the mixture was concentrated under reduced pressure. The residue was purified by silica gel chromatography to give PI-61c (0.5 g, 76%).

To a solution of PI-61c (600 mg, 2.58 mmol, 1.0 eq) in THF (20 mL) was added NaH (103 mg, 2.58 mmol, 1 eq, 60%) at 0° C. under nitrogen atmosphere. The mixture was stirred at 0° C. for 1 h. Then 4-chloronicotinaldehyde (365 mg, 2.58 mmol, 1.0 eq) was added. The mixture was stirred at room temperature for 12 h. The mixture was diluted with water (50 mL) and extracted with ethyl acetate (30 mL×3). The organic layer was washed with brine, dried over anhydrous $Na_2SO_4$ and concentrated under reduced pressure. The residue was purified by silica gel chromatography to afford PI-61d (250 mg, 29%)

To a solution of PI-61d (200 mg, 0.59 mmol, 1.0 eq) in MeOH (5 mL) was added $(NH_4)_2CO_3$ (227 mg, 2.37 mmol, 4.0 eq) and KCN (77 mg, 1.19 mmol, 2.0 eq). The mixture was stirred at 45° C. for 16 h. The reaction was added 3 M HCl to adjust pH=1~2 and stirred at room temperature for 1 h, then a saturated aqueous solution of $NaHCO_3$ was added to adjust pH=7~8 and extracted with ethyl acetate. The organic layer was washed with brine, dried over anhydrous $Na_2SO_4$ and concentrated under reduced pressure. The residue was purified by silica gel chromatography to give PC-61 (104 mg, 43%) as a white solid.

Preparation of Compound PC-62:

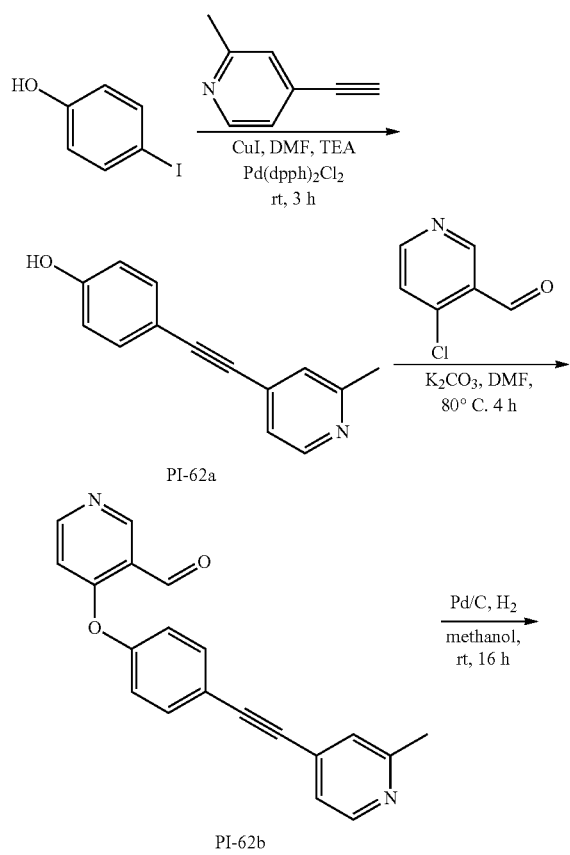

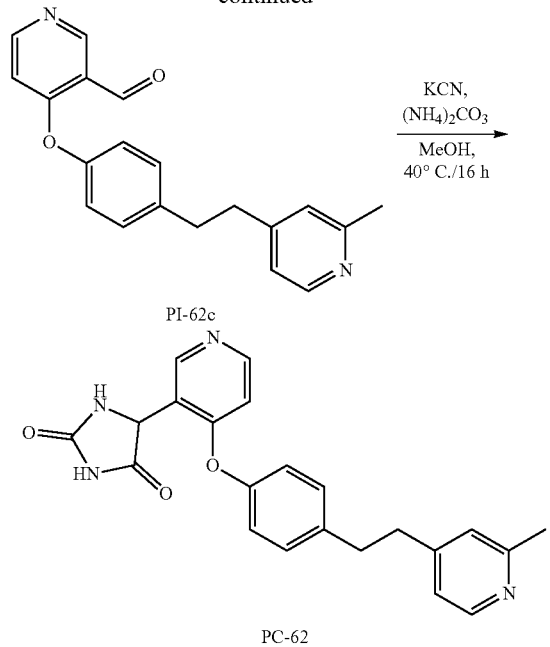

To a solution of 4-iodophenol (2.2 g, 10 mmol, 1.0 eq) and 4-ethynyl-2-methylpyridine (1.29 g, 11 mmol, 1.1 eq) in DMF (30 mL) was added TEA (3.2 g, 30 mmol, 3 eq), $Pd(Ph_3P)_2Cl_2$ (1.4 g, 2 mmol, 0.2 eq) and CuI (0.38 g, 2 mmol, 0.2 eq) under nitrogen atmosphere. The mixture was stirred at room temperature for 3 h under nitrogen atmosphere. Then the mixture was quenched with saturated $NH_4Cl$ (50 mL) solution. The mixture was extracted with ethyl acetate (30 mL×3). The combined organic phases were washed with brine, dried over anhydrous $Na_2SO_4$ and concentrated under reduced pressure. The residue was purified by silica gel chromatography to afford PI-62a (1.05 g, 45%).

To a solution of PI-62a (0.8 g, 3.82 mmol, 1.0 eq) in DMF (40 mL) was added 4-chloronicotinaldehyde (0.54 g, 3.82 mmol, 1.0 eq) and $K_2CO_3$ (1.05 g, 7.64 mmol, 2 eq). The mixture was stirred at 80° C. for 4 h. Then the mixture was diluted with water (100 mL) and extracted with ethyl acetate (50 mL×3). The organic layer was washed with brine, dried over anhydrous $Na_2SO_4$ and concentrated under reduced pressure. The residue was purified by silica gel chromatography to afford PI-62b (0.45 g, 37%).

To a solution of PI-62b (1.0 eq) in methanol (10 mL) is added Pd/C (20 mg). The mixture is stirred under hydrogen atmosphere (20 psi) at room temperature for 16 h. The mixture is filtered, and the filtrate is concentrated to give PI-62c without further purification.

To a solution of PI-62c (1.0 eq) in MeOH (5 mL) is added $(NH_4)_2CO_3$ (4.0 eq) and KCN (2.0 eq). The mixture is stirred at 45° C. for 16 h. The reaction is added with 3 M HCl to adjust pH=1~2 and stirred at room temperature for 1 h, then a saturated aqueous solution of $NaHCO_3$ is added to adjust pH=7~8 and extracted with ethyl acetate. The organic layer is washed with brine, dried over anhydrous $Na_2SO_4$ and concentrated under reduced pressure to give PC-62.

Preparation of Compound PC-63:

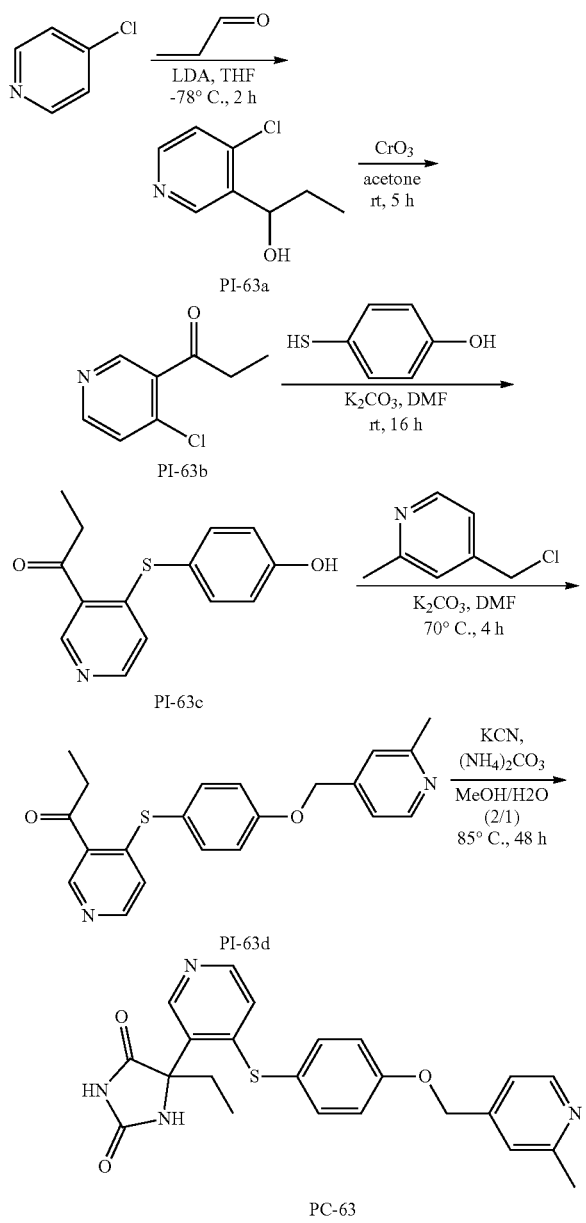

trated under reduced pressure. The residue was purified by silica gel chromatography to afford PI-63b (16.0 g, 62%)

To a mixture of PI-63b (1 g, 4.67 mmol, 1.0 eq) and 4-mercaptophenol (590 mg, 4.67 mmol, 1.0 eq) in DMF (50 mL) was added $K_2CO_3$ (1.29 g, 9.34 mmol, 2 eq). The mixture was stirred at room temperature for 16 h under nitrogen atmosphere. Then the mixture was quenched with $H_2O$ (100 mL) and extracted with ethyl acetate (50 mL×3). The combined organic phases were washed with brine, dried over anhydrous $Na_2SO_4$ and concentrated under reduced pressure. The residue was purified by silica gel chromatography to afford PI-63c (1.2 g, 99%).

To a mixture of PI-63c (500 mg, 1.93 mmol, 1.0 eq) and 4-(chloromethyl)-2-methylpyridine (409 mg, 2.89 mmol, 1.5 eq) in DMF (20 mL) was added $K_2CO_3$ (798 mg, 5.78 mmol, 3 eq). The mixture was stirred at 70° C. for 4 h under nitrogen atmosphere. Then the mixture was quenched with $H_2O$ (60 mL) and extracted with ethyl acetate (30 mL×3). The combined organic phases were washed with brine, dried over anhydrous $Na_2SO_4$ and concentrated under reduced pressure. The residue was purified by silica gel chromatography to afford PI-63d (610 mg, 87%).

To a solution of PI-63d (610 mg, 1.68 mmol, 1.0 eq) in $MeOH/H_2O$ (12 mL, 5/1) was added $(NH_4)_2CO_3$ (644 mg, 6.71 mmol, 4.0 eq) and KCN (218 mg, 3.36 mmol, 2.0 eq). The mixture was stirred at 45° C. for 16 h. The reaction was added with 3 M HCl to adjust pH=1~2 and stirred at room temperature for 1 h, then a saturated aqueous solution of $NaHCO_3$ was added to adjust pH=7~8 and extracted with ethyl acetate. The organic layer was washed with brine, dried over anhydrous $Na_2SO_4$ and concentrated under reduced pressure. The residue was purified by silica gel chromatography to give PC-63 (80 mg, 11%) as a white solid.

Preparation of Compound PC-64:

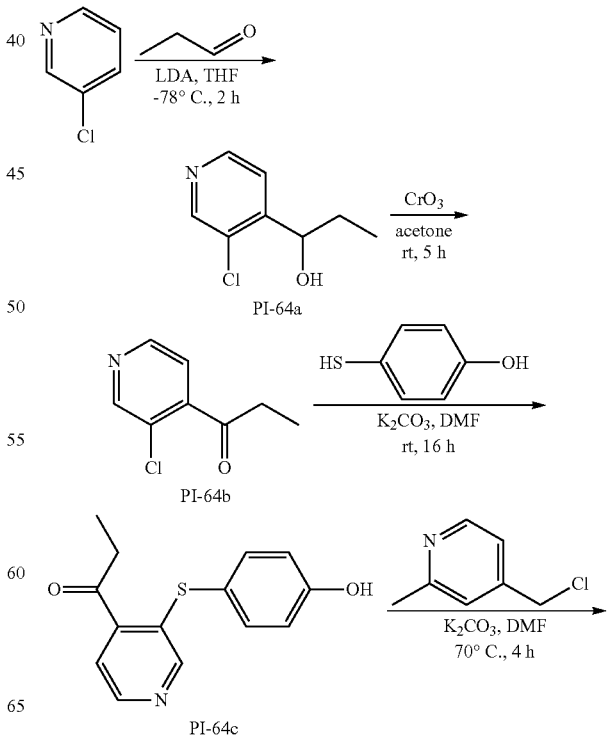

To a mixture of 4-chloropyridine (100 g, 0.667 mol, 1.0 eq) in dry THF (1 L) was quickly added LDA (2 M in THF, 733.26 mL, 1.467 mol, 2.2 eq) at −78° C. under nitrogen atmosphere. The mixture was stirred at −78° C. for 1 h. Then propionaldehyde (74.1 g, 0.999 mol, 1.5 eq) was added dropwise and the mixture was stirred for 1 h. TLC analysis of the reaction mixture showed full conversion to the desired product. The reaction was quenched with a saturated aqueous solution of $NH_4Cl$ and extracted with ethyl acetate (3×500 mL). The organic layer was washed with brine and water, dried over $Na_2SO_4$ and concentrated under vacuum. The residue was purified by column chromatography on silica gel (PE:EA, 3:1) to give PI-63a (45 g, 48%).

To a mixture of PI-63a (26.3 g, 0.154 mol, 1.0 eq) in acetone (300 mL) was added $CrO_3$ (30.8 g, 0.308 mol, 2.0 eq). The mixture was stirred at room temperature for 5 h. Then the mixture was filtered and the filtrate was concen- -continued

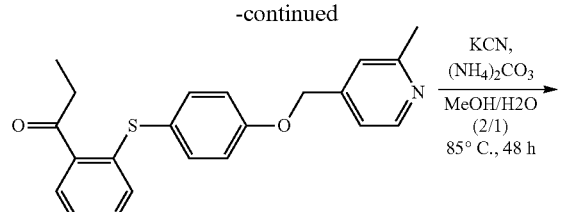

PI-64d

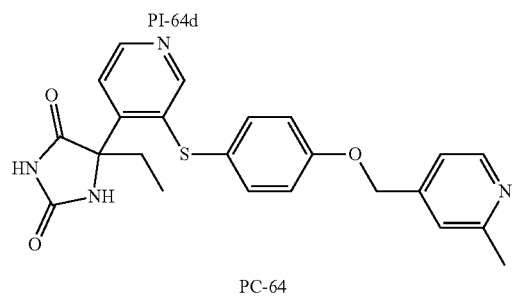

PC-64

To a mixture of 3-Chloropyridine (100 g, 0.667 mol, 1.0 eq) in dry THF (1 L) was quickly added LDA (2 M in THF, 733.26 mL, 1.467 mol, 2.2 eq) at −78° C. under nitrogen atmosphere. The mixture was stirred at −78° C. for 1 h. Then propionaldehyde (74.1 g, 0.999 mol, 1.5 eq) was added dropwise and the mixture was stirred for 1 h. TLC analysis of the reaction mixture showed full conversion to the desired product. The reaction was quenched with a saturated aqueous solution of NH$_4$Cl and extracted with ethyl acetate (3×500 mL). The organic layer was washed with brine and water, dried over Na$_2$SO$_4$ and concentrated under vacuum. The residue was purified by column chromatography on silica gel (PE:EA, 3:1) to give PI-64a (45 g, 48%).

To a mixture of PI-64a (26.3 g, 0.154 mol, 1.0 eq) in acetone (300 mL) was added CrO$_3$ (30.8 g, 0.308 mol, 2.0 eq). The mixture was stirred at room temperature for 5 h. Then the mixture was filtered and the filtrate was concentrated under reduced pressure. The residue was purified by silica gel chromatography to afford PI-64b (16.0 g, 62%)

To a mixture of PI-64b (1 g, 4.67 mmol, 1.0 eq) and 4-mercaptophenol (590 mg, 4.67 mmol, 1.0 eq) in DMF (50 mL) was added K$_2$CO$_3$ (1.29 g, 9.34 mmol, 2 eq). The mixture was stirred at room temperature for 16 h under nitrogen atmosphere. Then the mixture was quenched with H$_2$O (100 mL) and extracted with ethyl acetate (50 mL×3). The combined organic phases were washed with brine, dried over anhydrous Na$_2$SO$_4$ and concentrated under reduced pressure. The residue was purified by silica gel chromatography to afford PI-64c (1.2 g, 99%).

To a mixture of PI-64c (500 mg, 1.93 mmol, 1.0 eq) and 4-(chloromethyl)-2-methylpyridine (409 mg, 2.89 mmol, 1.5 eq) in DMF (20 mL) was added K$_2$CO$_3$ (798 mg, 5.78 mmol, 3 eq). The mixture was stirred at 70° C. for 4 h under nitrogen atmosphere. Then the mixture was quenched with H$_2$O (60 mL) and extracted with ethyl acetate (30 mL×3). The combined organic phases were washed with brine, dried over anhydrous Na$_2$SO$_4$ and concentrated under reduced pressure. The residue was purified by silica gel chromatography to afford PI-64d (610 mg, 87%).

To a solution of PI-64d (700 mg, 1.92 mmol, 1.0 eq) in MeOH/H2O (12 mL, 5/1) was added (NH$_4$)$_2$CO$_3$ (637 mg, 7.68 mmol, 4.0 eq) and KCN (248 mg, 3.83 mmol, 2.0 eq). The mixture was stirred at 45° C. for 16 h. The reaction was added with 3 M HCl to adjust pH=1~2 and stirred at room temperature for 1 h, then a saturated aqueous solution of NaHCO$_3$ was added to adjust pH=7~8 and extracted with ethyl acetate. The organic layer was washed with brine, dried over anhydrous Na$_2$SO$_4$ and concentrated under reduced pressure. The residue was purified by silica gel chromatography to give PC-64 (242 mg, 29%) as a white solid.

Preparation of Compounds OC-1 and OC-2:

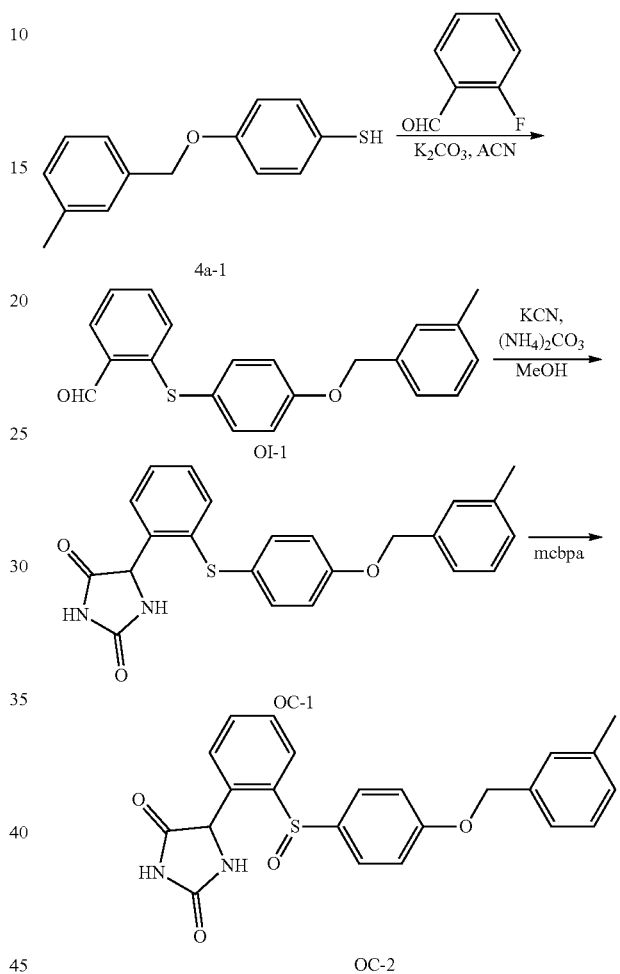

To a mixture of compound 4a-1 (0.5 g, 2.17 mmol, 1.0 eq) in ACN (15 mL) was added 2-fluorobenzaldehyde (0.271 g, 2.17 mmol, 1.0 eq) and K$_2$CO$_3$ (0.906 g, 6.52 mmol, 3.0 eq). The mixture was stirred at 85° C. overnight under nitrogen atmosphere. Then the mixture was concentrated under vacuum. The residue was purified by Prep-TLC to give compound OI-1 (490 mg, 68%).

To a mixture of OI-1 (200 mg, 0.6 mmol, 1.0 eq) in MeOH (10 mL) was added KCN (78 mg, 1.2 mmol, 2.0 eq) and (NH$_4$)$_2$CO$_3$ (230 mg, 2.4 mmol, 4.0 eq). The mixture was stirred at 40° C. overnight under nitrogen atmosphere. Then the mixture was concentrated in vacuum to give compound OC-1 (200 mg, 82%).

To a mixture of compound OC-1 (15 mg, 0.037 mmol, 1.0 eq) in dioxane (1 mL) was added m-CPBA (6.4 mg, 0.037 mmol, 1.0 eq). The mixture was stirred at room temperature for 12 h. Then the mixture was diluted with EA and washed with saturated NaHCO$_3$ aqueous. The organic layer was concentrated under reduced pressure. The residue was purified by silica gel chromatography to afford compound OC-2 (9.6 mg, 62%).

Preparation of Compounds OC-3 and OC-4:

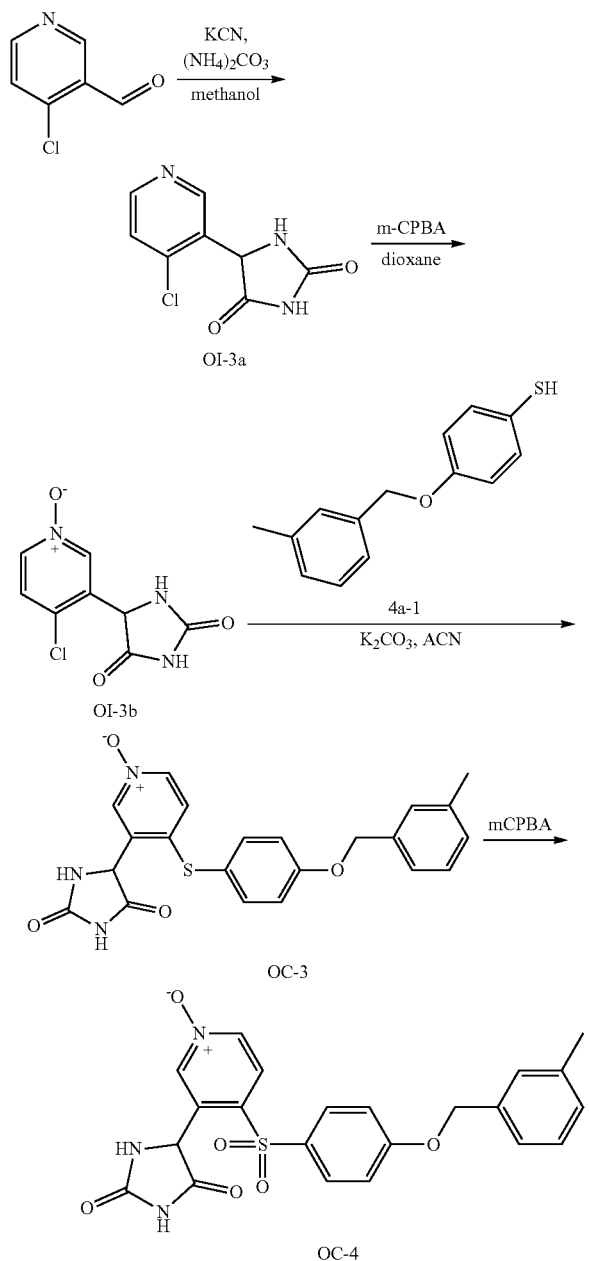

was concentrated under reduced pressure. The residue was purified by silica gel chromatography to afford OI-3b (200 mg, 19%).

To a mixture of OI-3b (100 mg, 0.43 mmol, 1.0 eq) and compound 4a-1 (99 mg, 0.43 mmol, 1 eq) in ACN (2 mL) was successively added $K_2CO_3$ (182 mg, 1.31 mmol, 3.0 eq). The mixture was stirred at 85° C. for 12 h under nitrogen atmosphere. TLC analysis of the reaction mixture showed full conversion to the desired product. Then the mixture was poured into water and extracted with EA (3×5 mL). The combined organic layers were washed with brine, dried over anhydrous $Na_2SO_4$ and concentrated under reduced pressure. The residue was purified by column chromatography on silica gel to give OC-3 (23.6 mg, 13%).

To a mixture of compound OC-3 (20 mg, 0.05 mmol, 1.0 eq) in dioxane (1 mL) was added m-CPBA (8.5 mg, 0.05 mmol, 1.0 eq). The mixture was stirred at room temperature for 12 h. Then the mixture was diluted with EA and washed with a saturated $NaHCO_3$ aqueous solution. The organic layer was concentrated under reduced pressure. The residue was purified by silica gel chromatography to afford OC-4 (8 mg, 40%).

Preparation of Compound OC-5:

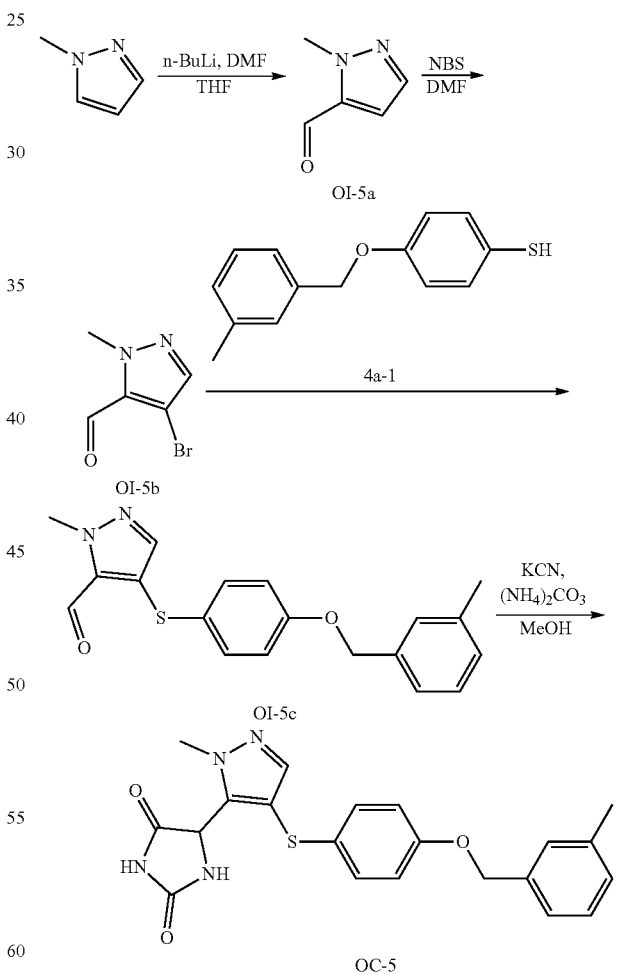

To a mixture of 4-chloronicotinaldehyde (1 g, 7.1 mmol, 1.0 eq) in MeOH (6 mL) was added KCN (0.92 mg, 14.2 mmol, 2.0 eq) and $(NH_4)_2CO_3$ (2.71 g, 28.2 mmol, 4.0 eq). The mixture was stirred at room temperature for 12 h. Then the mixture was diluted with water and extracted with ethyl acetate. The organic phase was dried over anhydrous $Na_2SO_4$ and concentrated under reduced pressure. The residue was purified by Prep-TLC to give compound OI-3a (1.0 g, 66%) as a white solid.

To a mixture of OI-3a (1.0 g, 4.73 mmol, 1.0 eq) in dioxane (10 mL) was added m-CPBA (0.82 g, 4.73 mmol, 1.0 eq). The mixture was stirred at room temperature for 12 h. Then the mixture was diluted with EA and washed with a saturated $NaHCO_3$ aqueous solution. The organic layer To a mixture of 1-methyl-1H-pyrazole (16.4 g, 0.2 mol, 1.0 eq) in dry THF (150 mL) was added n-BuLi (2.5 M in hexane, 96 mL, 0.24 mol, 1.2 eq) at −78° C. under nitrogen atmosphere. The mixture was stirred at −78° C. for 1 h. Then DMF (30.8 mL, 0.4 mol, 2.0 eq) was added dropwise and the mixture was stirred for 1 h. TLC analysis of the reaction mixture showed full conversion to the desired product. The reaction was quenched with a saturated aqueous solution of NH₄Cl and extracted with EA (3×500 mL). The organic layer was washed with brine and water, dried over Na₂SO₄ and concentrated under vacuum. The residue was purified by column chromatography on a silica gel to give compound OI-5a (12.7 g, 58%).

To a mixture of compound OI-5a (2 g, 18.2 mmol, 1.0 eq) in DMF (20 mL) was added NBS (4.86 g, 27.3 mmol, 1.5 eq). The mixture was stirred at room temperature for 16 h under nitrogen atmosphere. Then the mixture was filtered and extracted with water and ethyl acetate. The organic phase was dried over anhydrous Na₂SO₄ and concentrated under reduced pressure. The residue was purified by silica gel chromatography to afford compound OI-5b (2.3 g, 67%).

To a mixture of OI-5b (700 mg, 3.72 mmol, 1.0 eq), 4a-1 (1.27 g, 4.09 mmol, 1.1 eq), DPPF (42 mg, 0.503 mmol, 0.1 eq) and DIEA (942 mg, 7.55 mmol, 1.5 eq) in toluene (10 mL) was added Pd(dba)₂ (150 mg, 0.260 mmol, 0.07 eq) under nitrogen atmosphere. The mixture was stirred at 110° C. for 16 h. Then the mixture was filtered and extracted with water and ethyl acetate. The organic phase was dried over anhydrous Na₂SO₄ and concentrated under reduced pressure. The residue was purified by silica gel chromatography to afford OI-5c (120 mg, 10%)

To a mixture of compound OI-5c (140 mg, 0.414 mmol, 1.0 eq) in MeOH (5 mL) was added KCN (54 mg, 0.828 mmol, 2.0 eq) and (NH₄)₂CO₃ (159 mg, 1.66 mmol, 4.0 eq). The mixture was stirred at room temperature for 12 h. Then the mixture was diluted with water and extracted with ethyl acetate. The organic phase was dried over anhydrous Na₂SO₄ and concentrated under reduced pressure. The residue was purified by Prep-TLC to give compound OC-5 (67 mg, 40%) as a white solid.

Preparation of Compound OC-6:

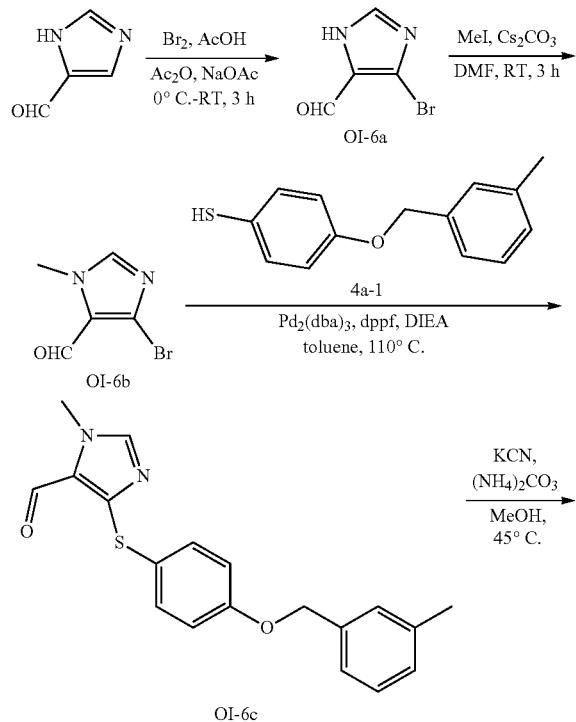

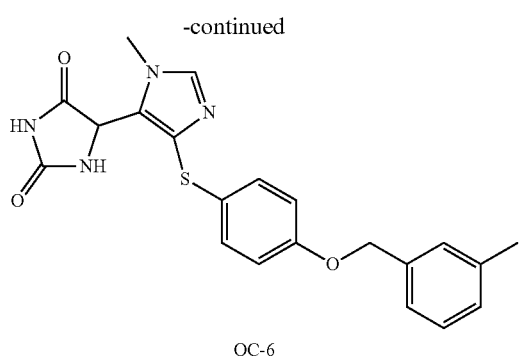

To a mixture of 4-Imidazolecarboxaldehyde (1 g, 10.4 mmol, 1.0 eq) and NaOAc (14.15 g, 104 mmol, 10 eq) in AcOH (100 mL) was dropwise added a solution of Br₂ (3.8 g, 23.77 mmol, 2.3 eq) in Ac₂O (20 mL) at 0° C. under nitrogen atmosphere. The mixture was stirred at RT for 3 h. TLC analysis of the reaction mixture showed full conversion to the desired product. The reaction was quenched with saturated NaHCO₃ aqueous and extracted with EA (3×20 mL). The organic layer was washed with brine and water, dried over Na₂SO₄ and concentrated in vacuum. The residue was purified by column chromatography to give OI-6a (0.8 g, 44%).

To a mixture of OI-6a (1 g, 5.71 mmol, 1.0 eq) and Cs₂CO₃ (1.86 g, 5.71 mmol, 1.0 eq) in DMF (50 mL) was successively added MeI (0.82 g, 5.71 mmol, 1.0 eq). The mixture was stirred at RT for 3 h under nitrogen atmosphere. TLC analysis of the reaction mixture showed full conversion to the desired product. Then the mixture was poured into water and extracted with EA (3×30 mL). The combined organic layers were washed with brine, dried over anhydrous Na₂SO₄ and concentrated under reduced pressure. The residue was purified by column chromatography on a silica gel to give OI-6b (0.7 g, 65%).

To a mixture of OI-6b (0.7 g, 3.7 mmol, 1.0 eq), 4a-1 (1.27 g, 5.56 mmol, 1.5 eq), CyPF-tBu (CAS: 158923-11-6) (21 mg, 0.04 mmol, 0.01 eq) and Cs₂CO₃ (942 mg, 7.55 mmol, 2.5 eq) in DME (10 mL) was added Pd(OAc)₂ (8 mg, 0.04 mmol, 0.01 eq) under nitrogen atmosphere. The mixture was stirred at 110° C. for 16 h. Then the mixture was filtered and extracted with water and ethyl acetate. The organic phase was dried over anhydrous Na₂SO₄ and concentrated under reduced pressure. The residue was purified by silica gel chromatography to afford OI-6c (0.28 g, 22%)

To a solution of OI-6c (280 mg, 0.83 mmol, 1.0 eq) in MeOH (5 mL) was added (NH₄)₂CO₃ (320 mg, 3.31 mmol, 4.0 eq) and KCN (108 mg, 1.65 mmol, 2.0 eq). The mixture was stirred at RT for 16 h. The reaction was added with 3 M HCl to adjust pH=1~2 and stirred at room temperature for 1 h, then a saturated aqueous solution of NaHCO₃ was added to adjust pH=6~7 and extracted with ethyl acetate. The organic layer was washed with brine, dried over anhydrous Na₂SO₄ and concentrated under reduced pressure. The residue was purified by silica gel chromatography to give OC-6 (200 mg, 59%) as a white solid.

Preparation of Compounds OC-7 and OC-10:

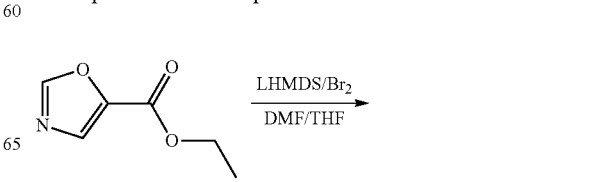

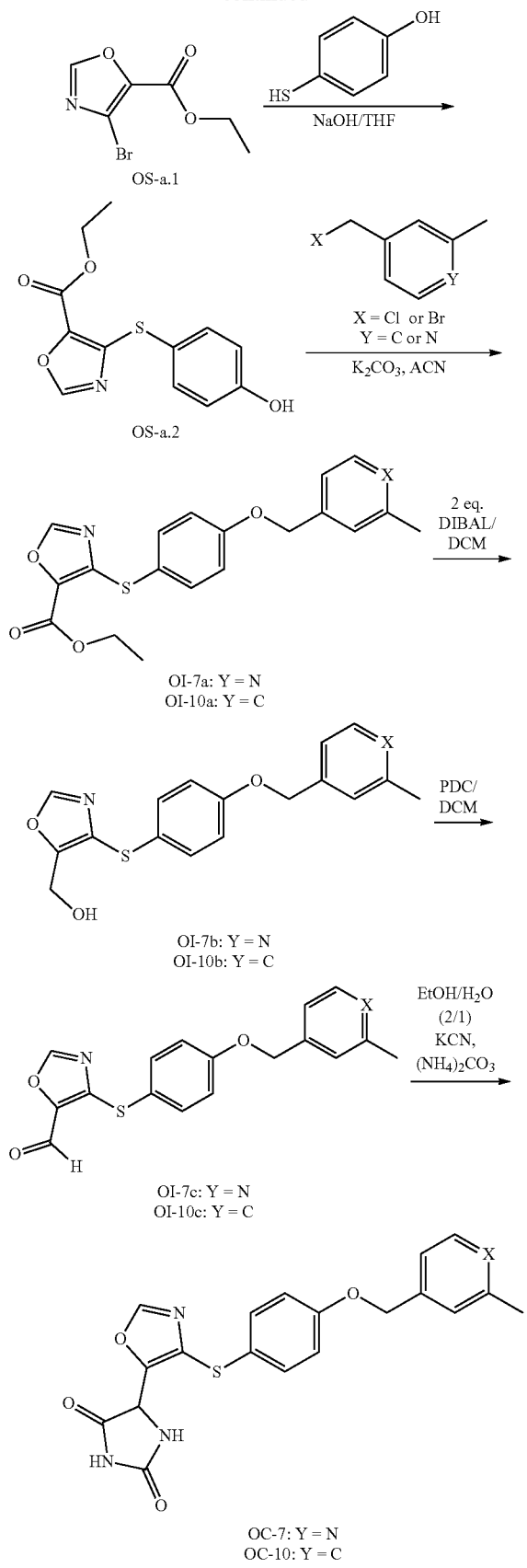

To a solution of ethyl oxazole-5-carboxylate (0.28 g, 2.00 mmol) in THF/DMF (2/2 mL) was added Br₂ (0.13 mL, 2.6 mmol, 1.3 eq.) and LHMDS (2.6 mL 2.6 mmol, 1.3 eq) to obtain a reaction mixture, which was stirred at –60° C. for 4 hours. The reaction mixture was extracted with EA and water and the combined organic layer was dried with MgSO₄. The residue was purified by flash chromatography with EA/Hex (EA/Hex=1:4) to give OS-a.1 as yellow oil (0.1 g, 30%).

To a solution of OS-a.1 (0.3 g, 1.36 mmol) in THF (10 mL) was added NaOH (81 mg, 2.05 mmol, 1.5 eq.) and 4-mercaptophenol (0.17 g, 1.36 mmol, 1 eq) was stirred overnight. The reaction mixture was extracted with EA and water and the combined organic layer was dried with MgSO₄. The residue was purified by flash chromagraphy with EA/Hex (EA/Hex=1:2) to give OS-a.2 as a yellow solid (0.25 g, 71%).

To a solution of compound OS-a.2 (4.2 g, 15.85 mmol, 1.0 eq) in DMF (40 mL) was added 4-(chloromethyl)-2-methylpyridine (2.2 g, 15.85 mmol, 1.0 eq) and K₂CO₃ (6.6 g, 47.55 mmol, 3.0 eq) at room temperature under nitrogen atmosphere. The mixture was stirred at 30° C. for 16 h. TLC analysis of the reaction mixture showed full conversion to the desired product. Then the mixture was diluted with water and extracted with ethyl acetate. The organic layer was washed with brine, dried over anhydrous Na₂SO₄ and concentrated under reduced pressure. The residue was purified by silica gel chromatography to afford compound OI-7a (2.5 g, 44%).

To a solution of OI-7a (1.4 g, 3.93 mmol, 1.0 eq) in anhydrous THF (10 mL) was added DIBAL-H (1 M in hexane, 7.87 mL, 7.87 mmol, 2.0 eq) dropwise at 0° C. The mixture was stirred at 0° C. for 2 h under nitrogen atmosphere. TLC analysis of the reaction mixture showed full conversion to the desired product. Then the mixture was quenched with saturated Na₂SO₄·10H₂O solution (50 mL). The mixture was extracted with DCM (3×30 mL). The combined organic phases were washed with brine (2×60 mL), dried over anhydrous Na₂SO₄ and concentrated under reduced pressure. The residue was purified by silica gel chromatography to afford OI-7b (620 mg, 48%).

To a solution of OI-7b (620 mg, 1.89 mmol, 1.0 eq) in DCM (5 mL) was added PDC (1.4 g, 3.78 mmol, 2.0 eq) and K₂CO₃ (782 mg, 5.67 mmol, 3.0 eq) at room temperature under nitrogen atmosphere. The mixture was stirred at 40° C. for 16 h. TLC analysis of the reaction mixture showed full conversion to the desired product. Then the mixture was diluted with water and extracted with DCM. The organic layer was washed with brine, dried over anhydrous Na₂SO₄ and concentrated under reduced pressure. The residue was purified by silica gel chromatography to afford OI-7c (205 mg, 33%).

To a solution of OI-7c (205 mg, 0.629 mmol, 1.0 eq) in MeOH (3 mL) was added (NH₄)₂CO₃ (241 mg, 2.52 mmol, 4.0 eq) and KCN (82 mg, 1.26 mmol, 2.0 eq). The mixture was stirred at room temperature for 16 h. The reaction was added with 3 M HCl to adjust the pH=1 to 2 and stirred at room temperature for 1 h, then a saturated aqueous solution of NaHCO₃ was added to adjust the pH=6 to 7 and extracted with ethyl acetate. The organic layer was washed with brine, dried over anhydrous Na₂SO₄ and concentrated under reduced pressure. The residue was purified by prep-TLC to give OC-7 (41 mg, 16%) as a white solid. Compound OC-10 was synthesized in the same fashion except that (chloromethyl)-2-methylpyridine was replaced with 1-(bromomethyl)-3-methylbenzene.

Preparation of Compound OC-8:
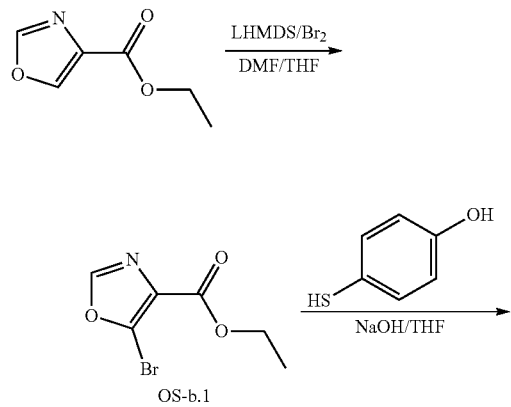
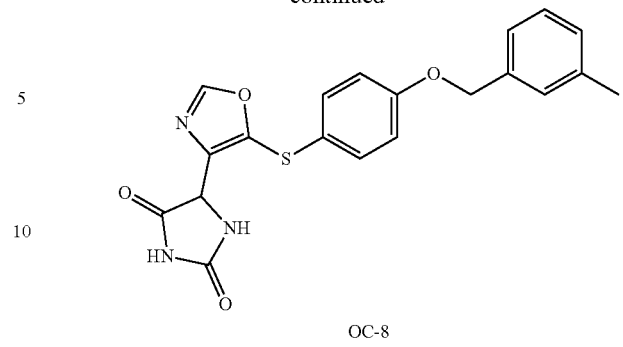
OC-8
Compound OC-8 was synthesized by the same procedure as the synthesis of compound OC-10 except that the starting material ethyl oxazole-5-carboxylate was replaced with ethyl oxazole-4-carboxylate.
Preparation of Compound OC-9:
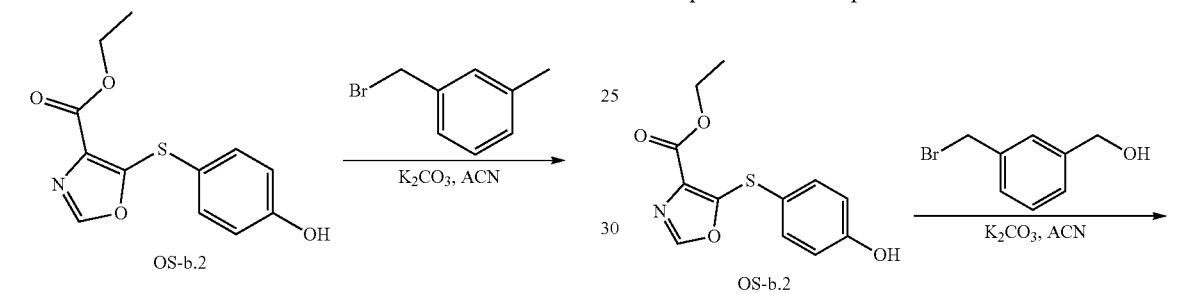
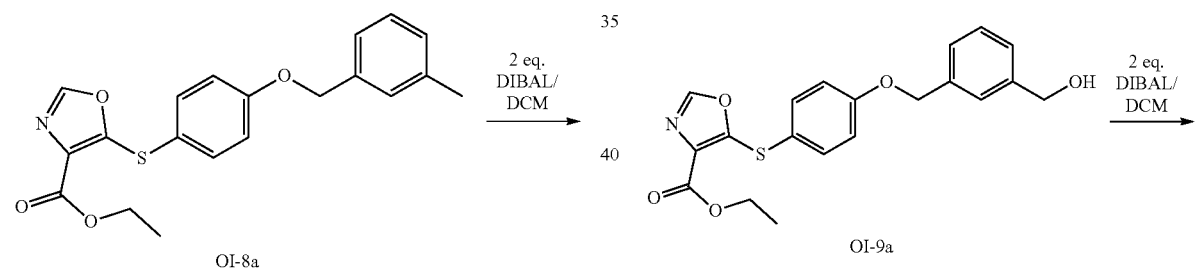
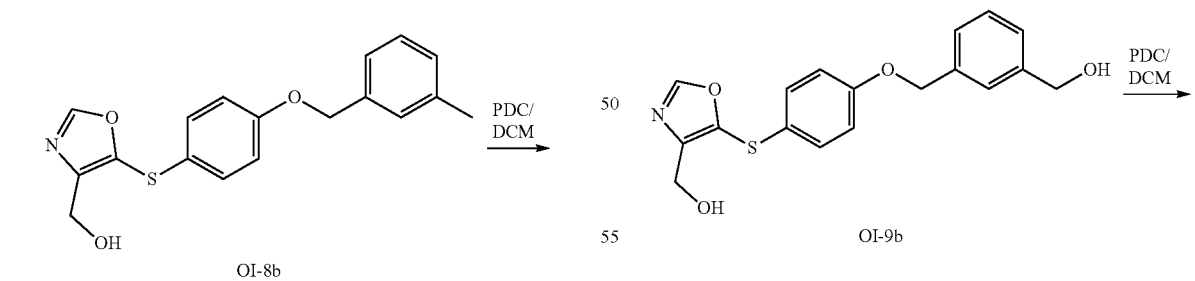
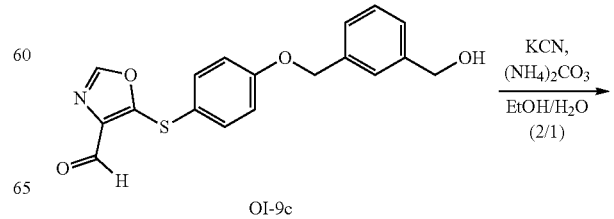

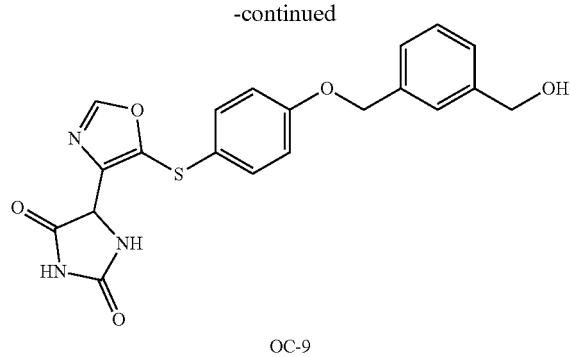

OC-9

Compound OC-9 was synthesized by the same procedure as the synthesis of OC-8 except that the starting material 1-(bromomethyl)-3-methylbenzene was replaced with (3-(bromomethyl)phenyl) methanol.

Preparation of Compound OC-11

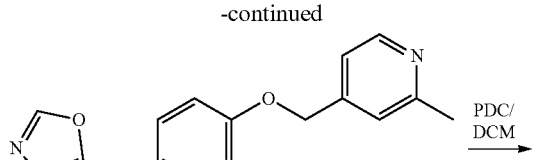

OI-11b

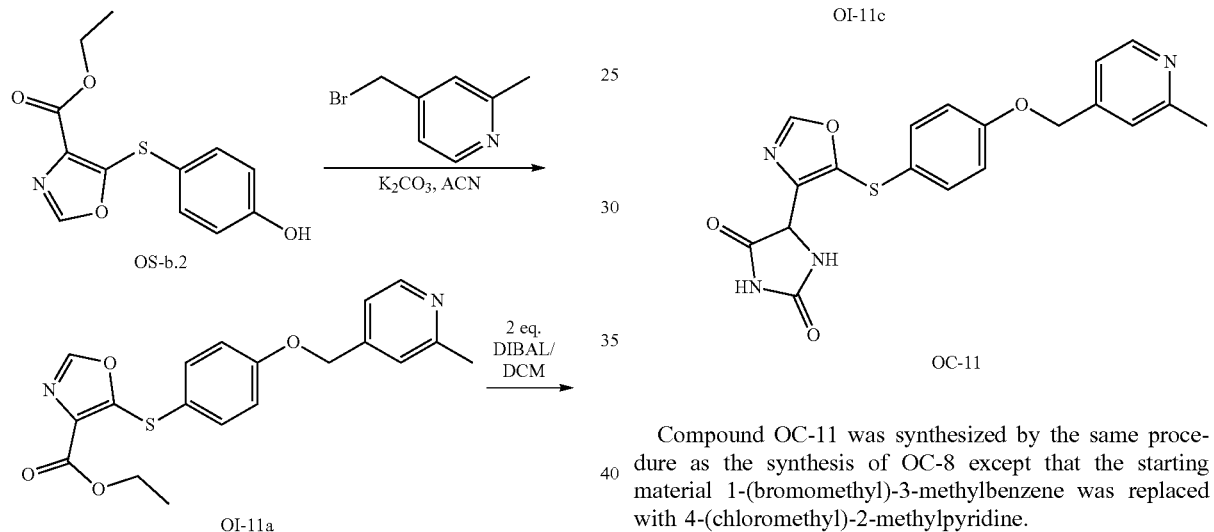

OC-11

Compound OC-11 was synthesized by the same procedure as the synthesis of OC-8 except that the starting material 1-(bromomethyl)-3-methylbenzene was replaced with 4-(chloromethyl)-2-methylpyridine.

Preparation of Compound OC-12:

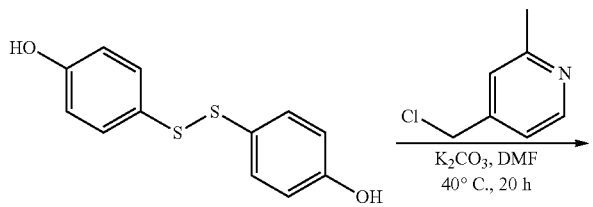

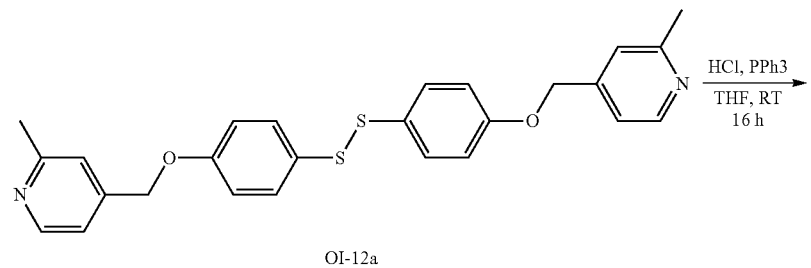

OI-12a

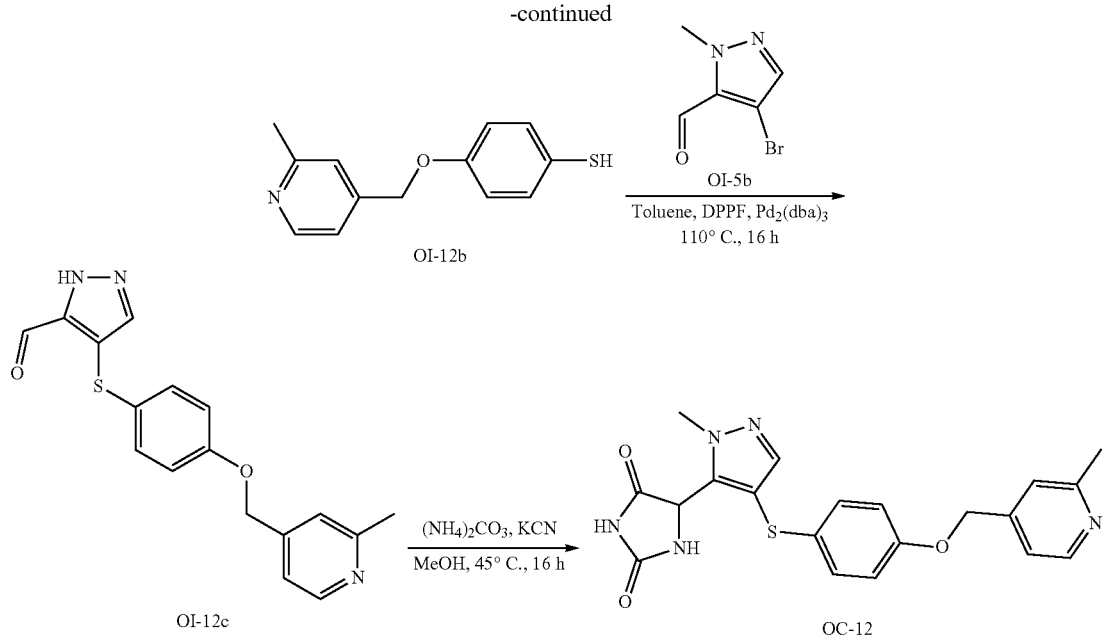

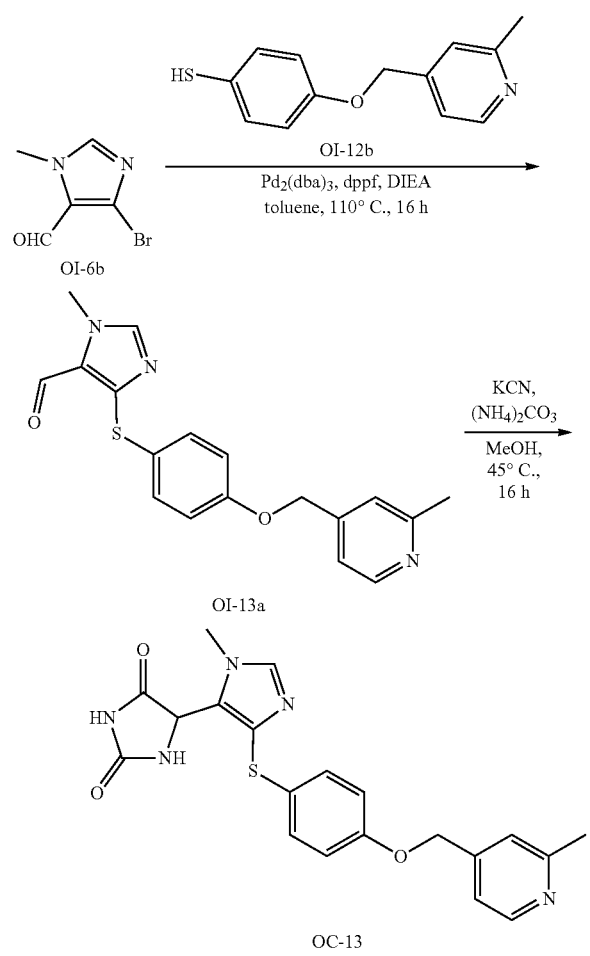

To a solution of Bis(4-Hydroxyphenyl)Disulfide (5.0 g, 19.97 mmol, 1.0 eq) in DMF (100 mL) was added 4-(chloromethyl)-2-methylpyridine (6.22 g, 43.94 mmol, 2.2 eq) and $K_2CO_3$ (8.2 g, 59.91 mmol, 3 eq). The mixture was stirred at 45° C. for 12 h. Then the mixture was diluted with water (200 mL) and extracted with ethyl acetate (100 mL*3). The organic layer was washed with brine, dried over anhydrous $Na_2SO_4$ and concentrated under reduced pressure. The residue was purified by silica gel chromatography to afford OI-12a (3.9 g, 42%).

To a solution of OI-12a (3.9 g, 8.46 mmol, 1.0 eq) in THF (50 mL) was added $PPh_3$ (2.22 g, 8.46 mmol, 1.0 eq) and concentrated HCl (8.8 mL, 84.6 mmol, 10 eq). The mixture was stirred at room temperature for 16 h. Then the mixture was diluted with water (100 mL) and extracted with ethyl acetate (50 mL×3). The organic layer was washed with brine, dried over anhydrous $Na_2SO_4$ and concentrated under reduced pressure. The residue was purified by silica gel chromatography to afford compound OI-12b (2.1 g, 53%).

To a mixture of OI-12b (296 mg, 1.28 mmol, 1.1 eq), OI-5b (220 mg, 1.16 mmol, 1.0 eq), DPPF (10 mg, 0.12 mmol, 0.1 eq) and DIEA (225 mg, 1.74 mmol, 1.5 eq) in toluene (10 mL) was added $Pd_2(dba)_3$ (47 mg, 0.08 mmol, 0.07 eq) under nitrogen atmosphere. The mixture was stirred at 110° C. for 16 h. Then the mixture was filtered and extracted with water and ethyl acetate. The organic phase was dried over anhydrous $Na_2SO_4$ and concentrated under reduced pressure. The residue was purified by silica gel chromatography to afford OI-12c (180 mg, 45%)

To a mixture of OI-12c (120 mg, 0.35 mmol, 1.0 eq) in MeOH (4 mL) was added KCN (46 mg, 0.7 mmol, 2.0 eq) and $(NH_4)_2CO_3$ (134 mg, 1.4 mmol, 4.0 eq). The mixture was stirred at 45° C. for 16 h. The reaction was added 3 M HCl to adjust pH=1~2 and stirred at room temperature for 1 h, then saturated aqueous of $NaHCO_3$ was added to adjust pH=7~8 and extracted with ethyl acetate. The organic layer was washed with brine, dried over anhydrous $Na_2SO_4$ and concentrated under reduced pressure. The residue was purified by prep-TLC to give compound OC-12 (50 mg, 35%) as a white solid.

Preparation of Compound OC-13:

To a mixture of OI-6b (310 mg, 1.63 mmol, 1.0 eq), OI-12b (414 mg, 1.79 mmol, 1.1 eq), DPPF (88 mg, 0.16 mmol, 0.1 eq) and DIEA (313 mg, 2.43 mmol, 1.5 eq) in toluene (16 mL) was added Pd$_2$(dba)$_3$ (104 mg, 0.11 mmol, 0.07 eq) under nitrogen atmosphere. The mixture was stirred at 110° C. for 16 h. Then the mixture was filtered and extracted with water (50 mL) and ethyl acetate (30 mL×3). The organic phase was dried over anhydrous Na$_2$SO$_4$ and concentrated under reduced pressure. The residue was purified by silica gel chromatography to afford OI-13a (400 mg, 72%)

To a mixture of OI-13a (370 mg, 1.09 mmol, 1.0 eq) in MeOH (10 mL) was added KCN (142 mg, 2.18 mmol, 2.0 eq) and (NH$_4$)$_2$CO$_3$ (418 mg, 4.36 mmol, 4.0 eq). The mixture was stirred at 45° C. for 16 h. The reaction was added with 3 M HCl to adjust pH=1~2 and stirred at room temperature for 1 h, then a saturated aqueous solution of NaHCO$_3$ was added to adjust pH=7~8 and extracted with ethyl acetate. The organic layer was washed with brine, dried over anhydrous Na$_2$SO$_4$ and concentrated under reduced pressure. The residue was purified by prep-TLC to give OC-13 (73 mg, 16%) as a white solid.

Preparation of Compound OC-14:

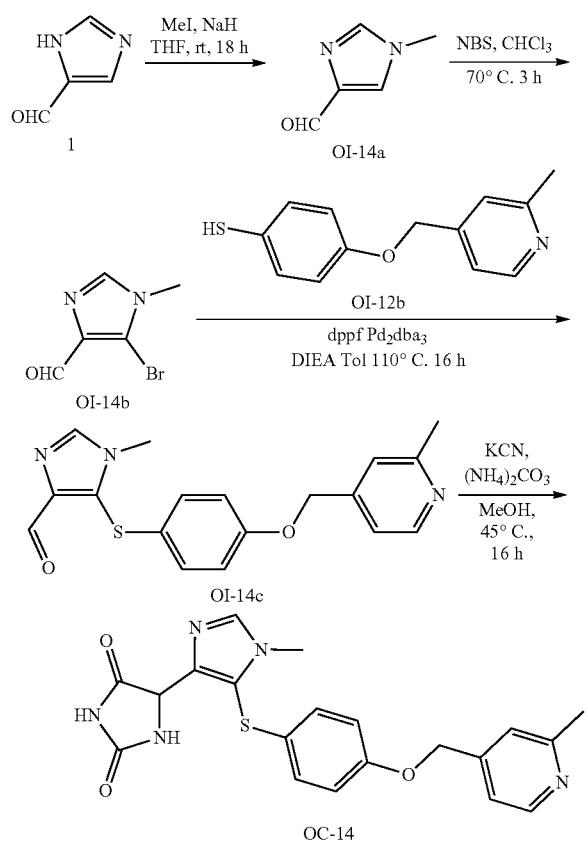

To a mixture of 4-Imidazolecarboxaldehyde (6 g, 62.44 mmol, 1.0 eq) in THF (60 mL) was added NaH (3 g, 74.9 mmol, 1.2 eq) at room temperature. After 10 min, the mixture was cooled to −78° C. and MeI (10.5 g, 74.9 mmol, 1.2 eq) was added. Then the mixture was gradually warmed to room temperature and stirred for 18 h. The reaction was quenched with methanol (10 mL) and concentrated under reduced pressure. The residue was purified by silica gel chromatography to afford OI-14a (4 g, 58%).

To a solution of OI-14a (4 g, 36.36 mmol, 1.0 eq) in chloroform (40 mL) was added NBS (7.12 g, 40 mmol, 1.1 eq). The mixture was stirred at 70° C. for 3 h. Then the mixture was cooled to room temperature and diluted with a saturated aqueous solution of Na$_2$CO$_3$ (50 mL) and DCM (100 mL). The organic layer washed with brine and water, dried over Na$_2$SO$_4$ and concentrated under vacuum. The residue was purified by column chromatography on silica gel to give OI-14b (333 mg, 4.8%).

To a mixture of OI-14b (333 mg, 1.76 mmol, 1.0 eq), compound OI-12b (448 mg, 1.94 mmol, 1.1 eq), DPPF (100 mg, 0.18 mmol, 0.1 eq) and DIEA (340 mg, 2.64 mmol, 1.5 eq) in toluene (20 mL) was added Pd$_2$(dba)$_3$ (113 mg, 0.12 mmol, 0.07 eq) under nitrogen atmosphere. The mixture was stirred at 110° C. for 16 h. Then the mixture was filtered and extracted with water (50 mL) and ethyl acetate (30 mL×3). The organic phase was dried over anhydrous Na$_2$SO$_4$ and concentrated under reduced pressure. The residue was purified by silica gel chromatography to afford OI-14c (261 mg, 43%)

To a mixture of OI-14c (261 mg, 0.77 mmol, 1.0 eq) in MeOH (5 mL) was added KCN (100 mg, 1.53 mmol, 2.0 eq) and (NH$_4$)$_2$CO$_3$ (295 mg, 3.08 mmol, 4.0 eq). The mixture was stirred at 45° C. for 16 h. The reaction was added with 3 M HCl to adjust pH=1~2 and stirred at room temperature for 1 h, then a saturated aqueous solution of NaHCO$_3$ was added to adjust pH=7~8 and extracted with ethyl acetate. The organic layer was washed with brine, dried over anhydrous Na$_2$SO$_4$ and concentrated under reduced pressure. The residue was purified by prep-TLC to give compound OC-14 (183 mg, 58%) as a white solid.

Biological Testing

Example 1: MMP Inhibitory Assays

The inhibitory effect of compounds on the rate of cleaving fluorogenic MMP substrate (Enzo, BML-P128) by recombinant human MMP-12 catalytic domain (Enzo, BML-SE138) was carried out by methods known in the art. Briefly, to each well of a 96-well black opaque plate, all the reagents were sequentially added by pipetting, and the final reaction contained 4 nM of recombinant human MMP-12 catalytic domain, 4 μM of fluorogenic MMP substrate, and various concentrations (0.15 nM to 10,000 nM) of tested compound dilutions in HEPES buffer (pH 7.5) containing 10 mM of CaCl$_2$), 0.01% Brij® 35 (polyoxyethylene (23) lauryl ether), and 0.1 mg/ml of BSA.

The enzyme and compounds were pre-incubated on a shaker to mix in wells. After an hour of mixing, fluorogenic substrate was added to each well. Reaction without enzyme was used as a blank control in the plate. The plate was then fed into a plate reader to measure fluorescence intensity at Excitation/Emission wavelengths of 340 nm/440 nm every 10 mins for at least 1 hour at 37° C. The IC$_{50}$ of each compound in MMP-12 inhibition was determined by using a readout obtained at time point 30 minutes. The results for each compound tested are show in Table 1.

Example 2: Selectivity Assay

The MMP selectivity assay was performed by using other recombinant human MMPs, including MMP-1, MMP-2, MMP-3, MMP-7, MMP-8, MMP-9, MMP-10, MMP-13, and MMP-14. The IC$_{50}$ of the compounds for the other recombinant human MMPs was determined as described above in Example 1, and are shown in Table 2.

TABLE 2

Selectivity Profile from MMP-12 of Compounds According to
Embodiments of the Application
Compound Activity

| ID | MMP-12 | MMP-1 | MMP-2 | MMP-3 | MMP-7 | MMP-8 | MMP-9 | MMP-10 | MMP-13 | MMP-14 |
|---|---|---|---|---|---|---|---|---|---|---|
| PC-8  | A | E | D | D | E | E | E | E | D | E |
| PC-10 | A | E | D | D | E | D | D | E | D | E |
| PC-12 | A | E | D | C | E | D | D | D | E | E |
| PC-13 | A | E | D | C | E | D | D | D | D | E |
| PC-16 | A | E | C | D | E | D | D | D | D | D |
| PC-22 | A | E | D | C | E | D | D | D | C | D |
| PC-28 | A | E | D | D | E | C | D | D | C | D |
| PC-48 | A | E | D | D | E | D | D | D | C | E |
| PC-50 | A | E | C | C | E | C | D | D | C | D |
| PC-51 | A | E | D | D | D | C | D | D | C | D |
| OC-7  | A | E | C | D | E | C | D | D | C | E |
| OC-12 | A | E | C | D | E | C | D | D | C | D |
| OC-13 | A | E | C | D | E | C | D | D | C | C |
| TC-4  | A | E | D | C | E | C | D | D | D | D |
| TC-5  | A | E | D | D | E | D | D | D | E | E |
| TC-8  | A | E | C | C | D | B | C | C | B | C |

A = less 10 nM,
B = 10 nM to 100 nM,
C = 100 nM to 1000 nM,
D = 1000 nM to 10000 nM,
E = greater than 10000 nM The results in Table 2 above show that compounds according to embodiments of the application have high selectivity for MMP-12 as compared to other MMPs, including MMP-1 MMP-2, MMP-3, MMP-7, MMP-8, MMP-9, MMP-10, MMP-13, and MMP-14.

Example 3: Efficacy Study of MMP-12 Inhibitors on SD Rat Kidney Fibrosis Model by Unilateral Ureteral Occlusion (UUO)

This study was to evaluate the therapeutic efficacy of MMP-12 inhibitor, PC-16 on a renal fibrosis model by unilateral ureteral occlusion (UUO). Male Sprague Dawley (SD) rats (180-220 g, n=71) were used in this study. Animals were randomly divided into 4 groups: vehicle group (group-1, n=8), PC-16 2 mg/kg/day group (group-2, n=9), PC-16 6 mg/kg/day group (group-3, n=10), PC-16 20 mg/kg/day group (group-4, n=9). Animals were anesthetized with 2.5% isoflurane inhelation. The left ureter was ligated to create a unilateral ureteral occlusion (UUO) model to induce renal fibrosis. The test article, PC-16 was administrated twice a day via oral delivery after modeling for 14 days. Peripheral blood serum was prepared at pre-modeling and day-15 (one day after last dosing). All animals were euthanized and processed for left kidney pathology studies.

PC-16 treatment at dose of 20 mg/kg/day did slightly limit the blood urea nitrogen (BUN) elevation as compared to vehicle group, however all data did not show a statistically significant difference as compared to model group. Serum creatinine levels did show a similar change as in the BUN.

Histologically, the left kidneys showed significant morphologic changes relative to the UUO including a pelvic dilatation, renal medula and cortex atropsy, tubular epithelial cell flattening and tubular dilatation, inflammation and necrosis. Interstitial fibrosis was clearly observed in the pelvic wall, medulla and cortex. PC-16 treatment showed a clear dose dependent effect, and a dose at 20 mg/kg/day was more effective than a dose of 2 mg/kg/day (p<0.01). The semi-quantitative evaluation of interstitial inflammation in the cortex indicated a significant reduction with the treatment of PC-16, and showed a dose dependent efficacy of PC-16. The semi quantitative evaluation of interstitial fibrosis in cortex indicated a significant reduction in the fibrosis score with the treatment of PC-16 at all dose groups. There was a clear dose dependent effect in PC-16 treatment groups.

The analysis of immunohistochemistry (IHC) staining in the cortex area of the left kidney for the animals treated with PC-16 showed a significant reduction in collagen-I deposition at a dose of 20 mg/kg/day (P<0.05) with a trance of dose dependent reduction with PC-16 treatment. It also showed a significant reduction in collagen-IV deposition at a dose of PC-16 6 mg/kg/day (P<0.05), PC-16 20 mg/kg/day with a trance of dose dependent reduction with PC-16 treatment.

In conclusion, UUO induced a significant kidney cortex damage, inflammation and interstitial fibrosis within 15 days of modeling. The treatment of PC-16 represented a clear dose dependent efficacy either in the limitation in the kidney damage, interstitial inflammation or interstitial fibrosis. Fibrosis related biomarker analysis indicated the treatment with PC-16 reduced the related collagen deposition (Collagen-I and IV) in the cortex area of damaged kidney.

Detailed Experimental Methods

Animals: Gender: Male, SD rats, 180-220 g, total 71. Certificate: 11400700272659, Beijing Vital River Laboratory Animal Technology Co., Ltd., China. Animal holding: Animals were maintained in a temperature-controlled environment with a 12 hours light/12 hours dark cycle and free access to food and water. Experimental procedures were performed according to IACUC guidelines in the KCl (Su-Zhou) Biotech Inc. (KCl) animal research facility. Model creation: Total 35 male SD rats were used in this study. After anesthesia with 2.5% isoflurane inhalation the animal abdomen was opened surgically. The left ureter was exposed and ligated close to the bladder to create the UUO model. After confirming no bleeding, the abdomen wall was closed in layers. The animals were maintained under temperature controlled pad (37° C.) for the recovery from anesthesia, and then were transferred to holding cages with regular food and water.

Experiment grouping: UUO modeling animals were divided into 7 groups randomizedly as vehicle (group-1, n=8), PC-16 2 mg/kg/day (group-5, n=9), PC-16 6 mg/kg/day (group-6, n=10), PC-16 20 mg/kg/day (group-7, n=9) (Table 4.1). Dosing regimen: All test articles were designed as an oral administration via a gastric perfusion. Test articles were designed to be delivered twice a day starting on the same day of modeling for 14 days (Table 4.1). Endpoints: 1) Blood collection: Peripheral blood was collected from all animals in each group and prepared for serum at pre-modeling and day-15 (one day after last dosing), stored at −80° C. All animals were euthanized according to KCl SOP. After confirming animal death without breath and heart bite the left kidneys were perfused with cold PBS followed by 10% neutral formalin and collected for further pathology study. 2) Detection of serum BUN and creatinine: The serum BUN and creatinine level were detected with Hitachi 7060 automatic biochemical analyzer and related test kits. 3) Kidney pathology examination: 3a) Kidney H&E staining and analysis: Following KCI's pathologic SOP all left kidneys were fixed in 10% formalin for at least 24 h at room temperature. After fixation, the kidney was cut longitudinally to get the largest surface and dehydrated in graded ethanol, cleared in xylene, and embedded in paraffin. Thin sections (3-μm) were mounted on glass slides, dewaxed, rehydrated to distilled water, and stained with hematoxylin and eosin (H&E). All stained slides were scanned with NanoZoomer Digital Pathology (S210, Hamamaci, Japan) scanner. Semi quantitative evaluation of the degree of tubular epithelial flattening and dilatation were graded from 0-5 according to the percentage of tubular involvement: score 0=no damage; score 1=1-10% damage; score 2=10-25% damage; score 3=25-50% damage; score 4=50-75% damage; score 5=75-100% damage. Semi quantitative evaluation of the tubular necrosis is graded from 0 to 3 according to the percentage of tubular involvement: score 0=no necrosis; score 1=<25% necrosis; score 2=25-50% necrosis; score 3=>50% necrosis. The average of tubular flattening and dilatation and necrosis as the total tubular damage was presented. Semi quantitative evaluation of the interstitial inflammation was graded from 0 to 4 according to the degree of inflammatory cell infiltration: score 0=no inflammatory cells; score 1=mild inflammatory cell infiltration; score 2=moderate inflammatory cell infiltration; score 3=severe inflammatory cell infiltration; score 4=extensive inflammatory cell infiltration. 3b) Kidney Masson Trichrome staining and analysis: Thin sections (3-μm) were mounted on glass slides, dewaxed, rehydrated to distilled water, and stained with Masson Trichrome. All stained slides were scanned with NanoZoomer Digital Pathology (S210, Hamamaci, Japan) scanner. Semi quantitative evaluation of cortex interstitial fibrosis with five different fields at ×10 magnification are selected randomly from kidney cortex, estimated using the following scoring system from 0-4 according to the percentage of interstitial fibrosis involvement: score 0=no fibrosis; score 1=<10% fibrosis; score 2=10-25% fibrosis; score 3=25-75% fibrosis; score 4=>75% fibrosis. 3c) Kidney IHC staining and analysis: All of left kidneys from each group (eight right kidneys from model group) were processed for biomarker analysis using IHC methods, such as Collagen-I (Abcam, Cat #ab34710), Collagen-IV (Abcam, Cat #ab6586). The IHC staining was processed according to the standard protocol of IHC at KCl. The stained slides were then scanned by Hamamatsu NanoZoomer Digital Pathology 5210 slide scanner and analyzed using the software to get the positive staining area/analysis area (%). 4) Statistical analysis: Graphpad, prism 5.0 was used for all statistical analyses with p value <0.05 considered significant. All data were reported as mean±SEM. Differences between groups were determined using either ANOVA tests with Bonferroni test or student T-test.

TABLE 4.1

Aninal Experiment Groups

| Group | N | OP | CPD | Conc. Mg/mL | Dosage mL/kg | Dosage mg/kg |
|---|---|---|---|---|---|---|
| Group-1 | 9 | UUO | Vehicle | N/A | 10 | N/A |
| Group-2 | 9 | UUO | PC-16 | 0.1 mg/ml | 10 | 2 mg/kg/d, bid |
| Gronp-3 | 9 | UUO | PC-16 | 0.3 mg/ml | 10 | 6 mg/kg/d, bid |
| Group-4 | 9 | UUO | PC-16 | 1 mg/ml | 10 | 20 mg/kg/d, bid |

Figure 1B:
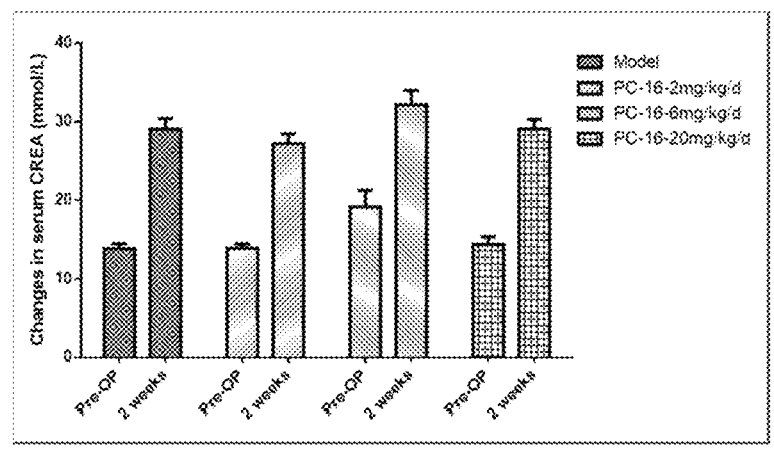
Figure 1C:
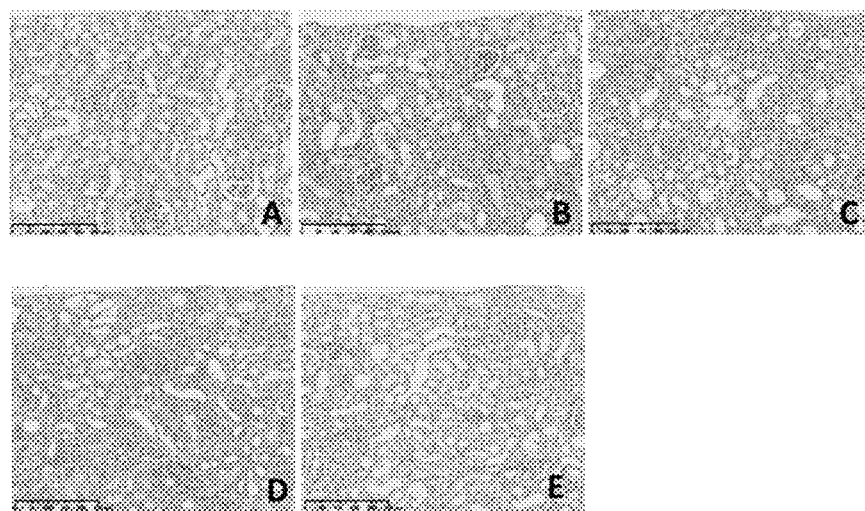
Figure 1D:
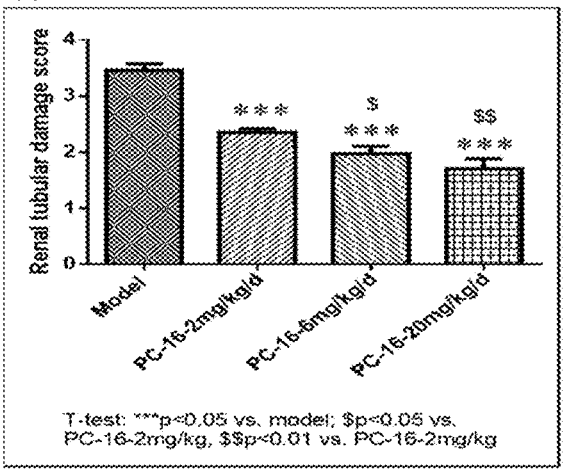
Figure 1D:
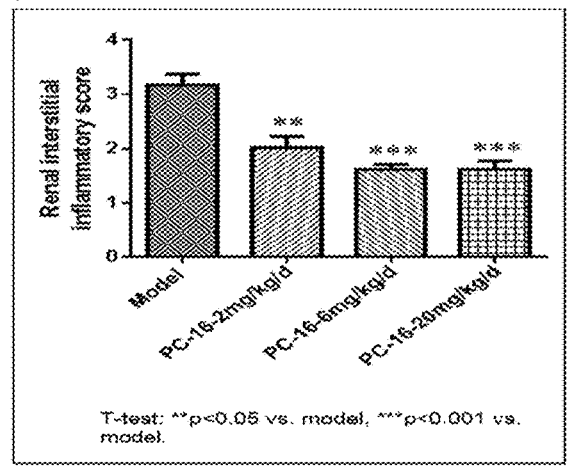
Figure 1F:
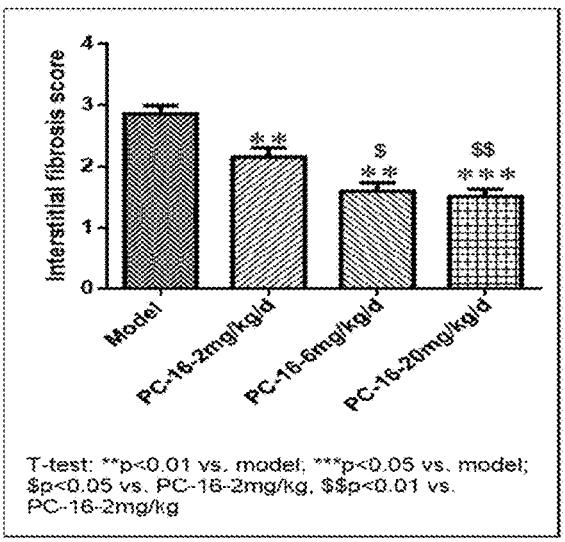
Figure 1E:
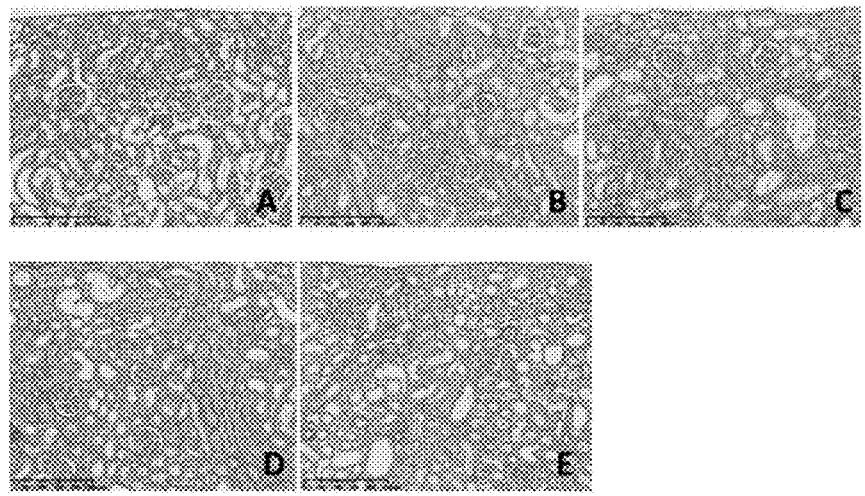
Figure 1G:
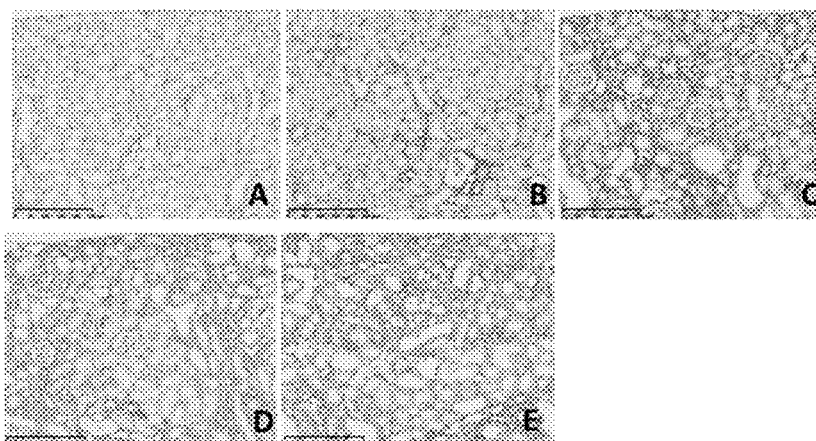
Figure 1G:
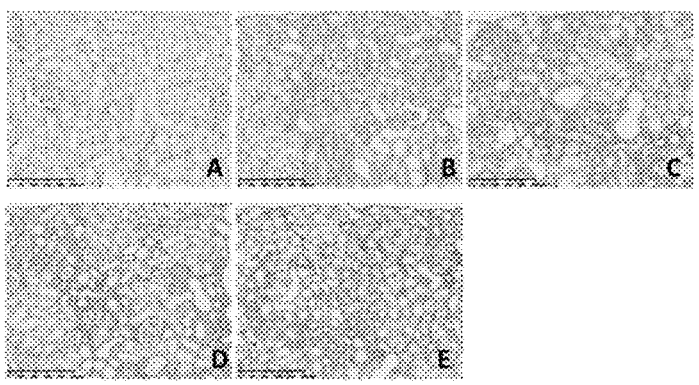
Figure 1H:
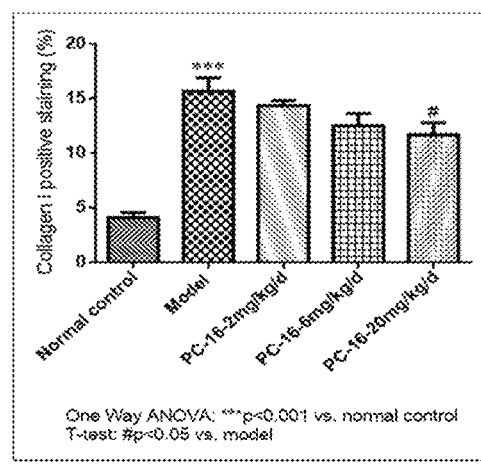
Figure 1H:
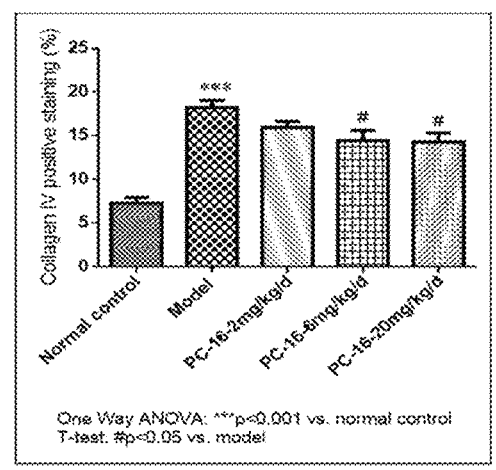

Results:
a) Animal physiological changes during the experimental periods: Several animals died during the experimental period, which was considered as the model failed such as the ureter ruptured during the operation, which induced peritonitis. The numbers of animals died in each group was showed in Table 4.1.
b) Changes in the serum BUN and creatitine: Serum BUN in all animals was raised after UUO at day-15 as compared to the pre modeling (p<0.001). PC-16 treatment at a dose of 20 mg/kg/day showed the same result (FIG. 1A); all data did not show a statistically significant difference as compared to model group. Serum creatinine levels did show a similar change as in the BUN (FIG. 1B).
c) Changes in the left kidney damage—The tubular damages: After 15 days of UUO, the left kidney showed pelvic cavity dilatation in all animals. The kidney cortex represented a significant atrophy with different degree of tubular epithelial cell flattening, tubular dilatation and interstitial inflammatory cell infiltration, and few foci of tubular necrosis (FIG. 1C). PC-16 treatment represented a clear dose dependent effect, and a dose at 20 mg/kg/day was more effect than a dose of 2 mg/kg/day (p<0.01) (FIG. 1D (I)).
d) Changes in the left kidney damage—The interstitial inflammation: The semi quantitative evaluation of interstitial inflammation in cortex indicated a significant reduction with the treatment of PC-16, and presented a dose dependent efficacy of PC-16 (FIG. 1D (II)).
e) Changes in the left kidney damage—The cortex interstitial fibrosis: After 15 days of UUO, the left kidney showed pelvic cavity, medulla area and cortex area with a significant interstitial fibrosis in all animals. The interstitial fibrosis in the cortex area was analyzed and represented a different degree with the test CPDs' treatment (FIG. 1E). The semi quantitative evaluation of interstitial fibrosis in cortex indicated a significant reduction in the fibrosis score with the treatment of PC-16 at dose of 20 mg/kg/day (p<0.001). There was a clear dose dependent effect in PC-16 treatment groups (FIG. 1F).
f) Pathological analysis of multiple biomarkers in left kidney: Collagen-I: The analysis of IHC staining in the cortex area of left kidney for the animals treated with PC-16 showed a significant reduction in collagen-I deposition at a dose of 20 mg/kg/day (p<0.05); a trance of dose dependent reduction in PC-16 treatment groups (FIG. 1G(I) and FIG. 1H(I)). Collagen-IV: IHC staining in the cortex area of the left kidney for the animals treated with PC-16 showed a significant reduction in collagen-IV deposition at dose of 20 mg/kg/day (p<0.05); a trance of dose dependent reduction with PC-16 treatment (FIG. 1G(II) and FIG. 1H(II)).

REFERENCES

1. U.S. Pat. No. 7,179,831
2. WO 02/096426
3. US 2004/0067996
4. WO 2004/108086
5. WO 02/074752
6. WO 2004/020415

We claim:
1. A compound of formula (I):

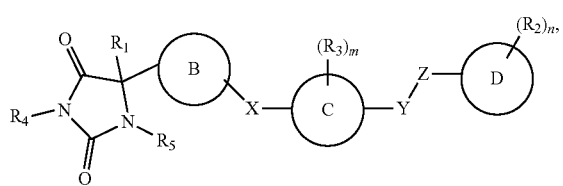

(I)

or a tautomer, stereoisomer, pharmaceutically acceptable salt thereof,
wherein:
  ring B is pyridinyl or thiophenyl;
  ring C is phenyl;
  ring D is pyridinyl;
  X is S;
  Y is O;
  Z is $CH_2$;
  $R_1$ is hydrogen or alkyl;
  each $R_2$ is independently selected from the group consisting of hydroxyl, amide, and hydroxyalkyl;
  each $R_3$ is independently selected from the group consisting of hydrogen, alkyl and halo;
  $R_4$ is hydrogen;
  $R_5$ is hydrogen;
  m is 1, 2, 3, or 4; and
  n is 1, 2, 3, 4, or 5.

2. The compound of claim 1, wherein each of $R_1$, $R_4$ and $R_5$ is hydrogen.

3. The compound of claim 1, wherein ring B is pyridinyl.

4. The compound of claim 3, wherein the compound is selected from the group consisting of a compound of formula (II-a), a compound of formula (II-b), a compound of formula (II-c), and a compound of formula (II-d):

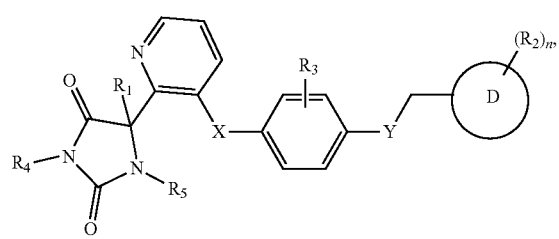

(II-a)

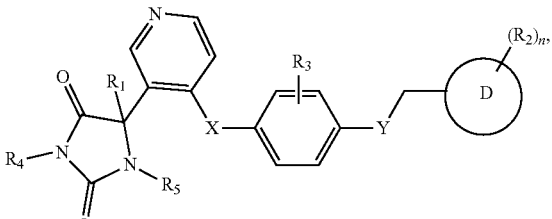

(II-b)

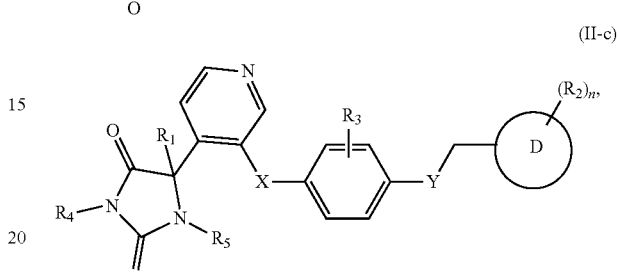

(II-c)

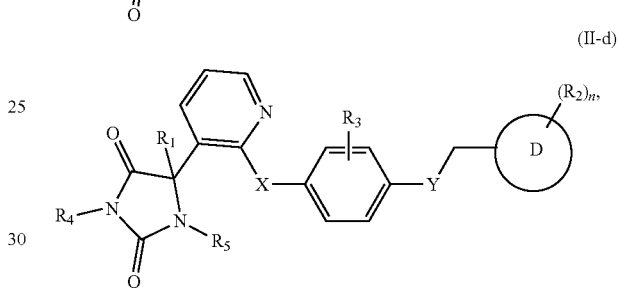

(II-d)

or a tautomer, stereoisomer, pharmaceutically acceptable salt thereof,
wherein:
  $R_1$ is hydrogen, —$CH_3$, or —$CH_2CH_3$;
  $R_3$ is hydrogen, —F, —Cl, or $CH_3$;
  $R_2$ is —$CH_2OH$, —OH, —C(O)$NH_2$, or —C(O)NH$CH_3$; and
  n is 0 or 1.

5. The compound of claim 1, wherein ring B is thiophenyl.

6. The compound of claim 5, wherein the compound is a compound of formula (IV):

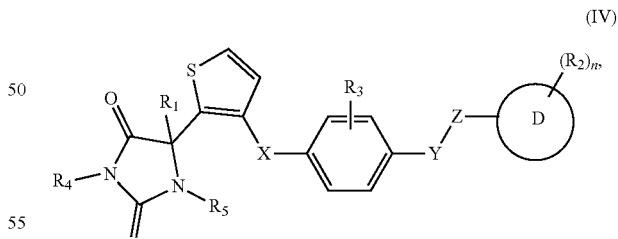

(IV)

or a tautomer, stereoisomer, pharmaceutically acceptable salt thereof,
wherein:
  each of $R_1$, $R_4$ and $R_5$ is hydrogen;
  X is S;
  Y is O;
  $R_3$ is hydrogen;
  $R_2$ is —C(O)$NH_2$, —$CH_2OH$, or —OH; and
  n is 0 or 1.

7. The compound of claim 1 being a compound of formula (I-a):

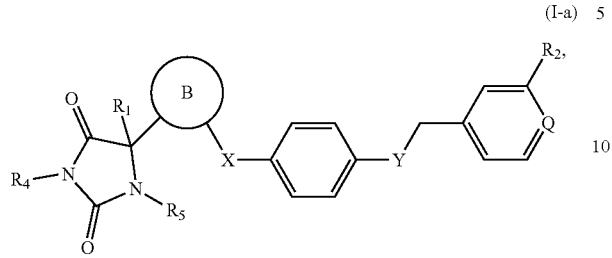

(I-a)

or a tautomer, stereoisomer, pharmaceutically acceptable salt thereof,
wherein:
ring B is pyridinyl;
Q is N;
$R_1$ is hydrogen, —$CH_3$, or —$CH_2CH_3$; and
$R_2$ is selected from the group consisting of —C(O)$NH_2$, —$CH_2OH$, or —OH.

8. The compound of claim 7, wherein each of $R_1$, $R_4$, and $R_5$ is hydrogen.

9. A compound selected from the group consisting of:

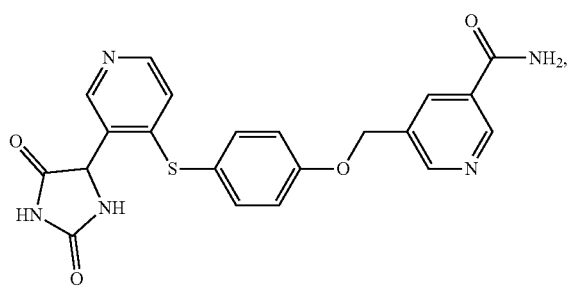

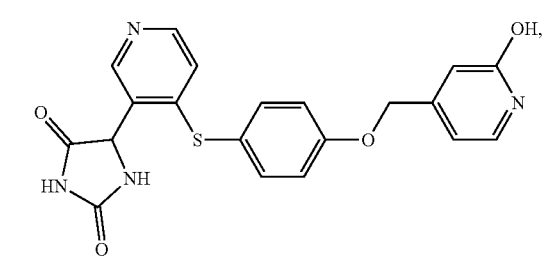

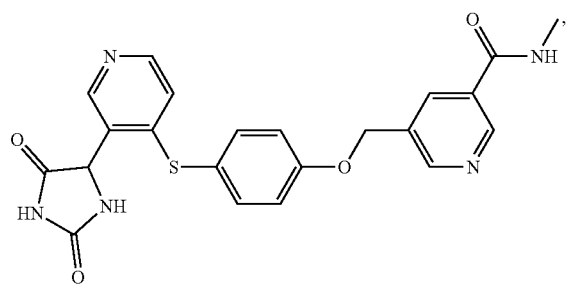

-continued

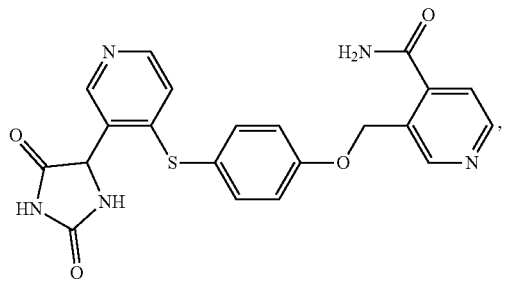

-continued

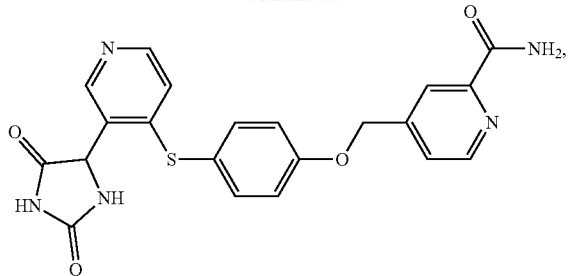

or a tautomer, stereoisomer, pharmaceutically acceptable salt thereof.

10. The compound of claim 9, or a pharmaceutically acceptable salt thereof.

11. A pharmaceutical composition comprising the compound of claim 1, and at least one pharmaceutically acceptable carrier.

12. A method of inhibiting macrophage elastase (MMP-12) in a subject in need thereof, the method comprising administering to the subject the pharmaceutical composition of claim 11.

13. A method of treating a disease mediated by macrophage elastase (MMP-12) in a subject in need thereof, the method comprising administering to the subject the pharmaceutical composition of claim 11, wherein the disease is selected from the group consisting of asthma, chronic obstructive pulmonary disease (COPD), a emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

* * * * *